US007117096B2

(12) United States Patent
Luo et al.

(10) Patent No.: US 7,117,096 B2
(45) Date of Patent: Oct. 3, 2006

(54) STRUCTURE-BASED SELECTION AND AFFINITY MATURATION OF ANTIBODY LIBRARY

(75) Inventors: Peizhi Luo, Sunnyvale, CA (US); Mark Hsieh, Palo Alto, CA (US); Pingyu Zhong, Mountain View, CA (US); Caili Wang, San Francisco, CA (US)

(73) Assignee: Abmaxis, Inc.

( * ) Notice: Subject to any disclaimer, the term of this patent is extended or adjusted under 35 U.S.C. 154(b) by 361 days.

(21) Appl. No.: 10/153,159

(22) Filed: May 20, 2002

(65) Prior Publication Data

US 2002/0177170 A1 Nov. 28, 2002

Related U.S. Application Data

(63) Continuation-in-part of application No. 10/125,687, filed on Apr. 17, 2002, now abandoned.

(60) Provisional application No. 60/284,407, filed on Apr. 17, 2001.

(51) Int. Cl.
*G01N 33/48* (2006.01)
*G01N 31/00* (2006.01)
*A61K 38/00* (2006.01)

(52) U.S. Cl. .......................... 702/19; 702/22; 530/300

(58) Field of Classification Search ................. 702/19, 702/27; 530/333
See application file for complete search history.

(56) References Cited

U.S. PATENT DOCUMENTS

| | | | |
|---|---|---|---|
| 6,403,312 | B1 | 6/2002 | Dahiyat et al. |
| 2003/0022240 | A1 | 1/2003 | Luo et al. |

FOREIGN PATENT DOCUMENTS

| | | |
|---|---|---|
| WO | WO 96/06625 | 3/1996 |
| WO | WO 98/45331 | 10/1998 |

OTHER PUBLICATIONS

Achim Knappik et al., "Fully Synthetic Human Combinatorial Antibody Libraries (HuCAL) Based on Modular Consensus Frameworks and CDRs Randomized with Trinucleotides", J. Mol. Biol. (2000) pp. 57-86.

Cyrus Chothia et al., "Structural Determinants in the Sequences of Immunoglobulin Variable Domain", J. Mol. Biol. (1998), pp. 457-479.

Yoshitaka Iba et al., "Changes in the Specificity of Antibodies Against Steriod Antigens by Introduction of Mutations into Complementarity-Determining Regions of the $V_H$ Domain," Protein Engineering, vol. 11, No. 5 (1998) pp. 361-370.

Mandal, C. et al., "ABGEN A Knowledge-Based Automated Approach for Antibody Structure Modeling", *Nature Biotechnology*, vol. 14, Mar. 1996, pp. 323-328.

Borrebaeck, C. et al., "Antibody evolution beyond Nature", *Nature Biotechnology*, vol. 20, Dec. 2002, pp. 1189-1190.

Bowie, J. et al., "A Method to Identify Protein Sequences That Fold into a Known Three-Dimensional Structure", *Science*, vol. 253, Jul. 1991, pp. 164-170.

Voigt, C. et al., "Computational method to reduce the search space for directed protein evolution", *Proc. Natl. Acad. Sci. USA*, vol. 98, No. 7, Mar. 2001, pp. 3778-3783.

Moore, G. et al., "Computational Challenges in Combinatorial Library Design for Protein Engineering", *AIChE Journal*, vol. 50, No. 2, Feb. 2004, pp. 262-272.

Kono, H. et al., "Statistical Theory for Protein Combinatorial Libraries. Packing Interactions, Backbone Flexibility, and the Sequence Variability of a Main-chain Structure", *J. Mol. Biol.*, vol. 306 (2001), pp. 607-628.

Wu, H. et al., "Stepwise *in vitro* affinity maturation of Vitaxin, an $\alpha_v\beta_3$-specific humanized mAb", *Proc. Natl. Acad. Sci. USA*, vol. 95, May 1998, pp. 6037-6042.

Al-Lazikani, B. et al. Standard Conformation for the Canonical Structures of Immunoglobulins. *J. Mol. Biol.* 1997; 273: 927-948.

(Continued)

*Primary Examiner*—Andrew Wang
*Assistant Examiner*—Anna Skibinsky

(57) ABSTRACT

The present invention provides a structure-based methodology for efficiently generating and screening protein libraries for optimized proteins with desirable biological functions, such as antibodies with high binding affinity and low immunogenicity in humans. In one embodiment, a method is provided for constructing a library of antibody sequences based on a three dimensional structure of a lead antibody. The method comprises: providing an amino acid sequence of the variable region of the heavy chain ($V_H$) or light chain ($V_L$) of a lead antibody, the lead antibody having a known three dimensional structure which is defined as a lead structural template; identifying the amino acid sequences in the CDRs of the lead antibody; selecting one of the CDRs in the $V_H$ or $V_L$ region of the lead antibody; providing an amino acid sequence that comprises at least 3 consecutive amino acid residues in the selected CDR, the selected amino acid sequence being a lead sequence; comparing the lead sequence profile with a plurality of tester protein sequences; selecting from the plurality of tester protein sequences at least two peptide segments that have at least 10% sequence identity with lead sequence, the selected peptide segments forming a hit library; determining if a member of the hit library is structurally compatible with the lead structural template using a scoring function; and selecting the members of the hit library that score equal to or better than or equal to the lead sequence. The selected members of the hit library can be expressed in vitro or in vivo to produce a library of recombinant antibodies that can be screened for novel or improved function(s) over the lead antibody.

46 Claims, 68 Drawing Sheets

OTHER PUBLICATIONS

Brinkmann, et al. Phage display of disulfide-stabilized Fv fragments. J. Immunol. Methods. 1995; 182(1):41-50 (Abstract).

Bruccoleri, R. et al. Structure of antibody hypervariable loops reproduced by a conformational search algorithm. *Nature.* 1988; 335: 564-568.

Bruccoleri. R. et al. Prediction of the Folding of Short Polypeptide Segments by Uniform Conformational Sampling. *Biopolymers.* 1987; 26: 137-168.

Chothia, C. et al. Canonical Structures for the Hypervariable Regions of Immunoglobulins. *J. Mol. Biol.* 1987; 196: 901-917.

Chothia, C. et al. Conformations of immunoglobulin hypervariable regions. *Nature.* 1989; 342: 877-883.

Eddy, Sean R. Profile hidden Markov models. Bioinformatics. 1998; 14:755-763.

Janway, et al. Structure of the antibody molecule and the immunoglobulin genes. In: Immunobiology. 1994; 3:1-3:3.

Johnson, G. et al. Kabat Database and its applications: 30 years after the first variability plot. *Nucleic Acids Research.* 2000; 28(1): 214-218.

Johnson, G. et al. Kabat Database and its applications: future directions. *Nucleic Acids Research.* 2001; 29(1): 205-206.

Kabat, E. A. et al. Sequences of Proteins of Immunological Interest. 4th Edition. National Institutes of Health, Bethesda, MD. 1987.

Laskoski, et al. Procheck: a program to check the stereochemical quality of protein structures. Journal of Applied Crystallography. 1993; 26(2):283-291.

MacCallum, R. et al. Antibody-antigen Interactions: Contact Analysis and Binding Site Topography. *J. Mol. Biol.* 1996; 262: 732-745.

Muller, et al. Tertiary structure of the major house dust mite allergen Der p. 2: Sequential and structural homologies. Biochemistry. 1998; 37:12707-12714.

Wu, T. T. et al. An Analysis of the Sequences of the Variable Regions of Bence Jones Proteins and Myeloma Light Chains and Their Implications for Antibody Complementarity. *J. Exp. Med.* 1970; 132: 211-250.

```
Kabat                               94   97   100 a b c d e f 101
Sequential scheme                   94   97   100101          107
Parental VH CDR3 (Lead):  CAKYPHYYGSSHWYFDVWG [SEQ ID NO: 5]
Mature VH CDR3:           CAKYPYYYGTSHWYFDVWG [SEQ ID NO: 6]
```

FIGURE 9B

```
kabat                    28   31
CDRs               |--CDR1---|                   |---CDR2---
Parental   CAASGYTFTNYGMNWVRQAPGKGLEWVGWINTYTGEPTY
Mature     CAASGYDFTHYGMNWVRQAPGKGLEWVGWINTYTGEPTY
contact              CC                          C CCC     C

Kabat                                 97    100a
CDRs       -----|                  |----CDR3----|
Parental   AADFKRRF---YYCAKYPHYYGSSHWYFDVWGQGTLVT
Mature     AADFKRRF---YYCAKYPYYYGTSHWYFDVWGQGTLVT
contact                              CCCCC  C  C
```

FIGURE 9C

```
Kabat                                94  97  100 a b c d e f 101
Sequential scheme                    94  97  100101          107
Parental VH CDR3 (Lead):   CAKYPHYYGSSHWYFDVWG [SEQ ID NO: 5]
Mature VH CDR3:            CAKYPYYYGTSHWYFDVWG [SEQ ID NO: 6]
```

Distribution of the hit sequences versus the sequence identity relative the parental $V_H$ CDR3 sequence Phylogenetic tree of a hit library of the anti-VEGF lead sequence

Variant Profile for $V_H$ CDR3

| AA: | A | C | D | E | F | G | H | I | K | L | M | N | P | Q | R | S | T | V | W | Y |
|---|---|---|---|---|---|---|---|---|---|---|---|---|---|---|---|---|---|---|---|---|
| #0: | 10 | 90 | 0 | 0 | 0 | 0 | 0 | 0 | 0 | 0 | 0 | 0 | 0 | 0 | 0 | 3 | 3 | 1 | 0 | 0 |
| #1: | 83 | 0 | 2 | 2 | 0 | 0 | 0 | 0 | 0 | 0 | 0 | 0 | 0 | 0 | 0 | 0 | 12 | 8 | 0 | 0 |
| #2: | 0 | 0 | 5 | 0 | 0 | 1 | 0 | 1 | 14 | 0 | 1 | 0 | 0 | 0 | 70 | 1 | 4 | 3 | 0 | 7 |
| #3: | 6 | 0 | 24 | 7 | 3 | 16 | 6 | 0 | 2 | 1 | 1 | 0 | 2 | 2 | 5 | 8 | 9 | 2 | 0 | 13 |
| #4: | 13 | 7 | 8 | 1 | 2 | 14 | 1 | 3 | 0 | 3 | 0 | 2 | 27 | 2 | 9 | 5 | 2 | 2 | 0 | 6 |
| #5: | 9 | 4 | 7 | 1 | 4 | 9 | 5 | 7 | 1 | 2 | 5 | 4 | 4 | 0 | 0 | 9 | 4 | 2 | 1 | 29 |
| #6: | 3 | 2 | 8 | 1 | 5 | 3 | 0 | 3 | 1 | 3 | 1 | 0 | 2 | 1 | 5 | 3 | 6 | 4 | 3 | 53 |
| #7: | 2 | 1 | 4 | 1 | 2 | 14 | 3 | 3 | 0 | 2 | 0 | 4 | 0 | 0 | 6 | 12 | 5 | 3 | 1 | 44 |
| #8: | 3 | 3 | 7 | 2 | 2 | 47 | 0 | 0 | 0 | 1 | 0 | 3 | 0 | 0 | 4 | 16 | 3 | 4 | 2 | 10 |
| #9: | 5 | 0 | 6 | 1 | 1 | 16 | 1 | 1 | 1 | 3 | 0 | 5 | 3 | 1 | 6 | 41 | 5 | 4 | 1 | 6 |
| #10: | 2 | 0 | 2 | 2 | 1 | 15 | 2 | 1 | 0 | 5 | 0 | 6 | 6 | 2 | 4 | 41 | 2 | 3 | 2 | 11 |
| #11: | 1 | 2 | 6 | 3 | 2 | 12 | 10 | 2 | 3 | 7 | 0 | 3 | 3 | 0 | 3 | 13 | 1 | 4 | 2 | 30 |
| #12: | 1 | 0 | 2 | 0 | 3 | 13 | 1 | 0 | 1 | 1 | 0 | 2 | 0 | 3 | 7 | 4 | 2 | 1 | 45 | 21 |
| #13: | 8 | 0 | 0 | 0 | 3 | 6 | 2 | 1 | 0 | 1 | 0 | 0 | 4 | 0 | 1 | 0 | 0 | 2 | 5 | 74 |
| #14: | 0 | 0 | 0 | 0 | 89 | 0 | 0 | 1 | 0 | 2 | 11 | 0 | 0 | 0 | 0 | 0 | 0 | 2 | 0 | 2 |
| #15: | 2 | 0 | 93 | 1 | 1 | 0 | 0 | 0 | 0 | 0 | 0 | 8 | 1 | 0 | 0 | 1 | 0 | 0 | 0 | 0 |
| #16: | 1 | 0 | 1 | 0 | 1 | 1 | 1 | 13 | 0 | 11 | 0 | 0 | 2 | 0 | 0 | 1 | 1 | 44 | 1 | 29 |
| #17: | 0 | 0 | 0 | 0 | 0 | 0 | 0 | 0 | 0 | 0 | 0 | 0 | 0 | 0 | 0 | 0 | 1 | 1 | 105 | 0 |
| #18: | 1 | 0 | 0 | 0 | 0 | 102 | 0 | 0 | 0 | 0 | 0 | 0 | 0 | 1 | 0 | 0 | 2 | 0 | 1 | 0 |

```
SEQ ID NO:
5      cakyphyygssnwyfdvwg
126    ..rd.y.....y.......
128    at.ggadgsggsyamnytt
129    svy.agrsydygggyaivq
130    tdttrstrdyp.rwlsl a
131    vedsddftvrnlnpvep w
132      veyivdraldshifd
133      shcpsnanvrqf zf
134      ias.ihnvrvfv pw
135      grimavfteetr  g
136      mklclitpwkdi  h
137       fqngaclqpvl  a
138       ptfwleqhnh   s
139       qvtpfwhack   t
140       vfvccletil
141       mnlqe idfa
141       lekew kfw
142        hwk  fia
143         em  w t
```

Cutoff at 10

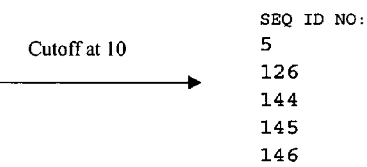

```
SEQ ID NO:
5      cakyphyygsshwyfdvwg
126    ..rd.y.....y.......
144     t.gg  gsggsy m y
145       .a  sy ygg   i
146                    l
```

Figure 11

Energy Correlation Between Antibody and Antibody-Antigen Complex of a Variant Library

Correlation between scores using refined vs simple scoring functions

Combinatorial Nucleic Acid Library Targeting the Peptide Library

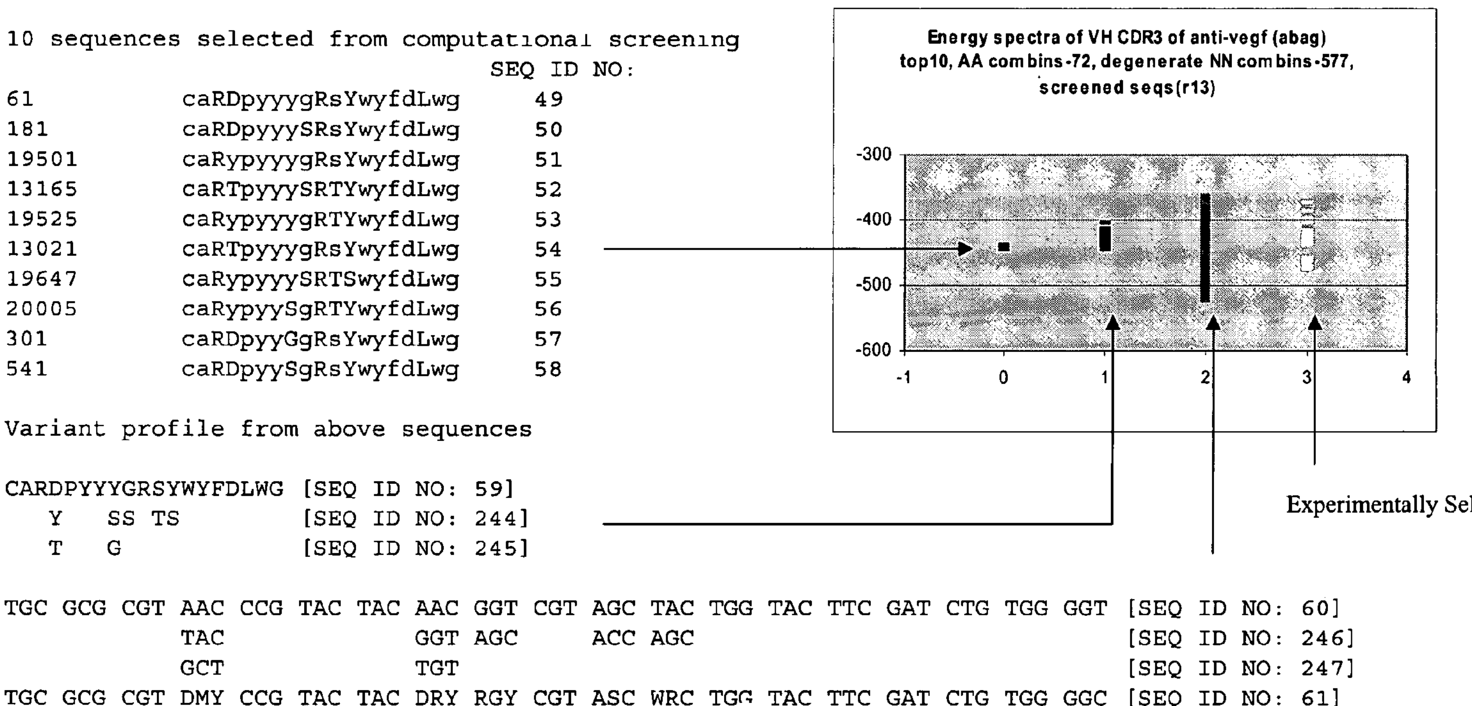

```
10 sequences selected from computational screening
                                     SEQ ID NO:
61          caRDpyyygRsYwyfdLwg     49
181         caRDpyyySRsYwyfdLwg     50
19501       caRypyyygRsYwyfdLwg     51
13165       caRTpyyySRTYwyfdLwg     52
19525       caRypyyygRTYwyfdLwg     53
13021       caRTpyyygRsYwyfdLwg     54
19647       caRypyyySRTSwyfdLwg     55
20005       caRypyySgRTYwyfdLwg     56
301         caRDpyyGgRsYwyfdLwg     57
541         caRDpyySgRsYwyfdLwg     58

Variant profile from above sequences

CARDPYYYGRSYWYFDLWG [SEQ ID NO: 59]
   Y   SS TS        [SEQ ID NO: 244]
   T   G            [SEQ ID NO: 245]

TGC GCG CGT AAC CCG TAC TAC AAC GGT CGT AGC TAC TGG TAC TTC GAT CTG TGG GGT [SEQ ID NO: 60]
            TAC             GGT AGC     ACC AGC                                 [SEQ ID NO: 246]
            GCT             TGT                                                 [SEQ ID NO: 247]
TGC GCG CGT DMY CCG TAC TAC DRY RGY CGT ASC WRC TGG TAC TTC GAT CTG TGG GGC [SEQ ID NO: 61]
```

Combinatorial peptide library size = 72

Combinatorial nucleotide library size = 4608

Figure 13A

Anti-VEGF $V_H$ CDR1 libraries: 10 selected sequences, combinatorial libraries of amino acids and nucleic acids

```
17102        gydftRygmnw      [SEQ ID NO: 147]
17108        gydftRygVnw      [SEQ ID NO: 148]
19796        gydfDRygVnw      [SEQ ID NO: 149]
17204        gydftRFgVnw      [SEQ ID NO: 150]
19790        gydfDRygmnw      [SEQ ID NO: 151]
3668         gyTfDRygVnw      [SEQ ID NO: 152]
41300        gFdftRygVnw      [SEQ ID NO: 153]
3662         gyTfDRygmnw      [SEQ ID NO: 154]
17105        gydftRygInw      [SEQ ID NO: 155]
17198        gydftRFgmnw      [SEQ ID NO: 156]

12345678901
GYDFTRYGVNW    [SEQ ID NO: 148]
 FT D F M      [SEQ ID NO: 157]
        I      [SEQ ID NO: 158]

---------------------------------------------
ggt tac gat ttc acc cgt tac ggt gtg aac tgg [SEQ ID NO: 159]
    ttc acc     gat     ttc     atg         [SEQ ID NO: 160]
                                atc         [SEQ ID NO: 161]

---------------------------------------------
ggt twc rmy ttc rmy cgt twc ggt rts aac tgg [SEQ ID NO: 162]

Combinatorial oligos: GGTTWCRMYTTCRMYCGTTWCGGTRTSAACTGG [SEQ ID NO:162]
Combinatorial peptide lib = 48
Combinatorial oligonucleotide lib = 1024
```

Figure 13B

Anti-VEGF $V_H$ CDR2 libraries: 10 selected sequences, combinatorial libraries of amino acids and nucleic acids

```
35584    wvntnngnttyvqdftr [SEQ ID NO: 163]
7168     wintnngestyvqdftr [SEQ ID NO: 164]
35016    wvntnngettyvqeftr [SEQ ID NO: 165]
35008    wvntnngettyvqdftr [SEQ ID NO: 166]
7176     wintnngestyvqeftr [SEQ ID NO: 167]
35012    wvntnngettyvqgftr [SEQ ID NO: 168]
7120     wintnngestyaqdftr [SEQ ID NO: 169]
7944     wintnngnttyvqeftr [SEQ ID NO: 170]
34816    wvntnngestyvqdftr [SEQ ID NO: 171]
34768    wvntnngestyaqdftr [SEQ ID NO: 172]


12345678901234567
WVNTNNGESTYVQDFTR [SEQ ID NO: 173]
 I     NT  A E    [SEQ ID NO: 174]
             G    [SEQ ID NO: 175]

-------------------------------------------------------------------
tgg gtg aac acc aac aac ggt gaa agc acc tac gtg cag gat ttc acc cgt [SEQ ID NO: 176]
    atc                     aac acc         gcg     gaa             [SEQ ID NO: 177]
                                                    ggt             [SEQ ID NO: 178]
-------------------------------------------------------------------
tgg rts aac acc aac aac ggt ram asc acc tac gyg cag grw ttc acc cgt [SEQ ID NO: 179]

                                    [SEQ ID NO: 179]
Combinatorial Oligos: TGGRTSAACACCAACAACGGTRAMASCACCTACGYGCAGGRWTTCACCCGT
Combinatorial peptide lib = 48
Combinatorial oligonucleotide lib = 256
```

Figure 13C

UV reading of ELISA positive clones selected from $V_H$ CDR3 library

Sequences of selected positive clones from rounds 1& 3 of $V_H$ CDR3

VEGF antibody, VH-CDR3

| SUMMARY | | SEQ ID NO: |
|---|---|---|
| Mature | TAVYYCAKYPYYYGTSHWYFDVWGQG | 62 |
| pVGD9-1-1B8 | TAVYYCARYPYYCGRTCWYFDLWGQG | 63 |
| pVGD9-1-1D7 | TAVYYCARYPYYCGRTCWYFDLWGQG | 64 |
| pVGD9-1-2A6 | TAVYYCARYPYYCGRTCWYFDLWGQG | 65 |
| pVGD9-1-3D10 | TAVYYCARYPYYCGRTCWYFDLWGQG | 66 |
| pVGD9-1-2A12 | TAVYYCARYPYYCGRTCWYFDLWGQG | 67 |
| pVGD9-1-1F8 | TAVYYCARYPYYCGRSCWYFDLWGQG | 68 |
| pVGD9-1-3B5 | TAVYYCARYPYYCGRSCWYFDLWGQG | 69 |
| pVGD9-1-1C4 | TAVYYCARYPYYCSRSCWYFDLWGQG | 70 |
| pVGD9-1-3F1 | TAVYYCARYPYYCSRSCWYFDLWGQG | 71 |
| pVGD9-1-2F7 | TAVYYCARYPYYCGRSNWYFDLWGQG | 72 |
| pVGD9-1-3B11 | TAVYYCARYPYYGSRTCWYFDLWGQG | 73 |
| pVGD9-1-3B10 | TAVYYCARYPYYSGRSYWYFDLWGQG | 74 |
| pVGD9-1-1A11 | TAVYYCARDPYYDSRSSWYFDLWGQG | 75 |
| pVGD9-1-2A1 | TAVYYCARDPYYDSRSYWYFDLWGQG | 76 |
| pVGD9-1-3A6 | TAVYYCARDPYYGGRSYWYFDLWGQG | 77 |
| pVGD9-1-2G8 | TAVYYCARDPYYGGRTSWYFDLWGQG | 78 |
| pVGD9-1-3B8 | TAVYYCARDPYYCGRSNWYFDLWGQG | 79 |
| pVGD9-1-1B7 | TAVSYCARDPYYYGRSNWYFDLWGQG | 80 |
| pVGD9-1-3H3 | TAVYYCARDPYYYGRTSWYFDLWGQG | 81 |
| pVGD9-1-1D2 | TAVYYCARAPYYCSRTCWYFDLWGQG | 82 |
| pVGD9-1-2A2 | TAVYYCARAPYYCSRTCWYFDLWGQG | 83 |
| pVGD9-1-2A11 | TAVYYCARAPYYCGRSCWYFDLWGQG | 84 |
| pVGD9-1-3A12 | TAVYYCARAPYYCGRSCWYFDLWGQG | 85 |
| pVGD9-1-1C2 | TAVYYYARAPYYCGRSYWYFDLWGQG | 86 |
| pVGD9-1-1B12 | TAVYYCARAPYYGGRSCWYFDLWGQG | 87 |
| pVGD9-1-2A3 | TAVYYCARSPYYCGRSCWYFDLWGQG | 88 |
| pVGD9-1-2G5 | TAVYYCARSPYYCGRSCWYFDLWGQG | 89 |
| pVGD9-1-2A8 | TAVYYCARSPYYCSRTCWYFDLWGQG | 90 |
| pVGD9-1-3A7 | TAVYYCARSPYYGGRSYWYFDLWGQG | 91 |
| pVGD9-1-2B7 | TAVYYCARNPYYCGRTCWYFDLWGQG | 92 |
| pVGD9-1-2G6 | TAVYYCARNPYYCGRTCWYFDLWGQG | 93 |
| pVGD9-1-3A11 | TAVYYCARTPYYGGRTNWYFDLWGQG | 94 |
| pVGD9-1-3H2 | TAVYYCARTPYYYGRTSWYFDLWGQG | 95 |
| Library9 | TAVYYCARXPYYXXRXXWYFDLWGQG | 96 |

| VH CDR3 Library round 3 selection | | SEQ ID NO: |
|---|---|---|
| PVG9-3-1G6 | TAVYYCARYPYYYSRSSWYFDLWGQG | 97 |
| PVG9-3-2A1 | TAVYYCARYPYYYSRSSWYFDLWGQG | 98 |
| PVG9-3-1D3 | TAVYYCARYPYYYSRSSWYFDLWGQG | 99 |
| PVG9-3-1D5 | TAVYYCARYPYYYSRSSWYFDLWGQG | 100 |
| PVG9-3-1G4 | TAVYYCARYPYYYSRSSWYFDLWGQG | 101 |
| PVG9-3-2E1 | TAVYYCARYPYYYSRSSWYFDLWGQG | 102 |
| PVG9-3-1E5 | TAVYYCARYPYYYSRSSWYFDLWGQG | 103 |
| PVG9-3-1A5 | TAVYYCARYPYYYSRSSWYFDLWGQG | 104 |
| PVG9-3-1A10 | TAVYYCARYPYYYSRSSWYFDLWGQG | 105 |
| PVG9-3-2E6 | TAVYYCARYPYYYSRSNWYFDLWGQG | 106 |
| PVG9-3-1B10 | TAVYYCARYPYYYSRSNWYFDLWGQG | 107 |
| PVG9-3-1D6 | TAVYYCARYPYYYSRSNWYFDLWGQG | 108 |
| PVG9-3-2F4 | TAVYYCARYPYYYGRSNWYFDLWGQG | 109 |
| PVG9-3-1E3 | TAVYYCARYPYYYGRSNWYFDLWGQG | 110 |
| PVG9-3-2A2 | TAVYYCARYPYYYGRSNWYFDLWGQG | 111 |
| PVG9-3-1G7 | TAVYYCARYPYYYGRSSWYFDLWGQG | 112 |
| PVG9-3-1E2 | TAVYYCARYPYYYGRSSWYFDLWGQG | 113 |
| PVG9-3-2B12 | TAVYYCARYPYYYGRTSWYFDLWGQG | 114 |
| PVG9-3-2D6 | TAVYYCARYPYYYGRTSWYFDLWGQG | 115 |
| PVG9-3-2F2 | TAVYYCARYPYYSGRSSWYFDLWGQG | 116 |
| PVG9-3-1D1 | TAVYYCARYPYYSGRSSWYFDLWGQG | 117 |
| PVG9-3-1A11 | TAVYYCARYPYYSGRSSWYFDLWGQG | 118 |
| PVG9-3-1E7 | TAVYYCARYPYYYSRTSWYFDLWGQG | 119 |
| PVG9-3-1C10 | TAVYYCARAPYYCGRSCWYFDLWGQG | 120 |
| PVG9-3-1F9 | TAVYYCARYPYYCGRSCWYFDLWGQG | 121 |
| PVG9-3-1F8 | TAVYYCARYPYYDGRSNWYFDLWGQG | 122 |
| PVG9-3-2G5 | TAVYYCARYPYYCGRSNWYFDLWGQG | 123 |
| PVG9-3-2B11 | TAVYYCARDPYYCSRSCWYFDLWGQG | 124 |
| PVG9-3-2G9 | TAVYYCARYPYYSGRSYWYFDLWGQG | 125 |

Figure 14B

The phylogenetic trees of the selected sequences of VH CDR3 with the parental and matured VH CDR3 sequences Experimentally selected anti-VEGF antibody sequences from designed $V_H$ CDR1, CDR2 and CDR3 libraries

| VH CDR1 libraries | SEQ ID NO: | VH CDR2 libraries | SEQ ID NO: | VH CDR3 libraries | SEQ ID NO: |
|---|---|---|---|---|---|
| GYNFTRYGI | 19 | WINTNNGESTYAQGFTR | 31 | RYPYYYSRSSWYFDL | 36 |
| GYNFTRYGM | 20 | WINTNNGDTTYAQEFTR | 32 | RYPYYYSRSNWYFDL | 37 |
| GYNFNRYGI | 21 | WINTNNGNSTYAQEFTR | 33 | RYPYYYGRSNWYFDL | 38 |
| GYDFTRYGV | 22 | WINTNNGDTTYVQDFTR | 34 | RYPYYYGRSSWYFDL | 39 |
| GYDFTRYGM | 23 | WVNTNNGDSTYAQGFTR | 35 | RYPYYYGRTSWYFDL | 40 |
| GYDFNRYGI | 24 | | | RYPYYYSRTSWYFDL | 41 |
| GYDFDRYGM | 25 | | | RYPYYSGRSSWYFDL | 42 |
| GYDFDRYGI | 26 | | | RAPYYCGRSCWYFDL | 43 |
| GYDFDRYGV | 27 | | | RYPYYDGRSNWYFDL | 44 |
| GYTFNRYGI | 28 | | | RYPYYCGRSNWYFDL | 45 |
| GYAFNRYGI | 29 | | | RDPYYCSRSCWYFDL | 46 |
| GYAFNRYGM | 30 | | | RYPYYSGRSYWYFDL | 47 |
| | | | | RPPYYYGSSHWYFDV | 48 |

FIGURE 16A

The distribution of the sequence identities of experimentally selected sequences relative to the corresponding parental sequence of anti-VEGF $V_H$ CDRs

The relationship among four libraries and distribution of the experimentally selected sequences among them:

designed peptide sequences, their combinatorial amino acid library and the degenerate nucleic acid library encoding combinatorial amino acid library of unique sequences, the whole degenerate nucleic acid library

The relationship among designed libraries of anti-VEGF $V_H$ CDR1,2,3 and the distribution of the selected sequences among them

| Library | AA_Seq/Comb. | NN_seq/peptide_seq | exp_seq/positive clones | distribution of the selected seqs | | |
|---|---|---|---|---|---|---|
| | | | | AA_seq | AA_comb | NN_peptide_seq |
| CDR1 | 10/48 | 1024/192 | 12 | 4 | 5 | 12 |
| CDR2 | 10/32 | 256/144 | 5 | 0 | 1 | 5 |
| CDR3_Round1 | 10/72 | 4608/576 | 23 | 1 | 5 | 23 |
| CDR3_Round3 | 10/72 | 4608/576 | 13 | 1 | 6 | 13 |

Notes:
(1) all positive clones are covered in the original degenerate nucleic acid library.
(2) Combinatorial degenerate nucleic acid library increases the size of library, but also expand diversity of the positive clones
(3) The degenerate nucleic acid library can be designed to increase the diversity of amino acid libraries while reduce the degeneracy of the encoded amino acid sequences by considering the library size as well as codon usage.
(4) The distribution of the experimentally selected sequences among the designed sequences, their combinatorial libraries of variant amino acids and degenerate nucleic acids should be examined by sampling a statistically meaningful number of samples.

FIGURE 17B

The lead sequence profile from structure-based multiple alignment

| Pdb id chain | sequences | motif color | |
|---|---|---|---|
| 1BJ1_H | cakyphyygsshwyfdvwg | magenta | [SEQ ID NO: 5] |
| 1HYX_H | carvshydgsrdwyfdvwg | green | [SEQ ID NO: 180] |
| 1DQD_H | casppgyygsgpyamdywg | yellow | [SEQ ID NO: 181] |
| 1ADQ_H | caktrsyvvaaeyyfhywg | cyan | [SEQ ID NO: 182] |
| 1OAK_H | cvrdpadygnydyaldywg | red | [SEQ ID NO: 183] |

Variant profile for the VH CDR3 lead sequence profile

Amino Acid Count by Position and Type

| Pos | A | C | D | E | F | G | H | I | K | L | M | N | P | Q | R | S | T | V | W | Y |
|---|---|---|---|---|---|---|---|---|---|---|---|---|---|---|---|---|---|---|---|---|
| 0 | 3 | 242 | 0 | 1 | 0 | 0 | 0 | 0 | 0 | 0 | 0 | 0 | 0 | 0 | 0 | 1 | 3 | 1 | 0 | 0 |
| 1 | 216 | 0 | 4 | 2 | 0 | 2 | 0 | 0 | 0 | 0 | 0 | 0 | 2 | 0 | 0 | 0 | 15 | 9 | 0 | 1 |
| 2 | 1 | 1 | 0 | 0 | 1 | 2 | 0 | 1 | 25 | 0 | 0 | 2 | 0 | 0 | 200 | 5 | 10 | 3 | 0 | 0 |
| 3 | 17 | 0 | 64 | 19 | 2 | 48 | 8 | 3 | 7 | 4 | 1 | 1 | 4 | 5 | 16 | 20 | 7 | 16 | 2 | 7 |
| 4 | 15 | 0 | 10 | 6 | 4 | 44 | 3 | 7 | 5 | 11 | 1 | 4 | 38 | 3 | 35 | 18 | 10 | 11 | 5 | 21 |
| 5 | 16 | 6 | 15 | 5 | 7 | 36 | 8 | 11 | 6 | 8 | 2 | 10 | 17 | 1 | 10 | 24 | 10 | 10 | 3 | 46 |
| 6 | 13 | 4 | 21 | 9 | 11 | 25 | 1 | 12 | 3 | 13 | 1 | 6 | 5 | 3 | 7 | 21 | 10 | 10 | 4 | 72 |
| 7 | 7 | 7 | 19 | 2 | 5 | 35 | 6 | 5 | 1 | 7 | 3 | 9 | 4 | 2 | 12 | 35 | 10 | 16 | 5 | 61 |
| 8 | 9 | 1 | 9 | 4 | 9 | 70 | 1 | 4 | 1 | 6 | 0 | 8 | 5 | 0 | 12 | 44 | 16 | 17 | 4 | 31 |
| 9 | 14 | 0 | 14 | 5 | 4 | 43 | 1 | 1 | 2 | 10 | 1 | 13 | 6 | 2 | 18 | 54 | 13 | 14 | 8 | 28 |
| 10 | 8 | 0 | 11 | 7 | 6 | 33 | 7 | 5 | 3 | 9 | 6 | 10 | 14 | 8 | 6 | 38 | 10 | 11 | 7 | 52 |
| 11 | 8 | 2 | 12 | 6 | 6 | 26 | 10 | 3 | 6 | 10 | 2 | 10 | 17 | 2 | 13 | 24 | 7 | 20 | 8 | 59 |
| 12 | 3 | 2 | 16 | 2 | 6 | 22 | 8 | 0 | 5 | 3 | 1 | 19 | 6 | 3 | 11 | 13 | 4 | 5 | 35 | 87 |
| 13 | 54 | 2 | 1 | 1 | 6 | 31 | 5 | 3 | 1 | 2 | 0 | 0 | 16 | 1 | 3 | 6 | 6 | 6 | 11 | 96 |
| 14 | 1 | 0 | 0 | 0 | 160 | 2 | 0 | 6 | 1 | 14 | 61 | 0 | 1 | 0 | 0 | 0 | 0 | 2 | 0 | 3 |
| 15 | 5 | 0 | 214 | 2 | 2 | 1 | 2 | 0 | 1 | 0 | 1 | 18 | 0 | 2 | 0 | 0 | 1 | 1 | 0 | 0 |
| 16 | 1 | 0 | 3 | 0 | 3 | 0 | 3 | 29 | 0 | 17 | 0 | 0 | 10 | 0 | 0 | 4 | 2 | 64 | 0 | 115 |
| 17 | 0 | 0 | 0 | 0 | 0 | 0 | 0 | 0 | 0 | 1 | 0 | 0 | 0 | 0 | 0 | 0 | 0 | 1 | 248 | 1 |
| 18 | 1 | 0 | 0 | 0 | 0 | 246 | 0 | 0 | 0 | 0 | 0 | 0 | 0 | 1 | 0 | 0 | 0 | 0 | 3 | 0 |

5% cutoff

```
Cakyphyygsshwyfdvwg [SEQ ID NO: 5]
-------------------
..rdgy....yyy...y.. [SEQ ID NO:184]
 t.g.ggssg.g.amn.   [SEQ ID NO:185]
 srssgyygsggl i     [SEQ ID NO:186]
   eypddvrpvnp  l   [SEQ ID NO:187]
   asaavtd pd       [SEQ ID NO:188]
   vadl  v rs       [SEQ ID NO:189]
   r     a          [SEQ ID NO:190]
         n          [SEQ ID NO:191]
         t          [SEQ ID NO:192]
```

FIGURE 19B

The distribution of hit libraries from a lead or lead profile versus identity relative the parental $V_H$ CDR3 sequence

Strategy to generate a focused intersection of sequence, structure and functional spaces while increasing the diversity in sequence and structure spaces

Sequences of coiled-coil domain in ccFv

Sequence for GR1 domain

```
XbaI     10          20          30          40          50
TCTAGAGGTGGAGGAGGTGAGGAGAAGTCCCGGCTGTTGGAGAAGGAGAA
 S  R  G  G  G  G  E  E  K  S  R  L  L  E  K  E  N
         60          70          80          90         100
CCGTGAACTGGAAAAGATCATTGCTGAGAAAGAGGAGCGTGTCTCTGAAC
  R  E  L  E  K  I  I  A  E  K  E  E  R  V  S  E
        110         120         130         140  AscI
TGCGCCATCAACTCCAGTCTGTAGGAGGTTGTTAATAGGGCGCGCC [SEQ ID NO: 9]
L  R  H  Q  L  Q  S  V  G  G  C [SEQ ID NO: 10]
```

Sequence for GR2 domain

```
 XhoI    10          20          30          40          50
TCTCGAGGAGGTGGTGGAACATCCCGCCTGGAGGGCCTACAGTCAGAAAA
 S  R  G  G  G  G  T  S  R  L  E  G  L  Q  S  E  N
         60          70          80          90         100
CCATCGCCTGCGAATGAAGATCACAGAGCTGGATAAAGACTTGGAAGAAG
  H  R  L  R  M  K  I  T  E  L  D  K  D  L  E  E
        110         120         130  NotI 140
TCACCATGCAGCTGCAAGACGTTGGCGGTTGCGCGGCCGCT [SEQ ID NO: 11]
V  T  M  Q  L  Q  D  V  G  G  C  A  A  A  [SEQ ID NO: 12]
```

FIGURE 21

VH for AM2 antibody (cDNA 1-369)

```
                                                                        NheI
         10        20        30        40        50        60        70        80
GAGGTGCAGCTGGTGGAGTCTGGGGGAGGCCTGGTCCAGCCTGGGGGGTCCCTGAGACTCTCCTGTGCAGCTAGCGGCTA
 E  V  Q  L  V  E  S  G  G  G  L  V  Q  P  G  G  S  L  R  L  S  C  A  A  S  G  Y>

                                             XmaI
         90       100       110       120       130       140       150       160
CACCTTCACTAACTATGGCATGAACTGGGTCCGCCAGGCTCCCGGGAAGGGGCTGGAGTGGGTTGGCTGGATAAACACAT
 T  F  T  N  Y  G  M  N  W  V  R  Q  A  P  G  K  G  L  E  W  V  G  W  I  N  T>
   CDR1

                                                               SpeI
        170       180       190       200       210       220       230       240
ATACTGGAGAGCCAACTTATGCAGCTGACTTCAAAAGACGATTCACCTTTTCCCTCGACACTAGTAAGTCCACGGCATAT
Y  T  G  E  P  T  Y  A  A  D  F  K  R  R  F  T  F  S  L  D  T  S  K  S  T  A  Y>
     CDR2

                                          PstI
        250       260       270       280       290       300       310       320
CTGCAAATGAACAGCCTGAGAGCCGAGGACACTGCAGTGTATTACTGTGCGAAGTACCCTCACTACTACGGTAGTTCCCA
 L  Q  M  N  S  L  R  A  E  D  T  A  V  Y  Y  C  A  K  Y  P  H  Y  Y  G  S  S  H>
                                                                     CDR3

            AatII      StyI
        330       340       350       360
CTGGTACTTCGACGTCTGGGGCCAAGGGACCCTTGTCACCGTCTCCTCA [SEQ ID NO: 13]
 W  Y  F  D  V  W  G  Q  G  T  L  V  T  V  S  S> [SEQ ID NO: 14]
```

FIGURE 22A

VL for AM2 antibody (cDNA 1-324)

```
                                                                BstEII
         10         20         30         40         50         60         70         80
GACATCCAGATGACACAGTCTCCATCCTCCCTGTCTGCATCTGTAGGAGACAGGGTCACCATCACTTGCAGCGCAAGTCA
 D  I  Q  M  T  Q  S  P  S  S  L  S  A  S  V  G  D  R  V  T  I  T  C  S  A  S  Q>

                                          SexA1    KasI
         90        100        110        120        130        140        150        160
GGACATTAGTAACTATTTAAATTGGTATCAGCAGAAACCAGGTAAGGCGCCTAAGGTCCTGATCTATTTCACATCCAGTT
 D  I  S  N  Y  L  N  W  Y  Q  Q  K  P  G  K  A  P  K  V  L  I  Y  F  T  S  S>
     CDR1                                                                    CDR2

      BspEI
       170        180        190        200        210        220        230        240
TGCACTCCGGAGTCCCATCAAGGTTCAGTGGCAGTGGATCTGGGACAGATTTCACTCTCACCATCAGCAGTCTGCAACCC
L  H  S  G  V  P  S  R  F  S  G  S  G  S  G  T  D  F  T  L  T  I  S  S  L  Q  P>

     BbsI                                                          KpnI
       250        260        270        280        290        300        310        320
GAAGACTTTGCAACTTACTACTGTCAACAGTACAGTACTGTCCCCTGGACTTTCGGTCAGGGTACCAAAGTGGAGATCAA
 E  D  F  A  T  Y  Y  C  Q  Q  Y  S  T  V  P  W  T  F  G  Q  G  T  K  V  E  I  K>
                                  CDR3

ACGT [SEQ ID NO: 15]
 R> [SEQ ID NO: 16]
```

FIGURE 22B

Vectors for AM2-ccFv display

Sequence for PABMD12 vector [SEQ ID NO: 17]

GCGCAACGCAATTAATGTGAGTTAGCTCACTCATTAGGCACCCCAGGCTTTACACTTTATGCTTCCGGCTCGTATGTTGTGTGGAATTGTGAGCGGATAACAATTTACCGGTTCTTTTAACTTTAGTAAGGAGGAATTAAA
AAATGAAAAAGTCTTTAGTCCTCAAAGCCTCCGTAGCCGTTGCTACCCTCGTTCCGATGCTAAGCTTCGCTGAGGTGCAGCTGGTGGAGTCTGGGGGAGGCCTGGTCCAGCCTGGGGGTCCCTGAGACTCTCCTGTGCAG
CTAGCGGCTACACCTTCACTAACTATGGCATGAACTGGGTCCGCCAGGCTCCCGGGAAGGGGCTGGAGTGGGTTGGCTGGATAAACACATATACTGGAGAGCCAACTTATGCAGCTGACTTCAAAAGACGATTCACCTTTT
CCCTCGACACTAGTAAGTCCACGGCATATCTGCAAATGAACAGCCTGAGAGCCGAGGACACTGCAGTGTATTACTGTGCGAAGTACCCTCACTACTACGGTAGTTCCCACTGGTACTTCGACGTCTGGGGCCAAGGGACCC
TTGTCACCGTCTCCTCATCTAGAGGTGGAGGAGGTGAGGAGAAGTCCCGGCTGTTGGAGAAGGAGAACCGTGAACTGGAAAAGATCATTGCTGAGAAAGAGGAGCGTGTCTCTGAACTGCGCCATCAACTCCAGTCTGTAG
GAGGTTGTTAATAGGGCGCGCCACAATTTCACAGTAAGGAGGTTTAACTTATGAAAAAATTATTATTCGCAATTCCTTTAGTTGTTCCTTTCTATTCTCACTCCGCTACGCGTGACATCCAGATGACACAGTCTCCATCCT
CCCTGTCTGCATCTGTAGGAGACAGGGTCACCATCACTTGCAGCGCAAGTCAGGACATTAGTAACTATTTAAATTGGTATCAGCAGAAACCAGGTAAGGCGCCTAAGGTCCTGATCTATTTCACATCCAGTTTGCACTCCG
GAGTCCCATCAAGGTTCAGTGGCAGTGGATCTGGGACAGATTTCACTCTCACCATCAGCAGTCTGCAACCCGAAGACTTTGCAACTTACTACTGTCAACAGTACAGTACTGTCCCCTGGACTTTCGGTCAGGGTACCAAAG
TGGAGATCAAACGTTCTCGAGGAGGTGGTGGAACATCCCGCCTGGAGGGCCTACAGTCAGAAAACCATCGCCTGCGAATGAAGATCACAGAGCTGGATAAAGACTTGGAAGAAGTCACCATGCAGCTGCAAGACGTTGGCG
GTTGCGCGGCCGCTTATCCATACGACGTACCAGACTACGCAGGAGGTCATCACCATCATCACCATTAGAGATCTGGAGGCGGTACTGTTGAAAGTTGTTTAGCAAAACCTCATACAGAAAATTCATTTACTAACGTCTGGA
AAGACGACAAAACTTTAGATCGTTACGCTAACTATGAGGGCTGTCTGTGGAATGCTACAGGCGTTGTGGTTTGTACTGGTGACGAAACTCAGTGTTACGGTACATGGGTTCCTATTGGGCTTGCTATCCCTGAAAATGAGG
GTGGTGGCTCTGAGGGTGGCGGTTCTGAGGGTGGCGGTTCTGAGGGTGGCGGTACTAAACCTCCTGAGTACGGTGATACACCTATTCCGGGCTATACTTATATCAACCCTCTCGACGGCACTTATCCGCCTGGTACTGAGC
AAAACCCCGCTAATCCTAATCCTTCTCTTGAGGAGTCTCAGCCTCTTAATACTTTCATGTTTCAGAATAATAGGTTCCGAAATAGGCAGGGTGCATTAACTGTTTATACGGGCACTGTTACTCAAGGCACTGACCCCGTTA
AAACTTATTACCAGTACACTCCTGTATCATCAAAAGCCATGTATGACGCTTACTGGAACGGTAAATTCAGAGACTGCGCTTTCCATTCTGGCTTTAATGAGGATCCATTCGTTTGTGAATATCAAGGCCAATCGTCTGACC
TGCCTCAACCTCCTGTCAATGCTGGCGGCGGCTCTGGTGGTGGTTCTGGTGGCGGCTCTGAGGGTGGCGGCTCTGAGGGTGGCGGTTCTGAGGGTGGCGGCTCTGAGGGTGGCGGTTCCGGTGGCGGCTCCGGTTCCGGTG
ATTTTGATTATGAAAAAATGGCAAACGCTAATAAGGGGGCTATGACCGAAAATGCCGATGAAAACGCGCTACAGTCTGACGCTAAAGGCAAACTTGATTCTGTCGCTACTGATTACGGTGCTGCTATCGATGGTTTCATTG
GTGACGTTTCCGGCCTTGCTAATGGTAATGGTGCTACTGGTGATTTTGCTGGCTCTAATTCCCAAATGGCTCAAGTCGGTGACGGTGATAATTCACCTTTAATGAATAATTTCCGTCAATATTTACCTTCCCTCCCTCAAT
CGGTTGAATGTCGCCCTTTTGTCTTTAGCGCTGGTAAACCATATGAATTTTCTATTGATTGTGACAAAATAAACTTATTCCGTGGTGTCTTTGCGTTTCTTTTATATGTTGCCACCTTTATGTATGTATTTTCTACGTTTG
CTAACATACTGCGTAATAAGGAGTCTTAAGTCGACCTCGACCAATTCGCCCTATAGTGAGTCGTATTACAATTCACTGGCCGTCGTTTTACAACGTCGTGACTGGGAAAACCCTGGCGTTACCCAACTTAATCGCCTTGCA
GCACATCCCCCTTTCGCCAGCTGGCGTAATAGCGAAGAGGCCCGCACCGATCGCCCTTCCCAACAGTTGCGCAGCCTGAATGGCGAATGGACGCGCCCTGTAGCGGCGCATTAAGCGCGGCGGGTGTGGTGGTTACGCGC
AGCGTGACCGCTACACTTGCCAGCGCCCTAGCGCCCGCTCCTTTCGCTTTCTTCCCTTCCTTTCTCGCCACGTTCGCCGGCTTTCCCCGTCAAGCTCTAAATCGGGGGCTCCCTTTAGGGTTCCGATTTAGTGCTTTACGG
CACCTCGACCCCAAAAAACTTGATTAGGGTGATGGTTCACGTAGTGGGCCATCGCCCTGATAGACGGTTTTTCGCCCTTTGACGTTGGAGTCCACGTTCTTTAATAGTGGACTCTTGTTCCAAACTGGAACAACACTCAAC
CCTATCTCGGTCTATTCTTTTGATTTATAAGGGATTTTGCCGATTTCGGCCTATTGGTTAAAAAATGAGCTGATTTAACAAAAATTTAACGCGAATTTTAACAAAATATTAACGCTTACAATTTAGGTGGCACTTTTCGGG
GAAATGTGCGCGGAACCCCTATTTGTTTATTTTTCTAAATACATTCAAATATGTATCCGCTCATGAGACAATAACCCTGATAAATGCTTCAATAATATTGAAAAAGGAAGAGTATGAGTATTCAACATTTCCGTGTCGCCC
TTATTCCCTTTTTTGCGGCATTTTGCCTTCCTGTTTTTGCTCACCCAGAAACGCTGGTGAAAGTAAAAGATGCTGAAGATCAGTTGGGTGCACGAGTGGGTTACATCGAACTGGATCTCAACAGCGGTAAGATCCTTGAGA
GTTTTCGCCCCGAAGAACGTTTTCCAATGATGAGCACTTTTAAAGTTCTGCTATGTGGCGCGGTATTATCCCGTATTGACGCCGGGCAAGAGCAACTCGGTCGCCGCATACACTATTCTCAGAATGACTTGGTTGAGTACT
CACCAGTCACAGAAAAGCATCTTACGGATGGCATGACAGTAAGAGAATTATGCAGTGCTGCCATAACCATGAGTGATAACACTGCGGCCAACTTACTTCTGACAACGATCGGAGGACCGAAGGAGCTAACCGCTTTTTTGC
ACAACATGGGGGATCATGTAACTCGCCTTGATCGTTGGGAACCGGAGCTGAATGAAGCCATACCAAACGACGAGCGTGACACCACGATGCCTGTAGCAATGGCAACAACGTTGCGCAAACTATTAACTGGCGAACTACTTA
CTCTAGCTTCCCGGCAACAATTAATAGACTGGATGGAGGCGGATAAAGTTGCAGGACCACTTCTGCGCTCGGCCCTTCCGGCTGGCTGGTTTATTGCTGATAAATCTGGAGCCGGTGAGCGTGGGTCTCGCGGTATCATTG
CAGCACTGGGGCCAGATGGTAAGCCCTCCCGTATCGTAGTTATCTACACGACGGGGAGTCAGGCAACTATGGATGAACGAAATAGACAGATCGCTGAGATAGGTGCCTCACTGATTAAGCATTGGTAACTGTCAGACCAAG
TTTACTCATATATACTTTAGATTGATTTAAAACTTCATTTTTAATTTAAAAGGATCTAGGTGAAGATCCTTTTTGATAATCTCATGACCAAAATCCCTTAACGTGAGTTTTCGTTCCACTGAGCGTCAGACCCCGTAGAAA
AGATCAAAGGATCTTCTTGAGATCCTTTTTTTCTGCGCGTAATCTGCTGCTTGCAAACAAAAAAACCACCGCTACCAGCGGTGGTTTGTTTGCCGGATCAAGAGCTACCAACTCTTTTTCCGAAGGTAACTGGCTTCAGCA
GAGCGCAGATACCAAATACTGTCCTTCTAGTGTAGCCGTAGTTAGGCCACCACTTCAAGAACTCTGTAGCACCGCCTACATACCTCGCTCTGCTAATCCTGTTACCAGTGGCTGCTGCCAGTGGCGATAAGTCGTGTCTTA
CCGGGTTGGACTCAAGACGATAGTTACCGGATAAGGCGCAGCGGTCGGGCTGAACGGGGGGTTCGTGCACACAGCCCAGCTTGGAGCGAACGACCTACACCGAACTGAGATACCTACAGCGTGAGCTATGAGAAAGCGCCA
CGCTTCCCGAAGGGAGAAAGGCGGACAGGTATCCGGTAAGCGGCAGGGTCGGAACAGGAGAGCGCACGAGGGAGCTTCCAGGGGGAAACGCCTGGTATCTTTATAGTCCTGTCGGGTTTCGCCACCTCTGACTTGAGCGTC
GATTTTTGTGATGCTCGTCAGGGGGGCGGAGCCTATGGAAAAACGCCAGCAACGCGGCCTTTTTACGGTTCCTGGCCTTTTGCTGGCCTTTTGCTCACATGTTCTTTCCTGCGTTATCCCCTGATTCTGTGGATAACCGTA
TTACCGCCTTTGAGTGAGCTGATACCGCTCGCCGCAGCCGAACGACCGAGCGCAGCGAGTCAGTGAGCGAGGAAGCGGAAGAGCGCCCAATACGCAAACCGCCTCTCCCCGCGCGTTGGCCGATTCATTAATGCAGCTGGC
ACGACAGGTTTCCCGACTGGAAAGCGGGCAGTGA

FIGURE 23B

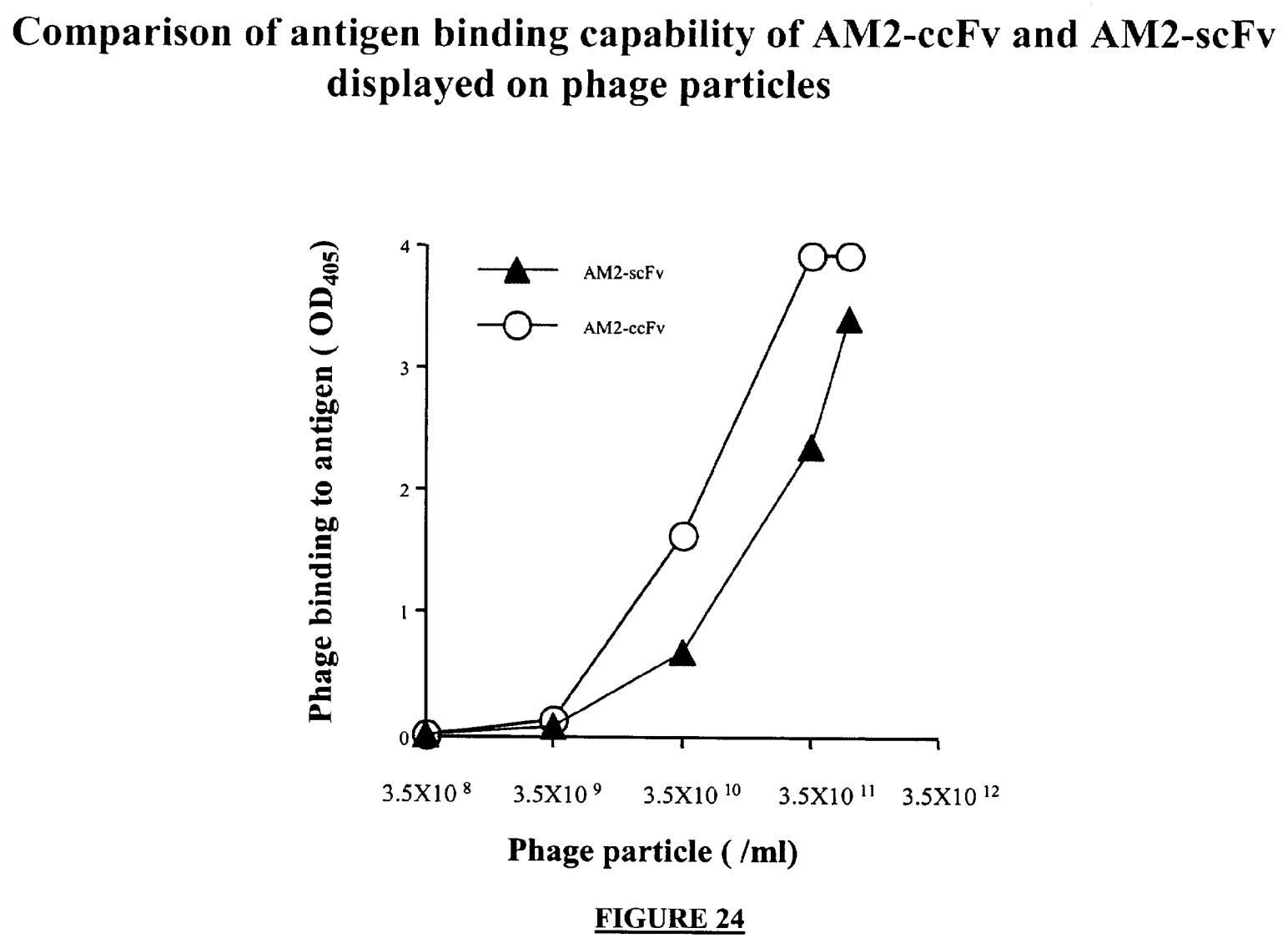

Comparison of antigen binding capability of AM2-ccFv and AM2-scFv displayed on phage particles Phage binding to antigen ( $OD_{405}$)

4
3
2
1
0

AM2-scFv
AM2-ccFv $3.5X10^{8}$
$3.5X10^{9}$
$3.5X10^{10}$
$3.5X10^{11}$
$3.5X10^{12}$

Phage particle ( /ml)

FIGURE 24

Enrichment of phages displaying AM2-ccFv antibody in panning of "model library"

Sequences of Anti-VEGF ccFv Antibodies Selected from Designed Libraries

| VH CDR1 libraries | SEQ ID NO: | VH CDR2 libraries | SEQ ID NO: | VH CDR3 libraries | SEQ ID NO: |
|---|---|---|---|---|---|
| GYNFTRYGI | 19 | WINTNNGESTYAQGFTR | 31 | RYPYYYSRSSWYFDL | 36 |
| GYNFTRYGM | 20 | WINTNNGDTTYAQEFTR | 32 | RYPYYYSRSNWYFDL | 37 |
| GYNFNRYGI | 21 | WINTNNGNSTYAQEFTR | 33 | RYPYYYGRSNWYFDL | 38 |
| GYDFTRYGV | 22 | WINTNNGDTTYVQDFTR | 34 | RYPYYYGRSSWYFDL | 39 |
| GYDFTRYGM | 23 | WVNTNNGDSTYAQGFTR | 35 | RYPYYYGRTSWYFDL | 40 |
| GYDFNRYGI | 24 | | | RYPYYYSRTSWYFDL | 41 |
| GYDFDRYGM | 25 | | | RYPYYSGRSSWYFDL | 42 |
| GYDFDRYGI | 26 | | | RAPYYCGRSCWYFDL | 43 |
| GYDFDRYGV | 27 | | | RYPYYDGRSNWYFDL | 44 |
| GYTFNRYGI | 28 | | | RYPYYCGRSNWYFDL | 45 |
| GYAFNRYGI | 29 | | | RDPYYCSRSCWYFDL | 46 |
| GYAFNRYGM | 30 | | | RYPYYSGRSYWYFDL | 47 |
| | | | | RPPYYYGSSHWYFDV | 48 |

FIGURE 27

Parsing VH CDR3 library into 3 segments

```
1234567890123456789
CAKYPHYYGSSHWYFDVWG (parental anti-VEGF sequence of VH CDR3) [SEQ ID NO:5]
CARYPYYYGSSHWYFDVWG (variant profile) [SEQ ID NO:193]
  KGGHFSSRGSY   L   [SEQ ID NO:194]
   PTGDG GAY    Y   [SEQ ID NO:195]
   TY    TT         [SEQ ID NO:196]
   D      Y         [SEQ ID NO:197]

CAKYPHYYGSSHWYFDVWG (1-3) segment [SEQ ID NO:5]
  RDGG      Y   L [SEQ ID NO:198]
   GTY          Y [SEQ ID NO:199]
   PY             [SEQ ID NO:200]
   T              [SEQ ID NO:201]
CAKYPHYYGSSHWYFDVWG (4) segment [SEQ ID NO:5]
    GGDGS          [SEQ ID NO:202]
    TYFS           [SEQ ID NO:203]
    Y              [SEQ ID NO:204]
CAKYPHYYGSSHWYFDVWG (5) segment [SEQ ID NO:5]
        SRASY      [SEQ ID NO:205]
         GGY       [SEQ ID NO:206]
         TT        [SEQ ID NO:207]
          Y        [SEQ ID NO:208]
```

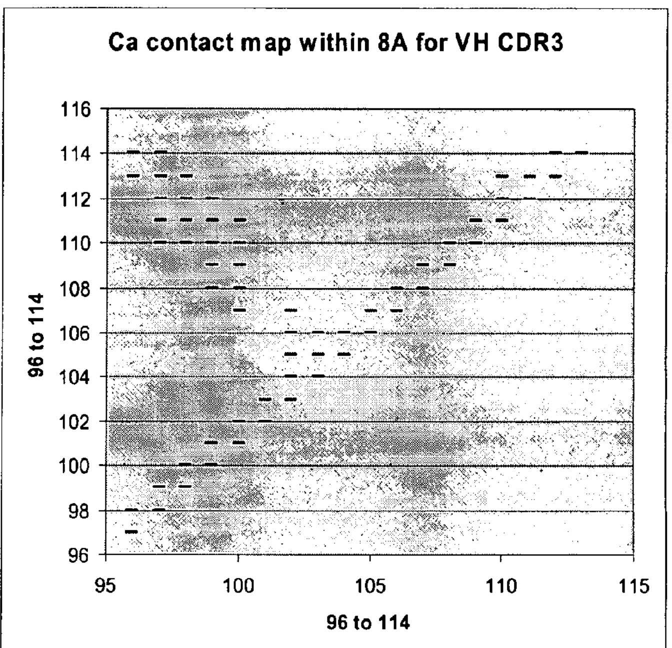

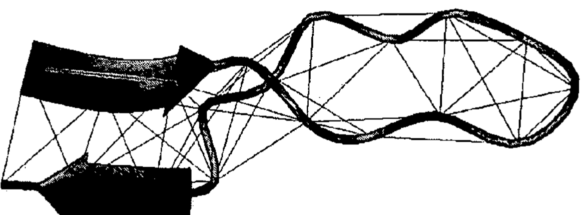

Figure 28A

First segment of parsed CDR3 libraries (1-3)

```
1234567890123456789        # underlined number is the mutation position
CAKYPHYYGSSHWYFDVWG        # Wild type [SEQ ID NO:5]
  RDGG      Y   L           [SEQ ID NO:198]
   GTY          Y           [SEQ ID NO:199]
   PY                       [SEQ ID NO:200]
   T                        [SEQ ID NO:201]

TGC GCG AAA TAC CCG CAC TAC TAC GGT AGC AGC CAC TGG TAC TTC GAT GTG TGG GGT [SEQ ID NO:209]
        CGT GAT GGT                             TAC             CTG          [SEQ ID NO:210]
            GGT ACC                                             TAC          [SEQ ID NO:211]
            CCG TAC                                                          [SEQ ID NO:212]
            ACA                                                              [SEQ ID NO:213]

TGC GCG MRW NVN NVB CAC TAC TAC GGT AGC AGC CAC TRS TAC TTC GAT BWS TGG GGT [SEQ ID NO:214]

Combinatorial  peptide lib = 240
Combinatorial  oligonucleotide lib = 6.6 x 10^5

Oligo Synthesis:
TGCGCGMRWNVNNVBCACTACTACGGTAGCAGCCACTRSTACTTCGATGTGTGGGGC    [SEQ ID NO:215]
TGCGCGMRWNVNNVBCACTACTACGGTAGCAGCCACTRSTACTTCGATCTGTGGGGC    [SEQ ID NO:216]
TGCGCGMRWNVNNVBCACTACTACGGTAGCAGCCACTRSTACTTCGATTACTGGGGC    [SEQ ID NO:217]
```

Figure 28B

Second segment of parsed CDR3 library (4)

```
1234567890123456789    # underlined number is the mutation position
CAKYPHYYGSSHWYFDVWG    # Wild type [SEQ ID NO:5]
    GGDGS          [SEQ ID NO:202]
    TYFS           [SEQ ID NO:203]
    Y              [SEQ ID NO:204]
```

```
TGC GCG AAA TAC CCG CAC TAC TAC GGT AGC AGC CAC TGG TAC TTC GAT GTG TGG GGT [SEQ ID NO:218]
                GGT GGT GTA GGT AGC                                         [SEQ ID NO:219]
                ACC TAC TTC AGC                                             [SEQ ID NO:220]
                TAC                                                         [SEQ ID NO:221]

TGC GCG AAA TAC NVB BRY KWM DRY RGY AGC AGC CAC TGG TAC TTC GAT GTG TGG GGT [SEQ ID NO:222]
```

Combinatorial peptide lib = 216

Combinatorial oligonucleotide lib =1.7 X 10^5

Oligo-Synthesis:

TGCGCGAAATACNVBBRYKWMDRYRGYAGCAGCCACTGGTACTTCGATGTGTGGGGC [SEQ ID NO:223]

Figure 28C

Third segment of parsed CDR3 library (5)

```
1234567890123456789      # underlined number is the mutation position
CAKYPHYYGSSHWYFDVWG      # Wild type [SEQ ID NO:5]
        SGASY        [SEQ ID NO:205]
         RGY         [SEQ ID NO:206]
         TT          [SEQ ID NO:207]
          Y          [SEQ ID NO:208]

TGC GCG AAA TAC CCG CAC TAC TAC GGT AGC AGC CAC TGG TAC TTC GAT GTG TGG GGT [SEQ ID NO:224]
                                AGC GGT GCG AGC TAC                         [SEQ ID NO:225]
                                    CGT GGT TAC                             [SEQ ID NO:226]
                                    ACC ACC                                 [SEQ ID NO:227]
                                        TAC                                 [SEQ ID NO:228]

TGC GCG AAA TAC CCG CAC TAC TAC RGY VSY DWB HRC TRS TAC TTC GAT GTG TGG GGT [SEQ ID NO:229]

Combinatorial  peptide lib = 240
Combinatorial  oligonucleotide lib =3.1X10^4
Oligo_Synthesis:
TGCGCGAAATACCCGCACTACTACRGYVSYDVBHRCTRSTACTTCGATGTGTGGGGC [SEQ ID NO:230]
```

Figure 28D

Figure 29 Summary of library L14 panning process

| Panning | Antigen | Input Phage | Binding | Dissociation | Enrichment (folds)* |
|---|---|---|---|---|---|
| p1 | 1 ug/ml | $10^{12}$ | RT | Brief rinse at RT | 1 |
| p2 | 1 ug/ml | $10^{12}$ | RT | Brief rinse at RT | 3.3 |
| p3 | 1 ug/ml | $10^{12}$ | RT | PBS 1 hr at 37°C | 33.3 |
| p4 | 1 ug/ml | $10^{12}$ | RT | PBS 2 hrs at 37°C | 33.3 |
| p5 | 0.5 ug/ml | $10^{12}$ | 37°C | PBST 1 hr at RT, followed by PBS 2 hrs at 37°C | 6.7 |
| p6 | 0.5 ug/ml | $10^{12}$ | 37°C | 20 ml PBS overnight at RT | 6.7 |
| p7 | 0.1 ug/ml | $10^{11}$ | 37°C | 50 ml PBST 24 hrs at 30°C | 26.7 |

* Enrichment was calculated by $(\text{output phage/input phage})_n$ / $(\text{output phage/input phage})_1$

Variants of VH CDR3 of anti-VEGF ccFv selected from library L14

| Variants | Sequence | | % of Hits (seq#/col. #) |
|---|---|---|---|
| | kabat 94 97 100 a b c d e f 101 | | |
| | 94 97 100 101 102 | | |
| Refseq | K Y P H Y Y G S S H W Y F D V | [SEQ ID NO:231] | |
| Panning 5 | | | |
| HR(S100aR) | - - - - - - - - R - - - - - - - - | [SEQ ID NO:232] | 35 (7/20) |
| HT(S100aT) | - - - - - - - - T - - - - - - - - | [SEQ ID NO:233] | 30 (6/20) |
| WT | - - - - - - - - - - - - - - - - - | [SEQ ID NO:234] | 20 (4/20) |
| HG(S100aG) | - - - - - - - - G - - - - - - - - | [SEQ ID NO:235] | 10 (2/20) |
| HA(S100aA) | - - - - - - - - A - - - - - - - - | [SEQ ID NO:236] | 5 (1/20) |
| Panning 7 | | | |
| HR mutant | - - - - - - - - R - - - - - - - - | [SEQ ID NO;232] | 70 (7/10) |
| HT mutant | - - - - - - - - T - - - - - - - - | [SEQ ID NO:233] | 30 (3/10) |

Figure 30

Enrichment of HR mutant from L14 library

ScFv antibody displayed by adapter-mediated phage display system

Map of UltraHelper phage GMCT

Sequence of modified gene III in GMCT phage genome

```
         KpnI   Gene III Leader                              GR2 domain
--TTAGTGGTACCTTTCTATTCTCACTCCGCT ACATCCCGCCTGGAGGGCCTACAGTCAGAAAACCATCGCCTGCGAATGAAGATCACAGAGCTGGATAAA
[SEQ ID NO:237]
 - L  V  V  P  F  Y  S  H  S  A   T  S  R  L  E  G  L  Q  S  E  N  H  R  L  R  M  K  I  T  E  L  D  K
[SEQ ID NO:238]
                                                NotI                Myc-tag
GACTTGGAAGAGGTCACCATGCAGCTGCAGGACGTCGGAGGTTGC GCGGCCGCAGAACAAAAACTGATCTCAGAAGAGGATCTGACGCGTGCT GGCGGC
 D  L  E  E  V  T  M  Q  L  Q  D  V  G  G  C   A  A  A  E  Q  K  L  I  S  E  E  D  L  T  R  A   G  G
   CT domain of Gene III
GGCTCTGGTGGTGGTTCTGGTGGCGGCTCTGAGGGTGGCGGCTCTGAGGGTGGCGGTTCTGAGGGTGGCGGCTCTGAGGGTGGCGGTTCCGGTGGCGGCTCC
 G  S  G  G  G  S  G  G  G  S  E  G  G  G  S  E  G  G  G  S  E  G  G  G  S  E  G  G  G  S  G  G  G  S
GGTTCCGGTGATTTTGATTATGAAAAAATGGCAAACGCTAATAAGGGGGCTATGACCGAAAATGCCGATGAAAACGCGCTACAGTCTGACGCTAAAGGCAAA
 G  S  G  D  F  D  Y  E  K  M  A  N  A  N  K  G  A  M  T  E  N  A  D  E  N  A  L  Q  S  D  A  K  G  K
CTTGATTCTGTCGCTACTGATTACGGTGCTGCTATCGATGGTTTCATTGGTGACGTTTCCGGCCTTGCTAATGGTAATGGTGCTACTGGTGATTTTGCTGGC
 L  D  S  V  A  T  D  Y  G  A  A  I  D  G  F  I  G  D  V  S  G  L  A  N  G  N  G  A  T  G  D  F  A  G
TCTAATTCCCAAATGGCTCAAGTCGGTGACGGTGATAATTCACCTTTAATGAATAATTTCCGTCAATATTTACCTTCCCTCCCTCAATCGGTTGAATGTCGC
 S  N  S  Q  M  A  Q  V  G  D  G  D  N  S  P  L  M  N  N  F  R  Q  Y  L  P  S  L  P  Q  S  V  E  C  R
CCTTTTGTCTTTGGCGCTGGTAAACCATATGAATTTTCTATTGATTGTGACAAAATAAACTTATTCCGTGGTGTCTTTGCGTTTCTTTTATATGTTGCCACC
 P  F  V  F  G  A  G  K  P  Y  E  F  S  I  D  C  D  K  I  N  L  F  R  G  V  F  A  F  L  L  Y  V  A  T
                                                          AscI                S/D
TTTATGTATGTATTTTCTACGTTTGCTAACATACTGCGTAATAAGGAGTCTTAATAA GGCGCGCCACAATTTCACAGTAAGGAGGTTTAATAA ATGAAA
 F  M  Y  V  F  S  T  F  A  N  I  L  R  N  K  E  S  *  *                                       M  K
OmpA leader                                              BglII             Gene III
AAGACAGCTATTGCGATTGCAGTGGCACTGGCTGGTTTCGCTACCGTAGCGCAGGCT AGATCTGGAGGCGGT ACTGTTGAAAGTTGTTTAGCAAAA---
 K  T  A  I  A  I  A  V  A  L  A  G  F  A  T  V  A  Q  A   R  S  G  G  G   T  V  E  S  C  L  A  K  -
```

Figure 33B

Phagemid vector for protein-GR1 expression

Complete sequence of vector pABMX14

[SEQ ID NO:239]

GCGCAACGCAATTAATGTGAGTTAGCTCACTCATTAGGCACCCCAGGCTTTACACTTTATGCTTCCGGCTCGTATGTTGTGTGGAATTGTGAGCGGATAACAATTTACCGG
TTCTTTAAGGAGGAATTAAAAAATGAAATACCTATTGCCTACGGCAGCCGCTGGATTGTTATTACTCGCGGCCCAGCCGGCCATGGCGGCCCTGCAGGCCTCTAGAGCGGC
CGCTGGAGGTGAGGAGAAGTCCCGGCTGTTGGAGAAGGAGAACCGTGAACTGGAAAAGATCATTGCTGAGAAAGAGGAGCGTGTCTCTGAACTGCGCCATCAACTCCAGTC
TGTAGGAGGTTGTAGATCTTATCCATACGACGTACCAGACTACGCAGGAGGTCATCACCATCATCACCATTAATGAGTCGACCTCGACCAATTCGCCCTATAGTGAGTCGT
ATTACAATTCACTGGCCGTCGTTTTACAACGTCGTGACTGGGAAAACCCTGGCGTTACCCAACTTAATCGCCTTGCAGCACATCCCCCTTTCGCCAGCTGGCGTAATAGCG
AAGAGGCCCGCACCGATCGCCCTTCCCAACAGTTGCGCAGCCTGAATGGCGAATGGGACGCGCCCTGTAGCGGCGCATTAAGCGCGGCGGGTGTGGTGGTTACGCGCAGCG
TGACCGCTACACTTGCCAGCGCCCTAGCGCCCGCTCCTTTCGCTTTCTTCCCTTCCTTTCTCGCCACGTTCGCCGGCTTTCCCCGTCAAGCTCTAAATCGGGGGCTCCCTT
TAGGGTTCCGATTTAGTGCTTTACGGCACCTCGACCCCAAAAAACTTGATTAGGGTGATGGTTCACGTAGTGGGCCATCGCCCTGATAGACGGTTTTTCGCCCTTTGACGT
TGGAGTCCACGTTCTTTAATAGTGGACTCTTGTTCCAAACTGGAACAACACTCAACCCTATCTCGGTCTATTCTTTTGATTTATAAGGGATTTTGCCGATTTCGGCCTATT
GGTTAAAAAATGAGCTGATTTAACAAAAATTTAACGCGAATTTTAACAAAATATTAACGCTTACAATTTAGGTGGCACTTTTCGGGGAAATGTGCGCGGAACCCCTATTTG
TTTATTTTTCTAAATACATTCAAATATGTATCCGCTCATGAGACAATAACCCTGATAAATGCTTCAATAATATTGAAAAAGGAAGAGTATGAGTATTCAACATTTCCGTGT
CGCCCTTATTCCCTTTTTTGCGGCATTTTGCCTTCCTGTTTTTGCTCACCCAGAAACGCTGGTGAAAGTAAAAGATGCTGAAGATCAGTTGGGTGCACGAGTGGGTTACAT
CGAACTGGATCTCAACAGCGGTAAGATCCTTGAGAGTTTTCGCCCCGAAGAACGTTTTCCAATGATGAGCACTTTTAAAGTTCTGCTATGTGGCGCGGTATTATCCCGTAT
TGACGCCGGGCAAGAGCAACTCGGTCGCCGCATACACTATTCTCAGAATGACTTGGTTGAGTACTCACCAGTCACAGAAAAGCATCTTACGGATGGCATGACAGTAAGAGA
ATTATGCAGTGCTGCCATAACCATGAGTGATAACACTGCGGCCAACTTACTTCTGACAACGATCGGAGGACCGAAGGAGCTAACCGCTTTTTTGCACAACATGGGGGATCA
TGTAACTCGCCTTGATCGTTGGGAACCGGAGCTGAATGAAGCCATACCAAACGACGAGCGTGACACCACGATGCCTGTAGCAATGGCAACAACGTTGCGCAAACTATTAAC
TGGCGAACTACTTACTCTAGCTTCCCGGCAACAATTAATAGACTGGATGGAGGCGGATAAAGTTGCAGGACCACTTCTGCGCTCGGCCCTTCCGGCTGGCTGGTTTATTGC
TGATAAATCTGGAGCCGGTGAGCGTGGGTCTCGCGGTATCATTGCAGCACTGGGGCCAGATGGTAAGCCCTCCCGTATCGTAGTTATCTACACGACGGGGAGTCAGGCAAC
TATGGATGAACGAAATAGACAGATCGCTGAGATAGGTGCCTCACTGATTAAGCATTGGTAACTGTCAGACCAAGTTTACTCATATATACTTTAGATTGATTTAAAACTTCA
TTTTTAATTTAAAAGGATCTAGGTGAAGATCCTTTTTGATAATCTCATGACCAAAATCCCTTAACGTGAGTTTTCGTTCCACTGAGCGTCAGACCCCGTAGAAAAGATCAA
AGGATCTTCTTGAGATCCTTTTTTTCTGCGCGTAATCTGCTGCTTGCAAACAAAAAAACCACCGCTACCAGCGGTGGTTTGTTTGCCGGATCAAGAGCTACCAACTCTTTT
TCCGAAGGTAACTGGCTTCAGCAGAGCGCAGATACCAAATACTGTCCTTCTAGTGTAGCCGTAGTTAGGCCACCACTTCAAGAACTCTGTAGCACCGCCTACATACCTCGC
TCTGCTAATCCTGTTACCAGTGGCTGCTGCCAGTGGCGATAAGTCGTGTCTTACCGGGTTGGACTCAAGACGATAGTTACCGGATAAGGCGCAGCGGTCGGGCTGAACGGG
GGGTTCGTGCACACAGCCCAGCTTGGAGCGAACGACCTACACCGAACTGAGATACCTACAGCGTGAGCTATGAGAAAGCGCCACGCTTCCCGAAGGGAGAAAGGCGGACAG
GTATCCGGTAAGCGGCAGGGTCGGAACAGGAGAGCGCACGAGGGAGCTTCCAGGGGGAAACGCCTGGTATCTTTATAGTCCTGTCGGGTTTCGCCACCTCTGACTTGAGCG
TCGATTTTTGTGATGCTCGTCAGGGGGGCGGAGCCTATGGAAAAACGCCAGCAACGCGGCCTTTTTACGGTTCCTGGCCTTTTGCTGGCCTTTTGCTCACATGTTCTTTCC
TGCGTTATCCCCTGATTCTGTGGATAACCGTATTACCGCCTTTGAGTGAGCTGATACCGCTCGCCGCAGCCGAACGACCGAGCGCAGCGAGTCAGTGAGCGAGGAAGCGGA
AGAGCGCCCAATACGCAAACCGCCTCTCCCCGCGCGTTGGCCGATTCATTAATGCAGCTGGCACGACAGGTTTCCCGACTGGAAAGCGGGCAGTGA

Figure 34B

Figure 35A Summary of Library L17 Panning process

| Panning | Antigen | Input Phage | Binding | Dissociation | Enrichment (folds)* |
|---|---|---|---|---|---|
| p1 | 1 ug/ml | $10^{12}$ | 37°C | PBST 1 hr at 25°C | 1 |
| p2 | 1 ug/ml | $10^{12}$ | 37°C | PBST 1 hrs at 25°C | 200 |
| p3 | 0.5 ug/ml | $10^{12}$ | 37°C | PBST 2 hrs at 25°C | 36.4 |
| p4 | 0.5 ug/ml | $10^{12}$ | 37°C | PBST 2 hrs at 25°C then 150 ml PBST for 18 hrs at 25°C | 45.5 |
| p5 | 0.5 ug/ml | $10^{12}$ | 37°C | PBST 2 hrs at 25°C then 150 ml PBST for 18 hrs at 37°C | 15.5 |

Variants of VH CDR3 of anti-VEGF scFv selected from library L17

| Variants | Sequence | | % of Hits(seq#/col.#) |
|---|---|---|---|
| kabat | 94 97 100 a b c d e f 101 | | |
| | 94 97 100 101 102 103 | | |
| Ref(parent) | K Y P H Y Y G S S H W Y F D V | [SEQ ID NO: 234] | |
| Panning 4 | | | |
| HT(S100aT) | - - - - - - - T - - - - - - - | [SEQ ID NO:233] | 30 (3/10) |
| HA(S100aA) | - - - - - - - A - - - - - - - | [SEQ ID NO:236] | 30 (3/10) |
| YS(H97Y) | - - - Y - - - - - - - - - - - | [SEQ ID NO:240] | 20 (2/10) |
| WT | - - - - - - - - - - - - - - - | [SEQ ID NO:234] | 10 (1/10) |
| (H97Y,Y99N) | - - - Y - N - - - - - - - - - | [SEQ ID NO:241] | 10 (1/10) |
| Panning 5 | | | |
| HR(S100aR) | - - - - - - - R - - - - - - - | [SEQ ID NO:232] | 37.5(3/8) |
| S101R,H103Q | - - - - - - - R - Q - - - - - | [SEQ ID NO:242] | 12.5(1/8) |
| HA(S100aA) | - - - - - - - A - - - - - - - | [SEQ ID NO:236] | 25.0(2/8) |
| HT(S100aT) | - - - - - - - T - - - - - - - | [SEQ ID NO:233] | 12.5(1/8) |
| S101G,S102C | - - - - - - - G C - - - - - - | [SEQ ID NO:243] | 12.5(1/8) |

Figure 36

STRUCTURE-BASED SELECTION AND AFFINITY MATURATION OF ANTIBODY LIBRARY

CROSS REFERENCE TO RELATED APPLICATIONS

This application is a continuation-in-part of U.S. patent application Ser. No. 10/125,687 entitled "Structure-based construction of human antibody library" filed Apr. 17, 2002 now abandoned, which claims the benefit of U.S. Provisional Application Ser. No. 60/284,407 entitled "Structure-based construction of human antibody library" filed Apr. 17, 2001. These applications are incorporated herein by reference.

BACKGROUND OF THE INVENTION

1. Field of the Invention

The present invention relates generally to a computer-aided design of a protein with binding affinity to a target molecule and, more particularly, relates to methods for screening and identifying antibodies (or immunoglobulins) with diverse sequences and high affinity to a target antigen by combining computational prediction and experimental screening of a biased library of antibodies.

2. Description of Related Art

Antibodies are made by vertebrates in response to various internal and external stimuli (antigens). Synthesized exclusively by the B cells, antibodies are produced in millions of forms, each with a different amino acid sequence and a different binding site for an antigen. Collectively called immunoglobulins (abbreviated as Ig), they are among the most abundant protein components in the blood, constituting about 20% of the total plasma protein by weight.

A naturally occurring antibody molecule consists of two identical "light" (L) protein chains and two identical "heavy" (H) protein chains, all held together by both hydrogen bonding and precisely located disulfide linkages. Chothia et al. (1985) J. Mol. Biol. 186:651–663; and Novotny and Haber (1985) Proc. Natl. Acad. Sci. USA 82:4592–4596. The N-terminal domains of the L and H chains together form the antigen recognition site of each antibody.

The mammalian immune system has evolved unique genetic mechanisms that enable it to generate an almost unlimited number of different light and heavy chains in a remarkably economical way by joining separate gene segments together before they are transcribed. For each type of Ig chain—κ light chains, λ light chains, and heavy chain—there is a separate pool of gene segments from which a single peptide chain is eventually synthesized. Each pool is on a different chromosome and usually contains a large number of gene segments encoding the V region of an Ig chain and a smaller number of gene segments encoding the C region. During B cell development a complete coding sequence for each of the two Ig chains to be synthesized is assembled by site-specific genetic recombination, bringing together the entire coding sequences for a V region and the coding sequence for a C region. In addition, the V region of a light chain is encoded by a DNA sequence assembled from two gene segments—a V gene segment and short joining or J gene segment. The V region of a heavy chain is encoded by a DNA sequence assembled from three gene segments—a V gene segment, a J gene segment and a diversity or D segment.

The large number of inherited V, J and D gene segments available for encoding Ig chains makes a substantial contribution on its own to antibody diversity, but the combinatorial joining of these segments greatly increases this contribution. Further, imprecise joining of gene segments and somatic mutations introduced during the V-D-J segment joining at the pre-B cell stage greatly increases the diversity of the V regions.

After immunization against an antigen, a mammal goes through a process known as affinity maturation to produce antibodies with higher affinity toward the antigen. Such antigen-driven somatic hypermutation fine-tunes antibody responses to a given antigen, presumably due to the accumulation of point mutations specifically in both heavy-and light-chain V region coding sequences and a selected expansion of high-affinity antibody-bearing B cell clones.

Structurally, various functions of an antibody are confined to discrete protein domains (regions). The sites that recognize and bind antigen consist of three hyper-variable or complementarity-determining regions (CDRs) that lie within the variable ($V_H$ and $V_L$) regions at the N-terminal ends of the two H and two L chains. The constant domains are not involved directly in binding the antibody to an antigen, but are involved in various effector functions, such as participation of the antibody in antibody-dependent cellular cytotoxicity.

The domains of natural light and heavy chains have the same general structures, and each domain comprises four framework regions, whose sequences are somewhat conserved, connected by three CDRs. The four framework regions largely adopt a β-sheet conformation and the CDRs form loops connecting, and in some cases forming part of, the β-sheet structure. The CDRs in each chain are held in close proximity by the framework regions and, with the CDRs from the other chain, contribute to the formation of the antigen binding site.

Generally all antibodies adopt a characteristic "immunoglobulin fold". Specifically, both the variable and constant domains of an antigen binding fragment (Fab, consisting of $V_L$ and $C_L$ of the light chain and $V_H$ and $C_H1$ of the heavy chain) consist of two twisted antiparallel β-sheets which form a β-sandwich structure. The constant regions have three- and four-stranded β-sheets arranged in a Greek key-like motif, while variable regions have a further two short β strands producing a five-stranded β-sheet.

The $V_L$ and $V_H$ domains interact via the five-stranded β sheets to form a nine-stranded β barrel of about 8.4 Å radius, with the strands at the domain interface inclined at approximately 50° to one another. The domain pairing brings the CDR loops into close proximity. The CDRs themselves form some 25% of the $V_L/V_H$ domain interface.

The six CDRs, (CDR-L1, -L2 and -L3 for the light chain, and CDR-H1, -H2 and -H3 for the heavy chain), are supported on the β barrel framework, forming the antigen binding site. While their sequences are hypervariable in comparison with the rest of the immunoglobulin structure, some of the loops show a relatively high degree of both sequence and structural conservation. In particular, CDR-L2 and CDR-H1 are highly conserved in conformation.

Chothia and co-workers have shown that five of the six CDR loops (all except CDR-H3) adopt a discrete, limited number of main-chain conformations (termed canonical structures of the CDRs) by analysis of conserved key residues. Chothia and Lesk (1987) J. Mol. Biol. 196:901–917; Chothia et al. (1989) Nature (London) 342:877; and Chothia et al. (1998) J. Mol. Biol. 278:457–479. Chothia and Lesk (1987) ibid. described in their report that "from an analysis of the immunoglobulins of known atomic structure we determine the limits of the β-sheet framework common to the known structure (see section 4 below)" (page 902, column 1, 3rd paragraph). In section 4 of Chothia and Lesk (1987) ibid. it is described that "the conservation of the frame work structure extends to the residues immediately adjacent to the hypervarible regions"; and "if the conserved frameworks of a pair of molecules are superimposed, the differences in the positions of these residues is in most cases less than 1 Å and in all but one case less than 1.8 Å (Table 5)" (page 904, column 1, 2nd paragraph). Table 5 in Chothia and Lesk (1987) ibid. demarcates the hypervariable regions (i.e., CDRs) and framework regions. The adopted structure depends on both the CDR length and the identity of certain key amino acid residues, both in the CDR and in the contacting framework, involved in its packing. The canonical conformations were determined by specific packing, hydrogen bonding interactions, and stereochemical constraints of only these key residues which serve as structural determinants.

Various methods have been developed for modeling the three dimensional structures of the antigen binding site of an antibody. Other than x-ray crystallography, nuclear magnetic resonance (NMR) spectroscopy has been used in combination with computer model building to study the atomic details of antibody-ligand interactions. Dwek et al. (1975) Eur. J. Biochem. 53:25–39. Dwek and coworkers used spin-labeled hapten to deduce the combining site of the MoPC 315 myeloma protein for dinitrophenyl. Similar analysis has also been done using anti-spin labeled monoclonal antibodies (Anglister et al. (1987) Biochem. 26: 6958–6064) and on the anti-2-phenyloxazolone Fv fragments (McManus and Riechmann (1991) Biochem. 30:5851–5857).

Computer-implemented analysis and modeling of antibody combining site (or antigen binding site) are based on homology analysis comparing the target antibody sequence with those of antibodies with known structures or structural motifs in existing data bases (e.g. the Brookhaven Protein Data Bank). By using such homology-based modeling methods approximate three-dimensional structure of the target antibody is constructed. Early antibody modeling was based on the conjecture that CDR loops with identical length and different sequence may adopt similar conformations. Kabat and Wu (1972) Proc. Natl. Acad. Sci. USA 69: 960–964. A typical segment match algorithm is as follows: given a loop sequence, the Protein Data Bank can be searched for short, homologous backbone fragments (e.g. tripeptides) which are then assembled and computationally refined into a new combining site model.

More recently, the canonical loop concept has been incorporated into the computer-implemented structural modeling of an antibody combining site. In its most general form, the canonical structure concept assumes that (1) sequence variation at other than canonical positions is irrelevant for loop conformation, (2) canonical loop conformations are essentially independent of loop-loop interactions, and (3) only a limited number of canonical motifs exist and these are well represented in the database of currently known antibody crystal structures. Based on this concept, Chothia predicted all six CDR loop conformations in the lysozyme-binding antibody D1.3 and five canonical loop conformations in four other antibodies. Chothia (1989), supra. It is also possible to improve the modeling of CDRs of antibody structures by combining the homology-based modeling with conformational search procedures. Martin, A. C. R. (1989) PNAS 86, 9268–72.

Besides modeling a specific antibody structure, efforts have been made in generating artificial (or synthetic) libraries of antibodies which are screened against a specific target antigen. A fully synthetic combinatorial antibody library has been designed based on modular consensus frameworks and CDRs randomized with trinucleotides. Knappik et al. (2000) J. Mol. Biol. 296:57–86. In this study, the human antibody repertoire was analyzed in terms of structure, amino acid sequence diversity and germline usage. Modular consensus framework sequences with seven $V_H$ and seven $V_L$ were derived to cover 95% of variable germline families and optimized for expression in *E. coli*. After cloning the genes in all 49 combinations into a phagemid vector, a set of antibody phage display libraries were created, totaling $2\times10^9$ members in the libraries.

Phage display technology has been used extensively to generate large libraries of antibody fragments by exploiting the capability of bacteriophage to express and display biologically functional protein molecule on its surface. Combinatorial libraries of antibodies have been generated in bacteriophage lambda expression systems which may be screened as bacteriophage plaques or as colonies of lysogens (Huse et al. (1989) Science 246: 1275; Caton and Koprowski (1990) Proc. Natl. Acad. Sci. (U.S.A.) 87: 6450; Mullinax et al (1990) Proc. Natl. Acad. Sci. (U.S.A.) 87: 8095; Persson et al. (1991) Proc. Natl. Acad. Sci. (U.S.A.) 88: 2432). Various embodiments of bacteriophage antibody display libraries and lambda phage expression libraries have been described (Kang et al. (1991) Proc. Natl. Acad. Sci. (U.S.A.) 88: 4363; Clackson et al. (1991) Nature 352: 624; McCafferty et al. (1990) Nature 348: 552; Burton et al. (1991) Proc. Natl. Acad. Sci. (U.S.A.) 88: 10134; Hoogenboom et al. (1991) Nucleic Acids Res. 19: 4133; Chang et al. (1991) J. Immunol. 147: 3610; Breitling et al. (1991) Gene 104: 147; Marks et al. (1991) J. Mol. Biol. 222: 581; Barbas et al. (1992) Proc. Natl. Acad. Sci. (U.S.A.) 89: 4457; Hawkins and Winter (1992) J. Immunol. 22: 867; Marks et al. (1992) Biotechnology 10: 779; Marks et al. (1992) J. Biol. Chem. 267: 16007; Lowman et al (1991) Biochemistry 30: 10832; Lerner et al. (1992) Science 258: 1313). Also see review by Rader, C. and Barbas, C. F. (1997) "Phage display of combinatorial antibody libraries" Curr. Opin. Biotechnol. 8:503–508.

Generally, a phage library is created by inserting a library of random oligonucleotides or a cDNA library encoding antibody fragment such as $V_L$ and $V_H$ into gene 3 of M13 or fd phage. Each inserted gene is expressed at the N-terminal of the gene 3 product, a minor coat protein of the phage. As a result, peptide libraries that contain diverse peptides can be constructed. The phage library is then affinity screened against immobilized target molecule of interest, such as an antigen, and specifically bound phage particles are recovered and amplified by infection into *Escherichia coli* host cells. Typically, the target molecule of interest such as a receptor (e.g., polypeptide, carbohydrate, glycoprotein, nucleic acid) is immobilized by a covalent linkage to a chromatography resin to enrich for reactive phage particles by affinity chromatography and/or labeled for screening plaques or colony lifts. This procedure is called biopanning. Finally, high affinity phage clones can be amplified and sequenced for deduction of the specific peptide sequences.

A method for humanizing antibody by using computer modeling has also been developed by Queen et al. U.S. Pat. No. 5,693,762. The structure of a non-human, donor antibody (e.g., a mouse monoclonal antibody) is predicted based on computer modeling and key amino acids in the framework are predicted to be necessary to retain the shape, and thus the binding specificity of the CDRs. These few key murine donor amino acids are selected based on their positions and characters within a few defined categories and substituted into a human acceptor antibody framework along with the donor CDRs. For example, category 1: The amino acid position is in a CDR as defined by Kabat et al. Kabat and Wu (1972) Proc. Natl. Acad. Sci. USA 69: 960–964. Category 2: If an amino acid in the framework of the human acceptor immunoglobulin is unusual, and if the donor amino acid at that position is typical for human sequences, then the donor amino acid rather than the acceptor many be selected. Category 3: In the position immediately adjacent to one or more of the 3 CDR's in the primary sequence of the humanized immunoglobulin chain, the donor amino acid(s) rather than the acceptor amino acid may be selected. Based on these criteria, a series of elaborate selections of individual amino acids from the donor antibody is conducted. The resulting humanized antibody usually includes about 90% human sequence. The humanized antibody designed by computer modeling is tested for antigen binding. Experimental results such as binding affinity are fed back to the computer modeling process to fine-tune the structure of the humanized antibody. The redesigned antibody can then be tested for improved biological functions. Such a reiterate fine tuning process can be labor intensive and unpredictable.

SUMMARY OF THE INVENTION

The present invention provides an innovative methodology for efficiently generating and screening protein libraries for optimized proteins with desirable biological functions, such as improved binding affinity towards biologically and/or therapeutically important target molecules. The process is carried out computationally in a high throughput manner by mining the ever-expanding databases of protein sequences of all organisms, especially human. The evolutionary data of proteins are utilized to expand both sequence and structure space of the protein libraries for functional screening in vitro or in vivo. By using the inventive methodology, an expanded and yet functionally biased library of proteins such as antibodies can be constructed based on computational evaluation of extremely diverse protein sequences and functionally relevant structures in silico.

In particular, the inventive methodology is implemented in designing antibodies that are diverse in sequence and yet functionally related to each other. Based on the designed antibody sequences, a library of antibodies can be constructed to include diverse sequences in the complementary determining regions (CDRs) and/or humanized frameworks (FRs) of a non-human antibody in a high throughput manner. This library of antibodies can be screened against a wide variety of target molecules for novel or improved functions.

In one aspect of the invention, a method is provided for in silico selection of antibody sequences based on the amino acid sequence of a region in a lead antibody, herein after referred to as the "lead sequence". The lead sequence is employed to search databases of protein sequences. The choice of the database depends on the specific functional requirement of the designed motifs. For example: in order to design the framework regions of variable chains for therapeutic application, collections of protein sequences that are evolutionarily related such as fully human immunoglobulin sequences and human germline immunoglobulin sequences should be used except for a few structurally critical sites. This would reduce the immunogenic response by preserving the origin of the sequences by introducing as few foreign mutants as possible in this highly conserved region (for framework regions). On the other hand, diverse sequence databases such as immunoglobulin sequences of various species or even unrelated sequence in genbank can be used to design the CDRs in order to improve binding affinity with antigens in this highly variable region. By using the method, a library of diverse antibody sequences can be constructed and screened experimentally in vitro or in vivo for antibody mutants with improved or desired function(s).

In one embodiment, the method comprises the steps of:

providing an amino acid sequence of the variable region of the heavy chain ($V_H$) or light chain ($V_L$) of a lead antibody;

identifying the amino acid sequences in the CDRs of the lead antibody;

selecting one of the CDRs in the $V_H$ or $V_L$ region of the lead antibody;

providing an amino acid sequence that comprises at least 3 consecutive amino acid residues in the selected CDR, the selected amino acid sequence being a lead sequence;

comparing the lead sequence with a plurality of tester protein sequences; and selecting from the plurality of tester protein sequences at least two peptide segments that have at least 15% sequence identity with the lead sequence, the selected peptide segments forming a hit library.

The method may further comprise the step of:

constructing a nucleic acid library comprising DNA segments encoding the amino acid sequences of the hit library.

Optionally, the method may further comprise the steps of:

building an amino acid positional variant profile of the hit library;

converting amino acid positional variant profile of the hit library into a nucleic acid positional variant profile by back-translating the amino acid positional variants into their corresponding genetic codons; and constructing a degenerate nucleic acid library of DNA segments by combinatorially combining the nucleic acid positional variants.

Optionally, the genetic codons may be the ones that are preferred for expression in bacteria. Optionally, genetic codons may be the ones that can reduce the size chosen such that the diversity of the degenerate nucleic acid library of DNA segments within the experimentally coverable diversity (<10^6 or 7) without undue experimental effort.is reduced to be below $1\times10^7$, preferably below $1\times10^6$.

In another embodiment, the method comprises the steps of:

providing an amino acid sequence of the variable region of the heavy chain ($V_H$) or light chain ($V_L$) of a lead antibody;

identifying the amino acid sequences in the CDRs and FRs of the lead antibody;

selecting one of the CDRs in the $V_H$ or $V_L$ region of the lead antibody;

providing a first amino acid sequence that comprises at least 3 consecutive amino acid residues in the selected CDR, the selected amino acid sequence being a CDR lead sequence;

comparing the CDR lead sequence with a plurality of CDR tester protein sequences;

selecting from the plurality of CDR tester protein sequences at least two peptide segments that have at least 15% sequence identity with the CDR lead sequence, the selected peptide segments forming a CDR hit library;

selecting one of the FRs in the $V_H$ or $V_L$ region of the lead antibody;

providing a second amino acid sequence that comprises at least 3 consecutive amino acid residues in the selected FR, the selected amino acid sequence being a FR lead sequence;

comparing the FR lead sequence with a plurality of FR tester protein sequences; and selecting from the plurality of FR tester protein sequences at least two peptide segments that have at least 15% sequence identity with the FR lead sequence, the selected peptide segments forming a FR hit library; and combining the CDR hit library and the FR hit library to form a hit library.

According to the method, the plurality of CDR tester protein sequences may comprise amino acid sequences of human or non-human antibodies.

Also according to the method, the plurality of FR tester protein sequences may comprise amino acid sequences of human origins, preferably human or humanized antibodies (e.g., antibodies with at least 50% human sequence, preferably at least 70% human sequence, more preferably at least 90% human sequence, and most preferably at least 95% human sequence in $V_H$ or $V_L$), more preferably fully human antibodies, and most preferably human germline antibodies.

Also according to the method, at least one of the plurality of CDR tester protein sequences is different from the plurality of FR tester protein sequences.

Also according to the method, the plurality of CDR tester protein sequences are human or non-human antibody sequences and the plurality of FR tester protein sequences are human antibody sequences, preferably human germline antibody sequences.

The method may further comprise the step of:

constructing a nucleic acid library comprising DNA segments encoding the amino acid sequences of the hit library.

Optionally, the method may further comprise the steps of:

building an amino acid positional variant profile of the CDR hit library;

converting the amino acid positional variant profile of the CDR hit library into a first nucleic acid positional variant profile by back-translating the amino acid positional variants into their corresponding genetic codons; and constructing a degenerate CDR nucleic acid library of DNA segments by combinatorially combining the nucleic acid positional variants.

Optionally, the genetic codons may be the ones that are preferred for expression in bacteria. Optionally, genetic codons may be the ones that can reduce the size chosen such that the diversity of the degenerate nucleic acid library of DNA segments within the experimentally coverable diversity (<10ˆ6 or 7) without undue experimental effort.is below $1\times10^7$, preferably below $1\times10^6$.

In yet another embodiment, the method comprises the steps of:

providing an amino acid sequence of the variable region of the heavy chain ($V_H$) or light chain ($V_L$) of a lead antibody;

identifying the amino acid sequences in the FRs of the lead antibody;

selecting one of the FRs in the $V_H$ or $V_L$ region of the lead antibody;

providing a first amino acid sequence that comprises at least 3 consecutive amino acid residues in the selected FR, the selected amino acid sequence being a first FR lead sequence;

comparing the first lead FR sequence with a plurality of FR tester protein sequences; and selecting from the plurality of FR tester protein sequences at least two peptide segments that have at least 15% sequence identity with the first FR lead sequence, the selected peptide segments forming a first FR hit library.

The method may further comprise the steps of providing a second amino acid sequence that comprises at least 3 consecutive amino acid residues in a FR that is different from the selected FR, the selected amino acid sequence being a second FR lead sequence;

comparing the second FR lead sequence with the plurality of FR tester protein sequences; and selecting from the plurality of FR tester protein sequences at least two peptide segments that have at least 15% sequence identity with the second FR lead sequence, the selected peptide segments forming a second FR hit library; and combining the first FR hit library and the second FR hit library to form a hit library.

According to the method, the lead CDR sequence may comprise at least 5 consecutive amino acid residues in the selected CDR. The selected CDR may be selected from the group consisting of $V_H$ CDR1, $V_H$ CDR2, $V_H$ CDR3, $V_L$ CDR1, $V_L$ CDR2, and $V_L$ CDR3 of the lead antibody.

Also according to the method, the lead FR sequence may comprise at least 5 consecutive amino acid residues in the selected FR. The selected FR may be selected from the group consisting of $V_H$ FR1, $V_H$ FR2, $V_H$ FR3, $V_H$ FR4, $V_L$ FR1, $V_L$ FR2, $V_L$ FR3 and $V_L$ FR4 of the lead antibody.

The method may further comprise the step of:

constructing a nucleic acid or degenerate nucleic acid library comprising DNA segments encoding the amino acid sequences of the hit library.

In another aspect of the invention, a method is provided for in silico selection of antibody sequences based on the amino acid sequence of a region in a lead antibody, i.e., the "lead sequence", and its 3D structure. The structure of the lead sequence is employed to search databases of protein structures for segments having similar 3D structures. These segments are aligned to yield a sequence profile, herein after referred to as the "lead sequence profile". The lead sequence profile is employed to search databases of protein sequences for remote homologues of the lead sequence having low sequence identity and yet structurally similar. By using the method, a library of diverse antibody sequences can be constructed and screened experimentally in vitro or in vivo for antibody mutants with improved or desired function(s).

In one embodiment, the method comprises the steps of:

providing an amino acid sequence of the variable region of the heavy chain ($V_H$) or light chain ($V_L$) of a lead antibody;

identifying the amino acid sequences in the CDRs of the lead antibody;

selecting one of the CDRs in the $V_H$ or $V_L$ region of the lead antibody;

providing an amino acid sequence that comprises at least 3 consecutive amino acid residues in the selected CDR, the selected amino acid sequence being a lead sequence;

providing a three-dimensional structure of the lead sequence;

building a lead sequence profile based on the structure of the lead sequence;

comparing the lead sequence profile with a plurality of tester protein sequences; and selecting from the plurality of tester protein sequences at least two peptide segments that have at least 10% sequence identity with lead sequence, the selected peptide segments forming a hit library.

According to the method, the three-dimensional structure of the lead sequence may be a structure derived from X-crystallography, nuclear magnetic resonance (NMR) spectroscopy or theoretical structural modeling.

According to the method, the step of building a lead sequence profile may include:

comparing the structure of the lead sequence with the structures of a plurality of tester protein segments;

determining the root mean square difference of the main chain conformations of the lead sequence and the tester protein segments;

selecting the tester protein segments with root mean square difference of the main chain conformations less than 5 Å, preferably less than 4 Å, more preferably less than 3 Å, and most preferably less than 2 Å; and aligning the amino acid sequences of the selected tester protein segments with the lead sequence to build the lead sequence profile.

Optionally, the structures of the plurality of tester protein segments are retrieved from the protein data bank.

Optionally, the step of building a lead sequence profile may include:

comparing the structure of the lead sequence with the structures of a plurality of tester protein segments;

determining the Z-score of the main chain conformations of the lead sequence and the tester protein segments;

selecting the segments of the tester protein segments with the Z-score higher than 2, preferably higher than 3, more preferably higher than 4, and most preferably higher than 5; and aligning the amino acid sequences of the selected tester protein segments with the lead sequence to build the lead sequence profile.

Optionally, the step of building a lead sequence profile may be implemented by an algorithm selected from the group consisting of CE, MAPS, Monte Carlo and 3D clustering algorithms.

The method may further comprise the step of:

constructing a nucleic acid library comprising DNA segments encoding the amino acid sequences of the hit library.

Optionally, the method may further comprise the steps of:

building an amino acid positional variant profile of the hit library;

converting amino acid positional variant profile of the hit library into a nucleic acid positional variant profile by back-translating the amino acid positional variants into their corresponding trinucleotide codons; and constructing a degenerate nucleic acid library of DNA segments by combinatorially combining the nucleic acid positional variants.

Any of the above methods may further comprise the following steps:

introducing the DNA segments in the nucleic acid or degenerate nucleic acid library into cells of a host organism;

expressing the DNA segments in the host cells such that recombinant antibodies containing the amino acid sequences of the hit library are produced in the cells of the host organism; and selecting the recombinant antibody that binds to a target antigen with affinity higher than $10^6$ $M^{-1}$, preferably $10^7$ $M^{-1}$, more preferably $10^8$ $M^{-1}$, and most preferably $10^9$ $M^{-1}$.

In yet another aspect of the invention, a method is provided for in silico selection of antibody sequences based on a 3D structure of a lead antibody. A lead sequence or sequence profile from a specific region of the lead antibody to be employed to search databases of protein sequences for remote homologues of the lead sequence having low sequence identity and yet structurally similar. These remote homologues form a hit library. The sequences in the hit library are subjected to evaluation for their structural compatibility with a 3D structure of the lead antibody, hereinafter referred to as the "lead structural template". Sequences in the hit library that are structurally compatible with the lead structural template are selected and screened experimentally in vitro or in vivo for antibody mutants with improved or desired function(s).

In one embodiment, the method comprises the steps of:

providing an amino acid sequence of the variable region of the heavy chain ($V_H$) or light chain ($V_L$) of a lead antibody, the lead antibody having a known three dimensional structure which is defined as a lead structural template;

identifying the amino acid sequences in the CDRs of the lead antibody;

selecting one of the CDRs in the $V_H$ or $V_L$ region of the lead antibody;

providing an amino acid sequence that comprises at least 3 consecutive amino acid residues in the selected CDR, the selected amino acid sequence being a lead sequence;

comparing the lead sequence profile with a plurality of tester protein sequences;

selecting from the plurality of tester protein sequences at least two peptide segments that have at least 10% sequence identity with lead sequence, the selected peptide segments forming a hit library;

determining if a member of the hit library is structurally compatible with the lead structural template using a scoring function; and selecting the members of the hit library that score equal to or better than or equal to the lead sequence.

According to the method, the scoring function is an energy scoring function selected from the group consisting of electrostatic interactions, van der Waals interactions, electrostatic salvation energy, solvent-accessible surface salvation energy, and conformational entropy.

Optionally, the scoring function is one incorporating a forcefield selected from the group consisting of the Amber forcefield, Charmm forcefield, the Discover cvff forcefields, the ECEPP forcefields, the GROMOS forcefields, the OPLS forcefields, the MMFF94 forcefield, the Tripos forcefield, the MM3 forcefield, the Dreiding forcefield, and UNRES forcefield, and other knowledge-based statistical forcefield (mean field) and structure-based thermodynamic potential functions.

Also according to the method, the step of selecting the members of the hit library includes selecting the members of the hit library that have a lower or equal total energy than that of the lead sequence calculated based on a formula of $$\Delta E_{total}=E_{vdw}+E_{bond}+E_{angel}+E_{electrostatics}+E_{solvation}$$

Also according to the method, the step of selecting the members of the hit library includes selecting the members of the hit library that have a lower binding free energy than that of the lead sequence calculated as the difference between the bound and unbound states using a refined scoring function $$\Delta G_b=\Delta G_{MM}+\Delta G_{sol}-T\Delta S_{ss}$$

where $$\Delta G_{MM}=\Delta G_{ele}+\Delta G_{vdw} \quad (1)$$

$$\Delta G_{sol}=\Delta G_{ele\text{-}sol}+\Delta G_{ASA} \quad (2)$$

The method may further comprise the step of:

constructing a nucleic acid library comprising DNA segments encoding the amino acid sequences of the hit library.

Optionally, the method may further comprise the steps of:

building an amino acid positional variant profile of the hit library;

converting amino acid positional variant profile of the hit library into a nucleic acid positional variant profile by back-translating the amino acid positional variants into their corresponding trinucleotide codons; and constructing a degenerate nucleic acid library of DNA segments by combinatorially combining the nucleic acid positional variants.

In yet another aspect of the invention, a method is provided for in silico selection of antibody sequences based on a 3D structure or structure ensemble of a lead antibody, i.e., or a structure ensemble of multiple antibodies, hereinafter collectively referred to as the lead structural template. A lead sequence or sequence profile from a specific region of the lead antibody to be employed to search databases of protein sequences for remote homologues of the lead sequence having low sequence identity and yet structurally similar. These remote homologues form a hit library. An amino acid positional variant profile (AA-PVP) of the hit library is built based on frequency of amino acid variant appearing at each position of the lead sequence. Based on the AA-PVP, a hit variant library is constructed by combinatorially combining the amino acid variant at each position of the lead sequence with or without cutoff of low frequency variants. The sequences in the hit variant library are subjected to evaluation for their structural compatibility with the lead structural template. Sequences in the hit library that are structurally compatible with the lead structural template are selected and screened experimentally in vitro or in vivo for antibody mutants with improved or desired function(s).

In one embodiment, the method comprises the steps of:

providing an amino acid sequence of the variable region of the heavy chain ($V_H$) or light chain ($V_L$) of a lead antibody, the lead antibody having a known three dimensional structure which is defined as a lead structural template;

identifying the amino acid sequences in the CDRs of the lead antibody;

selecting one of the CDRs in the $V_H$ or $V_L$ region of the lead antibody;

providing an amino acid sequence that comprises at least 3 consecutive amino acid residues in the selected CDR, the selected amino acid sequence being a lead sequence;

comparing the lead sequence with a plurality of tester protein sequences;

selecting from the plurality of tester protein sequences at least two peptide segments that have at least 10% sequence identity with lead sequence, the selected peptide segments forming a hit library;

building an amino acid positional variant profile of the hit library based on frequency of amino acid variant appearing at each position of the lead sequence;

combining the amino acid variants in the hit library to produce a combination of hit variants which form a hit variant library;

determining if a member of the hit variant library is structurally compatible with the lead structural template using a scoring function; and selecting the members of the hit variant library that score equal to or better than the lead sequence.

According to the method, the step of combining the amino acid variants in the hit library includes:

selecting the amino acid variants with frequency of appearance higher than 4 times, preferably 6 times, more preferably 8 times, and most preferably 10 times (2% to 10% and preferably 5% of the frequency for the cutoff and then include some of the amino acids from the lead sequence if they are missed after cutoff); and combining the selected amino acid variants in the hit library to produce a combination of hit variants which form a hit variant library.

According to the method, the scoring function is an energy scoring function selected from the group consisting of electrostatic interactions, van der Waals interactions, electrostatic solvation energy, solvent-accessible surface solvation energy, and conformational entropy.

Optionally, the scoring function is one incorporating a forcefield selected from the group consisting of the Amber forcefield, Charmm forcefield, the Discover cvff forcefields, the ECEPP forcefields, the GROMOS forcefields, the OPLS forcefields, the MMFF94 forcefield, the Tripos forcefield, the MM3 forcefield, the Dreiding forcefield, and UNRES forcefield, and other knowledge-based statistical forcefield (mean field) and structure-based thermodynamic potential functions.

The method may further comprise the step of:

constructing a nucleic acid library comprising DNA segments encoding the amino acid sequences of the selected members of the hit variant library.

Optionally, the method may further comprise the steps of:

partitioning the parsing the selected members of hit variant library into at least two sub-hit variant libraries;

selecting a sub-hit variant library;

building an amino acid positional variant profile of the selected sub-hit variant library;

converting the amino acid positional variant profile of the selected sub-hit variant library into a nucleic acid positional variant profile by back-translating the amino acid positional variants into their corresponding trinucleotide codons; and constructing a degenerate nucleic acid library of DNA segments by combinatorially combining the nucleic acid positional variants.

The step of parsing the hit variant library may include:

randomly selecting 10–30 members of the hit variant library that score equal to or better than the lead sequence, the selected members forming a sub-variant library.

Optionally, the step of parsing the hit variant library may include:

building an amino acid positional variant profile of the hit variant library, resulting a hit variant profile;

Route V. Library construction by parsingparsing the hit variant profile into segments of sub-variant profile based on the contact maps of the Calfa, or Cbeta or heavy atoms of the structure or structure ensembles of a lead sequence within certain distance cutoff (8A to 4.5 A). A structural model or lead structural template within a distance of 4.5 Å, preferably within 5 Å, more preferably within 6 Å, and most preferably within 8 Å.

ensemble structure models can serve the purpose. See example shown for anti-VEGF VH CDR3; show the map and figures. Good for cases without X-ray structure or only low resolution structure model can be constructed.

In another embodiment, the method comprises the steps of:

providing an amino acid sequence of the variable region of the heavy chain ($V_H$) or light chain ($V_L$) of a lead antibody, the lead antibody having a known three dimensional structure;

providing 3D structures of one or more antibodies with different sequences in $V_H$ or $V_L$ region than that of the lead antibody;

forming a structure ensemble by combining the structures of the lead antibody and the one or more antibodies; the structure ensemble being defined as a lead structural template;

identifying the amino acid sequences in the CDRs of the lead antibody;

selecting one of the CDRs in the $V_H$ or $V_L$ region of the lead antibody;

providing an amino acid sequence that comprises at least 3 consecutive amino acid residues in the selected CDR, the selected amino acid sequence being a lead sequence;

comparing the lead sequence with a plurality of tester protein sequences;

selecting from the plurality of tester protein sequences at least two peptide segments that have at least 10% sequence identity with lead sequence, the selected peptide segments forming a hit library;

building an amino acid positional variant profile of the hit library based on frequency of amino acid variant appearing at each position of the lead sequence;

combining the amino acid variants in the hit library to produce a combination of hit variants which form a hit variant library;

determining if a member of the hit variant library is structurally compatible with the lead structural template using a scoring function; and selecting the members of the hit variant library that score equal to or better than the lead sequence.

[Route VII. Claim the sequential steps by using a lead sequence from sequence to structure to functional space shown in FIG. 2B]

In a particular embodiment, the method comprises the steps of:

a) providing an amino acid sequence of the variable region of the heavy chain ($V_H$) or light chain ($V_L$) of a lead antibody, the lead antibody having a known three dimensional structure;

b) identifying the amino acid sequences in the CDRs of the lead antibody;

c) selecting one of the CDRs in the $V_H$ or $V_L$ region of the lead antibody;

d) providing an amino acid sequence that comprises at least 3 consecutive amino acid residues in the selected CDR, the selected amino acid sequence being defined as a lead sequence;

e) comparing the lead sequence with a plurality of tester protein sequences;

f) selecting from the plurality of tester protein sequences at least two peptide segments that have at least 10% sequence identity with lead sequence, the selected peptide segments forming a hit library;

g) building an amino acid positional variant profile of the hit library based on frequency of amino acid variant appearing at each position of the lead sequence;

h) combining the amino acid variants in the hit library to produce a combination of hit variants which form a hit variant library;

i) determining if a member of the hit variant library is structurally compatible with the lead structural template using a scoring function;

j) selecting the members of the hit variant library that score equal to or better than the lead sequence;

k) constructing a degenerate nucleic acid library comprising DNA segments encoding the amino acid sequences of the selected members of the hit variant library;

l) determining the diversity of the nucleic acid library, if the diversity is higher than $1\times10^6$, repeating steps j) through l) until the diversity of the diversity of the nucleic acid library is equal to or lower than $1\times10^6$;

m) introducing the DNA segments in the degenerate nucleic acid library into cells of a host organism;

n) expressing the DNA segments in the host cells such that recombinant antibodies containing the amino acid sequences of the hit library are produced in the cells of the host organism;

o) selecting the recombinant antibody that binds to a target antigen with affinity higher than $10^6$ $M^{-1}$; and p) repeating steps e) through o) if no recombinant antibody is found to bind to the target antigen with affinity higher than $10^6$ $M^{-1}$.

In another particular embodiment, the method comprises the steps of:

a) providing an amino acid sequence of the variable region of the heavy chain ($V_H$) or light chain ($V_L$) of a lead antibody, the lead antibody having a known three dimensional structure which is defined as a lead structural template;

b) identifying the amino acid sequences in the CDRs of the lead antibody;

c) selecting one of the CDRs in the $V_H$ or $V_L$ region of the lead antibody;

d) providing an amino acid sequence that comprises at least 3 consecutive amino acid residues in the selected CDR, the selected amino acid sequence being defined as a lead sequence;

e) mutating the lead sequence by substituting one or more of the amino acid residues of the lead sequence with one or more different amino acid residues, resulting in a lead sequence mutant library;

f) determining if a member of the lead sequence mutant library is structurally compatible with the lead structural template using a first scoring function;

g) selecting the lead sequence mutants that score equal to or better than the lead sequence;

h) comparing the lead sequence with a plurality of tester protein sequences;

i) selecting from the plurality of tester protein sequences at least two peptide segments that have at least 10% sequence identity with lead sequence, the selected peptide segments forming a hit library;

j) building an amino acid positional variant profile of the hit library based on frequency of amino acid variant appearing at each position of the lead sequence;

k) combining the amino acid variants in the hit library to produce a combination of hit variants;

l) combining the selected lead sequence mutants with the combination of hit variants to produce a hit variant library;

m) determining if a member of the hit variant library is structurally compatible with the lead structural template using a second scoring function;

n) selecting the members of the hit variant library that score equal to or better than the lead sequence;

o) constructing a degenerate nucleic acid library comprising DNA segments encoding the amino acid sequences of the selected members of the hit variant library;

p) determining the diversity of the nucleic acid library, and if the diversity is higher than $1\times10^6$, repeating steps n) through p) until the diversity of the diversity of the nucleic acid library is equal to or lower than $1\times10^6$;

q) introducing the DNA segments in the degenerate nucleic acid library into cells of a host organism;

r) expressing the DNA segments in the host cells such that recombinant antibodies containing the amino acid sequences of the hit library are produced in the cells of the host organism;

s) selecting the recombinant antibody that binds to a target antigen with affinity higher than $10^6$ $M^{-1}$; and t) repeating steps e) through s) if no recombinant antibody is found to bind to the target antigen with affinity higher than $10^6$ $M^{-1}$.

In yet another aspect of the present invention, a computer-implemented method is provided for constructing a library of mutant antibodies based on a lead antibody. In one embodiment, the method comprises:

taking as an input an amino acid sequence that comprises at least 3 consecutive amino acid residues in a CDR region of the lead antibody, the amino acid sequence being a lead sequence;

employing a computer executable logic to compare the lead sequence with a plurality of tester protein sequences;

selecting from the plurality of tester protein sequences at least two peptide segments that have at least 15% sequence identity with lead sequence; and generating as an output the selected peptide segments which form a hit library.

According to any of the above methods, the length of the lead sequence is preferably between 5–100 aa, more preferably between 6–80 aa, and most preferably between 8–50 aa.

According to any of the above methods, the step of identifying the amino sequences in the CDRs is carried out by using Kabat criteria; other criteria such as Chothia etc can be also used (quote them).

or Chothia criteria.

Also according to any of the above methods, the lead sequence may comprise an amino acid sequence from a particular region within the $V_H$ or $V_L$ of the lead antibody, CDR1, CDR2 or CDR3, or from a combination of the CDR and FRs, such as CDR1-FR2, FR2-CDR2-FR3, and the full length $V_H$ or $V_L$ sequence. The lead sequence preferably comprises at least 6 consecutive amino acid residues in the selected CDR, more preferably at least 7 consecutive amino acid residues in the selected CDR, and most preferably all of the amino acid residues in the selected CDR.

Also according to any of the above methods, the lead sequence may further comprise at least one of the amino acid residues immediately adjacent to the selected CDR.

Also according to any of the above methods, the lead sequence may further comprise at least one of the FRs flanking the selected CDR.

Also according to any of the above methods, the lead sequence may further comprise one or more CDRs or FRs adjacent the C-terminus or N-terminus of the selected CDR.

Also according to any of the above methods, the lead structural template may be a 3D structure of a fully assembled lead antibody, or a heavy chain or light chain variable region of the lead antibody (e.g., CDR, FR and a combination thereof).

Also according to any of the above methods, the plurality of tester protein sequences includes preferably antibody sequences, more preferably human antibody sequences, and most preferably human germline antibody sequences (V-database), especially for the framework regions.

Also according to any of the above methods, the plurality of tester protein sequences is retrieved from genbank of the NIH or Swiss-Prot database or the Kabat database for CDRs of antibodies.

Also according to any of the above methods, the step of comparing the lead sequence with the plurality of tester protein sequences is implemented by an algorithm selected from the group consisting of BLAST, PSI-BLAST, profile HMM, and COBLATH.

Also according to any of the above methods, the sequence identity of the selected peptide segments in the hit library with the lead sequence is preferably at least 25%, preferably at least 35%, and most preferably at least 45%.

According to any of the above method, the method further comprises the following steps:

introducing the DNA segments in the nucleic acid or degenerate nucleic acid library into cells of a host organism;

expressing the DNA segments in the host cells such that recombinant antibodies containing the amino acid sequences of the hitencoded by the nucleic acid or degenerate nucleic acid library are produced in the cells of the host organism; and selecting the recombinant antibody that binds to a target antigen with affinity higher than $10^6$ $M^{-1}$, preferably $10^7$ $M^{-1}$, more preferably $10^8$ $M^{-1}$, and most preferably $10^9$ $M^{-1}$.

The recombinant antibodies may be fully assembled antibodies, Fab fragments, Fv fragments, or single chain antibodies.

The host organism includes any organism or its cell line that is capable of expressing transferred foreign genetic sequence, including but not limited to bacteria, yeast, plant, insect, and mammals.

The recombinant antibodies may be fully assembled antibodies, Fab fragments, Fv fragments, or single chain antibodies. For example, the recombinant antibodies may be expressed in bacterial cells and displayed on the surface of phage particles. The recombinant antibodies displayed on phage particles may be a double-chain heterodimer formed between $V_H$ and $V_L$. The heterodimerization of $V_H$ and $V_L$ chains may be facilitated by a heterodimer formed between two non-antibody polypeptide chains fused to the $V_H$ and $V_L$ chains, respectively. For example, these two non-antibody polypeptide may be derived from a heterodimeric receptors $GABA_B$ R1 (GR1) and R2 (GR2), respectively.

Alternatively, the recombinant antibodies displayed on phage particles may be a single-chain antibody containing $V_H$ and $V_L$ linked by a peptide linker. The display of the single chain antibody on the surface of phage particles may be facilitated by a heterodimer formed between a fusion of the single chain antibody with GR1 and a fusion of phage pIII capsid protein with GR2.

The target antigen to be screened against includes small molecules and macromolecules such as proteins, peptides, nucleic acids and polycarbohydrates.

In yet another aspect of the present invention, a computer-readable medium is provided. The computer medium comprises logic for constructing a library of mutant antibodies based on a lead antibody, the logic comprising:

logic which

- takes as an input an amino acid sequence that comprises at least 3 consecutive amino acid residues in a CDR of the lead antibody, the amino acid sequence being a lead sequence;
- compares the lead sequence with a plurality of tester protein sequences;
- selects from the plurality of tester protein sequences at least two peptide segments that have at least 15% sequence identity with lead sequence; and
- generates as an output the selected peptide segments which form a hit library.

In yet another aspect of the present invention, monoclonal antibodies are provided that are capable of binding to human vascular endothelial growth factor (VEGF) with a binding affinity higher than $10^6$ $M^{-1}$. The monoclonal antibody may be a fully assembled antibody, a Fab fragment, a Fv fragment or a single chain antibody (scFv).

In one embodiment, the heavy chain CDR3 of the monoclonal antibody comprises an amino acid sequence selected from group consisting of SEQ ID Nos: 36–48 and 63–125.

In another embodiment, the heavy chain CDR1 of the monoclonal antibody comprises an amino acid sequence selected from group consisting of SEQ ID Nos: 19–30.

In yet another embodiment, the heavy chain CDR2 of the monoclonal antibody comprises an amino acid sequence selected from group consisting of SEQ ID Nos: 31–35.

Optionally, the heavy chain CDR3 of the monoclonal antibody comprises an amino acid sequence selected from group consisting of SEQ ID Nos: 36–48 and 63–125, and the heavy chain CDR1 of the monoclonal antibody comprises an amino acid sequence selected from group consisting of SEQ ID Nos: 19–30.

Also optionally, the heavy chain CDR3 of the monoclonal antibody comprises an amino acid sequence selected from group consisting of SEQ ID Nos: 36–48 and 63–125, and the heavy chain CDR2 of the monoclonal antibody comprises an amino acid sequence selected from group consisting of SEQ ID Nos: 31–35.

Also optionally, the heavy chain CDR1 of the monoclonal antibody comprises an amino acid sequence selected from group consisting of SEQ ID Nos: 19–30, and the heavy chain CDR2 of the monoclonal antibody comprises an amino acid sequence selected from group consisting of SEQ ID Nos: 31–35.

The antibodies designed by using the methods of present invention may be used for diagnosing or therapeutic treatment of various diseases, including but not limited to, cancer, autoimmune diseases such as multiple sclerosis, rheumatoid arthritis, systemic lupus erythematosus, Type I diabetes, and myasthenia gravis, graft-versus-host disease, cardiovascular diseases, viral infection such as HIV, hepatitis viruses, and herpes simplex virus, bacterial infection, allergy, Type II diabetes, hematological disorders such as anemia.

The antibodies can also be used as conjugates that are linked with diagnostic or therapeutic moieties, or in combination with chemotherapeutic or biological agents. The antibodies can also be formulated for delivery via a wide variety of routes of administration. For example, the antibodies may be administered or coadministered orally, topically, parenterally, intraperitoneally, intravenously, intraarterially, transdermally, sublingually, intramuscularly, rectally, transbuccally, intranasally, via inhalation, vaginally, intraoccularly, via local delivery (for example by a catheter or a stent), subcutaneously, intraadiposally, intraarticularly, or intrathecally.

In sequence space, the lead sequence(s) or profile is used to search the specific database for evolutionarily related sequences. Sequence profile based on the structural alignment of the lead structure can be used to search for remote homologues of the lead sequence. The variant profile of the hit library describes the positional frequency and entropy of the amino acid sequence. The variant profile can be filtered and re-profiled at a given cutoff to give the evolutionally preferred variant profile. This procedure can be iterated with various searching methods on related sequence database.

In structure space, an in silico variant profile is generated using a structure-based screening of random or evolutionally pooled sequence library. The variant profile can be filtered and refined to give the structurally preferred variant profile. This procedure can be iterated and refined with better scoring functions and representative structure ensemble.

The variant profile generated using either evolutionally- or structurally-based approaches can be used in sequential (2B: from sequence to structure to function space; 2C: from structure to sequence to function space) or parallel fashion (from sequence space to function space and from structure space to function space) to give an overall variant profile or library of amino acids. The resulting variant library of amino acids is back-translated into nucleic acid library by using preferred or optimized codons. This procedure can be iterated with different filtering and partitioning procedure to adjust the library size to within experimentally manageable range.

To select for functional mutants in function space, the synthesized nucleic acid library is introduced into vectors by transformation and functionally expressed or displayed, for example, on phage particles. Rounds of selection and enrichment against immobilized antigen are carried out. The whole or part of the procedure can be iterated and refined until the desired candidates are selected experimentally.

Figure 2A:
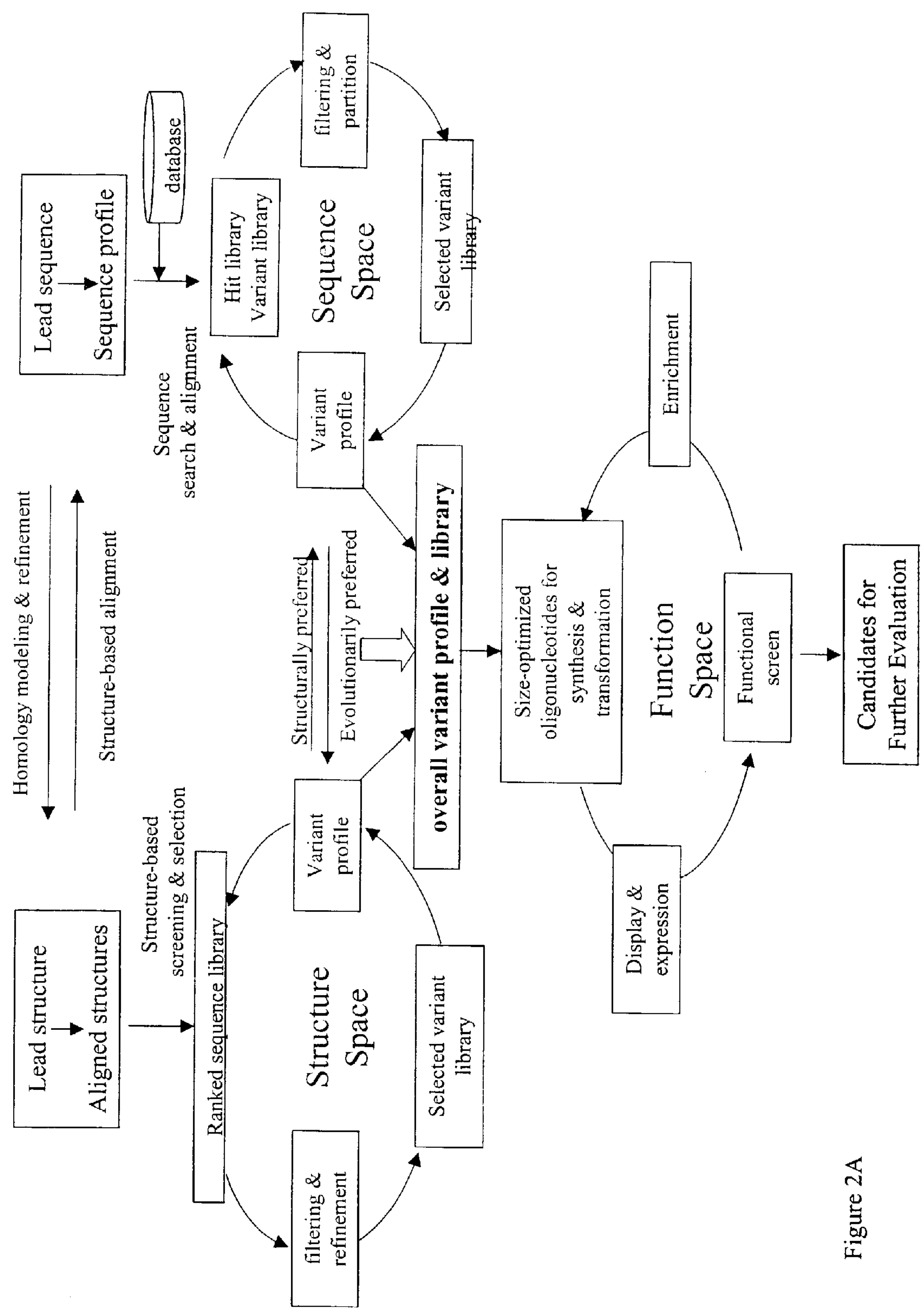
FIG. 2A is a schematic overview of the in silico protein evolution system provided by the present invention. The triangular relationship among sequence, structure and function spaces is shown to illustrate potential paths traversing from the lead structure/lead structural profile or lead sequence/lead sequence profile to candidate sequences through sequence, structure and function spaces.
Figure 2B:
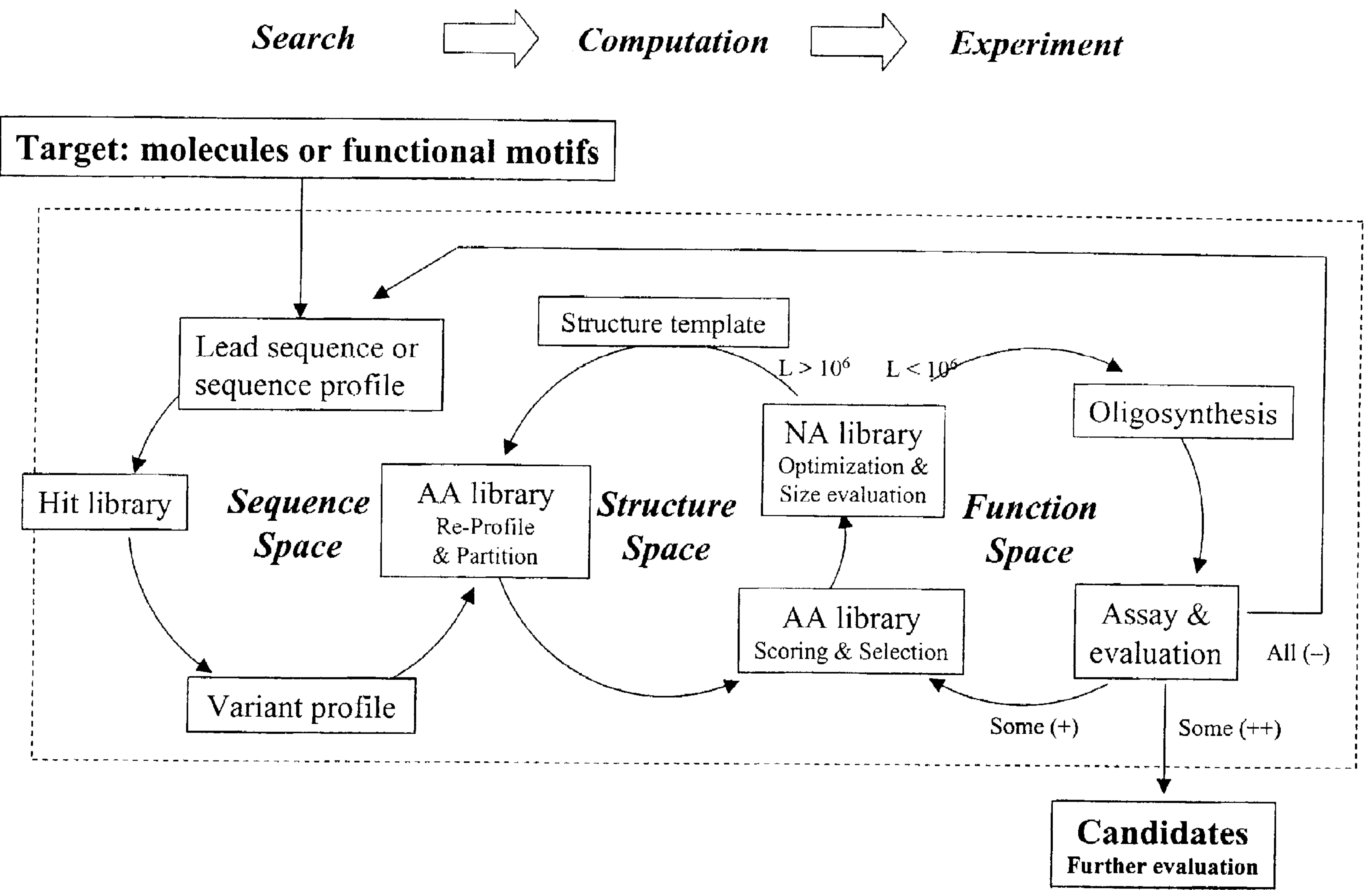

FIG. 2B. A schematic diagram of an embodiment of the methodology provided in the present invention for antibody library design. A sequential procedure moves from sequence first to structure and to function space. The design starts from a lead sequence or sequence profile (multiple aligned sequences from structure-based alignment). A hit library is generated by searching the sequence database. The hit profile given by the hit library at certain cutoff will give the hit variant library. Either the hit library or hit variant libraries can be screened computationally using the lead structure or structure ensemble as the template structure. The resulting sequence library is ranked based on their compatibility with the template structure or structure ensemble.

Sequences with scores better than or equal to the lead sequence are selected and profiled to generate nucleic acid (NA) library. The in silico NA library size is evaluated and passed on to oligonucleotide synthesis if the library size is acceptable. Otherwise, the hit variant library is repartitioned into smaller segments and smaller NA libraries are generated. In the function space, the nucleic acid library is experimentally screened and positive sequences are fed back into the computational cycle for library refinement. Strong positive clones are passed on for further evaluation and potential therapeutic development. If no hits occur in the experimental screening, the lead or its new lead profile is selected for the target system and the process is reiterated.

Figure 2C:
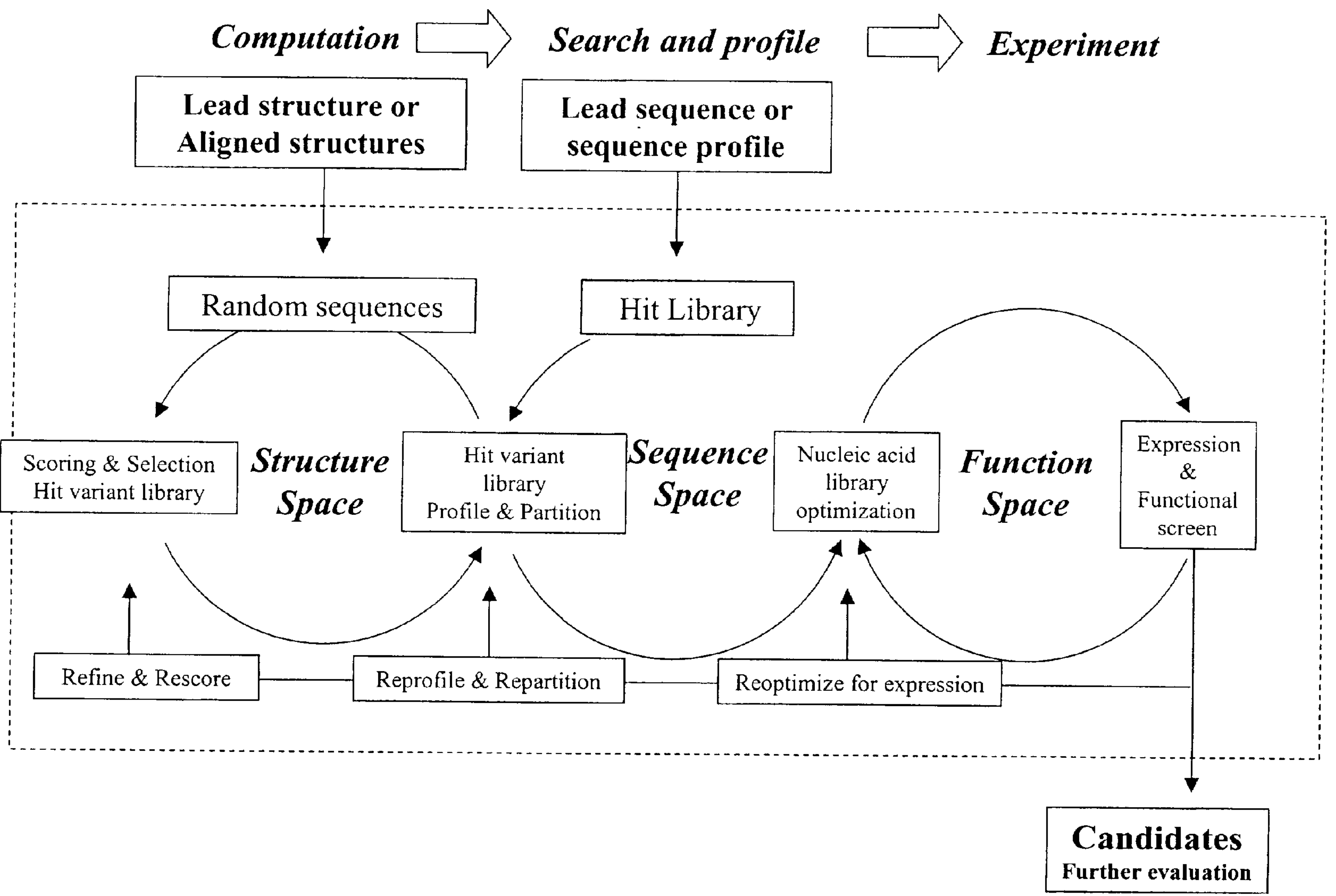

FIG. 2C. A schematic diagram of another embodiment of the methodology provided in the present invention for antibody library design. An alternative sequential procedure moves from the structure first to sequence and to function space. The design starts from a lead structure or structure ensemble. A combination of random mutations at target positions is screened computationally for their compatibility with the structure template. A variant profile of the sequences that score better than or equal to the lead sequence is generated. This variant profile can be compared and/or combined with those given by searching the sequence database. Novel mutants might be included or excluded based on the consensus frequency shown in sequence and structure space to generate a nucleic acid library. The rest of the procedure is similar to those described in FIG. 2B. This approach emphasizes the importance of finding novel mutants by structure-based computational screening without relying on the evolutionary sequence information. The sequence profile from searching database will help to assess the variant profile obtained from computational screening that lies on the accuracy of the scoring function as well as on the sampling algorithm used.

Figure 3:
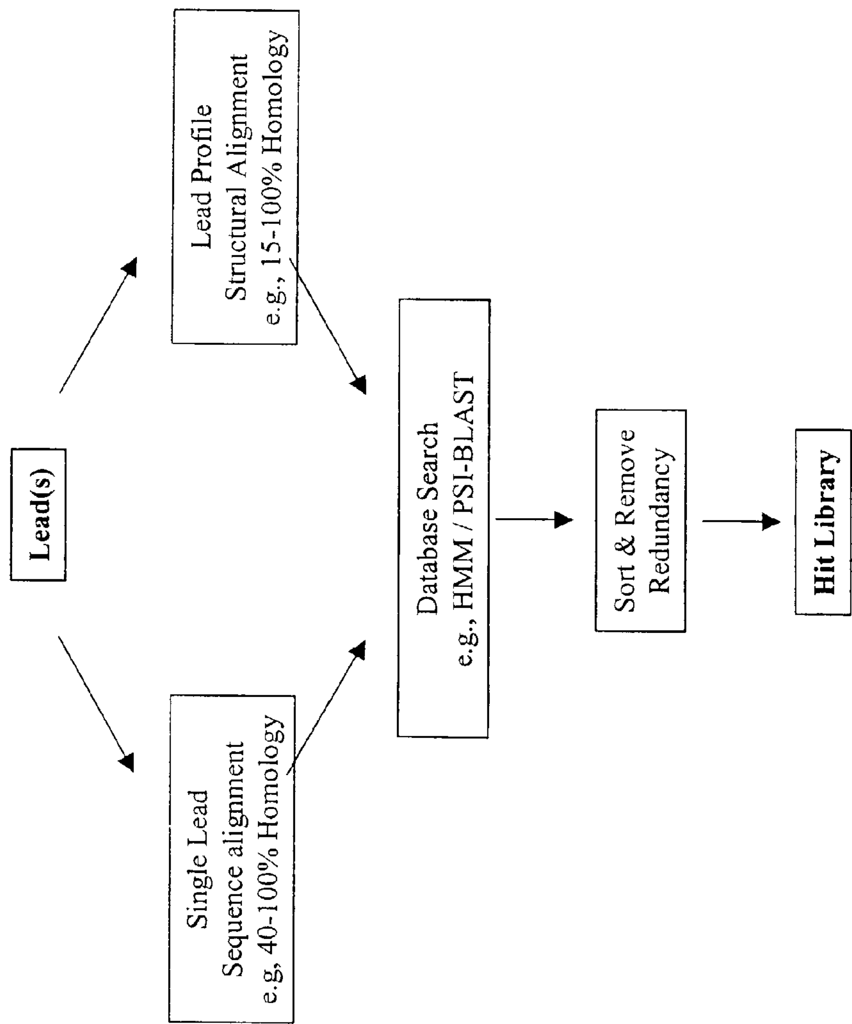

FIG. 3 illustrates a process for constructing a hit library in silico via database search using either the single lead or the lead profile based on structural alignment. The search results are sorted and redundant sequences (even if the background is different) are removed to produce a list of unique sequences in the hit library. Impact of the lead sequence/sequence profile, sequence searching methods, and various database are shown in FIGS. 4–6.

Figure 4:
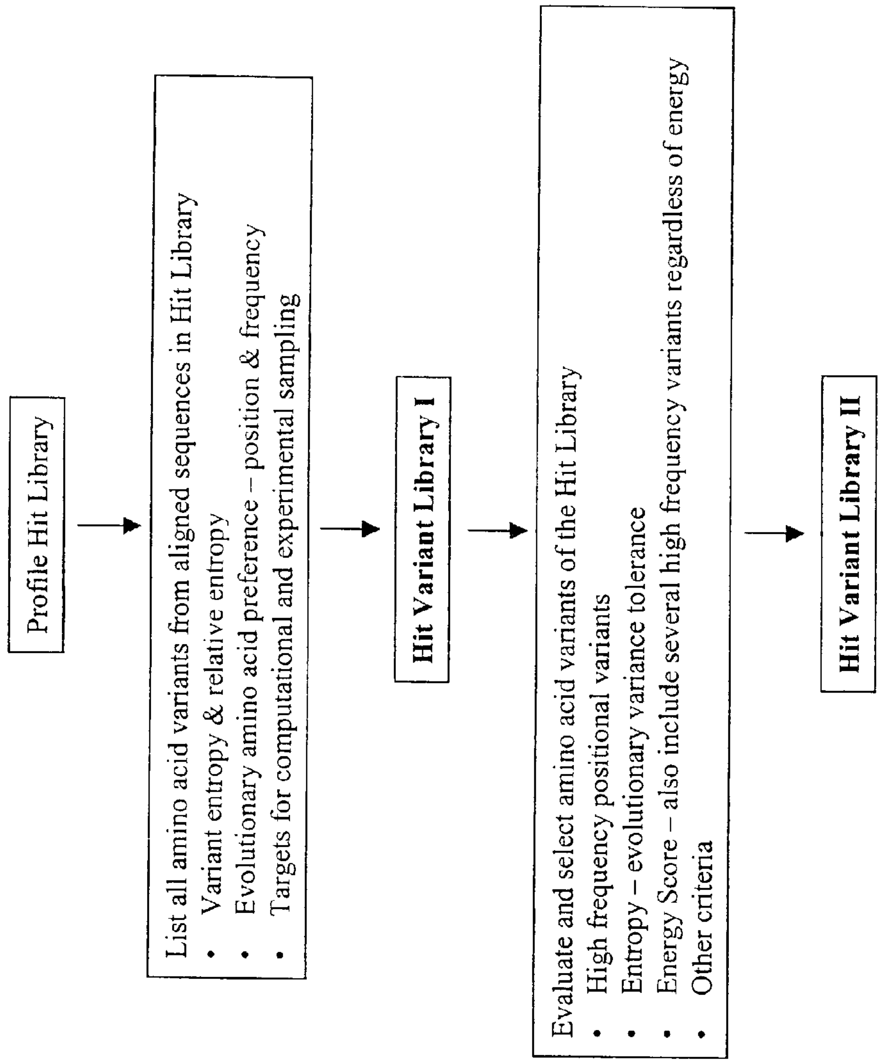

FIG. 4 illustrates a process for constructing a hit variant library I based on the variant profile from the hit library that is used to analyze the evolutionary positional preferences for amino acids. A refined variant profile is derived by filtering based on selection criteria that include frequency, variation entropy, and energy score of the amino acid variants at each position. The hit variant library II is combinatorially enumerated from the refined variant profile.

Figure 5:
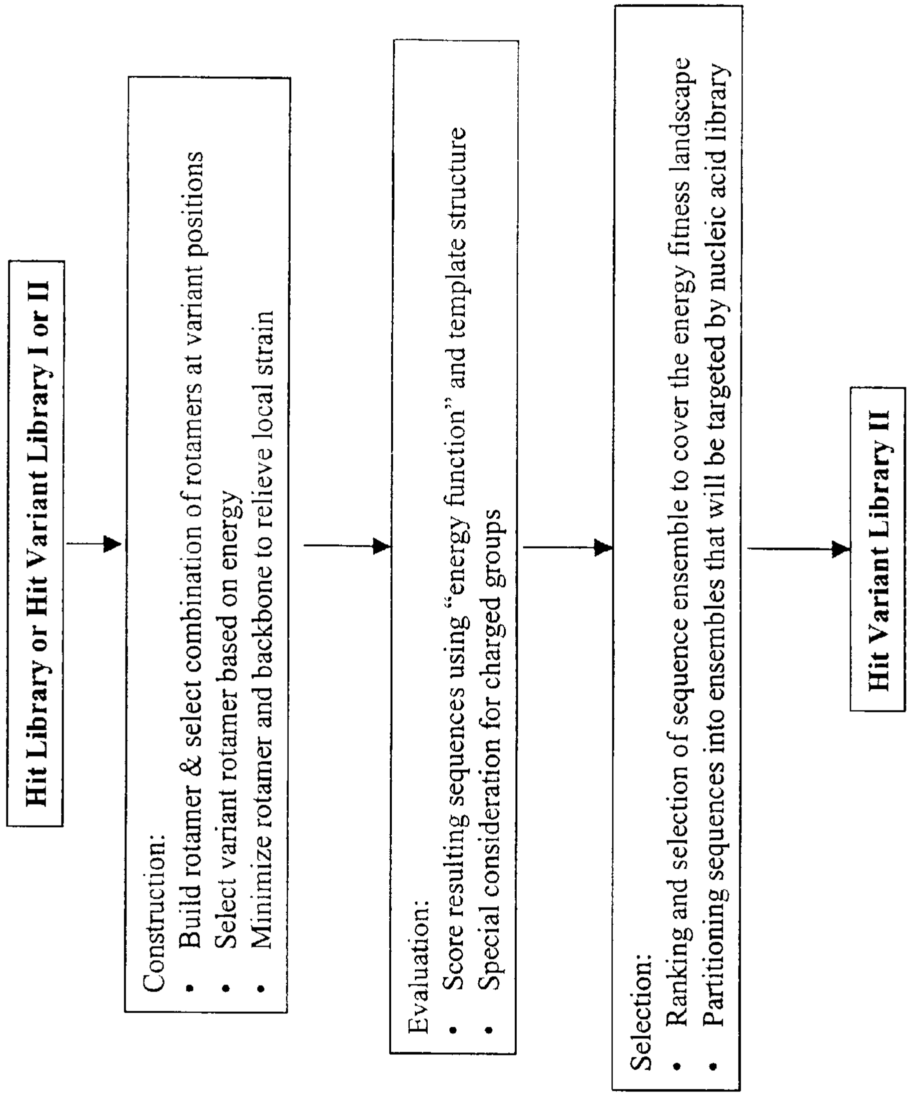

FIG. 5 illustrates a process for structural evaluation and selection of a hit variant library I or II to create a structurally screened version of hit variant library II. The computational selection uses simple as well as custom energy function to score and rank the hit variant library I or II sequences applied to a lead structural template. For each sequence, the side chains are generated using a backbone-dependent rotamer library and the side chains and backbone are energy minimized against the template background to relieve any local strain. The fitness of the hit variant library I or II in the template structure is scored and ranked using simple as well as custom energy functions. Several ensembles of the “best” sequences are selected to build a new hit variant library II for translation into a nucleic acid (NA) library. The selection criteria may include sequence clustering, structural considerations or functional considerations. The ensembles of amino acid sequences are re-profiled for generating the nucleic acid library within experimentally manageable limit (FIG. 6).

Figure 6:
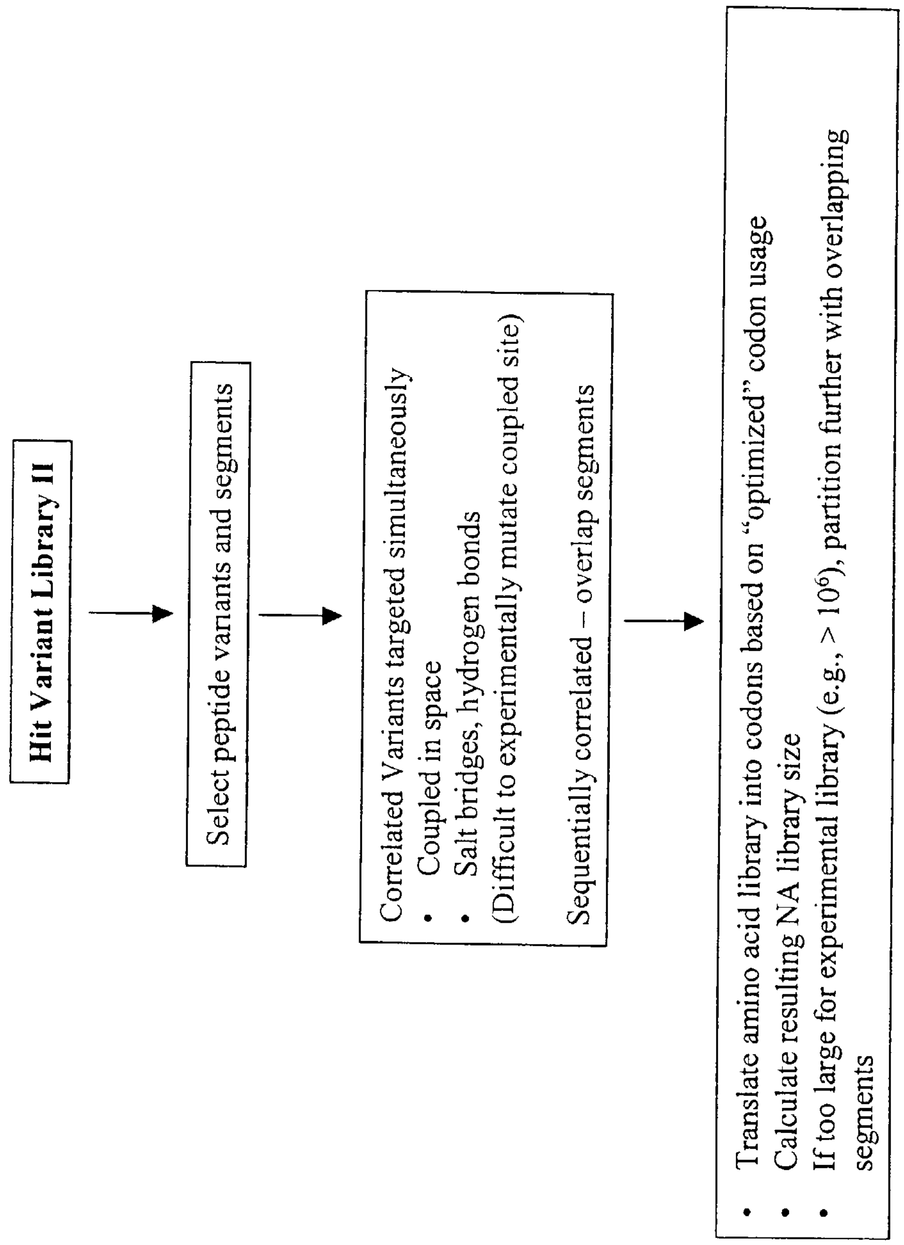

FIG. 6 illustrates a process for constructing a nucleic acid (NA) library by back-translation from hit variant library II. The back translation of amino acids into nucleic acids is intended to keep the size of the nucleic acid library within experimentally manageable limit while optimizing the prefered codon usage. The size of the nucleic acid library is calculated and kept within the experimental limit or the hit variant profile is modified by reducing the variant number or partitioned into shorter segments. Partitioning may be accomplished either by using structurally correlated segments or series of overlapping sequentially correlated segments.

Figure 7:
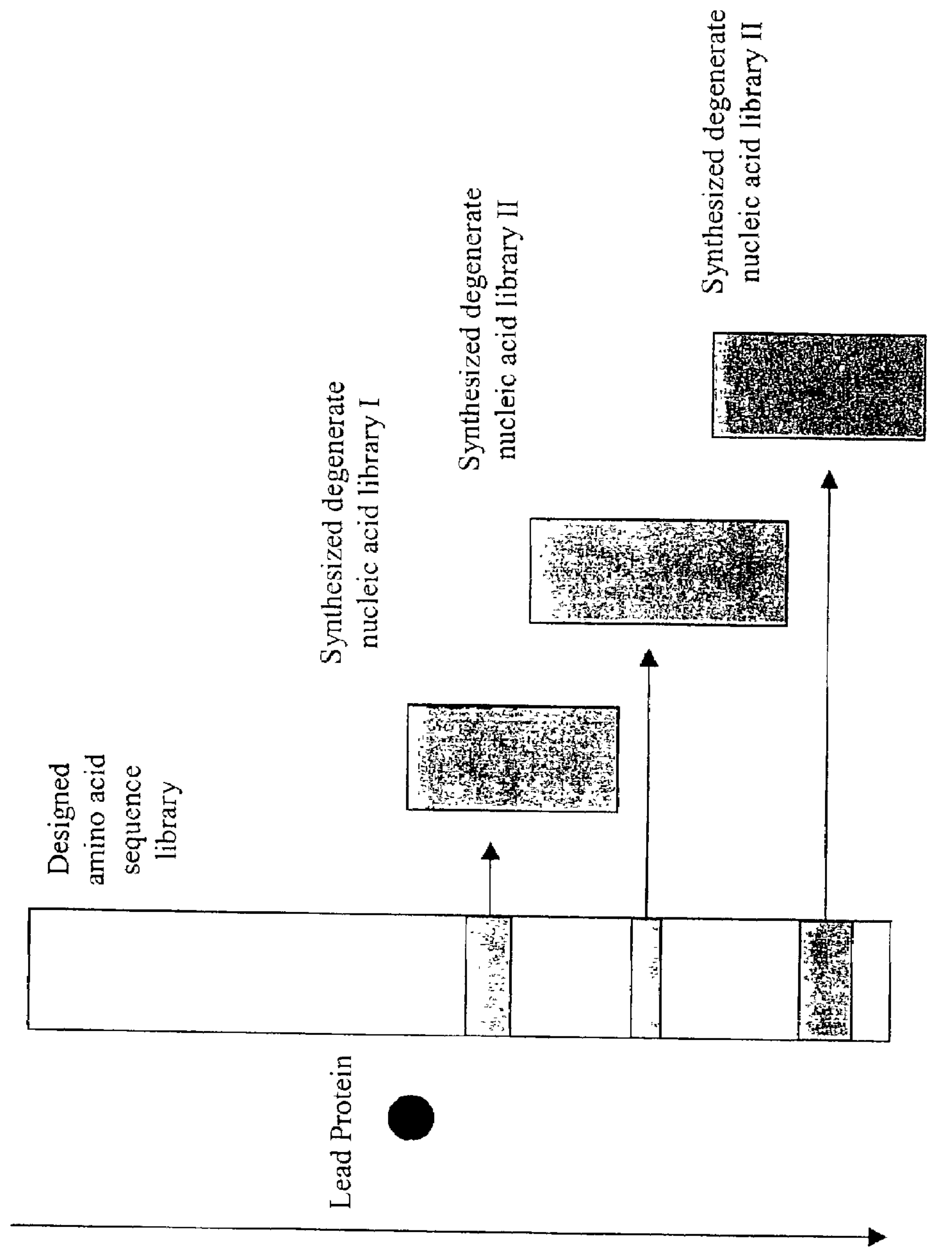

FIG. 7 is an overview of a strategy of sampling a library at several regions of the fitness landscape. The fitness landscape of the selected peptide sequences can be expanded to cover a larger fitness landscape if the combinatorial amino acid or its degenerate nucleic acid libraries can be designed to sample a larger function space. Strategic sampling from a designed library leads to overlapping and expanded diversity that can include significant evolutionary jumps in the fitness landscape of the function space.

Figure 8:
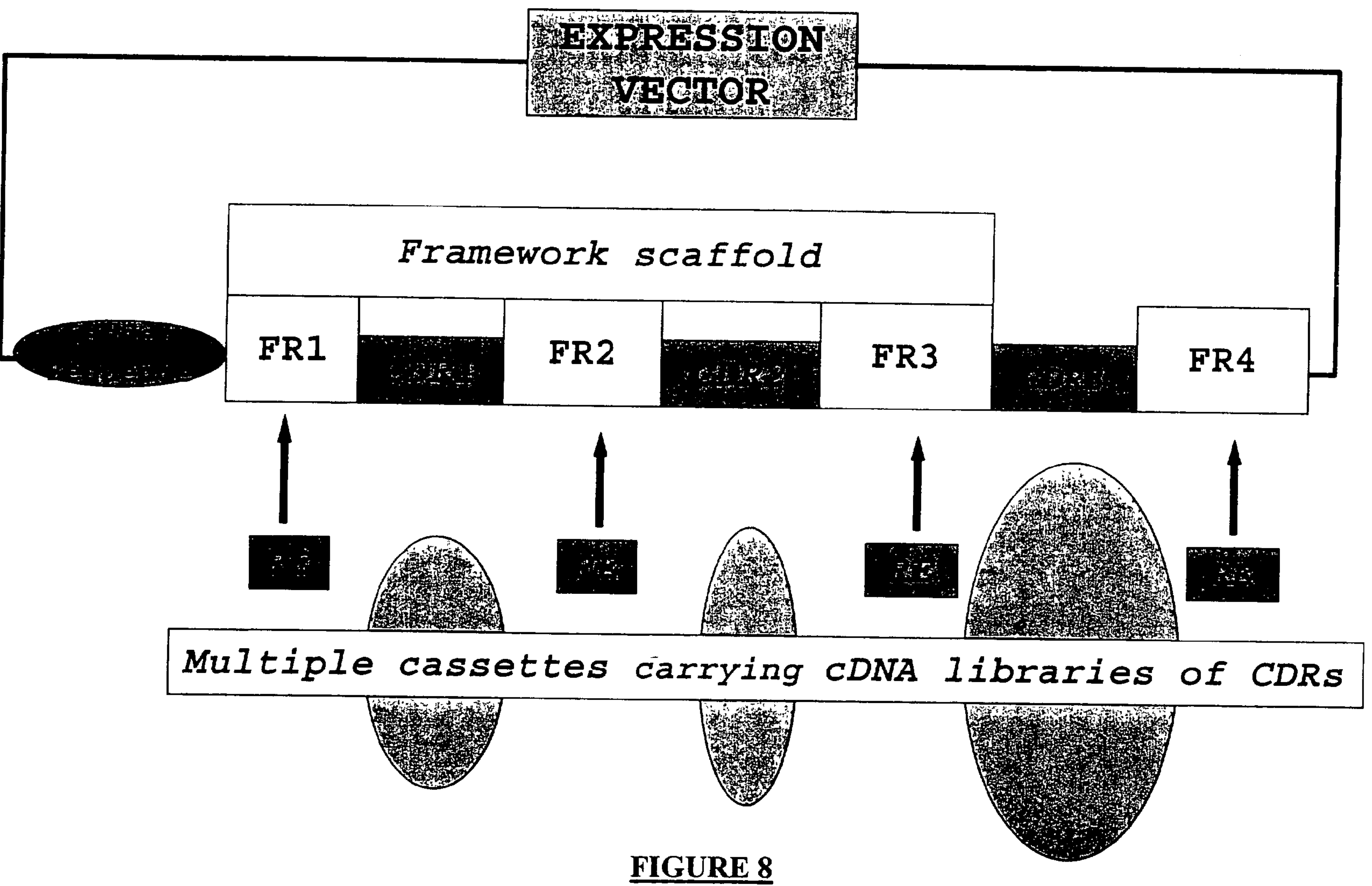

FIG. 8 shows modular elements of a typical library plasmid for antibody engineering. The libraries of framework and CDR sequences can be designed, respectively or combinatorially in iteration. FR=framework region. CDR=complementarity determining region. RE=restriction enzyme site.

Figures 9A, 9B:
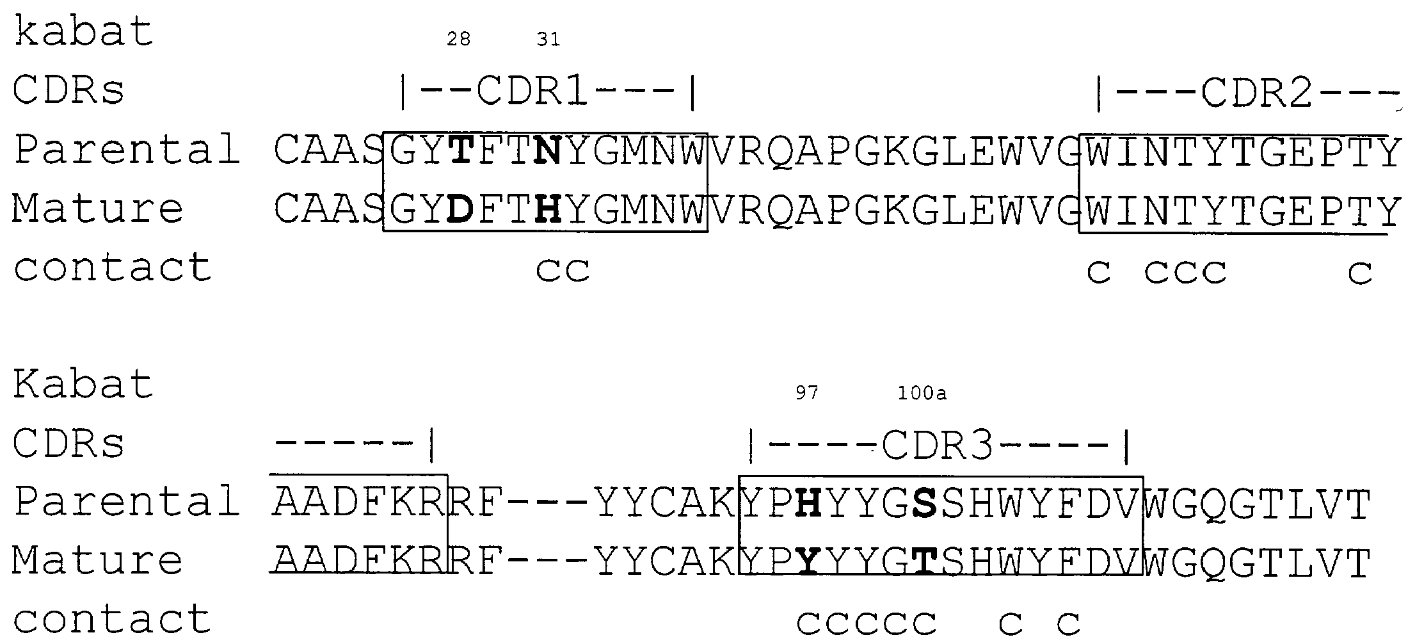

FIG. 9A is a sequence comparison between the parental [SEQ ID NO: 1] and matured [SEQ ID NO: 3] anti-VEGF antibody in $V_H$ CDRs. “c” indicates where atoms of the antigen-antibody complex contact within 4.5 Å in the X-ray structure. Bold letters highlight the differences in amino acids between the parental and matured antibody in $V_H$ CDRs (CDR1 and CDR3). The numbering for $V_H$ CDRs follows the convention by Kabat and a sequential scheme (100, 101 rather than 100, 100a etc).

FIG. 9B is a sequence comparison between the parental and matured anti-VEGF antibody in $V_H$ CDR3 with its adjacent regions. The sequence (SEQ ID NO: 5) from parental antibody is the lead sequence used for searching database. The numbering for $V_H$ CDRs are both Kabat and a sequential scheme used here also.

Figure 10A:
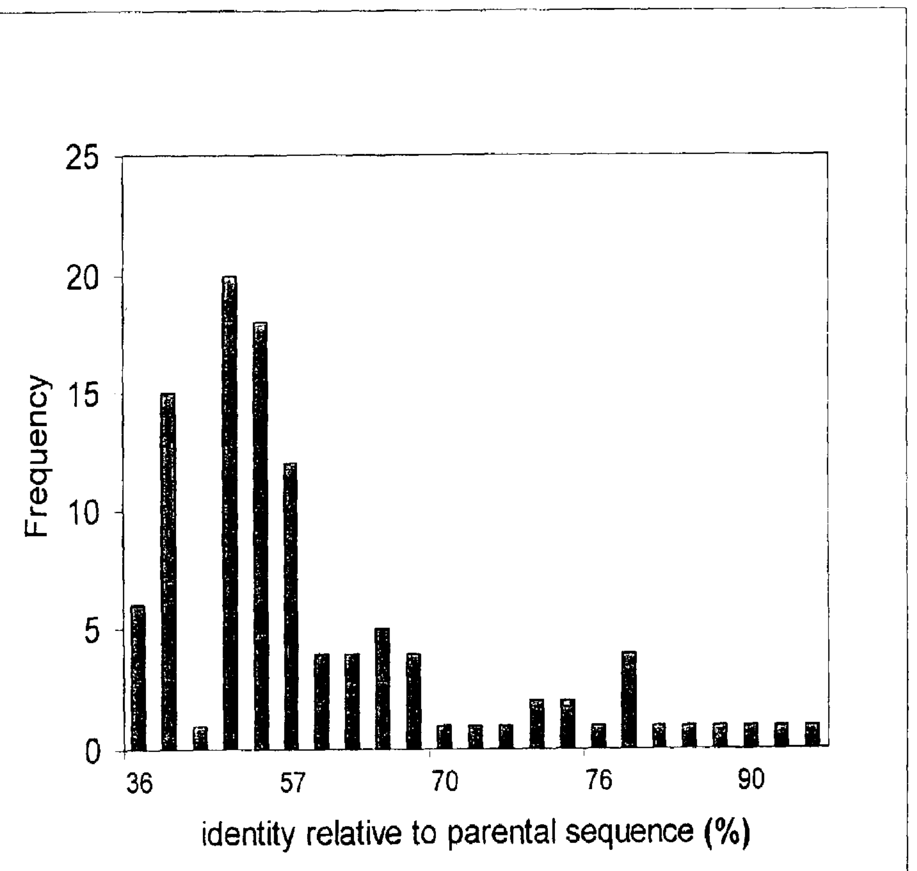

FIG. 10A is a plot showing the distribution of the frequency of a hit library versus their sequence identity (in %) relative to the lead sequence of $V_H$ CDR3 of parental anti-VEGF antibody. The lead sequence is shown in FIG. 9B and the profile HMM (HAMMER2.1.1) was used to search the Kabat database (Johnson, G and Wu, T T (2001) Nucleic Acids Research, 29, 205–206).

Figure 10B:
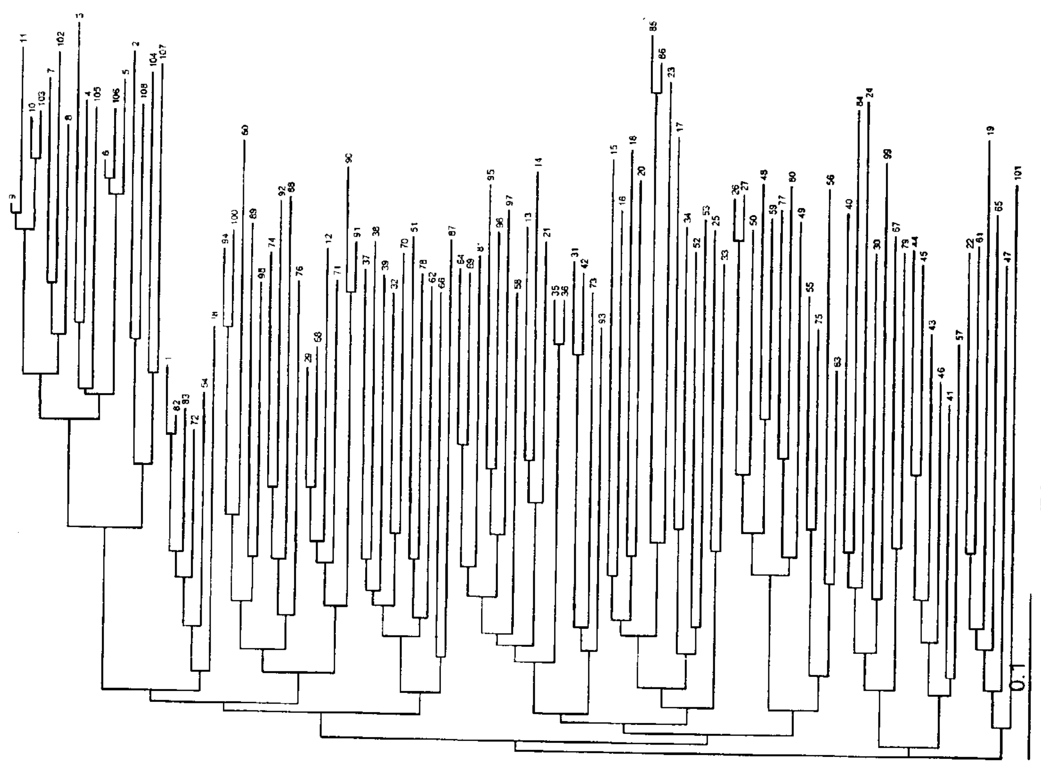

FIG. 10B illustrates the phylogenetic tree of the sequences of a hit library shown in FIG. 10A in order to show the phylogenetic diversity of the hit library resulting from the database search in FIG. 10A.

FIG. 11 shows a variant profile for the 107 sequences of the hit library generated based on the lead sequence of $V_H$ CDR3 of parental anti-VEGF antibody. The upper portion shows a table listing the amino acid frequency of 20 amino acids at each position of the lead sequence. The variant profile at the bottom shows the amino acid positional diversity. A complete enumeration of a combinatorial library with no selective control of amino acid diversity (shown in lower left portion of the figure) will require a library size on the order of $10^{19}$. The lower right portion of the figure shows a filtered variant profile obtained by using a cutoff frequency of 10. All positional amino acids occurring 10 or less times among the 107 members of the hit list are filtered. This filtered variant profile can be further screened computationally to reflect the ranking order of the structural compatibility if only the antibody structure is used, or binding affinity with the antigen if the complex structure between antibody and antigen is used. The variant profile shows no correlation with the contact sites between antigen and antibody as indicated in FIG. 9A.

Figures 12A, 12B:
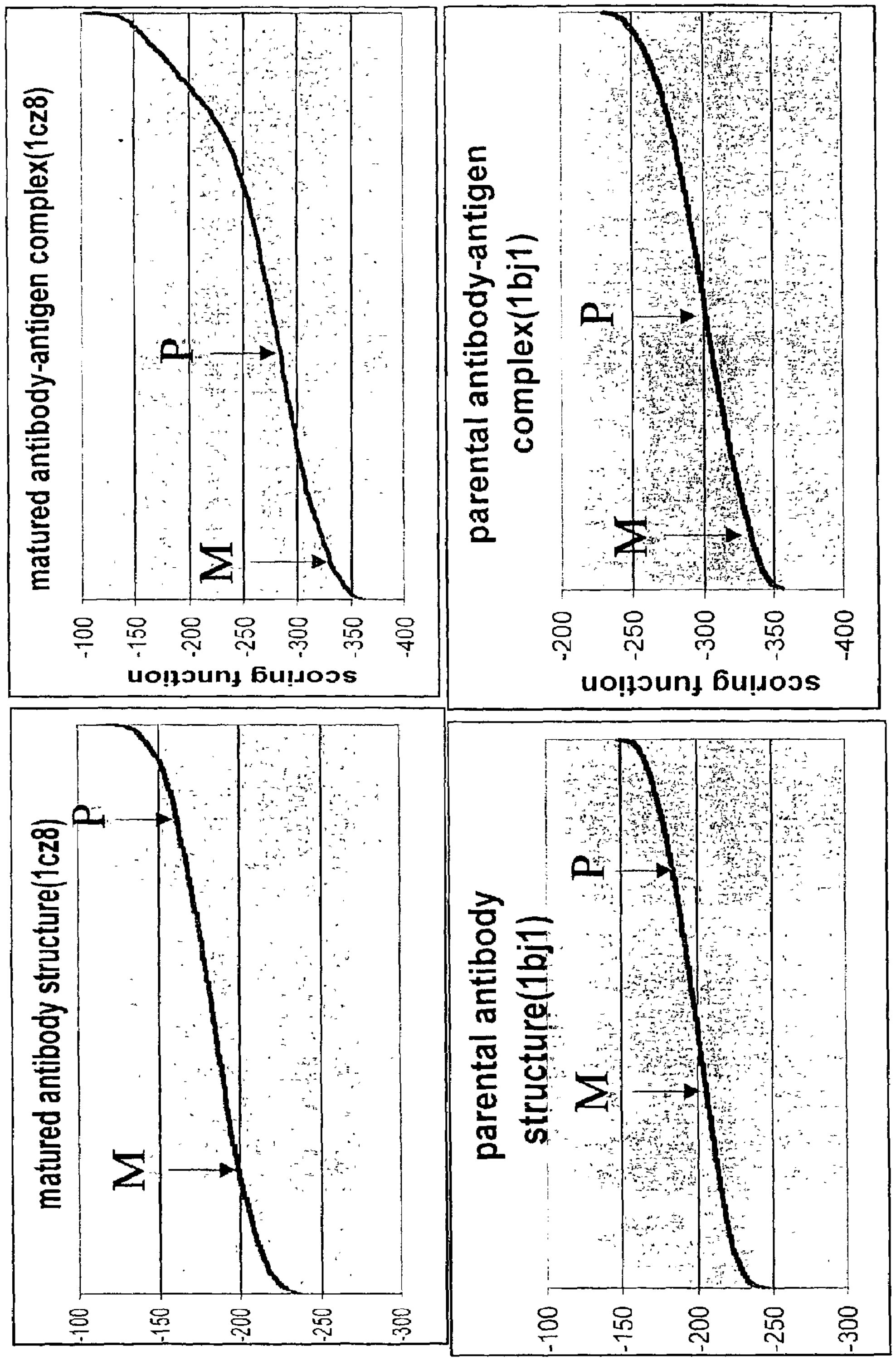
Figure 12C:
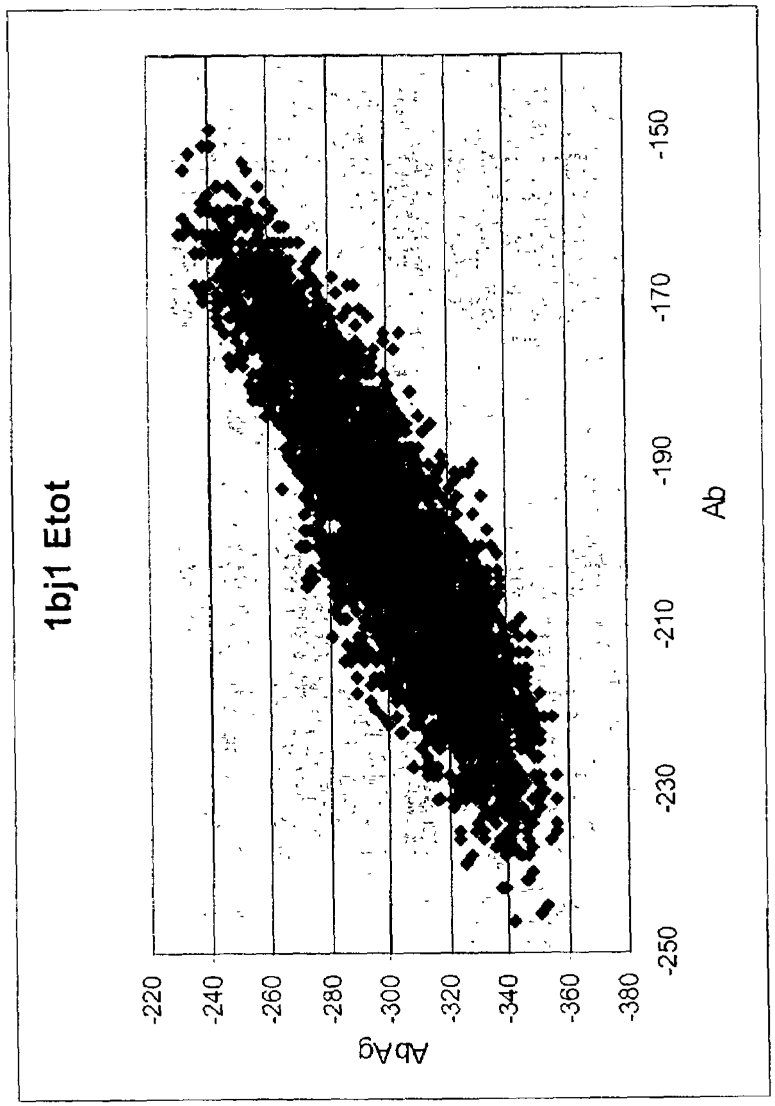
Figures 12D, 12E:
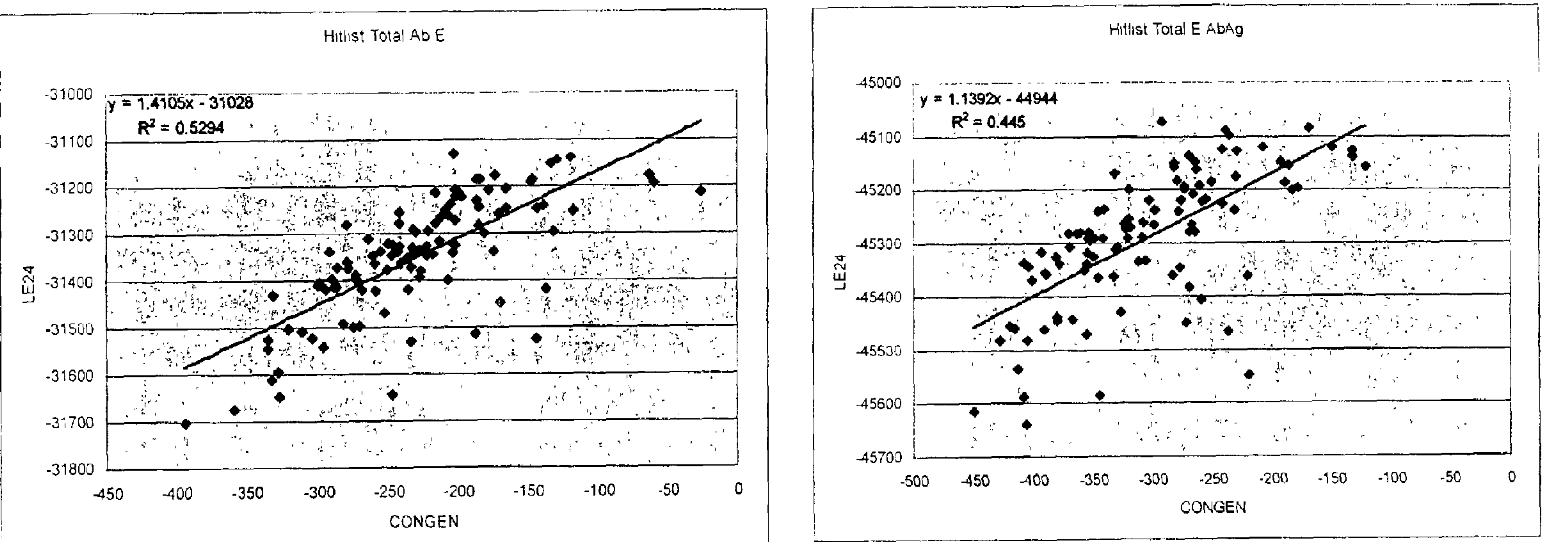

FIGS. 12A and 12B show a typical plot of the scores of an anti-VEGF antibody variant library in the parental (1bj1) and matured (1cz8) antibody structure, respectively, in the absence (A) and presence of VEGF antigen (B), using a scoring function of the total energy of the Amber94 force-field implemented in CONGEN. The scores of the matured (M) and parental (P) sequences are marked by the arrows. The mature sequence scores better than that of the parental sequence in the absence and presence of the antigen in both template structures. FIG. 12C shows the correlation between the scores of the variant library in the presence and absence of the antigen. FIGS. 12D and E show that the simple scoring function used here is also in general correlated with a refined scoring function for the hit library (FIGS. 10 & 11) using the template structure of the matured antibody (1cz8), although some scattering in the correlation plot suggest that some terms involving the solvation etc should be added into the simple scoring function to improve the correlation.

FIG. 13A shows how the present inventive methods can select the top ten sequences from a computational screening of an anti-VEGF $V_H$ CDR3 hit variant library for experimental screening, to demonstrate that diverse, functional sequences, different from the parental or matured ones, can be selected. The amino acid variant profile and the corresponding variant library in the degenerate nucleic acids are listed. An energy diagram at the upper right portion of the figure shows from left to right the energy distribution of the 10 selected sequences from computational screening, their variant amino acid combinatorial library, nucleic acid combinatorial library and positive clones selected from experimental screening in vitro. The sequence library that corresponds to each of sequence pools shown in the energy diagram is indicated with arrows. FIGS. 13B & C show the top 10 sequences from computational screening of the variant libraries for $V_H$ CDR1 and CDR2, respectively, the amino acid variant profile and corresponding variant library in degenerate nuclei acids for $V_H$ CDR1 and CDR2 libraries of anti-VEGF antibodies.

Figure 14A:
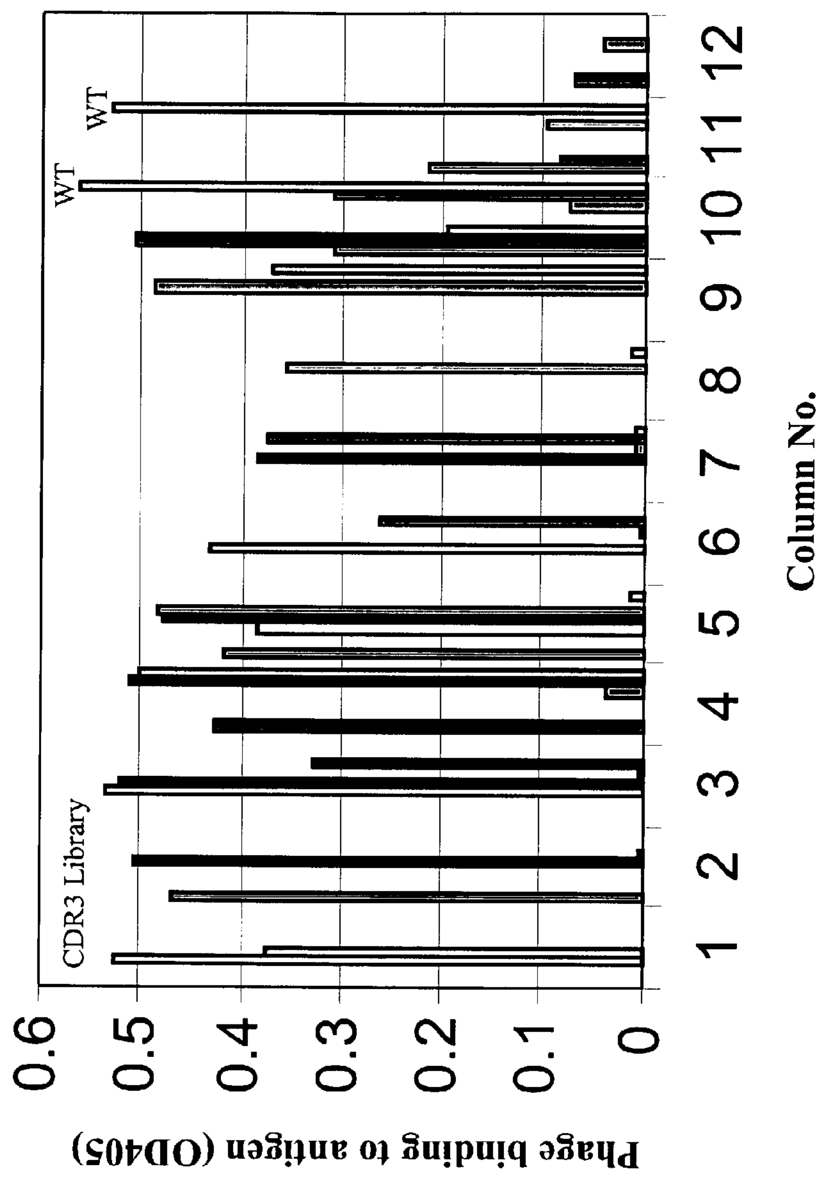

FIG. 14A shows UV reading of the ELISA positive clones identified in round 1 and round 3 selections of functional anti-VEGF ccFv antibodies with $V_H$ CDR3 encoded by the designed nucleic acid library (FIG. 13A). The bottom numbers indicate the column numbers in a 96-well (8×12) ELISA plate. Different bar shadings indicated different rows.

FIG. 14B shows $V_H$ CDR3 sequences of the positive clones from round 1 and 3 selection via phage display of the nucleic acid library shown in FIG. 13A. It is clear that many diverse sequences are selected with large variations at several positions that are different from $V_H$ CDR3 of parental and matured anti-VEGF antibody (FIGS. 9A & B).

Figure 14C:
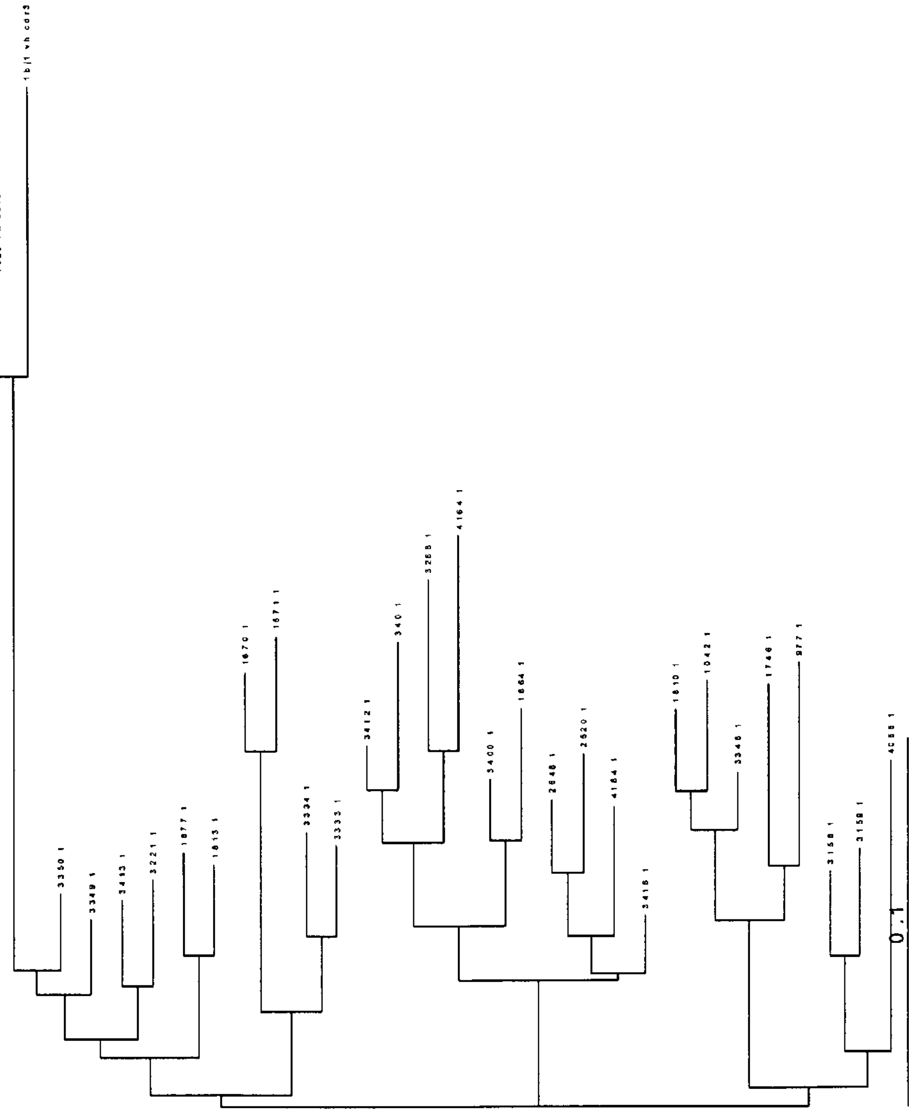

FIG. 14C illustrates a phylogenetic tree of the positive clones showing the diversity of the screened sequences. The sequence identities of the selected positive clones from $V_H$ CDR3 shown in FIGS. 14A & B ranged from 57 to 73 percent relative to the parental $V_H$ CDR3 sequence, with N-terminal CAK and C-terminal WG residues included (see FIG. 9B).

Figure 15A:
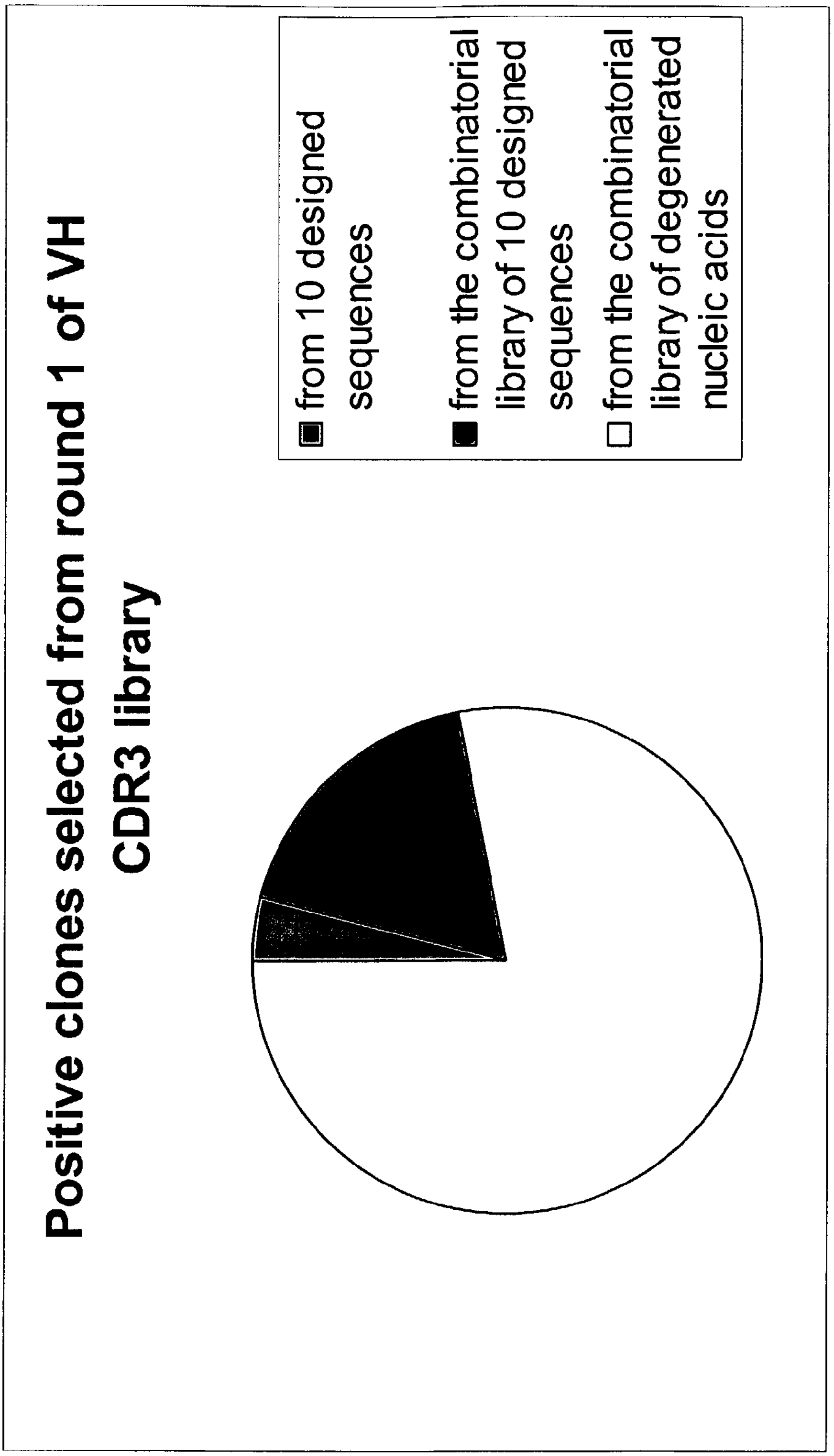
Figure 15B:
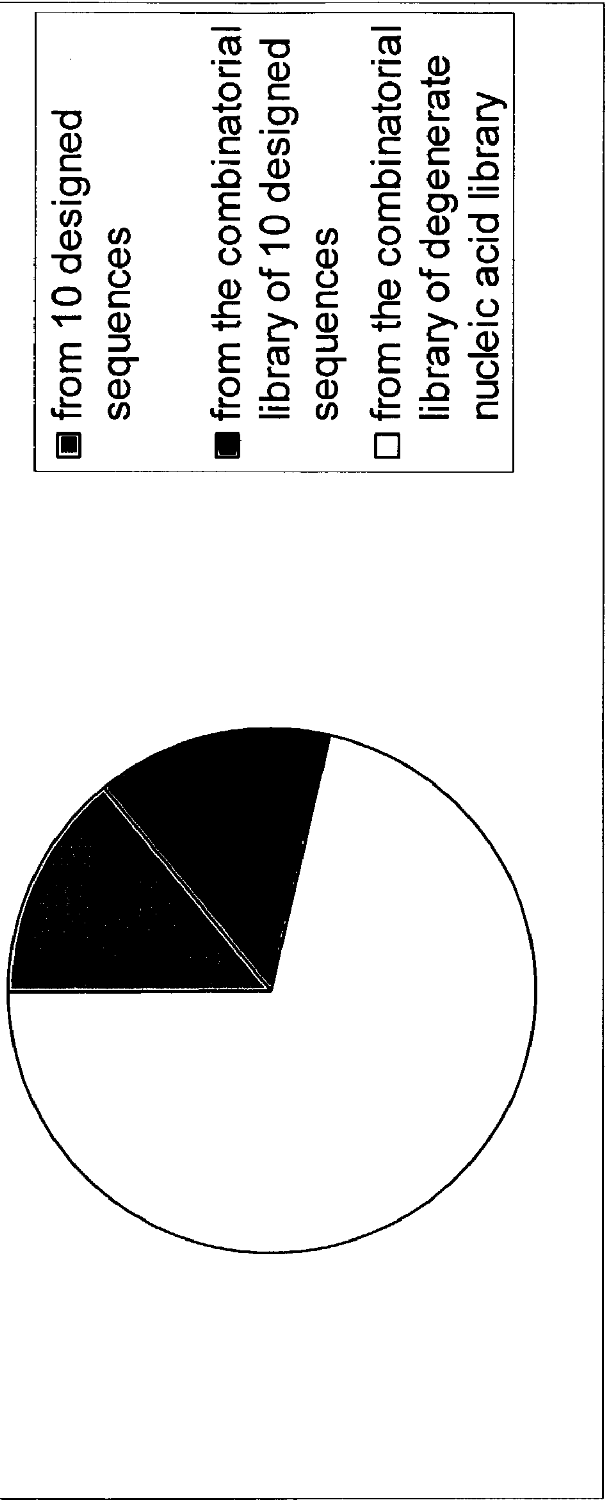

FIGS. 15A–B are pie charts showing the breakdown of the origins of the screened sequences in the first and third rounds into three groups: designed amino acid sequences, combinatorial amino acid sequences from the designed sequences, and the novel combinatorial amino acid sequences encoded by the synthesized degenerate nucleic acid library. A: $V_H$ CDR3 clones from the first round screening in vitro with distribution of experimentally selected sequences from positive clones in 3 libraries. B: $V_H$ CDR3 clones from the third round screening in vitro with distribution of experimentally selected sequences from positive clones in 3 libraries. Because only limited number of positive clones from each round are selected for sequence analysis, the figures are only used to illustrate rough percentages of the selected sequences from designed, its combinatorial amino acid and nucleic acid libraries.

Figure 16B:
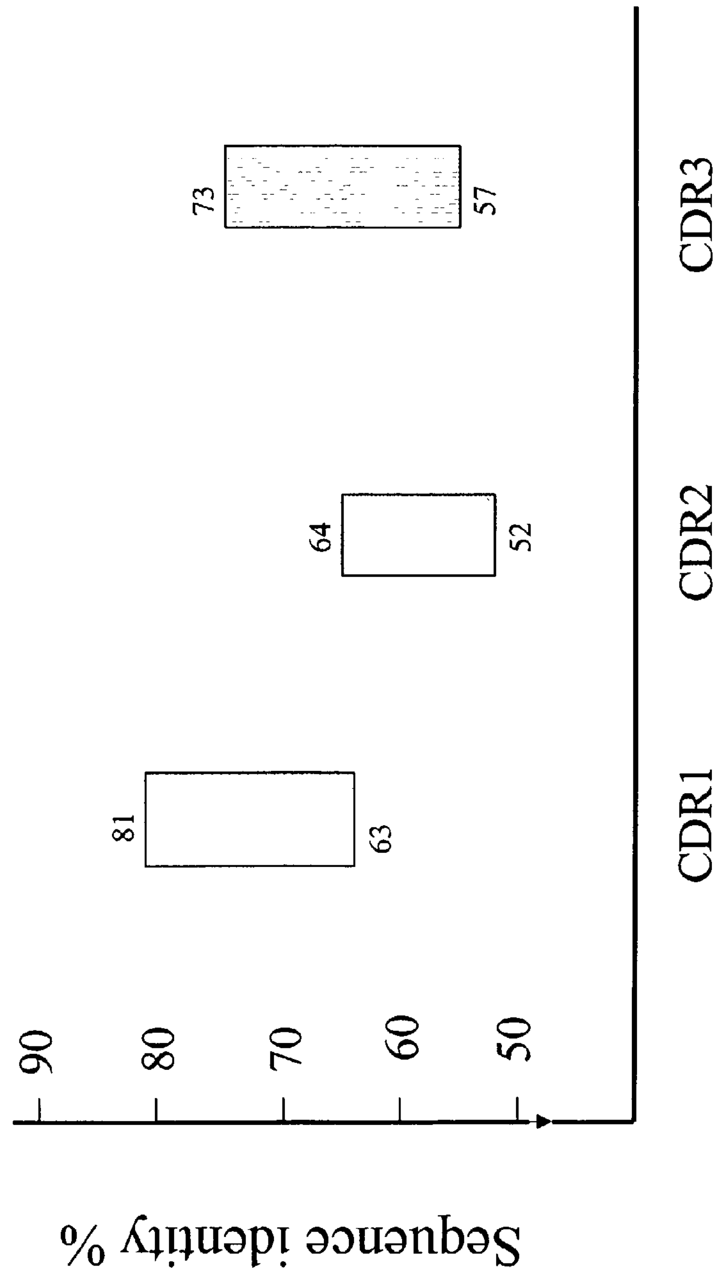

FIG. 16A is a table that lists the experimentally selected amino acids sequences from $V_H$ CDR1, CDR2 and CDR3 libraries of degenerate nucleic acids shown in FIGS. 13A–C. FIG. 16B shows the distribution of the sequence identities of selected sequences from $V_H$ CDR1, CDR2 and CDR3 libraries relative to the corresponding parental sequence of anti-VEGF $V_H$ CDR1, 2, and 3 respectively. It is clear that functional, diverse sequences different from the corresponding parental sequences can be selected experimentally.

Figure 17A:
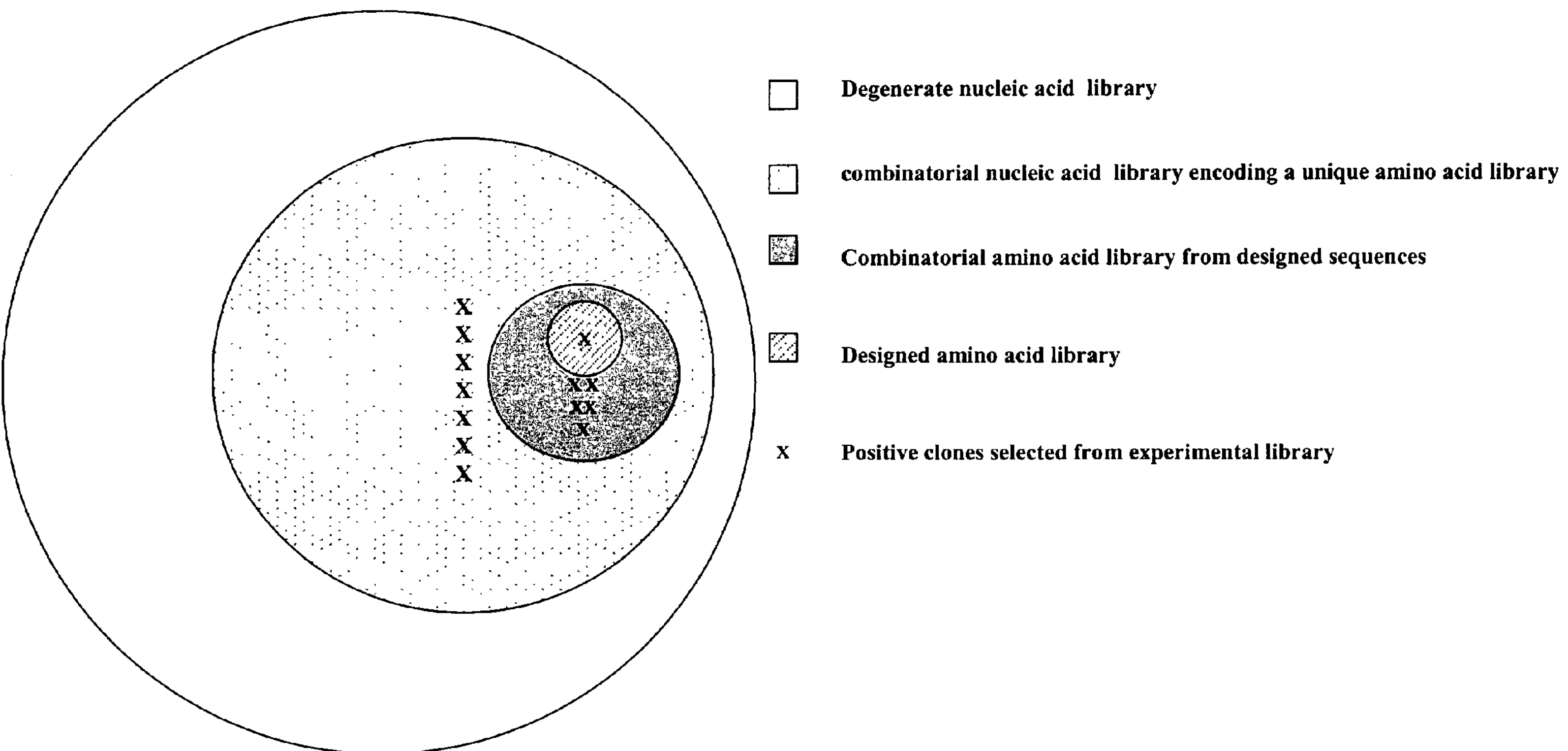

FIG. 17A shows the schematic relationship among 4 different libraries (designed amino acid sequences, the combinatorial library of amino acid variant of the designed sequences, and combinatorial degenerate nucleic acid libraries encoding the unique amino acid sequences and the entire degenerate nucleic acid library) and the distribution of the experimentally selected positive clones shown in X. The innermost (striped) circle represents the designed amino acid sequence library selected, for example, based on energy scores of the hit variant library. The shaded circle represents combinatorial amino acid library of the selected sequences from computational screening of a hit variant library. The third (stippled) circle represents the combinatorial amino acid library encoding the unique combinatorial amino acid library. The outermost circle represents the degenerate nucleic acid library for all amino acid sequences derived from the back-translation of the amino acid library. The relative size of the outermost versus the third (stippled circle) depends on the efficiency of the back-translation procedure from amino acids to nucleic acid sequences with consideration for other factors such as the codon usage. "X" indicates experimentally selected sequences. For example, anti-VEGF $V_H$ CDR3 library from round 3 is shown here (see table in FIG. 17B). The distribution among different libraries depends on selection conditions, the effectiveness of library design, the relative size of the selected clones versus library or number of sequenced clones etc.

FIG. 17B shows a table delineating the relationships among the four libraries (FIG. 17A) and the distribution of the experimentally selected sequences of the positive clones for anti-VEGF $V_H$ CDR1, 2, and 3 libraries. The "AA_Seq/Comb" column indicates the number of selected amino acid sequences by computational screening (designed library I) and the number of recombinant sequences of the selected sequences (variant library II). The "NN_seqs/peptide seq" column indicates the number of nucleic acid sequences of the degenerate nucleic acid library, and the unique amino acid sequences encoded by the degenerate nucleic acid library. The "exp_seq" column shows the number of the experimentally selected, unique sequences from positive clones. The "distribution of the selected sequences" column indicates the numbers of unique sequences from designed amino acid sequences, their combinatorial library of amino acid variants and the combinatorial library of the degenerate nucleic acids encoding unique peptide sequences.

Figure 18:
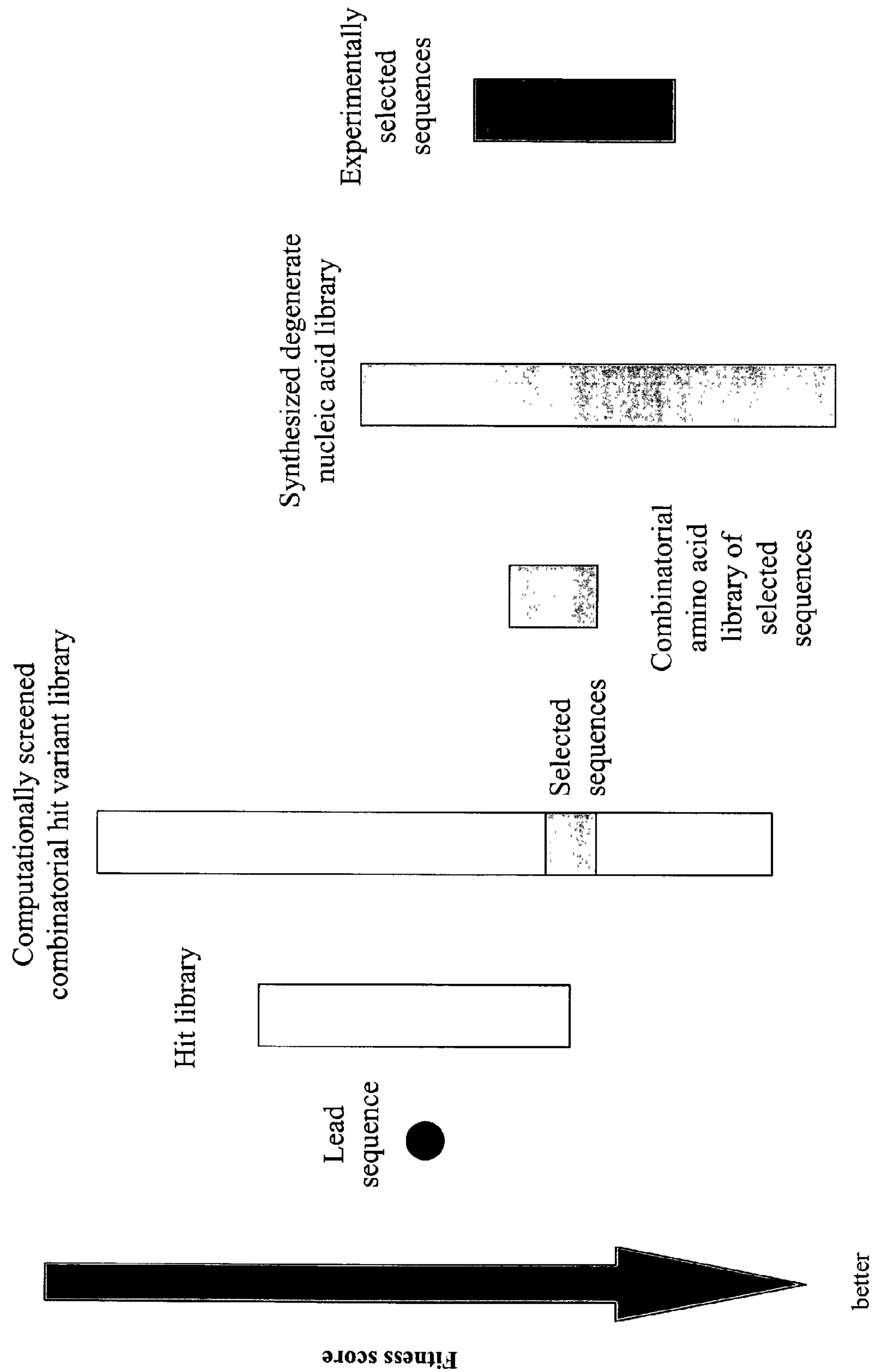

FIG. 18 shows the evolution of the sequence fitness scores for anti-VEGF $V_H$ CDR3 libraries at various stages in the procedure, starting from left to right: a lead sequence, hit library, hit variant library I, selected sequences from computational screening (shaded band), the combinatorial library of selected sequences (hit variant library II), combinatorial nucleic acid library encoding the combinatorial amino acid sequences, and experimentally selected sequences. A lead sequence was used to identify evolutionary hit library from a database of sequences. An in silico combinatorial library was designed based on the diversity of the hit library. A subset of the computationally screened sequences with scores better than the lead was used to generate a combinatorial amino acid library. A degenerate nucleic acid library coding the combinatorial amino acid library was generated using degenerate nucleic acid synthesis strategy to expand the diversity. Experimental screening of the library led to sequences with potentially improved function.

Figure 19A:
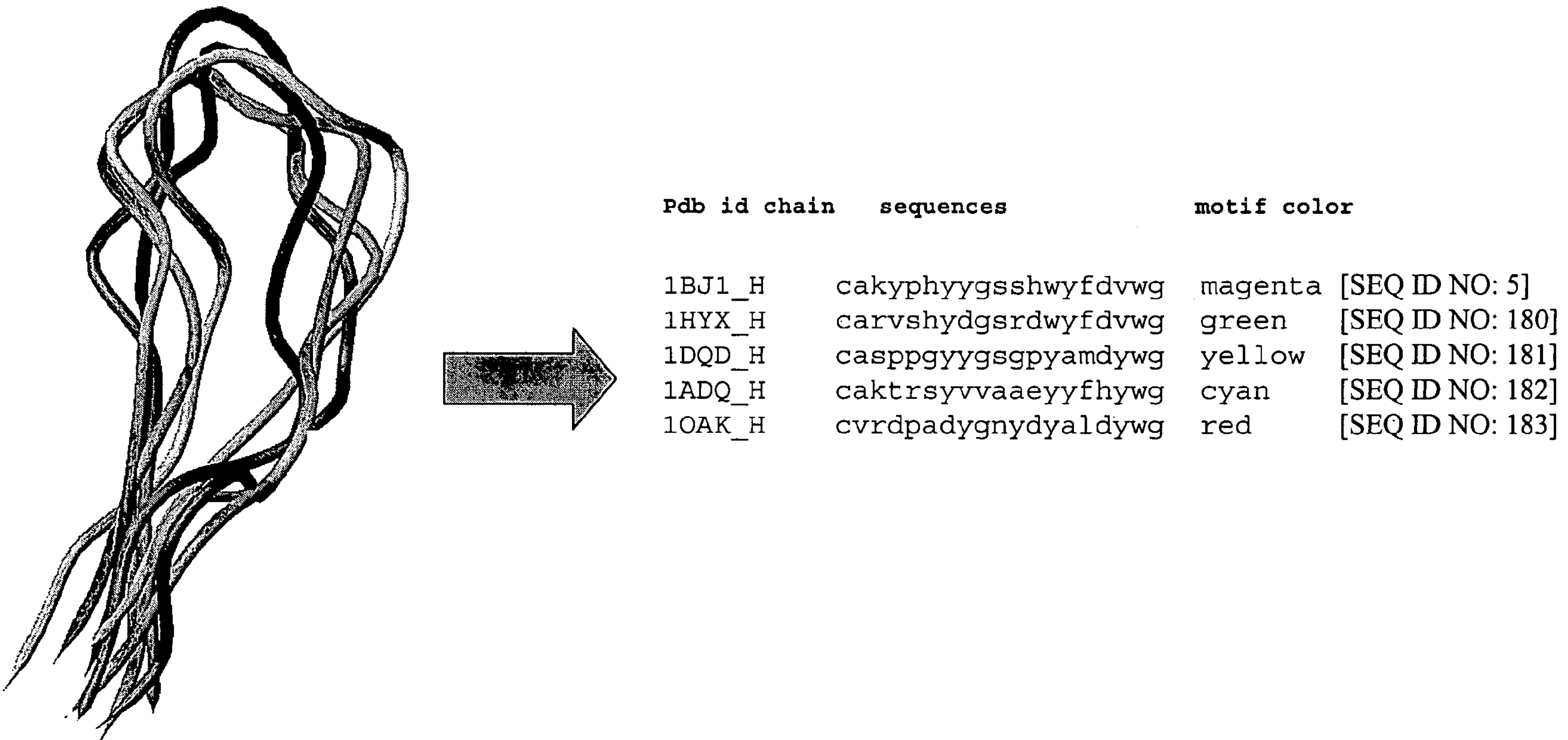

FIG. 19A shows the lead profile generated from structure-based mutiple seqeuce alignment. The structural motif of the lead sequence is used to search protein structure database (PDB databank) for similar structures within certain distance cutoff. The five structures are superimposed using $C_\alpha$ atoms of the $V_H$ CDR3. The average root mean square deviation (RMSD) between each structure and $V_H$ CDR3 structural motif (colored in magenta) is about 2 Å. The corresponding mutiple sequence alignment is shown to the right, together with their PDB IDs and corresponding colors.

FIG. 19B shows a variant profile for the 251 unique sequences of the hit library generated based on the lead sequence profile of $V_H$ CDR3 of parental anti-VEGF antibody. The upper portion shows a table listing the amino acid frequency of 20 amino acids at each position of the lead sequence. The lower portion of the figure shows a filtered variant profile obtained by using a 5% cutoff of the frequency or 12 in this case. All positional amino acids occurring 12 or less times among the 251 members of the hit list are removed. This filtered variant profile can be further screened computationally using the structure ensembles.

Figure 19C:
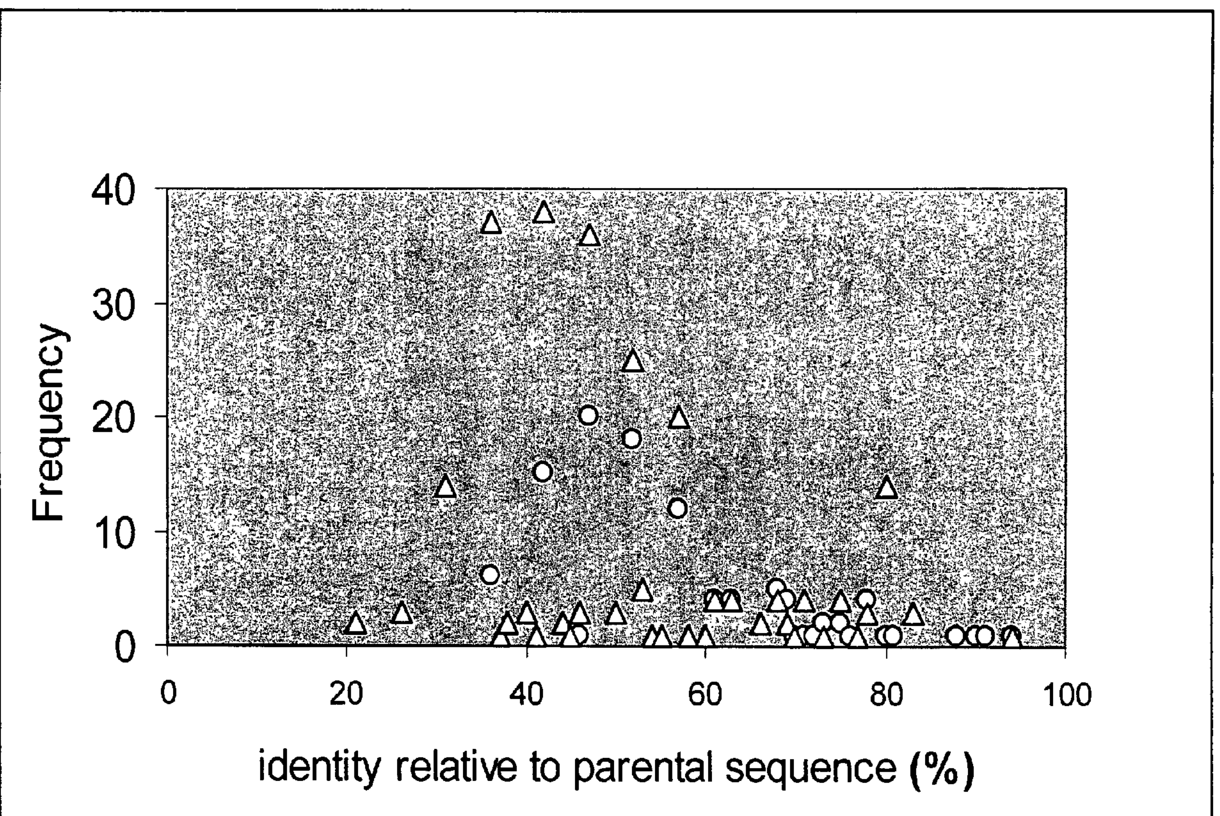

FIG. 19C shows the distribution of the sequences from the hit library relative to the parental $V_H$ CDR3 sequence (FIG. 9B). The circles indicate that the sequence identity up to 36% can be identified using the single parental sequence for HMM search. The triangles indicate that even lower sequence identity up to ~20% can be found using the lead sequence profile from a structure-based multiple sequence alignment. The sequence searching strategy used here can find diverse hits with remote homology (as low as 20%) to the lead sequence.

Figure 19D:
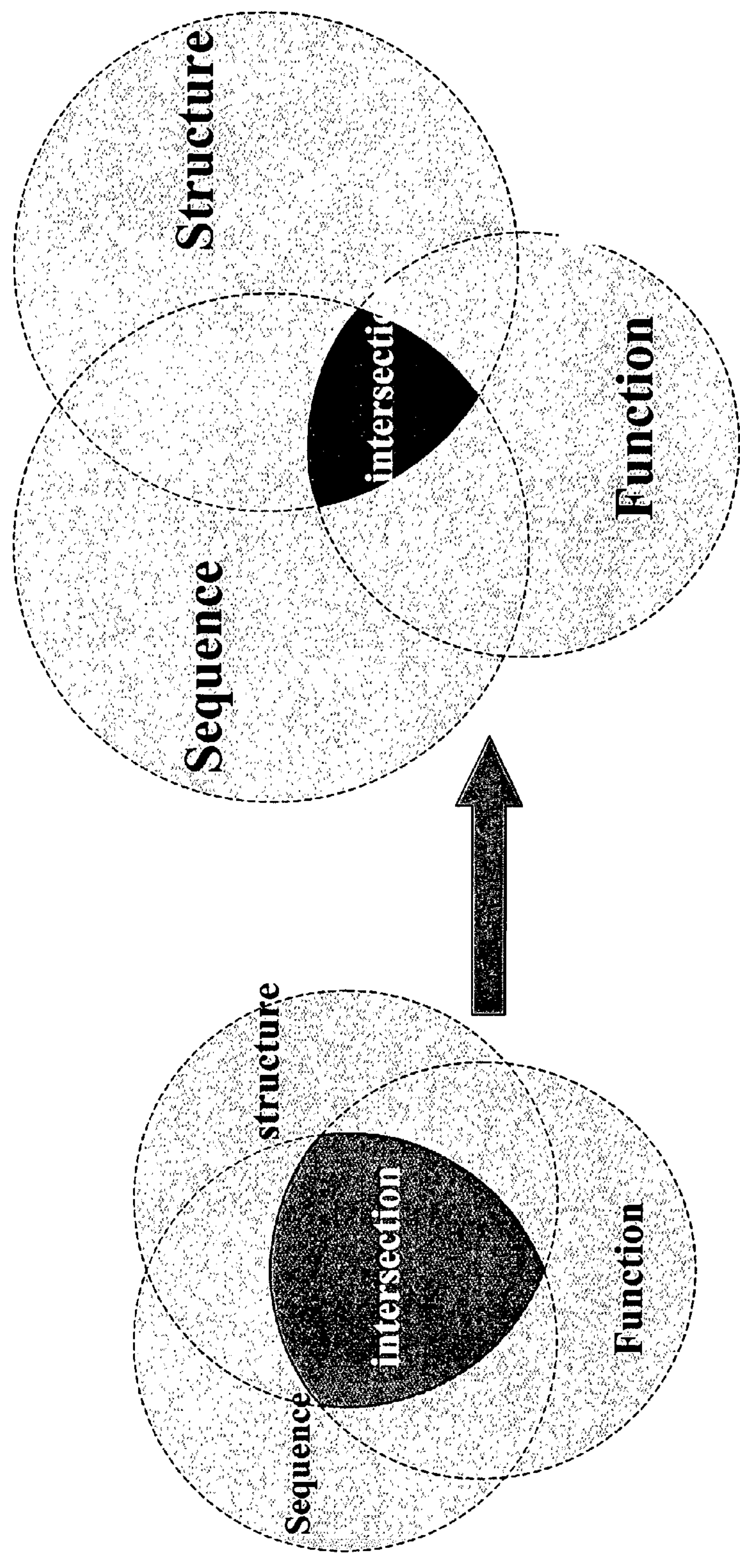

FIG. 19D shows the general strategy in generating a focused library that lies within the intersection of the sequence, structure and function spaces. As shown in FIG. 19A-C, the diversity of the hit sequences is increased by using a structure-based mutiple alignment. It is possible to expand the diversity in both sequence and structure spaces, good hits can be identified in the intersection of all three spaces.

Figure 20:
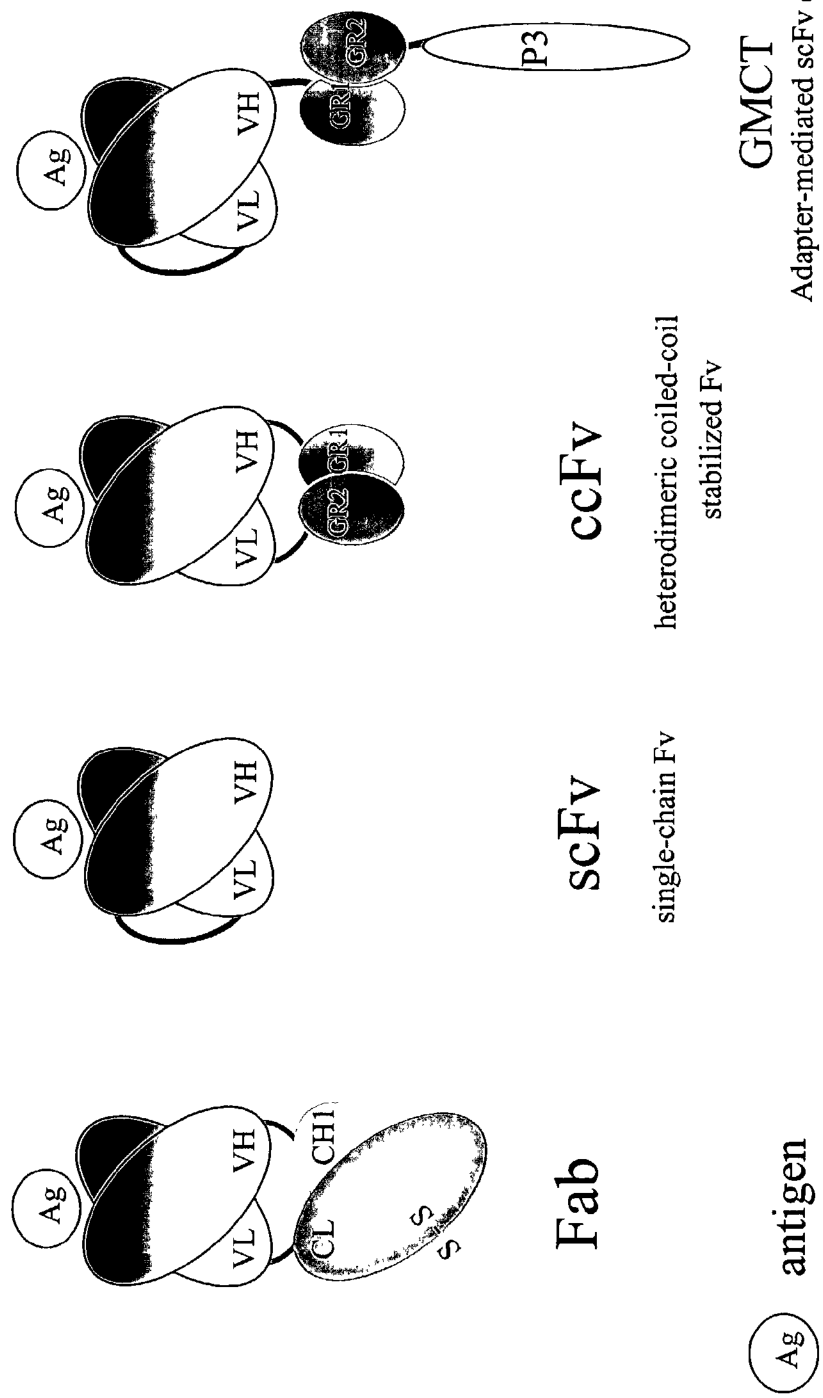

FIG. 20 is a schematic representation depicting various antigen-binding unit (Abu) configurations. Note two novel display systems employed in the current inventive methods: ccFv system, heterodimeric coiled-coil stabilized Fv with a disulfide bond between GR1 and GR2, and GMCT system, adapter-mediated scFv display system.

FIG. 21 depicts the nucleotide and amino acid sequences of $GABA_b$ receptor 1 and 2 that were used in constructing the subject ccFv Abu. The coiled-coil sequences are derived from human $GABA_b$-R1 and $GABA_b$-R2 receptors. The coding amino acid sequences from $GABA_b$ receptors are written as bold letters. A flexible GlyGlyGlyGly spacer was added to the amino-terminus of R1 and R2 heterodimerization sequences to favor the functional Fv heterodimer formation. To further stabilize the heterodimer, we introduced a ValGlyGlyCys spacer to lock the heterodimeric coiled-coil pair by a disulfide bond. The additional SerArg coding sequences at N-terminus of GGGG spacer provides XbaI or XhoI sites for the fusion of the GR1 and GR2 domains to the carboxy-terminus of $V_H$ and $V_L$ fragment, respectively.

FIGS. 22A–B depict the nucleotide and amino acid sequences of $V_H$ and $V_L$ of anti-VEGF ccFv antibody AM2, respectively.

Figure 23A:
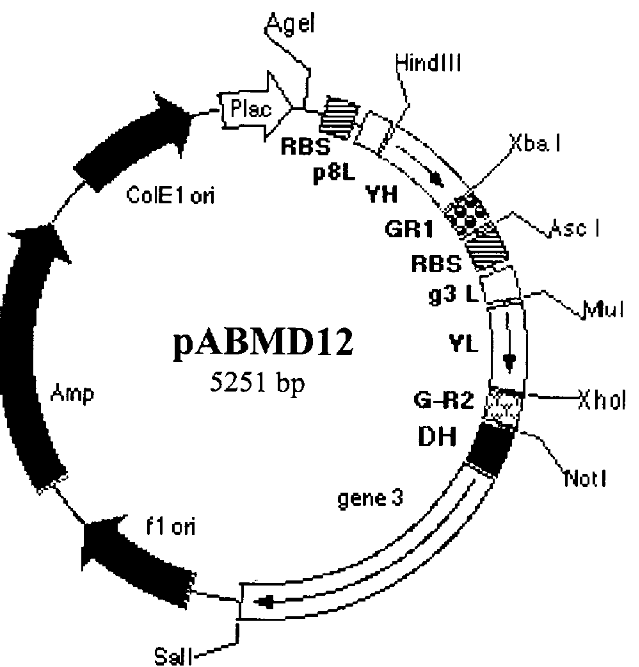

FIG. 23A is a schematic representation of the phagemid vectors pABMD12.

FIG. 23B depicts the sequence of pABMD12 vector.

FIG. 24 depicts a comparison of the binding capability of phage displayed AM2 ccFv and scFv to the immobilized VEGF antigen. The results demonstrate that ccFv can be assembled and displayed on phage particles.

Figure 25A:
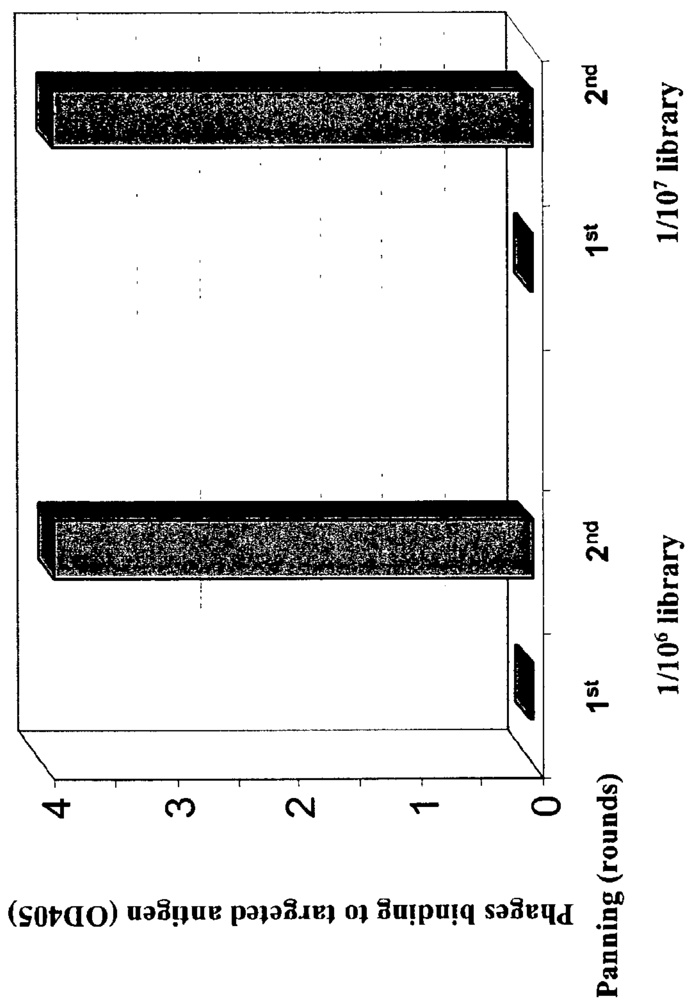

FIG. 25A depicts the results of an ELISA using AM2-ccFv phages from model library pannings. The results demonstrate the enrichment of phages displaying AM2-ccFv antibody in panning of model libraries.

Figure 25B:
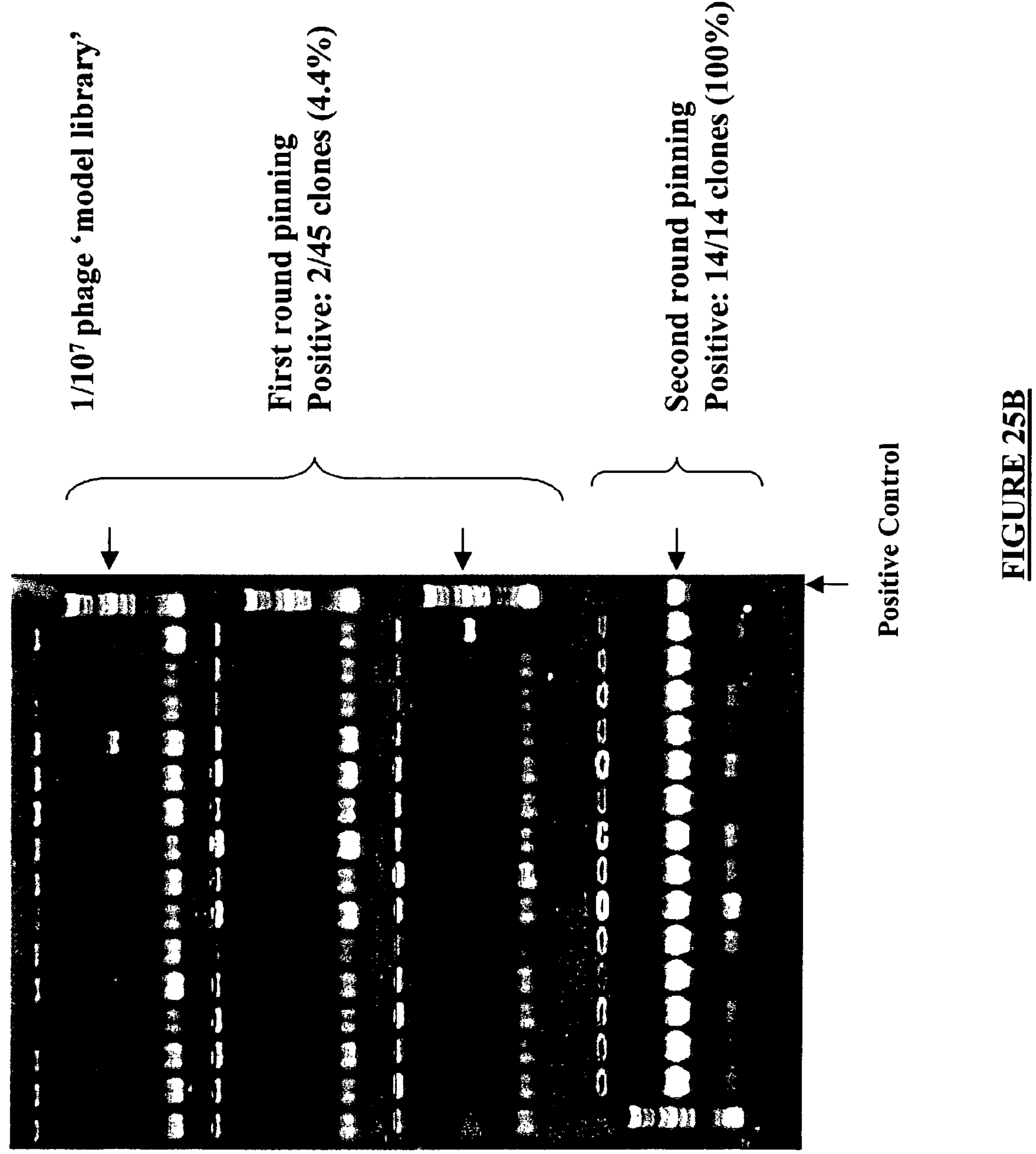

FIG. 25B show the PCR results from $1/10^7$ model library panning which shows that the test sequence can be selected from the model library.

Figure 26:
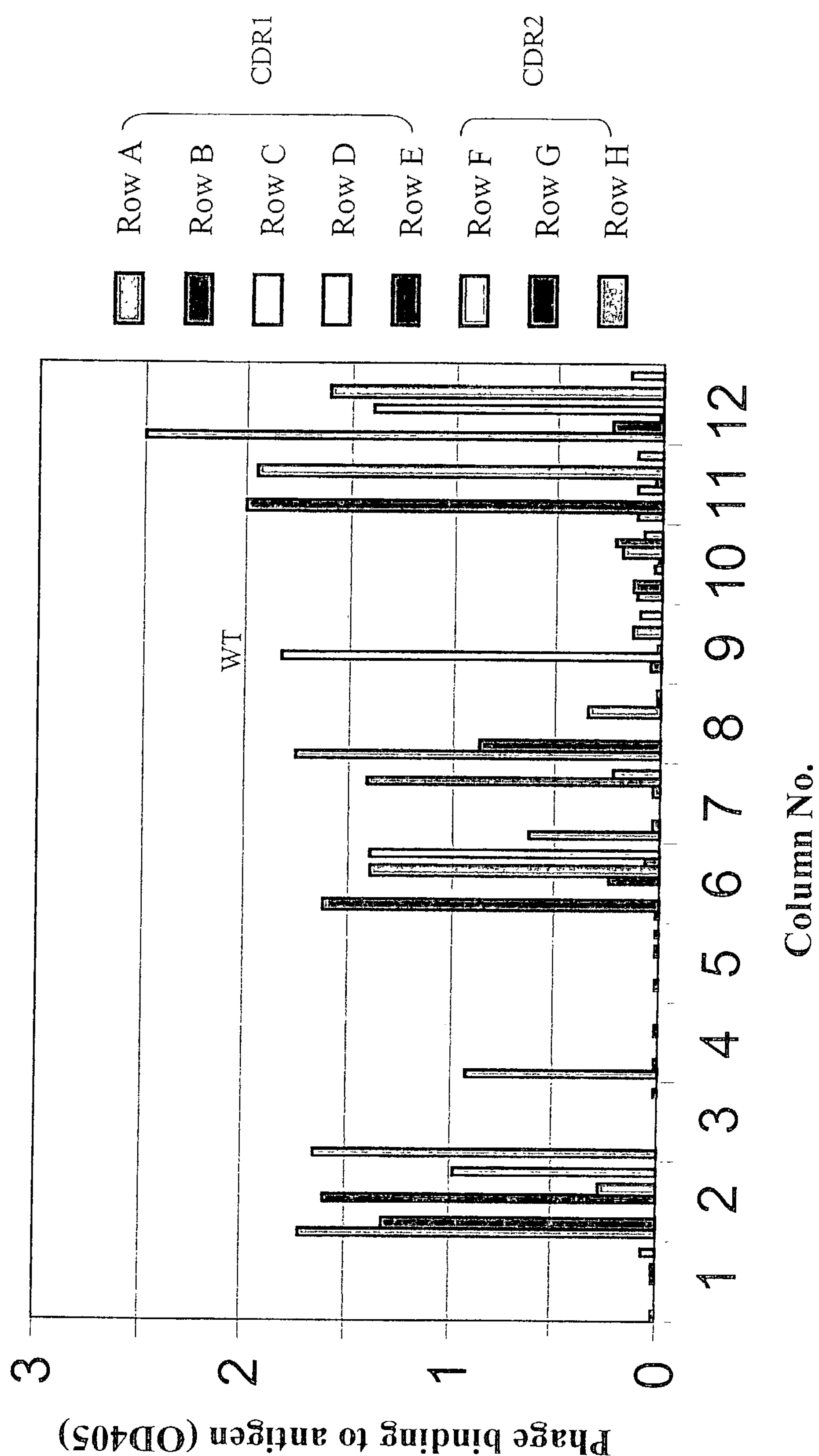
Figure 26B:
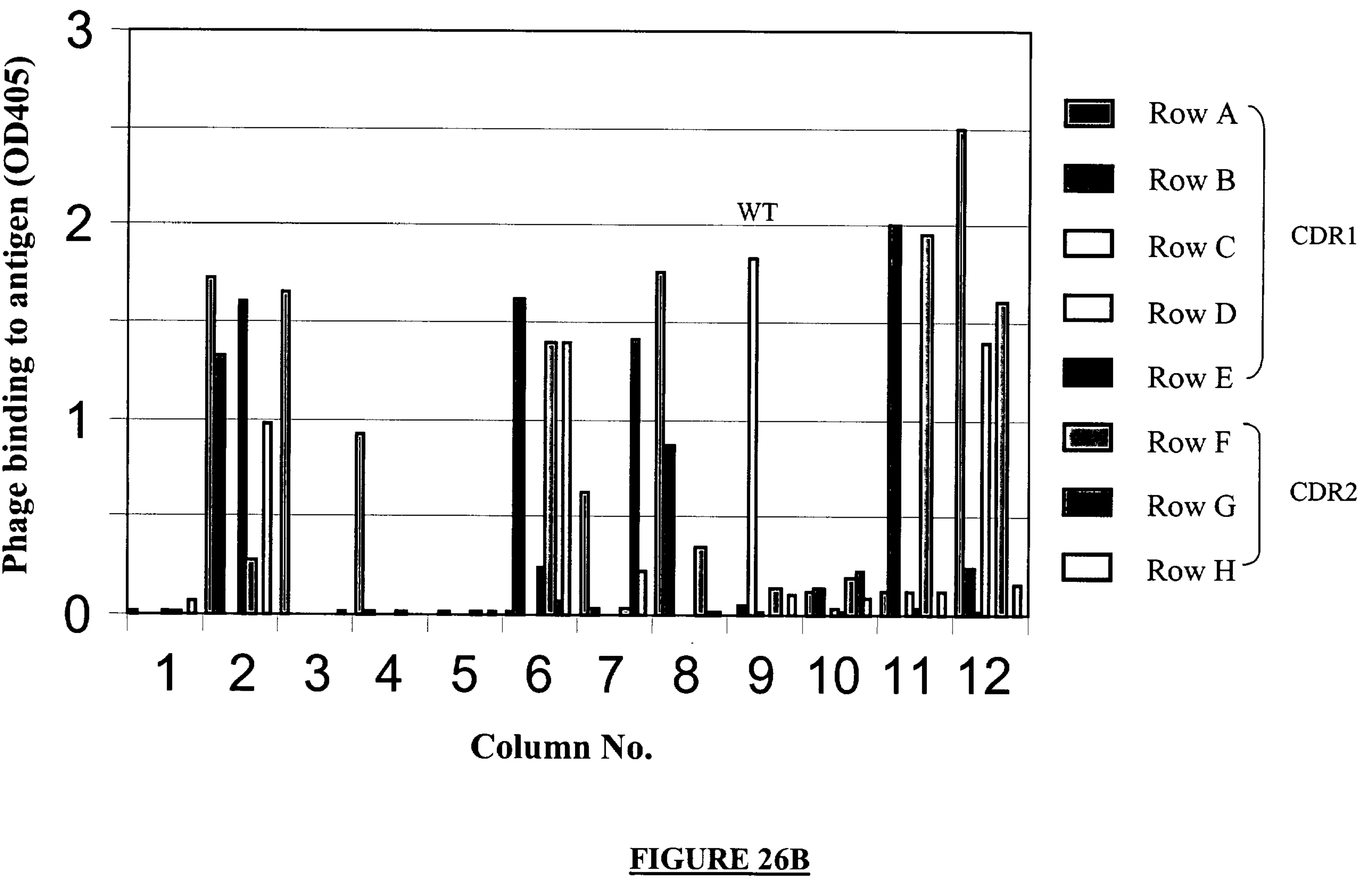

FIG. 26 depicts the results of ELISA using phages from library panning. The results show that the VEGF-binding phages were selected out from $V_H$ CDR1, CDR2 libraries (see FIG. 14A for $V_H$ CDR3).

FIG. 27 (same as FIG. 16A) is a table listing the amino acids sequences of experimentally selected clones encoding designed for anti-VEGF VH CDR1, CDR2 and CDR3 libraries (see FIGS. 13A–C).

FIG. 28A show the sequence library of a composite anti-VEGF $V_H$ CDR3 library. Because the library size is too big to be covered by one or several degenerate nucleic acid library, the variant profile is parsed into 3 segments with their variant profiles shown in FIG. 28A. The segments are parsed based on the contact map of $C_\alpha$ atoms within 8 Å shown on the right side of FIG. 28A. FIG. 28A also shows the ribbon diagram of the anti-VEGF $V_H$ CDR3 as well as contact distances among $C_\alpha$ atoms within 8 Å. The approach provide a general way to parse a large variant profile into smaller segments based on the topology of the structure. Low resolution structure or structure model can serve the purpose here because only structural constraints from topological features is required for sequence segmentation in order to capture covariants distant in primary sequence such as N- and C-termini residues close in the loop.

FIG. 28B covers the N- and C-termini that might contain coupled variants (1–3). The variant profiles of both amino acid library and nucleic acid library are listed, together with the combinatorial size of the libraries and final synthesized degenerate oligonucleotides. FIG. 28C contains segment (4) and FIG. 28D contains another segment (5). All three segments are covered by nucleic acid libraries with sizes less than $10^6$: (1–3) in FIG. 28B are targeted by 3 degenerate nucleic acid libraries, whereas (4) and (5) in FIGS. 28C–D are targeted by a separate degenerate nucleic acid library.

FIG. 29 summarizes the procedures and conditions used for panning ccFv library L14 as well as the enrichment factor from each panning. L14 library is constructed in FIGS. 28A–D by pooling together all 5 degenerate oligonucleotides shown in FIGS. 28B–D.

FIG. 30 shows the amino acid sequences of the $V_H$ CDR3 variants selected from panning 5 and 7 of library L14 using ccFv display platform. Note that after panning 5, all variants are located at position 101. Only two variants, S101R and S101T, are selected after round 7.

Figure 31:
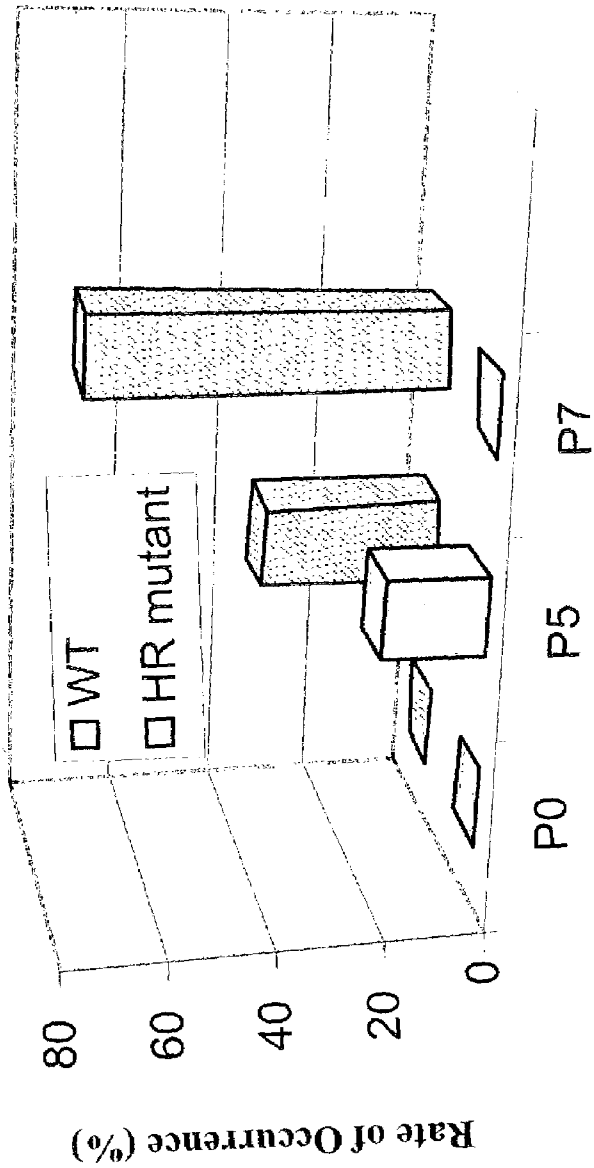

FIG. 31 shows the enrichment of HR (H97, S101R) phage from panning of library L14 for $V_H$ CDR3. The enrichment for HR and parental antibody WT (see also FIG. 9B) at round 0, 5 and 7 were highlighted.

Figure 32:
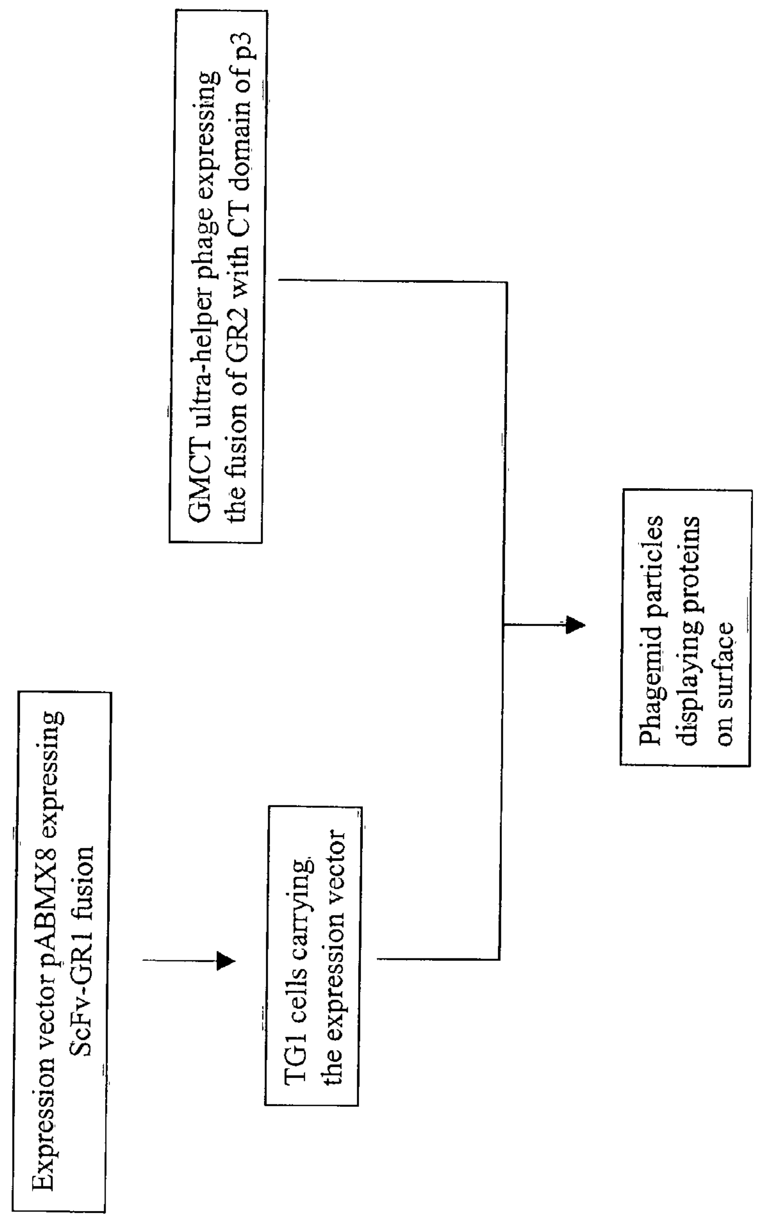

FIG. 32 shows a simple diagram of a novel Coiled-coil Domain Interaction Mediated Display (CDIM) adapter-directed display system for single chain antibody library. Transformation Infection of expression vector pGDH1 alone in *E. coli* bacteria permits expression and production of soluble proteins fused with GR1 in bacterial periplasmic space. Additional superinfection of the same bacteria with the UltraHelper phage vector expressing the engineered coat protein fused with GR2 and other phage proteins permits the display of antibody fragments (or other proteins) on the surface of filamentous phage following synthesis of phage particles in periplasmic space of bacteria.

Figure 33A:
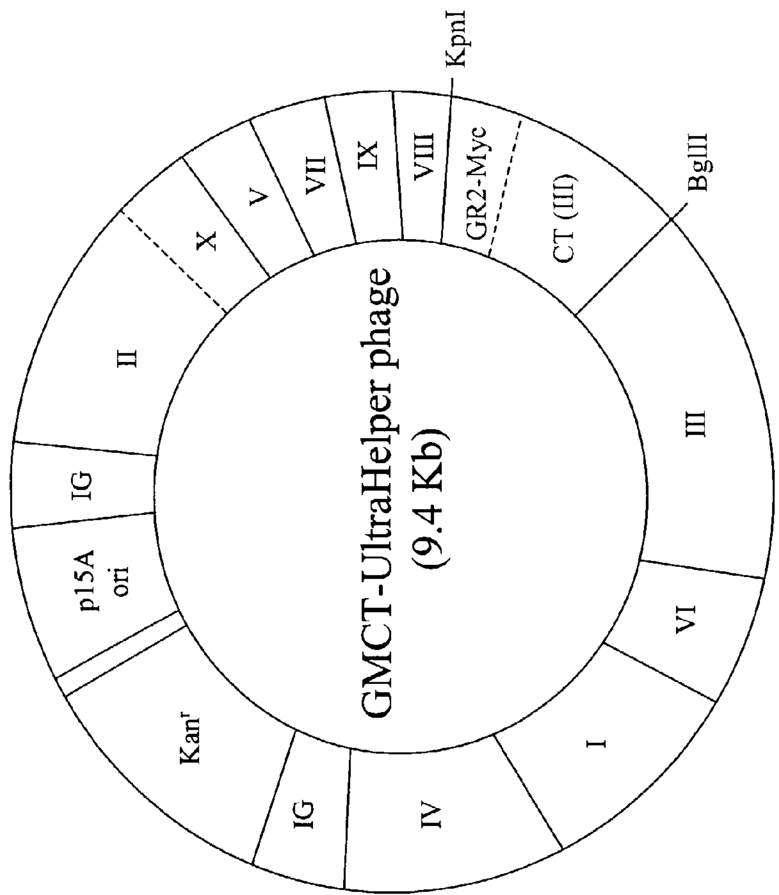

FIG. 33A shows the map of the GMCT-UltraHelper phage plasmid. The construct contains a nucleotide sequence encoding an additional copy of the engineered gene III fused to adaptor GR2 and myc protein tag in KO7kpn phage vector, and ribosome binding sequence-OmpA leader sequence adjacent to the wild-type gene III sequence. FIG. 33B shows the genetically modified region of KO7Kpn to produce GMCT-UltraHelper phage at the nucleotide and amino acid sequence level.

Figure 34A:
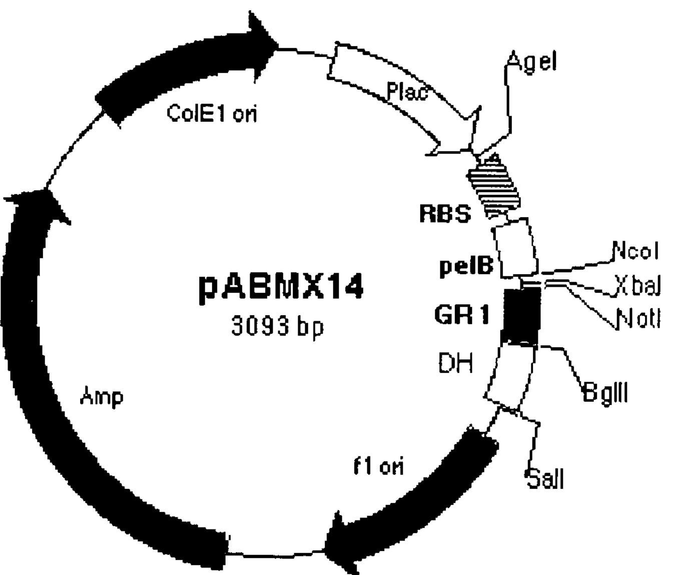

FIGS. 34A & B show the protein expression vector map (A) and the complete nucleotide sequence (B) for pABMX14, which includes an ampicillin-resistance gene for antibiotic selection (Amp), a plasmid origin of replication (ColE1 ori), a f1 phage origin of replication (f1 ori), lac promoter/lac O1 controlled protein expression cassette (plac-RBS-pelB-GR1-DH), and restriction endonuclease sites are also shown. The NcoI/XbaI or NcoI/NotI or XbaI/NotI restriction sites can be used to insert nucleotide sequence encoding proteins of interest.

Figure 35B:
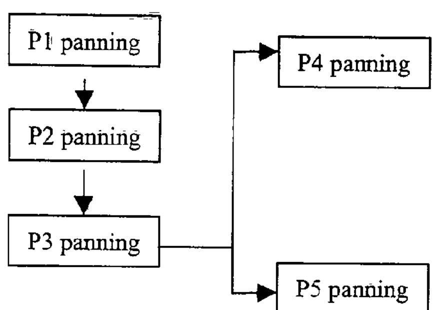

FIG. 35A summarizes the procedure and conditions used for panning scFv library L17, together with the enrichment factor from each round (A). The sequences of L17 library in $V_H$ CDR3 region are exactly the same as those of L14 (see FIG. 28A-D). FIG. 35B shows the flowchart of the panning process.

FIG. 36 shows the amino acid sequences of the $V_H$ CDR3 variants selected from library L17 by off-rate panning from two parallel steps 4 and 5, respectively, using the adapter-mediated phage display system. Note in off-rate panning 4, sequences were selected with variants located at positions 97 and/or 101 (100a in Kabat nomenclature). In off-rate panning 5, sequences were selected with variants located at 101(100a) and/or 102 (100b) and/or 103 (100c). Two important mutants YS (H97Y-S101) and HT (H97-S101T or H97-S100aT) in the mature sequence were selected from panning 4 and panning 5, separately. The combination of variants at these two positions might give the mature sequence H97Y and S100aT in $V_H$ CDR3 (FIG. 9B). But this combination is deliberately avoided in the parsed segments (see FIG. 28A-D). Also, note that HR (H97-S100aR) is again shown in higher frequency (3/1) than HT (H97-S100aT), the mature sequence (FIG. 9B), consistent with the similar observation (7/3) in panning 7 of FIG. 30.

DEFINITION

Structural cluster: a group of structures that are clustered into a family based on some empirically chosen cutoff values of the root mean square deviation (RMSD) (for example, of the $C_\alpha$ atoms of the aligned residues) and statistical significance (Z-score). These values are empirically decided after an overall comparison among structures of interest. Several programs can be used for searching structural clusters. For CE (combinatorial extension) algorithms (Shindyalov I N, Bourne P E (1998) Protein Engineering 11, 739–747), the criteria used are RMSD<2 Å and Z-score>4. MAPS (Multiple Alignment of Protein Structures) is an automated program for comparisons of multiple protein structures. The program can automatically superimpose the 3d models of common structural similarities, detect which residues are structural equivalent among all the structures and provide the residue-to-residue alignment. The structurally equivalent residues are defined according to the approximate position of both main-chain and side-chain atoms of all the proteins. According to structure similarity, the program calculate a score of structure diversity, which can be used to build a phylogenetic tree (Lu, G. (1998) "An Approach for Multiple Alignment of Protein Structures"). In structural clustering, members within a structural cluster are analyzed to understand some consensus information about the distribution of all structural templates within a family and constraints on their sequences or sequence profiles within a structural family.

Ensemble structures: It is well-known in the structural determination by NMR (nuclear magnetic resonance), the ensemble of structures rather than a single structure, with perhaps several members, all of which fit the NMR data and retain good stereochemistry, is deposited with the Protein Data Bank. Comparisons between the models in this ensemble provide some information on how well the protein conformation was determined by the NMR constraints. It should be pointed out that all the sequences corresponding to NMR-determined ensemble structures have the same sequences (one protein with variable conformations). The structural ensemble here, additionally, refers to different proteins with variations in sequence and/or length but have similar main chain conformations, in addition to those structures, such as from NMR determinations or from molecular dynamics simulations, have the same sequence but differ structurally due to natural shape fluctuations.

Ensemble sequences: A population of sequences that statistically defines a certain property of a target protein such as stability or binding affinity.

Ensemble average or representative structure: If all members within a structural cluster has the same length of amino acids, the positions of atoms in the main chain atoms of all structures are averaged, and the average model is then adjusted to obey normal bond distances and angles ("restrained minimization"), similar to NMR-determined average structure. If all members within a structural cluster vary in the length of amino acids, a member, which is representative of the average characteristics of all other members within the cluster, will be chosen as the representative structure.

Canonical structures: the commonly occurring main-chain conformations of the hypervariable regions.

Structural repertoire: the collection of all structures populated by a class of proteins such as the modular structures and canonical structures observed for antibody framework and CDRs.

Sequence repertoire: collection of sequences for a protein family.

Functional repertoire: the collection of all functions performed by proteins, which is related here, for example for antibodies, to the diverse functional CDRs that are capable of binding to various antigens.

Germline gene segments: refers to the genes from the germline (the haploid gametes and those diploid cells from which they are formed). The germline DNA contains multiple gene segments that encode a single immunoglubin heavy or light chains. These gene segments are carried in the germ cells but cannot be transcribed and translated into heavy and light chains until they are arranged into functional genes. During B-cell differentiation in the bone marrow, these gene segments are randomly shuffled by a dynamic genetic system capable of generating more than 108 specificities. Most of these gene segment sequences are accessible from the germline database. The variable heavy and light chains called V-gene database are classified into subfamilies based on sequence homology.

Rearranged immunoglobulin sequences: the functional immunoglobulin gene sequences in heavy and light chains that are generated by transcribing and translating the germline gene segments during B-cell differentiation and maturation process. Most of the rearranged immunoglobulin sequences used here are from Kabat-Wu database.

BLAST: Basic Local Alignment Search Tool for pairwise sequence analysis. Blast uses a heuristic algorithm with position-independent scoring parameters to detect similarity between two sequences, the default parameters are used with Expect at 10, Word Size 3 Scoring matrix BLOSUM62, Gap costs for existence 11 and extension 1.

PSI-BLAST: The Position-Specific Iterated BLAST, or PSI-BLAST program performs an iterative search in which sequences found in one round of searching are used to build a score model for the next round of searching. In PSI-BLAST the algorithm is not tied to a specific score matrix. Traditionally, it has been implemented using an AxA substitution matrix where A is the alphabet size. PSI-BLAST instead uses a QxA matrix, where Q is the length of the query sequence; at each position the cost of a letter depends on the position with respect to the query and the letter in the subject sequence. Two PSI-BLAST parameters have been adjusted: the pseudocount constant default has been changed from 10 to 7, and the E-value threshold for including matches in the PSI-BLAST model has been changed from 0.001 to 0.002.

Energy landscape: An energy distribution where peaks and wells define ensemble states of a molecule. It is believed that an energy landscape can provide a complete description of the folding process as well as descritions of local structural states, whereas the common optimized or minimized structure describes only a single structural species out of a collection of many possible states within a local energy minimum.

Fitness/Fitness score: A measure of an experimentally observable property of a molecule such as stability, activity and affinity.

Fitness landscape: A distribution of a fitness score defined by other intrinsic parameters of the molecule, such as sequence.

Sequence space: See sequence repertoire.

Structure Space: See structure repertoire.

Functional Space: See functional repertoire

Lead sequence: the sequence used for searching sequence database.

Variant profile/sequence profile/positional variant profile (PVP): description of the amino acid entropy at each position for a set of peptide sequences. This includes both the range and frequency of the amino acids (AA-PVP) or nucleic acids (NA-PVP).

Hit library/Hit list: the collection of sequences found by searching the sequence database using the lead sequence or sequence profile.

Hit variant library I/Library I: An in silico amino acid sequence library derived from the combinatorial enumeration of the variant profile of the hit library.

Hit variant library II/Library II/Designed amino acid library/Refined amino acid library: An in silico amino acid sequence library derived from the hit variant library I as a result of a re-profiling or specific design. Re-profiling of the variants can be accomplished 1) by selecting a sequence cluster(s) based energy ranking with a specific cut off value or a window of sequences containing key amino acid residues, 2) by including specific positional residues indentified by functional screening, and/or 3) by inclusion or exclusion of residues or sequence clusters as determined by those trained in the arts using any other means available for making such determinations.

Hit variant library III/Library III: An amino acid sequence library that is expressed in vitro by the degenerate oligonucleotide library (below) for functional screening. Library III expands the sequence space of Library II due to back translation, optimized codon usage, recombination at the nucleotide level and expression of the resulting combinatorial nucleic acid library.

Degenerate nucleic acid/oligonucleotide library: The library of mixed oligonucleotides that is used to target an amino acid variant profile that corresponds to a designed amino acid library (library II above). It is derived from the combinatorial enumeration of the corresponding nucleic acid positional variant profile that is back translated from the amino acid positional variant profile of library II using optimized codon(s).

Combinatorial amino acid/peptide library: Library generated from the complete combinatorial enumeration of an amino acid positional variant profile. Library I and II are such libraries.

Combinatorial nucleic acid/oligonucleotide library: Library generated from the complete combinatorial enumeration of a nucleic acid positional variant profile.

DNA shuffling: A method of generating recombinant oligonucleotides from a mixture of parental sequences through multiple iterations of oligonucleotide fragmentation and homologous recombination (Stemmer W P (1994) Nature 370, 389–391)

In silico rational library design: a method of designing a digital amino acid or nucleic acid library that incorporates evolutionary, structural, and functional data in order to define and efficiently sample ensembles in the sequence and structure spaces in order to identify those that have a desired fitness.

Profile Hidden Markov Model (profile HMM): A statistical model of the primary structure consensus of a sequence family based on the sequence profile of proteins. It uses position-specific scores for amino acids and for opening and extending an insertion and deletion to detect remote sequence homologues based on the statistical description of the consensus of a multiple sequence alignment. The multiple sequence alignments are given either by the multiple sequence alignment program such as ClustalW or structure-based multiple sequence alignment given by structural clustering.

Threading: a process of assigning the folding of the protein by threading its sequence to a library of potential structural templates by using a scoring function that incorporates the sequence as well as the local parameters such as secondary structure and solvent exposure. The threading process starts from prediction of the secondary structure of the amino acid sequence and solvent accessibility for each residue of the query sequence. The resulting one-dimensional (1D) profile of the predicted structure is threaded into each member of a library of known 3D structures. The optimal threading for each sequence-structure pair is obtained using dynamic programming. The overall best sequence-structure pair constitutes the predicted 3D structure for the query sequence.

Reverse threading: a process of searching for the optimal sequence(s) from sequence database by threading them onto a given target structure and/or structure cluster. Various scoring functions may be used to select for the optimal sequence(s) from the library comprising protein sequences with various lengths.

Side chain rotamer: the conformation of an amino acid side chain defined in terms of the dihedral angels or chi angles of side chains.

Rotamer library: a distribution of side chain rotamers either based on the backbone dihedral angles phi and psi called backbone-dependent rotamer library or independent of backbone dihedral angles called backbone-independent rotamer library for all amino acids derived from the analysis of side chain conformations in the protein structural database See Dunbrack R L and Karplus M (1993) JMB 230, 543–574.

DETAILED DESCRIPTION OF THE INVENTION

The present invention provides a system and method for efficiently generating and screening protein libraries for optimized proteins with improved biological functions, such as improved binding affinity towards biologically and/or therapeutically important target molecules. The process is carried out computationally in a high throughput manner by mining the ever-expanding databases of protein sequences of all organisms, especially human. With a combination of database-mining of evolutionary sequences from nature with computational design of structurally relevant variants of the natural sequences, the method of the present invention represents a distinct departure from other approaches in computational design and functional screening of protein libraries.

By using this innovative method, a biased library of proteins such as antibodies can be constructed based on computational evaluation of extremely diverse protein sequences and functionally relevant structures in silico. This ensemble-based statistical method of library construction and screening in silico efficiently maps out the distribution of the fitness and energy landscapes in protein sequence and structure spaces, a goal practically unachievable for in vitro or in vivo screening. Following screening in silico, an expanded nucleic acid library based on the sequences encoding the selected proteins is constructed, introduced into an expression system, and screened for proteins with improved or novel functions in vitro or vivo.

FIG. 1 is a series of flowcharts outlining various embodiments of the method of the present invention. Based on a lead protein with known sequence and/or structure, libraries of proteins can be constructed and screened for candidates with desired functions following at least four different routes (Route I–IV) shown in FIG. 1.

In one embodiment, the method comprises the steps of:

providing an amino acid sequence of the variable region of the heavy chain ($V_H$) or light chain ($V_L$) of a lead antibody;

identifying the amino acid sequences in the CDRs of the lead antibody;

selecting one of the CDRs in the $V_H$ or $V_L$ region of the lead antibody;

providing an amino acid sequence that comprises at least 3 consecutive amino acid residues in the selected CDR, the selected amino acid sequence being a lead sequence;

comparing the lead sequence with a plurality of tester protein sequences; and selecting from the plurality of tester protein sequences at least two peptide segments that have at least 15% sequence identity with the lead sequence, the selected peptide segments forming a hit library.

The method may further comprise the step of:

constructing a nucleic acid library comprising DNA segments encoding the amino acid sequences of the hit library.

Figure 1A:
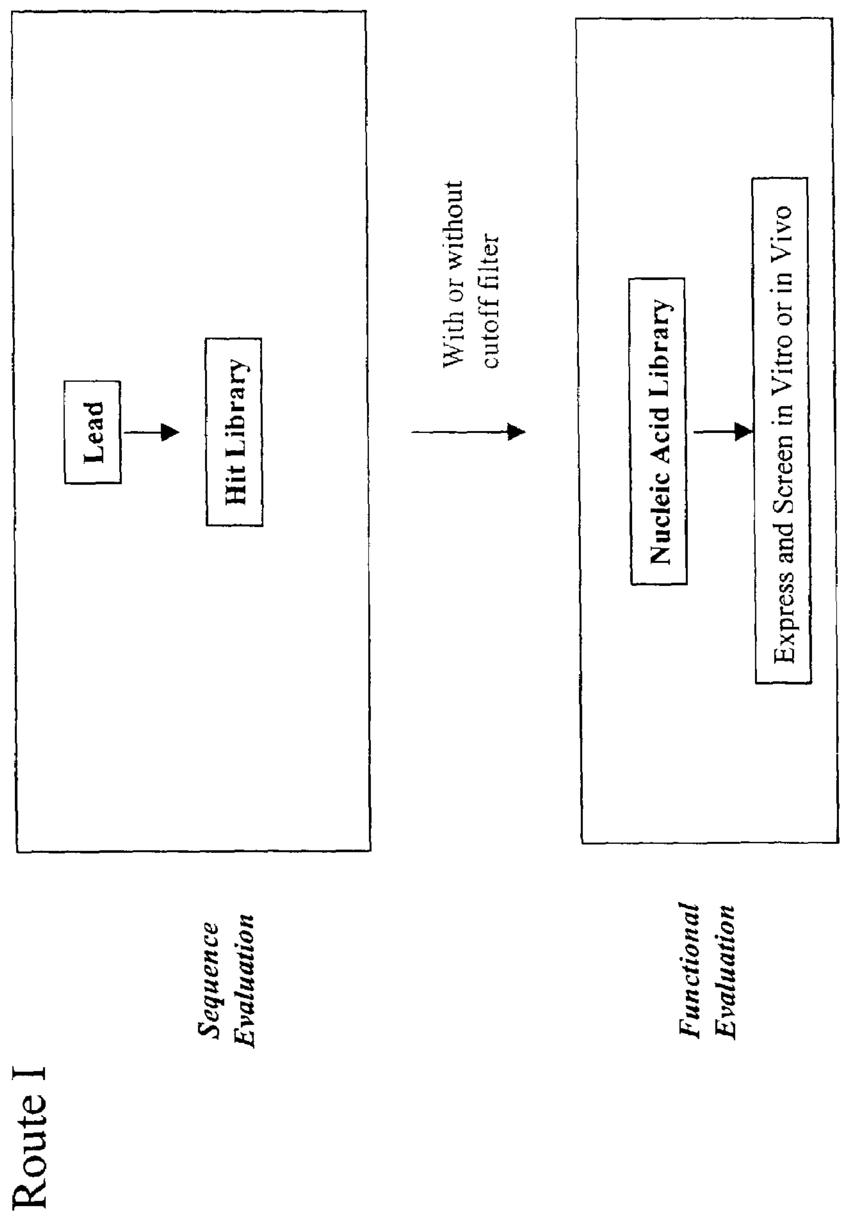
FIGS. 1A–D illustrate four embodiments of the method that can be used in the present invention to select for proteins with desired functions. Lead in FIGS. 1A–D can be either the lead sequence or sequence profile from multiple structure-based alignment. The hit library, hit variant library I and II are defined in the definition section.

Route I in FIG. 1A schematically represents this embodiment. According to this embodiment, a lead protein (e.g., an antibody), with known sequence and structure, is provided. A rich pool of protein sequences (e.g., human antibody repertoire) is screened for varying identity with a selected segment of the lead protein (herein after referred to as "the lead sequence"). From this screening, a list of protein sequences can selected with varying degrees of homology (herein after referred to as the "hit library") using a sequence alignment method such as Hidden Markov Model or HMM. Amino acid sequences of the hit library are then profiled against the lead sequence to show variance of amino acid residues in each position of the lead sequence. As will be described in more detail in Section 7 below, some or all of the profiled sequences in the hit library are selected and translated back to a library of nucleic acid for functional screening in vitro or vivo.

Optionally, the method may further comprise the steps of:

building an amino acid positional variant profile of the hit library;

converting amino acid positional variant profile of the hit library into a nucleic acid positional variant profile by back-translating the amino acid positional variants into their corresponding genetic codons; and constructing a degenerate nucleic acid library of DNA segments by combinatorially combining the nucleic acid positional variants.

Figure 1B:
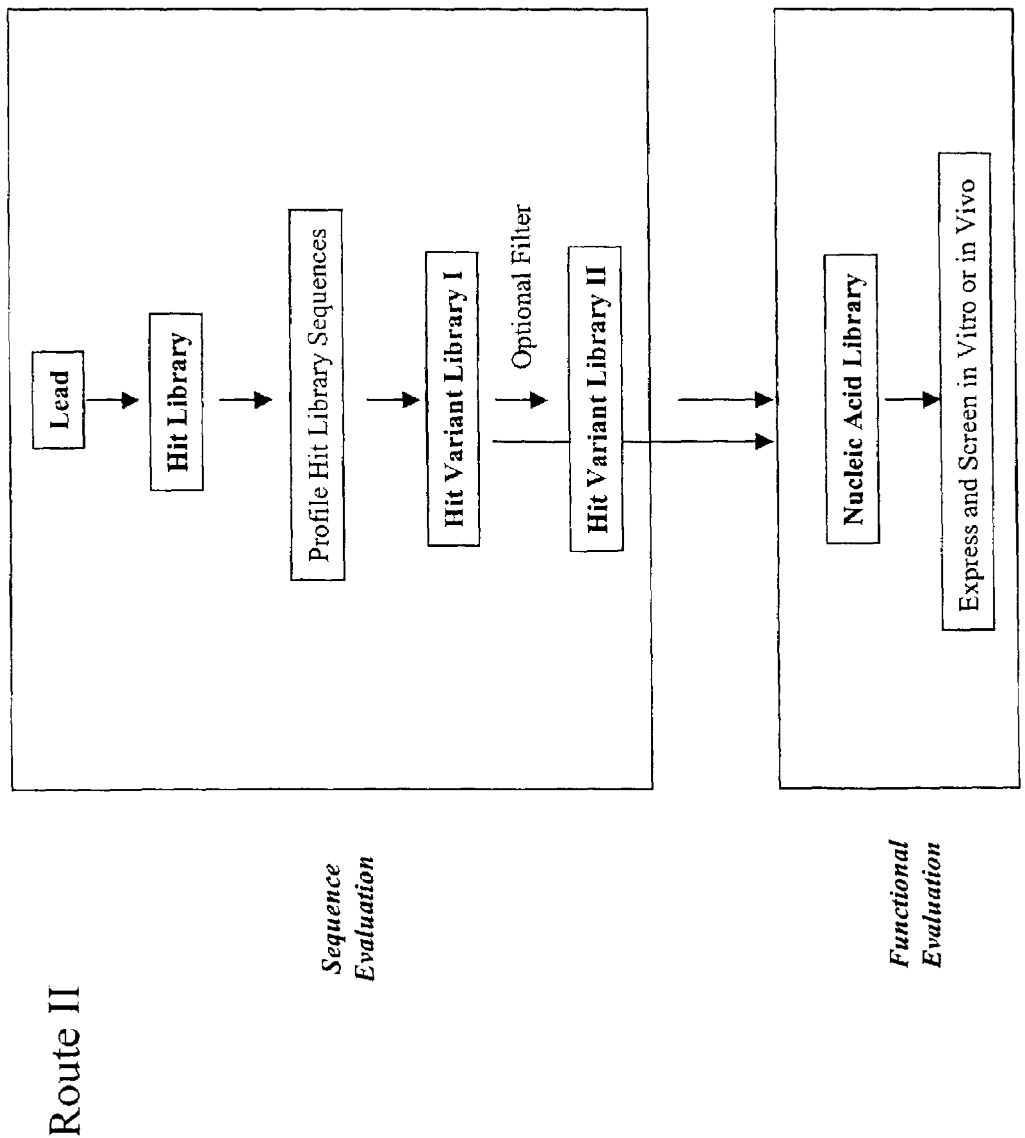

Route II in FIG. 1B schematically represents this embodiment. According to this embodiment, after amino acid sequences of the hit library are profiled against the lead sequence, a combinatorial library (herein after referred to as "hit variant library I" or "library I") is constructed based on the frequency of an amino acid in each residue position (also called amino acid positional variant profile or AA-PVP). Using this approach the hit variant library I is substantially larger than the hit library. By modifying (e.g., filtering) the AA-PVP to bias towards preferred mutants for each position, based on those observed at higher frequencies, indicating evolutionary preference, a reduced variant profile is generated and its combinatorial enumeration leads to hit variant library II. Hit variant library II profile is translated back to a library of nucleic acid for functional screening in vitro or vivo.

Optionally, the genetic codons may be the ones that are preferred for expression in bacteria. Optionally, genetic codons may be the ones that can reduce the size chosen such that the diversity of the degenerate nucleic acid library of DNA segments is within the experimentally coverable diversity without undue experimental effort, preferably below $1\times10^7$ and more preferably below $1\times10^6$.

In another embodiment, the method comprises the steps of:

providing an amino acid sequence of the variable region of the heavy chain ($V_H$) or light chain ($V_L$) of a lead antibody;

identifying the amino acid sequences in the CDRs and FRs of the lead antibody;

selecting one of the CDRs in the $V_H$ or $V_L$ region of the lead antibody;

providing a first amino acid sequence that comprises at least 3 consecutive amino acid residues in the selected CDR, the selected amino acid sequence being a CDR lead sequence;

comparing the CDR lead sequence with a plurality of CDR tester protein sequences;

selecting from the plurality of CDR tester protein sequences at least two peptide segments that have at least 15% sequence identity with the CDR lead sequence, the selected peptide segments forming a CDR hit library;

selecting one of the FRs in the $V_H$ or $V_L$ region of the lead antibody;

providing a second amino acid sequence that comprises at least 3 consecutive amino acid residues in the selected FR, the selected amino acid sequence being a FR lead sequence;

comparing the FR lead sequence with a plurality of FR tester protein sequences; and selecting from the plurality of FR tester protein sequences at least two peptide segments that have at least 15% sequence identity with the FR lead sequence, the selected peptide segments forming a FR hit library; and combining the CDR hit library and the FR hit library to form a hit library.

According to the method, the plurality of CDR tester protein sequences may comprise amino acid sequences of human or non-human antibodies.

Also according to the method, the plurality of FR tester protein sequences may comprise amino acid sequences of human origins, preferably human or humanized antibodies (e.g., antibodies with at least 50% human sequence, preferably at least 70% human sequence, more preferably at least 90% human sequence, and most preferably at least 95% human sequence in $V_H$ or $V_L$), more preferably fully human antibodies, and most preferably human germline antibodies.

Also according to the method, at least one of the plurality of CDR tester protein sequences is different from the plurality of FR tester protein sequences.

Also according to the method, the plurality of CDR tester protein sequences are human or non-human antibody sequences and the plurality of FR tester protein sequences are human antibody sequences, preferably human germline antibody sequences.

The method may further comprise the step of:

constructing a nucleic acid library comprising DNA segments encoding the amino acid sequences of the hit library.

Optionally, the method may further comprise the steps of:

building an amino acid positional variant profile of the CDR hit library;

converting the amino acid positional variant profile of the CDR hit library into a first nucleic acid positional variant profile by back-translating the amino acid positional variants into their corresponding genetic codons; and constructing a degenerate CDR nucleic acid library of DNA segments by combinatorially combining the nucleic acid positional variants.

Optionally, the genetic codons may be the ones that are preferred for expression in bacteria. Optionally, genetic codons may be the ones that can reduce the size chosen such that the diversity of the degenerate nucleic acid library of DNA segments within the experimentally coverable diversity (<10^6 or 7) without undue experimental effort.is below $1\times10^7$, preferably below $1\times10^6$.

In yet another embodiment, the method comprises the steps of:

providing an amino acid sequence of the variable region of the heavy chain ($V_H$) or light chain ($V_L$) of a lead antibody;

identifying the amino acid sequences in the FRs of the lead antibody;

selecting one of the FRs in the $V_H$ or $V_L$ region of the lead antibody;

providing a first amino acid sequence that comprises at least 3 consecutive amino acid residues in the selected FR, the selected amino acid sequence being a first FR lead sequence;

comparing the first lead FR sequence with a plurality of FR tester protein sequences; and selecting from the plurality of FR tester protein sequences at least two peptide segments that have at least 15% sequence identity with the first FR lead sequence, the selected peptide segments forming a first FR hit library.

The method may further comprise the steps of providing a second amino acid sequence that comprises at least 3 consecutive amino acid residues in a FR that is different from the selected FR, the selected amino acid sequence being a second FR lead sequence;

comparing the second FR lead sequence with the plurality of FR tester protein sequences; and selecting from the plurality of FR tester protein sequences at least two peptide segments that have at least 15% sequence identity with the second FR lead sequence, the selected peptide segments forming a second FR hit library; and combining the first FR hit library and the second FR hit library to form a hit library.

According to the method, the lead CDR sequence may comprise at least 5 consecutive amino acid residues in the selected CDR. The selected CDR may be selected from the group consisting of $V_H$ CDR1, $V_H$ CDR2, $V_H$ CDR3, $V_L$ CDR1, $V_L$ CDR2, and $V_L$ CDR3 of the lead antibody.

Also according to the method, the lead FR sequence may comprise at least 5 consecutive amino acid residues in the selected FR. The selected FR may be selected from the group consisting of $V_H$ FR1, $V_H$ FR2, $V_H$ FR3, $V_H$ FR4, $V_L$ FR1, $V_L$ FR2, $V_L$ FR3 and $V_L$ FR4 of the lead antibody.

The method may further comprise the step of:

constructing a nucleic acid or degenerate nucleic acid library comprising DNA segments encoding the amino acid sequences of the hit library.

In another aspect of the invention, a method is provided for in silico selection of antibody sequences based on the amino acid sequence of a region in a lead antibody, i.e., the "lead sequence", and its 3D structure. The structure of the lead sequence is employed to search databases of protein structures for segments having similar 3D structures. These segments are aligned to yield a sequence profile, herein after referred to as the "lead sequence profile". The lead sequence profile is employed to search databases of protein sequences for remote homologues of the lead sequence having low sequence identity and yet structurally similar. By using the method, a library of diverse antibody sequences can be constructed and screened experimentally in vitro or in vivo for antibody mutants with improved or desired function(s).

In one embodiment, the method comprises the steps of:

providing an amino acid sequence of the variable region of the heavy chain ($V_H$) or light chain ($V_L$) of a lead antibody;

identifying the amino acid sequences in the CDRs of the lead antibody;

selecting one of the CDRs in the $V_H$ or $V_L$ region of the lead antibody;

providing an amino acid sequence that comprises at least 3 consecutive amino acid residues in the selected CDR, the selected amino acid sequence being a lead sequence;

providing a three-dimensional structure of the lead sequence;

building a lead sequence profile based on the structure of the lead sequence;

comparing the lead sequence profile with a plurality of tester protein sequences; and selecting from the plurality of tester protein sequences at least two peptide segments that have at least 10% sequence identity with lead sequence, the selected peptide segments forming a hit library.

According to the method, the three-dimensional structure of the lead sequence may be a structure derived from X-crystallography, nuclear magnetic resonance (NMR) spectroscopy or theoretical structural modeling.

According to the method, the step of building a lead sequence profile may include:

comparing the structure of the lead sequence with the structures of a plurality of tester protein segments;

determining the root mean square difference of the main chain conformations of the lead sequence and the tester protein segments;

selecting the tester protein segments with root mean square difference of the main chain conformations less than 5 Å, preferably less than 4 Å, more preferably less than 3 Å, and most preferably less than 2 Å; and aligning the amino acid sequences of the selected tester protein segments with the lead sequence to build the lead sequence profile.

Optionally, the structures of the plurality of tester protein segments are retrieved from the protein data bank.

Optionally, the step of building a lead sequence profile may include:

comparing the structure of the lead sequence with the structures of a plurality of tester protein segments;

determining the Z-score of the main chain conformations of the lead sequence and the tester protein segments;

selecting the segments of the tester protein segments with the Z-score higher than 2, preferably higher than 3, more preferably higher than 4, and most preferably higher than 5; and aligning the amino acid sequences of the selected tester protein segments with the lead sequence to build the lead sequence profile.

Optionally, the step of building a lead sequence profile may be implemented by an algorithm selected from the group consisting of CE, MAPS, Monte Carlo and 3D clustering algorithms.

The method may further comprise the step of:

constructing a nucleic acid library comprising DNA segments encoding the amino acid sequences of the hit library.

Optionally, the method may further comprise the steps of:

building an amino acid positional variant profile of the hit library;

converting amino acid positional variant profile of the hit library into a nucleic acid positional variant profile by back-translating the amino acid positional variants into their corresponding trinucleotide codons; and constructing a degenerate nucleic acid library of DNA segments by combinatorially combining the nucleic acid positional variants.

Any of the above methods may further comprise the following steps:

introducing the DNA segments in the nucleic acid or degenerate nucleic acid library into cells of a host organism;

expressing the DNA segments in the host cells such that recombinant antibodies containing the amino acid sequences of the hit library are produced in the cells of the host organism; and selecting the recombinant antibody that binds to a target antigen with affinity higher than $10^6$ $M^{-1}$, preferably $10^7$ $M^{-1}$, more preferably $10^8$ $M^{-1}$, and most preferably $10^9$ $M^{-1}$.

In one embodiment, the method comprises the steps of:

providing an amino acid sequence of the variable region of the heavy chain ($V_H$) or light chain ($V_L$) of a lead antibody, the lead antibody having a known three dimensional structure which is defined as a lead structural template;

identifying the amino acid sequences in the CDRs of the lead antibody;

selecting one of the CDRs in the $V_H$ or $V_L$ region of the lead antibody;

providing an amino acid sequence that comprises at least 3 consecutive amino acid residues in the selected CDR, the selected amino acid sequence being a lead sequence;

comparing the lead sequence profile with a plurality of tester protein sequences;

selecting from the plurality of tester protein sequences at least two peptide segments that have at least 10% sequence identity with lead sequence, the selected peptide segments forming a hit library;

determining if a member of the hit library is structurally compatible with the lead structural template using a scoring function; and selecting the members of the hit library that score equal to or better than or equal to the lead sequence.

According to the method, the scoring function is an energy scoring function selected from the group consisting of electrostatic interactions, van der Waals interactions, electrostatic solvation energy, solvent-accessible surface salvation energy, and conformational entropy.

Optionally, the scoring function is one incorporating a forcefield selected from the group consisting of the Amber forcefield, Charmm forcefield, the Discover cvff forcefields, the ECEPP forcefields, the GROMOS forcefields, the OPLS forcefields, the MMFF94 forcefield, the Tripos forcefield, the MM3 forcefield, the Dreiding forcefield, and UNRES forcefield, and other knowledge-based statistical forcefield (mean field) and structure-based thermodynamic potential functions.

Also according to the method, the step of selecting the members of the hit library includes selecting the members of the hit library that have a lower or equal total energy than that of the lead sequence calculated based on a formula of $$\Delta E_{total}=E_{vdw}+E_{bond}+E_{angel}+E_{electrostatics}+E_{solvation}$$

Also according to the method, the step of selecting the members of the hit library includes selecting the members of the hit library that have a lower binding free energy than that of the lead sequence calculated as the difference between the bound and unbound states using a refined scoring function $$\Delta G_b=\Delta G_{MM}+\Delta G_{sol}-T\Delta S_{ss}$$

where $$\Delta G_{MM}=\Delta G_{ele}+\Delta G_{vdw} \quad (1)$$

$$\Delta G_{sol}=\Delta G_{ele\text{-}sol}+\Delta G_{ASA} \quad (2)$$

The method may further comprise the step of:

constructing a nucleic acid library comprising DNA segments encoding the amino acid sequences of the hit library.

Figure 1C:
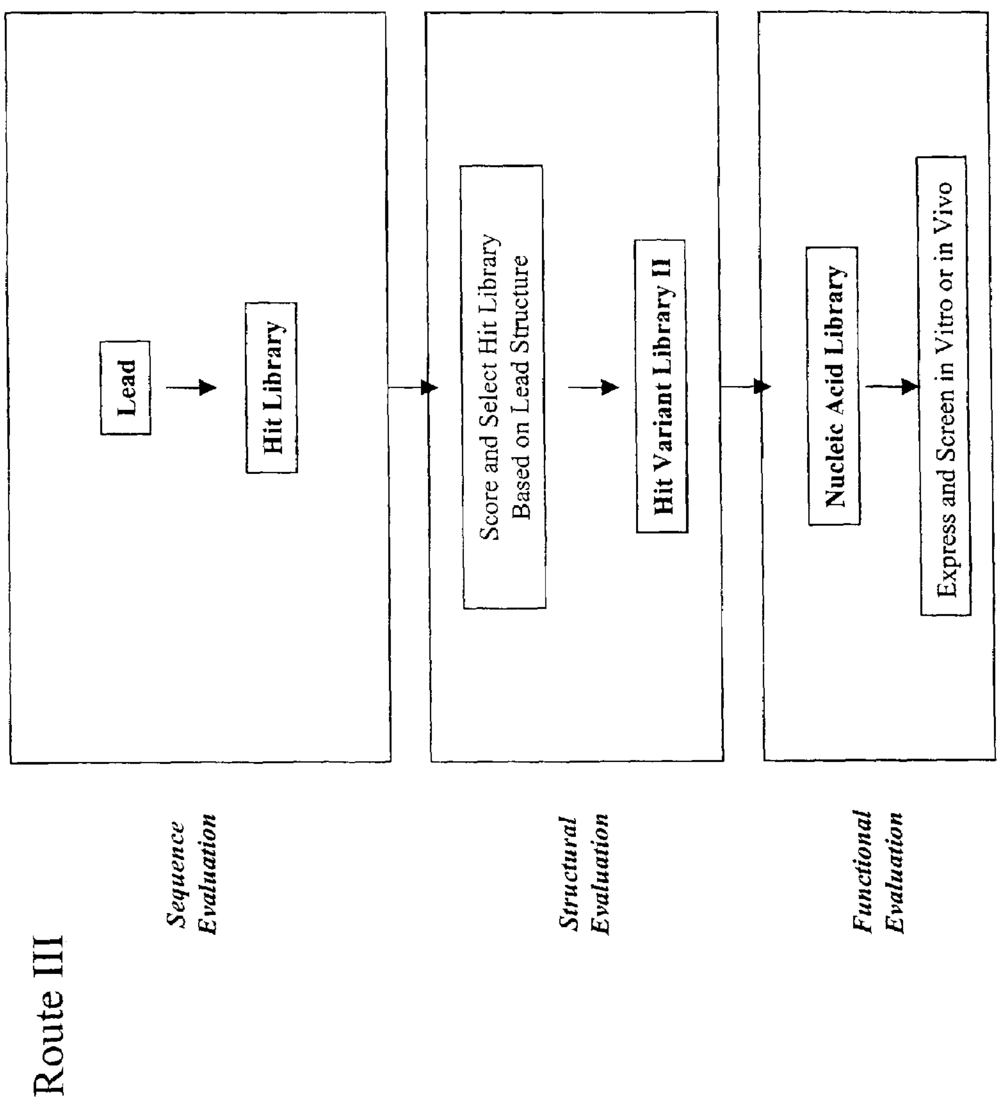

Route III in FIG. 1C schematically represents this embodiment. According to this embodiment, sequences of the hit library are built into the 3D structure of the lead protein by substituting side chains from a rotamer database, and scored for their structural compatibility with the 3D structure of the lead protein (herein after referred to as "the lead structural template". Based on the structural evaluation, the hit library is reprofiled by ranking according to the score in energy function. Some of the sequences in the hit library with a desired energy function are selected and translated back to a library of nucleic acid for functional screening in vitro or vivo. There is no amino acid sequence combinatorial step in this embodiment.

Optionally, the method may further comprise the steps of:

building an amino acid positional variant profile of the hit library;

converting amino acid positional variant profile of the hit library into a nucleic acid positional variant profile by back-translating the amino acid positional variants into their corresponding trinucleotide codons; and constructing a degenerate nucleic acid library of DNA segments by combinatorially combining the nucleic acid positional variants.

In yet another embodiment, the method comprises:

In one embodiment, the method comprises the steps of:

providing an amino acid sequence of the variable region of the heavy chain ($V_H$) or light chain ($V_L$) of a lead antibody, the lead antibody having a known three dimensional structure which is defined as a lead structural template;

identifying the amino acid sequences in the CDRs of the lead antibody;

selecting one of the CDRs in the $V_H$ or $V_L$ region of the lead antibody;

providing an amino acid sequence that comprises at least 3 consecutive amino acid residues in the selected CDR, the selected amino acid sequence being a lead sequence;

comparing the lead sequence with a plurality of tester protein sequences;

selecting from the plurality of tester protein sequences at least two peptide segments that have at least 10% sequence identity with lead sequence, the selected peptide segments forming a hit library;

building an amino acid positional variant profile of the hit library based on frequency of amino acid variant appearing at each position of the lead sequence;

combining the amino acid variants in the hit library to produce a combination of hit variants which form a hit variant library;

determining if a member of the hit variant library is structurally compatible with the lead structural template using a scoring function; and selecting the members of the hit variant library that score equal to or better than the lead sequence.

According to the method, the step of combining the amino acid variants in the hit library includes:

selecting the amino acid variants with frequency of appearance higher than 4 times, preferably 6 times, more preferably 8 times, and most preferably 10 times (2% to 10% and preferably 5% of the frequency for the cutoff and then include some of the amino acids from the lead sequence if they are missed after cutoff); and combining the selected amino acid variants in the hit library to produce a combination of hit variants which form a hit variant library.

According to the method, the scoring function is an energy scoring function selected from the group consisting of electrostatic interactions, van der Waals interactions, electrostatic solvation energy, solvent-accessible surface solvation energy, and conformational entropy.

Optionally, the scoring function is one incorporating a forcefield selected from the group consisting of the Amber forcefield, Charmm forcefield, the Discover cvff forcefields, the ECEPP forcefields, the GROMOS forcefields, the OPLS forcefields, the MMFF94 forcefield, the Tripos forcefield, the MM3 forcefield, the Dreiding forcefield, and UNRES forcefield, and other knowledge-based statistical forcefield (mean field) and structure-based thermodynamic potential functions.

The method may further comprise the step of:

constructing a nucleic acid library comprising DNA segments encoding the amino acid sequences of the selected members of the hit variant library.

Figure 1D:
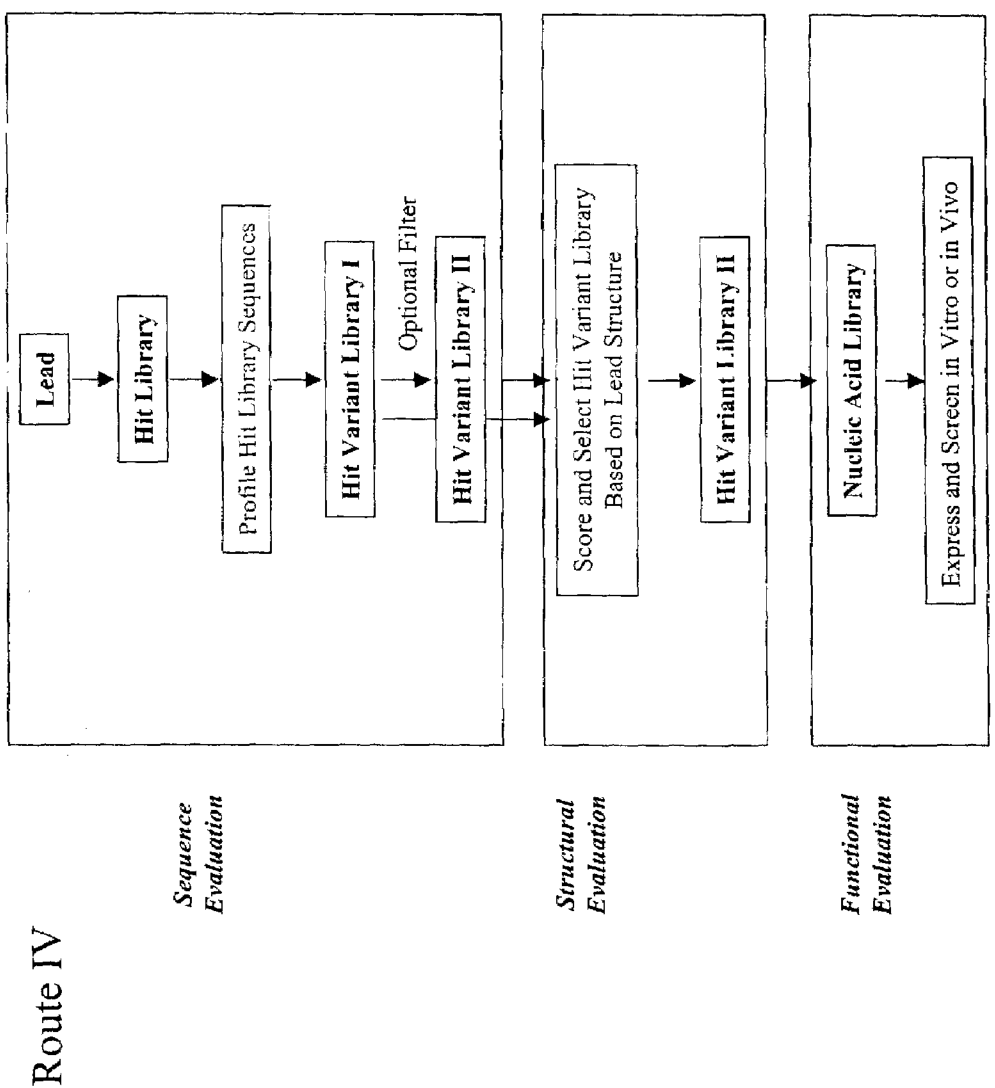
Figure 1E:
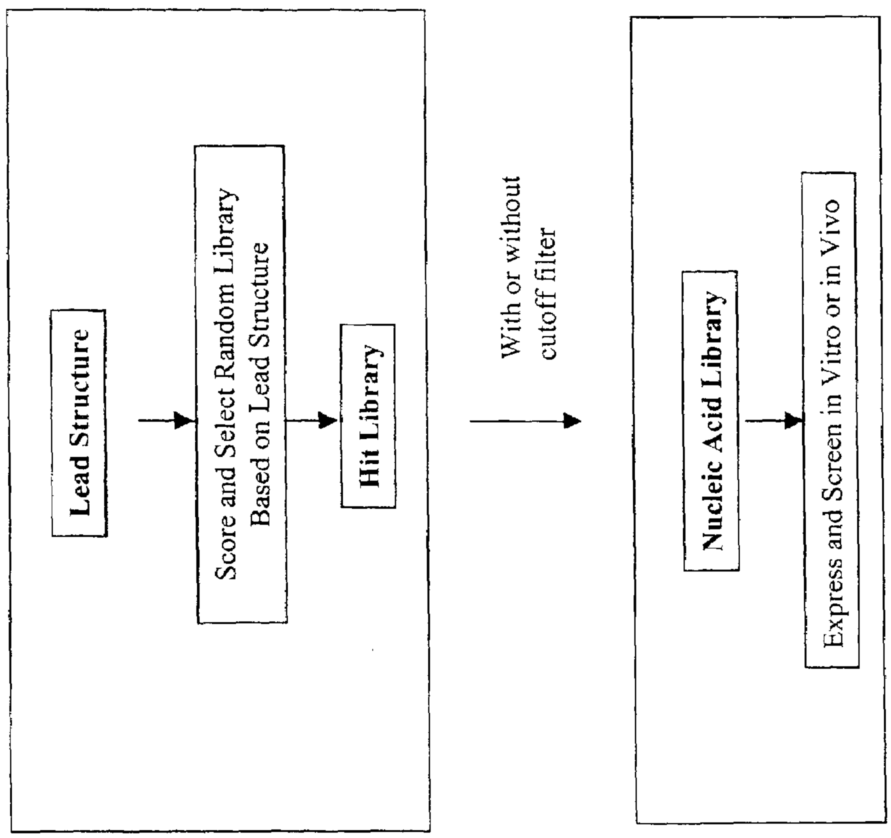
FIGS. 1E–H illustrate four of the possible embodiments of the method that can be used in the present invention to select for proteins with desired functions. Here, the lead refers to a structure or structure model or structure ensemble or profile (multiple superimposed structures), the corresponding sequence or sequence profile from the lead structure or structure ensemble can be then used to screen all possible sequences or random combinations for the hit sequence library based on structure-based screening. The resulting hit variant libraries can be used for direct experimental screening or compared with the sequence hit profile derived from the corresponding lead sequence or sequence profile (see FIGS. 2A–C). The structure template referes to structure, structure ensemble (more than 2 structures) from experimental determination and/or modeling.
Figure 1F:
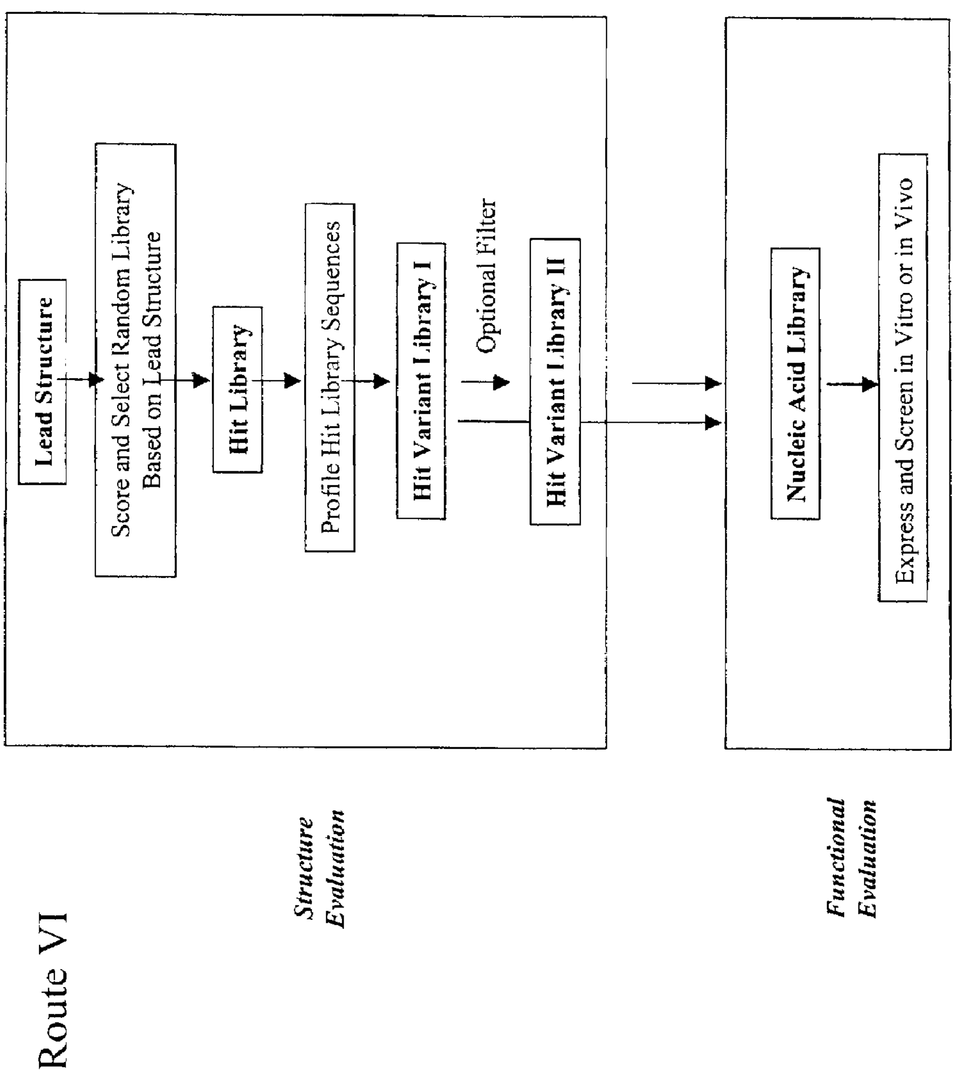
Figure 1G:
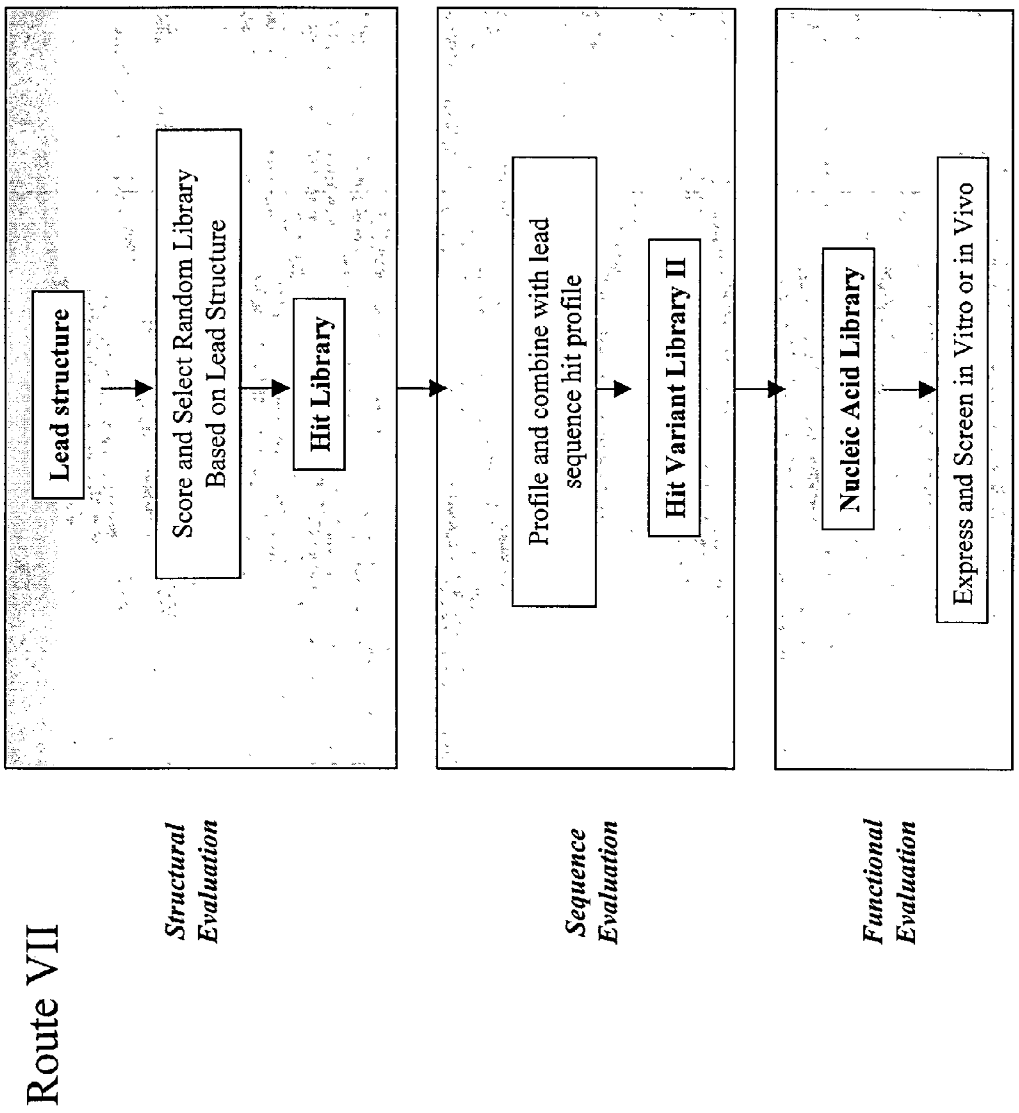
Figure 1H:
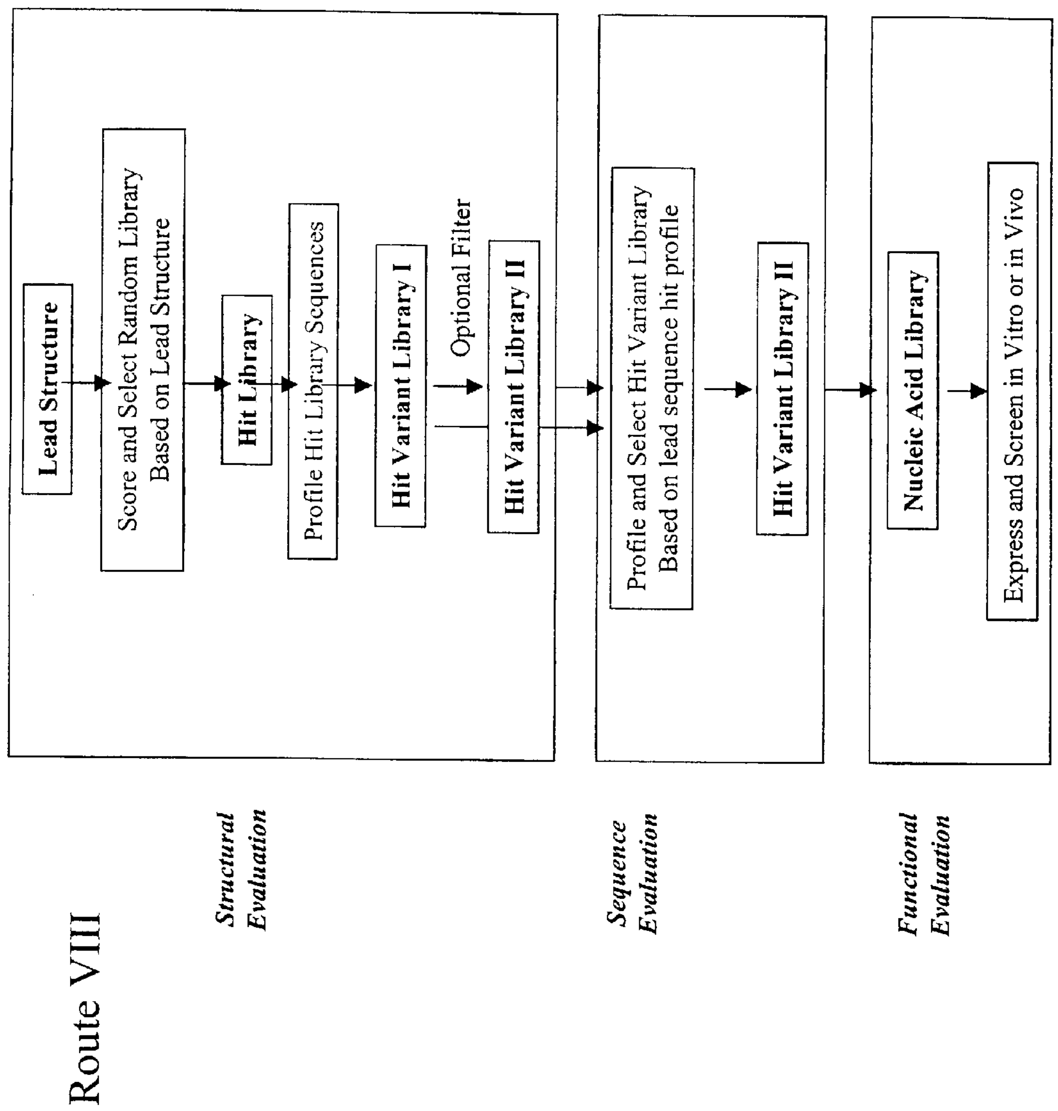

Route IV in FIG. 1D schematically represents this embodiment. According to this embodiment, after amino acid sequences of the hit library are profiled against the lead sequence, a combinatorial library of hit variants, i.e., hit variant library I. Hit variant library II is constructed based on the frequency of appearance of an amino acid in each residue position (as in Route III). Sequences of hit variant library II are built into the 3D structure of the template protein by substituting side chains from a rotamer database, and scored for their structural compatibility with the lead structural template. Based on the structural evaluation, the hit variant library II is re-profiled by ranking according to the score in energy function. Some of the sequences in the re-profiled hit variant library II with a desired energy function are selected and translated back to a library of nucleic acid for functional screening in vitro or in vivo. Additional modifications to the variant profile of library II can be applied based on other selective factors determined by those trained in the arts. Thus library II is a designed library based on evolutionary, structural, and/or functional data.

Based on the sequences of the selected hit list or hit variant library II that are generated in silico, a synthetic library of antibody can be constructed in the lab and screened against the target antigen. A wide variety of biological assays can be used for high throughput screening, such as phage display (Smith and Scott (1993) Method Enzymol. 217: 228–257), ribosome display (Hanes and Pluckthun (1997) Proc. Natl. Acad. Sci. USA 94:4937–4942), yeast display (Kieke et al. (1997) Protein Eng. 10:1303–1310), and other extra- or intra-cellular expression systems.

In another embodiment, the method comprises the steps of:

providing an amino acid sequence of the variable region of the heavy chain ($V_H$) or light chain ($V_L$) of a lead antibody, the lead antibody having a known three dimensional structure;

providing 3D structures of one or more antibodies with different sequences in $V_H$ or $V_L$ region than that of the lead antibody;

forming a structure ensemble by combining the structures of the lead antibody and the one or more antibodies; the structure ensemble being defined as a lead structural template;

identifying the amino acid sequences in the CDRs of the lead antibody;

selecting one of the CDRs in the $V_H$ or $V_L$ region of the lead antibody;

providing an amino acid sequence that comprises at least 3 consecutive amino acid residues in the selected CDR, the selected amino acid sequence being a lead sequence;

comparing the lead sequence with a plurality of tester protein sequences;

selecting from the plurality of tester protein sequences at least two peptide segments that have at least 10% sequence identity with lead sequence, the selected peptide segments forming a hit library;

building an amino acid positional variant profile of the hit library based on frequency of amino acid variant appearing at each position of the lead sequence;

combining the amino acid variants in the hit library to produce a combination of hit variants which form a hit variant library;

determining if a member of the hit variant library is structurally compatible with the lead structural template using a scoring function; and selecting the members of the hit variant library that score equal to or better than the lead sequence.

Such a process, i.e., computational prediction of a digital antibody library and experimental screening of the synthetic antibody library, can be reiterated to improve the binding affinity of selected antibodies. After the first round of screening, the three-dimensional structure of the selected antibody or antibodies can be modeled computationally. Also, the structure can be modified by expanding the sequence and conformation space and by subjecting it to soft docking by the target antigen to create a second generation of the digital antibody library. The second generation of the digital antibody library can then be screened experimentally to select for the antibodies with higher affinity than the first generation of selected antibodies. Such a reiterating process of structural modification and screening against the antigen effectively mimics the natural process of antibody maturation in vertebrates.

The conceptual framework and practical applications of the present invention are described in detail in the following sections.

1. Conceptual Framework of the Present Invention

The present invention provides innovative solutions to problems long existing in the field of molecular biology, in particular, protein folding and design. The approach developed by the inventors combines the best ideas in protein folding and design into a powerful integrated system that can develop novel protein products for practical applications in a high throughput and cost-effective manner.

The inventors believe that a central issue in molecular biology is to map out the functional repertoire of biopolymers such as proteins, RNA and DNA molecules in terms of their sequence and structure. The functional repertoire of biopolymers is shaped by a complex interplay of selective pressures during the course of evolution and by physical constraints on the folding and stability of biopolymers under various environmental conditions. What is the difference between the natural biopolymers and the random polymers? What is the best strategy to exploit the rich diversity of function, sequence and structure spaces of naturally occurring biopolymers to create novel biopolymers with stable structures and proper biological functions? Answers to these questions are of fundamental interest in molecular design and evolution, especially in the discovery of novel proteins with enhanced binding and catalytic activities.

The present invention addresses these issues in the following three steps: 1) discuss the general conceptual framework underlying protein folding and evolution to provide the basic knowledge needed for understanding the present invention; 2) describe the current experimental and theoretical methods used in protein folding and design and the problems related to these approaches; and 3) outline the inventive approaches to solve some of the longstanding problems in protein design and engineering.

1) Protein Folding and Evolution

Proteins are essential molecules for performing a diverse array of biological functions. Proteins acquire their biological functions by folding their linear sequences into unique three-dimensional structures. Predicting protein structure from sequence still remains an unsolved problem. However, important progress has been made in understanding the mechanisms of protein folding, especially with the advent of the statistical interpretation of the ensembles of intermediates and transition states in folding pathways.

The dynamics nature of protein conformation in solution has been well documented in both experimental and theoretical studies. Dynamic fluctuation in protein conformation can be essential for carrying out some of their biological functions such as in allosteric regulation (Monod, J., Wyman, J., and Changeux, J. P. (1965) J. Mol. Biol., 12:88–118) in protein-protein and protein-nucleic acid interactions, and conformational gating (Zhou, H-X, Wlodek, S. T., McCammon, J. A. (1998) PNAS 95, 9280–9283.) in enzymatic activities.

The continuous ensemble approach is favored over the classical discrete-state approach for describing protein folding mechanism because it provides, not only a more realistic view of biopolymers, as compared to the static x-ray structure, but a general framework for describing a growing body of experimental observations that would difficult to interpret, otherwise (Hong Qian (2002) Protein Science 11, 1–5). This view emphasizes the importance of using the statistical properties of the continuous distribution of conformational ensembles on an energy landscape in understanding biological functions of macromolecules (Baldwin R L (1995) 5, 103–109 J Biomol. NMR; Pande V J etc (1998) Curr. Opin. Struct. Biol., 8, 68–79).

The random energy model (REM) used to study heteropolymer freezing and design provides an excellent approximate physical model for protein folding and design (see Vijay S. Pande, Alexander Yu. Grosberg, and Toyoichi Tanaka, Review of Modern Physics, Vol. 72, No. 1, 2000 and references within). Much has been learned from the quantitative studies of simple models of protein folding and design based on the statistical properties of the freezing transition for heteropolymers. The phase transition between conformational states of ensembles distributed in continuous energy spectra provides a more realistic description of the folding and binding properties of proteins compared to the traditional view of a few discrete states populating a set of well-defined energy wells. The REM landscape suggests that a necessary and sufficient condition for any designed sequences to fold into a kinetically accessible and thermodynamic stable conformation is an energy distribution that shows a continuous energy spectrum in the upper portion and a pronounced energy minimum in the lower portion (See Vijay S. Pande, Alexander Yu. Grosberg, and Toyoichi Tanaka, Review of Modern Physics, Vol. 72, No. 1, 2000 and references within; Shakhnovich and Gutin, 1993 PNAS, 90, 7195–7199). Therefore, sequences should be designed to enlarge the energy gap between the ground state of the designed sequence and the bottom of the REM continuous energy spectrum. The energy gap is enlarged either by pulling down the energy of the native conformation of sequences (positive design for stability) or by pushing up the energy of alternative conformation of a sequence (negative design for specificity).

The general rules derived from this simple model of protein folding was strictly followed in a recent de novo computational protein design: the composition of amino acids is kept unchanged while the energy is minimized (Koehl P & Levitt M (1999) J Mol Biol 293, 1161–1181). It is argued that defining the ensemble characteristics of the sequences compatible to a given structure is more important than finding the specific optimal sequence (Koehl P & Levitt M (1999) J Mol Biol 293, 1183–1193). The multiple alignment of the designed sequences defines a sequence space that is measured by information entropy; a subset of this sequence space is similar in size to the sequence space derived from the same structural alignment observed in Nature (Koehl P; Levitt M (2001) PNAS 1–6). This work shows that topology and stability defines the sequence space of a given fold, while a subset of the sequence space can be defined by the functional fitness. However, this method poses too much restriction on the choice of amino acids at each position by keeping the composition of amino acids unchanged.

The dynamic nature of protein evolution has been actively pursued by theoretical and evolutionary biologists (Maynard-Smith, J (1970) Nature, 225, 563–564). Mapping sequences (genotypes) into values measuring the fitness landscape is a core issue of evolutionary biology. Although the relationship between genotype and phenotype is too complicated to be analyzed in general by a quantitative method, this relationship can be, however, simplified to relations between sequence (genotype) and structure (phenotype) and therefore, fitness values can be used to score the fitness of sequences to a given shape of biopolymers as shown below:

Genotype (sequences)←fitness score→Phenotype (structure)

Proteins observed in nature have evolved under selective pressures to perform specific functions. Interestingly, fitness landscape of functional proteins has been mapped and simulated using similar tools as in protein folding field. The fitness landscape is mapped out in sequence space in order to define the mutant ensemble that would enhance the functional property of a protein. Statistical properties of the sequence ensemble have been used to describe the neutral network in sequence space of the target protein (Stadler P F. Journal of Molecular Structure (Theochem) 463, 7–19 (1999); J Theor Biol 2001, 212, 35–46).

There are three essential ingredients embedded in the landscape theory: a set of configurations; a fitness function assigned to each configuration; and the connectivity between configurations that define the distance or relation between configurations. A fitness function can be broadly defined as a property of a protein such as the binding affinity between two proteins (receptor and ligand; antigen and antibody), the catalytic activity of an enzyme, or the structural stability of a target scaffold.

From the perspective of evolution, the fitness landscapes arising from mapping the sequence-structure relations of natural RNA and proteins predict the existence of neutral networks in sequence space evolved under partially correlated landscapes, providing an efficient route to adaptive evolution toward a new fitness function. In contrast, the random sequences evolved under rugged fitness landscapes without neutral neighbors are trapped in local optima, leading to localized populations in sequence space. The natural sequence has undergone evolutionary optimization under selective pressure through a mountain climbing process. An effective route to a new fitness function via sequence alteration is to follow the neutral networks in sequence space rather than by random mutation. (Stadler P F. Journal of Molecular Structure (Theochem) 463, 7–19 (1999); J Theor Biol 2001, 212, 35–46; Aderonke Babajide etc (1997) Folding & Design 2, 261–269). The relative efficiency of searching the fitness landscape via point-mutation versus gene recombination in protein space can be simulated and compared using the REM as well as heterpolymer-based model (Bogarad L, Deem M W (1999) PNAS 96, 2591–2595; Cui Y, Wong W H, Bornberg-Bauer E, Chan H S (2002) 99, 809–814).

The above-described theoretical studies of protein folding and evolution using simplified models have provided some insights into the statistical properties of ensemble states of protein structures and sequences during folding and evolution. The inventors believe that a theory that combines the concepts in molecular biology, physics of spin glass and physics of heteropolymer should provide a unified framework for the dynamic properties of biopolymers. The question now becomes how to turn such a conceptual framework based on models of proteins into a practical approach to map out the functional landscape of proteins in both sequence and structure spaces.

2) Current Experimental and Theoretical Methods for Protein Sequence Design in the Art and Problems that Lie therein A major goal in protein engineering is to generate proteins with novel or improved function. To this end, two alternative approaches have been used to obtain proteins, mainly enzymes, with desired properties: in vitro directed molecular evolution and structure-based computational design. The approach of in vitro directed evolution employs homologous sequences, random mutagenesis and gene shuffling to generate diverse sequence library. Mutants with desirable properties are selected in a high throughput screening and re-shuffled. This procedure is iterated until a desired level of functional enhancement is attained.

The first law in directed evolution that states, "You get what you screen for," underscores the importance of the screening method in evaluating the functional fitness of the protein libraries (Wintrode, P & Arnold, F H (2000) Adv Protein Chem. 55, 161–226). The availability and improved sensitivity of high throughput enzymatic screenings have led to some successes of directed evolution. Compared to rational engineering, the directed evolution requires little or no additional information such as the structure of the target enzyme, and can screen directly for biological activities from a large pool of molecules under defined selective pressure.

The dependence on the screening ability imposes an upper limit on the size of the generated combinatorial library and therefore the size of the sampled functional space. Because random mutagenesis by using error-prone PCR is biased and inefficient process for generating a diverse library, the probability of a significant functional improvement by any single random mutation is small and drops rapidly for multiple simultaneous random mutations. It is also difficult to generate several mutants simultaneously at a single codon position at the nucleic acid level.

Furthermore, the dependence of the DNA shuffling on homologous recombination of sequences with high homology (>70%) limits the sequence space that the resulting library can span. As a result, each successive iteration of shuffling and screening leads to sampling in a shrinking local sequence space. This may be efficient for identifying new homologous sequences with enhanced properties but may not be adequate for identifying truly novel sequences with potentially greater functional improvements.

Nonetheless, beneficial amino acid substitutions are generated and identified by incorporating random mutagenesis. Accumulating beneficial point mutations has been used successfully to evolve and screen a number of important enzymes with desired properties. Besides the simple random mutagenesis strategy, gene recombination by DNA shuffling, including family shuffling approach that combines genes from multiple parents of the same or different species, creates highly improved biocatalysts (Ness J E Del Cardayre, S B Minshull, J & Stemmer, W P C (2000) Adv Protein Chem 55, 261–292).

As a closely related problem to protein folding, protein design is considered as the inverse folding problem (Drexler, K E (1981) PNAS 78, 5275–5278; Pabo, C. (1983) Nature 301, 200): finding the sequences that give rise to the target structure. Designing protein sequences that would give rise to the target scaffold is considered to be an important step in engineering proteins with improved properties for a wide range of applications.

A major issue related to the inverse folding protocol is the necessity of maintaining a rigid protein backbone. Because conformational space needed to be sampled is enormous, for practical reasons, the static X-ray structure of a protein is still widely used as a starting point in rational structure-based protein or drug design. The inverse protein folding approach tries to compute the optimal sequence compatible with the protein structure based on semi-empirical all-atom energy functions describing the interactions between amino acids. While the native protein is known to tolerate small perturbation with robust conformational adaptation, the computational ground state of a rigid protein backbone is, however, not sufficiently adaptable to small perturbation in protein backbone or side chain rotamers to provide an accurate measure of stability.

Some efforts in backbone parameterization have been made to address these issues by adjusting the relative orientation between regular secondary structures (Harbury, P B, Tidor B. & Kim, P S (1995) Protein Science 92, 8408–8412; Su A & Mayo S L (1997) Prot Sci. 6, 1701–1707; Harbury P B, Plecs J J, Tidor B, Alber T, Kim P S (1998) Science 282, 1462–1467). The inventors believe that a simple but efficient solution to relieve the local constraints is energy minimization including backbone and side chains (Keating A E, Malashkevich V N, Tidor B, Kim P S (2001) PNAS 98, 14825–30) for any structure type of a protein as demonstrated in the present invention for protein loops, which are irregular and whose backbone movements are hard to parameterize in general.

Apart from a few cases with regular secondary structures (see below), most of the protein design strategy strictly follows the inverse folding protocols in sequence selection in order to reduce the immense task of searching the conformational space. Even with backbone fixed, powerful searching algorithms, including stochastic Monte Carlo or genetic algorithm and deterministic dead end elimination, are needed to search for the best solution to an empirical energy function that incorporates various factors in stabilizing a protein assembled from a rotamer library of protein side chains (Ponder, J. W. & Richards, F. M. (1983) J. Mol. Biol. 193, 775–791; Hellinga, H. W., Richards, F. M. (1994) PNAS 91, 5803–5807; Desjarlais, J. R. & Handel, T. M. (1995) Prot Sci. 4, 2006–2018; Dahiyat, B. I. & Mayo, S. L. (1996) Prot. Sci. 5, 895–903).

For amino acids exposed on the surface, evolutionary pressure may play a greater role in determining the sequence selection than in the core regions where packing constraints lead to conserved amino acid selections. But having fewer physical constraints on the surface and highly variable charge and polar solvation interactions poses a challenging design problem for exposed side chains. This limitation restricts most protein design methods to the core of proteins because the steric constraints are major determinants in designing amino acids in these positions.

Some algorithms try to divide proteins into discontinuous regions such as core, boundary and surface residues in order to have different scoring functions for different sites of protein structures (Dahiyat, B. I. & Mayo, S. L. (1996) Prot. Sci. 5, 895–903). However, for protein-protein interactions, the important residues are located on the surface of proteins, and most likely on the loops of proteins, the most difficult or irregular structure class of proteins. Upon interaction between proteins, some of the interacting residues become buried or half-exposed, making it difficult to model their interactions as specific class of residues in discrete regions of proteins. The inventors believe that although protein loops are widely involved in mediating protein-proteins interactions such as interactions between CDRs of antibodies and antigens or cytokines and their receptors, the methods existing in the art are still far from being capable of predicting the interactions, with high accuracy, of the loop structures of proteins by using force field-based approach alone, unless it is combined with a good homology model and database information (van Vlijmen H W, Karplus M (1997) J Mol Biol 267, 975–1001).

Given the inability of current force fields in predicting protein folding, a perpetual problem in protein folding and design is to develop an energy function that captures all factors known to contribute to protein stability, whose predictions compare favorably with experimental data. No matter how elaborate this procedure may be, calculating the small difference between two large numbers of stabilities for the folded and unfolded states of a protein is intrinsically difficult and error-prone. This difficulty becomes even greater if the region of interest lies at the interface between two proteins with the polar and charge residues whose forcefield parameters are still under active investigation for an accurate evaluation. The scoring function may also overfit the experimental feedback from a specific test system. In short, compared to the core packing inside proteins, accurate calculation of interactions between proteins that are dominated by polar and charged residues still remains a difficult task in this field. The inventor believes that side chain placing algorithms shown to be so effective in packing the hydrophobic core of proteins may not provide an effective solution to this standing problem.

The inventors stress that using the fixed backbone in the inverse folding protocol also over-restricts the positioning of the side chain rotamers and the steric repulsion between them. Such stiff constraints on the side chain rotamers are unrealistic. A real protein would accommodate side chain mutations or rotamers through dynamic fluctuations in solution that is reminiscent of an altered ensemble of conformational states. It is noted that a parametric representation between regular secondary structural elements has been used to drive the systematic folding of protein backbones (Harbury, P. B., Tidor, B. & Kim, P. S (1995); Su & Mayo (1997) Prot Sci.; Harbury P. B. etc (1999) Science 282, 1462–1467). However, it is still difficult to use such an approach on non-regular secondary structural element such as a loop to account for the fluctuating ensemble states.

Given the limitations of the computational methods, impatient evolutionary protein designers have chosen to avoid the rational structure-based approach altogether and to invent a set of powerful experimental tools. But no matter how powerful, creating a diverse library by random mutagenesis and screening them by experiment is a highly inefficient process. On the other hand, recombination of homologous genes by DNA shuffling allows only a limited sampling of the sequence and structure space.

The inventors believe that a computational method that has no a priori physical limitations can search a much larger sequence space. In addition, a key advantage and the main driving force of the rational approach is the ability to design and control the sequence library at every stage prior to experimental screening. This allows the protein designer to make greater virtual jumps in protein sequence space that sample greater distances which might lead to discovery of novel sequences and structures that has little or no homology to the starting sequences. Additionally, the virtual size and direction of these “jumps” can be controlled in accordance with experimental feedback to follow the functional landscape to a new peak. This capability is expected to increase dramatically with increasing computational power and development of novel algorithms and new software tools.

Obviously, computational power will not by itself make the computational protein design superior to in vitro protein evolution experimental method unless the subtle but important structural perturbations resulting from the directed evolution can be understood and captured. For example, it has been shown that the beneficial mutations are generally not localized to the catalytic sites but are distributed over large parts of proteins with perturbed protein backbone (Spiller B, Gershenson A, Arnold F H, Stevens R. (1999) PNAS 96, 12305–12310)

In the current art, the experimental screening for biological activities is still the only reliable approach available to evaluate the biological functions of molecules that are controlled by complicated competing factors under experimental conditions. It is extremely hard to correctly capture all the details simultaneously in a computational method and to pin point the answer without extensive experimental test. In addition, most of the scoring functions can only calculate the stability rather than activity or specificity.

Some statistics-based approaches have been developed that shed light on the evolutionary sequence design. Using a simplified model similar to the random energy model in protein folding, Bogarad and Deem have shown that DNA swapping of nonhomologous DNA segments with low energy structures is much more efficient in searching the fitness landscape in protein space than gene recombination of homologous DNA by DNA shuffling, which in turn is better than point mutations (Bogarad L, Deem M W (1999) PNAS 96, 2591–2595). Recently, a heteropolymer-based model has been used to explicitly map out the sequence-structure relationship in the fitness landscape in a structure-based evolutionary approach (Cui Y, Wong W H, Bornberg-Bauer E, Chan H S (2002) 99, 809–814). The point mutations are found to lead to diffusive walks on the evolutionary landscape, where crossovers can tunnel through barriers of diminished fitness. The smoothness of the energy or fitness landscape, together with the ratio between crossover and point-mutation rates, determines the effectiveness of crossovers in sampling the protein sequence and structure space. Thus, the inventors believe that evolutionary sequence design should not be limited to point mutations and homologous gene recombinations.

Experimental feedback is also essential to show any of the expected improvement in protein properties and to improve the agreement between theoretical prediction and experimental test (Desjarlais, J. R. & Handel, T. M. (1995) Prot Sci. 4, 2006–2018; Dahiyat, B. I. & Mayo, S. L. (1996) Prot. Sci. 5, 895–903; Keating A E, Malashkevich V N, Tidor B, Kim P S (2001) PNAS 98, 14825–30). Thus, the inventors believe that unless the agreement between experimental and computational values are confirmed (Keating A E, Malashkevich V N, Tidor B, Kim P S (2001) PNAS 98, 14825–30) and demonstrated extensively, including polar and charged residues at various regions of different kinds of proteins, experimental library should not be limited to sequences around the global optimal or suboptimal solution from computation. Instead, the experimental library should be constructed to cover a wide range of distributions over the energy landscapes that score as good as or better than the lead sequence.

Some convergence between in vitro directed evolution and computational sequence design has begun to emerge. For example, the structure-based de novo designed enzymes are usually not very active (Benson, D E, Wisz, M S & Hellinga H W (2000) PNAS 97, 6292–6297; Bolon D N, Mayo S L (2001) PNAS 98, 14274–14279). But these de novo design of the sequences in a different scaffold can serve as a starting point and subject to directed evolution for activity improvement (Altamirano, M M, Blackburn, J M, Aguayo C, Fersht A R (2000) Nature 403, 617–622). Conversely, structure-based computational method can be used to identify potential sites for concentrated point mutations in evolutionary design in order to reduce the search space in directed evolution, although these sites are found to be different from those from sequence profiling. (Voigt C A, Mayo S, Arnold, F H & Wang Z-G (2001) PNAS 98, 3778–3783).

However, the inventors believe that the strategies for directed evolution should be analyzed and measured in quantitative terms before launching the laborious experimental work. Some steps have been taken to simulate the DNA shuffling computationally to optimize the possible experimental conditions and possible limits for enhancement (Moore, G L, Maranas C D, Lutz S, Benkovic S (2001) PNAS 98, 3226–3231). Given the huge protein space that can be searched by various approaches, it is important to compare the efficiency and limitations inherent to each experimental or computational approach in order to determine the best route for the specific problem at hand.

The inventors also believe that, for structure-based protein design, the heart of the problem lies in the deterministic approach to a complicated problem with unrealistic assumptions. It is well known that interactions that stabilize a protein are very complex. The static structure used for design is an ensemble average of the dynamic fluctuations observed in solution that can change upon interacting with another protein or a ligand. Therefore, the idea of looking for the optimal solution to a target function is an interesting theoretical challenge but might be of little interest or practical relevance to real biological problems. Either the defect in energy function or the stringent restriction of using rigid backbone or both would contaminate the "optimal solution" to the design problem. Thus, again, the inventors believe that experimental library should not be limited to sequences around the global optimal or suboptimal solution from computation that might be biased by the assumption and parameters used in the computation. Instead, the sequences covering a preferred range that, for example, scores better than or equal to the lead sequence should be used for experimental screening.

For evolutionary protein design, current approaches to the design of proteins as biocatalysts (e.g., enzymes) still remain more art than science. But some methods are robust enough to be directly applied to solve real world problems in commercial biocatalyst design. Although DNA recombination by DNA shuffling and random mutagenesis have provided diverse protein libraries for functional screening, more efficient ways of library generation should be explored and the process should become predictable and routine rather than relying exclusively on the final screening results. So far, directed evolution has been applied most successfully to solve the biocatalyst design because it is easier to do high throughput screening for enzymatic activities where chemical reactions can be readily detected.

However, the inventors believe that the unexpected solution provided by directed evolution with mutations distributed throughout the entire protein sequence also poses problems for evolving certain proteins of pharmaceutical interest. In therapeutic antibody design, the mutations need to be limited to certain regions such as the CDR and modifications to a previously inert framework regions may render the protein potentially immunogenic. Such undesireable mutants during experimental shuffling has to be minimized or reduced by tedious backcrossing procedure; hopefully removal of these immunogenic mutants will not negate the activity improvement earned by hard experimental effort.

The rational structure-based protein design has undergone fast evolution in its development and has begun to deliver some impressive results. Over the years, exciting progress has been made in computationally designing protein variants possessing the target scaffold (Dahiyat, B. I. & Mayo, S. L. (1997) Science 278, 82–87) and markedly improved thermal stability by repacking the hydrophobic core (Malakauskas, S. M. & Mayo, S. L. (1998) Nature Struct. Biol. 5, 470–475) and discovering novel scaffold not yet observed in nature (Harbury P. B. etc (1998) Science 282, 1462–1467). For biological activity and affinity design, some interesting progress has been made to extend this rational approach to affect binding affinity by designing residues around the binding sites in three different conformational states with open, apo- and closed ligand-binding states that can modulate the binding activity through an allosteric effect on the binding sites (Marvin, J. S. & Hellinga H. W. (2001) Nat Struct Biol 8, 795–798.). However, for most proteins of biological and medical interest, the structural information required for such design is still unavailable or at a low resolution insufficient for such design, although structural genomic project is promised to increase the structural information at an accelerated pace.

3) The Inventive Approach

The present invention provides an innovative approach to efficiently map out the distribution of the fitness and energy landscape in protein sequence and structure space by using ensemble-based statistical methods.

Given the incomplete knowledge of principles underlying protein folding and design, the ensemble-based statistical approach to protein combinatorial library seeks to design sequence ensembles that are compatible to a given structure or structure family, that cover a distribution of the energy landscape with scores better than that of the lead sequence. It is statistical because it is the distribution of sequences or structures rather than a specific optimal solution to a given fixed structure that are designed. It is ensemble-based because it is structure/sequence ensembles that are targeted by nucleic acid libraries rather than a specific sequence or structure.

The inventors believe that partitioning of the energy distribution function into different ensemble states in sequence space allows for an effective sampling by subsequent experimental methods. This statistical approach to mapping the functional space of selected protein sequences provides a means to select protein sequences of real biological interest in the context of a fitness landscape described above. By defining the ensemble statistical properties rather than a single optimized sequence or a group of sub-optimal sequences, a protein designer is more likely to avoid getting trapped in a biased solution or move in a wrong direction resulting from the limitations inherent in current computational methods.

The inventive approach is developed by combining insights gleaned from theoretical studies of the simple models of protein folding and evolution based on the inventors' understanding of the problems associated with methods existing in the art. Through investigation and diligent experimentation, the inventors have developed practical solutions to the problems in the areas of protein folding, engineering and design, especially in the exciting field of antibody engineering.

FIG. 2A schematically outlines an in silico biopolymer evolution system developed by the inventors. As shown in FIG. 2A-C, the path from the initial target biopolymer (e.g., a protein) to the final candidate sequences with desired function(s) traverses in three spaces of biological importance: the sequence, structure and function spaces.

In the sequence space, the lead sequence(s) is employed to search the database(s) for evolutionarily related sequences. It is noted that this search may be applied to the structure space to obtain more distant sequences when structural alignment is used. The variant profile of the hit library describes the amino acid frequency and variants at the each position.

In the structure space, a hit variant library is generated in silico based on a reduced variant profile and partitioning (FIGS. 1C, 1D and 2A–C) or a complete sequence library or their random combinations (see FIGS. 1E–H, 2A and C). This hit variant library or random/complete sequence library is scored using a structural template, and preferred sequence ensembles are selected and re-profiled for the generation of an expanded nucleic acid (NA) library in silico. The size of the in silico NA library is evaluated and passed on for oligonucleotide synthesis if the library size is acceptable. Otherwise, the hit variant library is re-partitioned into smaller segments and smaller NA libraries are generated with overlapping sequences to maintain sequence and structural correlation among the resulting libraries (see Example section below and FIGS. 28A–C).

In the function space, the NA library is experimentally screened and positive sequences are input back into the computational cycle for library refinement. Strong positive clones are passed on for further evaluation and potential therapeutic development. If no hits occur in the experimental screening, new lead sequence ensembles in structure-based scoring and/or variant profile are selected for the target system and the process is restarted.

As can be appreciated from the depiction in FIG. 2A, an important distinction between the approach described here from other methods in the field of computational and evolutionary sequence design is that the present invention combines the best from both worlds to explore the fitness landscape in sequence and structure spaces more efficiently. Our approach combines the evolutionary information in protein sequence database with the physical constraints such as compatibility of the sequences with the 3D structure of a protein. The biological function of proteins can be computationally evaluated through sampling of a limited set of sequences that satisfies both evolutionary selection in sequence space and physical constraints in structure space.

In a particular application of the inventive methodology, antibodies are utilized as a model system for both experimental and computational tests. Antibodies are widely used in research, diagnostics and medical application. Antibodies can bind a variety of targets with good specificity and affinity. Catalytic antibodies are also being developed to catalyze chemical reactions.

In a more particular application, antibody hypervariable loops or complementarity determining regions (CDRs) as well as the framework regions (FRs) are targeted. The CDRs determine antibody-antigen binding and specificity, whereas the framework regions provide the scaffold on which the CDRs are correctly positioned for biological function. The antibody molecule is well suited for engineering because of its modular structure, with CDRs and framework regions that are well defined sequentially and structurally.

As outlined in FIG. 1A (Route I), polypeptide segments in an expressed protein database are computationally screened against a specific region (e.g., $V_H$ CDR3) of a lead antibody to be optimized and those that match in their sequence patterns with that of the lead antibody are selected. The selected sequences form a hit library.

Furthermore, as outlined in FIG. 1B (Route II), a variant profile can be generated by listing amino acid variants at each sequence position from the hit library, together with the number of the occurrence in the hit library. The combinatorial enumeration of this profile represents the hit variant library I. This variant profile can be edited either by including amino acids from the lead sequence or sequence profile at the corresponding positions where they are missed from the hit library or by eliminating amino acid variants that occur below a certain cut off frequency, or both. The resulting variant profile defines the hit variant library II, the designed library.

As outlined in FIGS. 1C and 1D, each member of the hit variant library I or II is "grafted" onto the corresponding region of the lead antibody template structure or model, if available, and selected, using a scoring function, for ones that are structurally compatible with the rest of the 3D structure. Optionally, the hit variant library can be evaluated in the presence or absence of a target antigen. Antibodies with favorable scores are selected and screened experimentally in a laboratory for their actual binding affinity towards the antigen. As will be shown in the EXAMPLE section, a large number of antibodies against human vascular endothelial growth factor (VEGF) are selected using this approach and proven to be able to bind to the target antigen VEGF. Some of them show affinity higher than that of the lead antibody (see FIGS. 30 & 36).

As will become more apparent with further disclosure in the sections below, the approach provided by the present invention is not only conceptually distinguishable from those in the art but also possesses many practical advantages in antibody engineering.

By exploiting the expressed protein sequences compiled in the protein databases, this approach, not only effectively mimics the natural process of affinity maturation in silico, but can potentially drastically hasten the evolution of proteins with improved binding affinity. For example, any set of amino acid sequences, including but not limited to sequences of immunological interest, from various species can be used to maximize the library diversity for profiling against a lead sequence for CDR affinity maturation. However, sequences of human germlines and/or origins should be used for profiling against a lead sequence for framework regions for humanization or framework design in order to minimize potential immunogenicity. Thus, the choice of the database, based on their application, sizes and origins of species such as human, mouse, etc. or all species available, permits the flexibility and control on the design proteins.

Further, the approach optionally includes modeling of the protein mutant (e.g., a mutant of the lead antibody) in the presence of the target molecule (e.g., the antigen of the lead antibody) if the complex structure or a model is available. By including the interaction between the antibody and antigen in the calculation, the screening process more closely mimics the natural process of affinity maturation, as an antigen-directed process, and the calculated binding affinities may correlate better with experimental values.

Moreover, the method of the present invention combines computational prediction of an antibody library, which is biased toward a specific target molecule or antigen, if the complex structure or structure model is available, with experimental screening of the library to select for those with high binding affinity to the antigen. Such a process can be reiterated to improve the binding affinity of selected antibodies. Given the availability of a high affinity complex structure as a template, the hit variant library can be computationally pre-screened to reduce the library size, yet remain functionally highly focused compared to traditional libraries generated through complete randomization of amino acids in each position of the lead antibody. Through prediction and construction of the hit variant library in silico, the whole process of protein evolution can be hastened, effectively mimicking the natural process of antibody affinity maturation in a high throughput manner.

In a preferred embodiment, the lead protein is an antibody or immunoglobulin and the target molecule is an antigen that binds to the template antibody. It should be noted that the lead protein may be any protein, preferably a protein with known three-dimensional structure which may be resolved using X-ray crystallography or nuclear magnetic resonance spectroscopy. Alternatively, the 3D structure or structure ensembles of the template protein may be provided by computer modeling using algorithms known in the art.

4) Comparison of the Inventive Methods with others in Antibody Selection and Engineering It is understood that selection of antibodies from a highly diverse library allows for a broad coverage of sequences, thereby maximizing the chance of finding the optimal sequence(s). However, for antibody sequences that are derived from random mutagenesis of the lead antibody, for example, in the CDRs, not all structures of the randomized CDRs are compatible with the 3D structure of the lead antibody. By using expressed proteins sequences as opposed to those from random mutagenesis and filtering out the incompatible sequences using the inventive method, a fewer number of sequences are selected. As a result, the sequence space of an antibody to be screened is reduced in size without losing sequences that may be highly relevant to affinity binding maturation and stabilization of the mutant antibody.

In contrast, the current methods in the art for constructing an antibody library involve in vitro isolation of cDNA libraries from immunized human antibody gene pool, naive B-cell Ig repertoire, or particular germline sequences. Barbas and Burton (1996), supra; De Haard et al. (1999), supra; and Griffiths et al (1994), supra. These libraries are very large and extremely diverse in terms of antibody sequences. Such a conventional approach attempts to create a library of antibody as large, and as diverse as possible to mimic immunological response to antigen in vivo. Typically, these large libraries of antibody are displayed on phage surface and screened for antibodies with high binding affinity to a target molecule. Such a "fishing in a large pond" or "finding a needle in a huge hay stack" approach is based on the assumption that a simple increase in the size of sequence repertoire should make it more likely to fish out the antibody that can bind to a target antigen with high affinity, but, in practice, is inefficient for affinity maturation due to inadequate sampling, insufficient diversity and indeterminate library composition.

The inventors believe that there are several problems associated with such a conventional approach. A simple increase in the size of sequence library may not necessarily correlate with an effective increase in functional diversity. Further, due to the physical limit on making an extremely large experimental library, it may be very difficult to construct a library with diversity over $10^{11}$ in vitro. The library that is actually screened experimentally probably presents only a fraction of the sequence repertoire at the theoretically predicted size. In addition, there is a legitimate concern that, with the difficulties and the under-representation problems associated with handling and manipulation of an extremely large library in vitro, time and money may be lost in an effort trying to increase the size of the library and yet not significantly increasing the functional diversity.

Another approach existing in the art is to design an artificial antibody library computationally and then construct a synthetic antibody library which is expressed in bacteria. Knappik et al., supra. The artificial antibody library was designed based the consensus sequence of each subgroup of the heavy chain and light chain sequences according to the germline families. The consensus was automatically weighted according to the frequency of usage. The most homologous rearranged sequences for each consensus sequence was identified by searching against the compilation of rearranged sequences, and all positions where the consensus differed from this nearest rearranged sequence were inspected. Furthermore, models for the seven $V_H$ and seven $V_L$ consensus sequences were built and analyzed according to their structural properties.

However, there are a few problems concerning such an approach as far as therapeutic applications of the selected antibody are concerned. The definition of consensus sequence may be too arbitrary and such artificial sequences defined may not be representative of a natural, functional structure, although experimental test and structural analysis may eliminate some unfavorable amino acid combinations. Although the consensus sequences may be designed to cover mainly those human germline sequences that are highly used in rearranged human sequences, it might bias the consensus sequence library toward a limited number of antigens exposed to human being so far in the course of evolution. Although these library construction method is mainly focused on finding a lead antibody or hit from a large antibody library, for the affinity maturation, most of the approach described above still quite limited for antibody affinity maturation. More tranditional approach such as CDR walk, random mutagenesis, or stepwise saturated mutagenesis at each position of CDRs etc are used for antibody affinity maturation. The present invention is specifically tailored to designing biased library for affinity maturation.

The inventors believe that sampling the functional space by mapping structures from different species covers a wider range of functional CDRs in an antibody library and will expand the range of antigens it can bind. This approach would be very important in the design of antibody libraries to target novel antigens. The method of the present invention typically relies on structural constraints derived from antibodies or from other natural sources. According to the present invention, a complete sequence space of all proteins available, preferably antibodies, including those from both human and other species, can be analyzed by fitting each library sequence into the 3D structural framework of the lead antibody.

Based on this analysis, the resulting mutant antibodies are not only novel in their sequences but also possess higher affinity than that of the lead antibody. As shown in the section of EXAMPLE below, a large number of mutant antibodies are selected using the inventive method and experimentally proven to bind to human VEGF with affinity similar to or higher than the lead anti-VEGF antibody.

2. General Description of Procedures Employed to Implement Protein Design Strategies of the Present Invention The procedures involve the exploration of sequence, structure and functional spaces and the evaluation of the relationships among them (FIGS. 1A–D, 1E–H, 2A–C). Starting point can be either a lead structure or a lead sequence or both, if available. The procedure systematically explores both the sequence space and structure space in order to identify variant profiles optimized for functional screening. There are three modes of information exchange: i) separate evaluation of information in sequence and/or structure space and then combined, ii) consecutive evaluation from sequence to structure, or from structure to sequence, or iii) from sequence or structure alone. While the sequence design can be explored in sequence and structure spaces separately (two separate cycles), the variant profiles from these two separate cycles can be compared and combined in order to arrive at the optimal overall variant profile with good consensus variant profile that is likely to produce strong candidates in the functional screen.

The two starting points are interrelated operationally because a sequence profile may be derived as a result of comparing the target sequence with homologous sequences or through structural alignment of known homologous structures. Sequence profiles may also be derived from mutational data that suggest functional or structural information. Similarly structure ensembles may be generated through molecular dynamic simulations but can also be derived from sequence alignments of know structures or from homology-based modeling.

The two filtering and refining cycles in sequence and structure spaces are further linked during the filtering and evaluative steps because the variant profiles arrived by each cycle are compared and/or passed to the other cycle for further refinement. For the sequence-derived variant profile, it is structurally evaluated on a known template in structure space in order to rank and refine the variant profile. Conversely, the structure-derived variant profile can be passed on to the sequence space to evaluate if they belong to the same superfamily of the hit or variant library or for comparison and partitioning to control the final library size.

1) Sequence Space

In sequence space, the goal is to determine the variant profile that is optimized for the target function. The cycle begins with the identification of the hit library through database sequence search and alignment using the sequence profile. This may be a simple BLAST search or a probabilistic approach such as profile HMM. Based on the variations within the hit library, the sequence can be filtered and partitioned. This is achieved by evaluating the amino acid frequency and distribution at each position. Commonly, the residues with the highest frequencies at each position as well as the residues from the target sequence are included in the variant profile. A cutoff value, such 5% or higher, depending on the distribution of the variant frequency, or amino acids ranked relatively higher at each position can be included in the variant profile.

Partitioning may be necessary to set a practical limit on the final size of the oligonucleotide library. Partitioning can be determined by calculating the size of the oligonucleotide library as a function of the degenerate nucleic acid library of the various variant profile segments. Thus, a highly variable variant profile can be partitioned so that the size of the resulting oligonucleotide library can be set within the limit for effective and efficient experimental synthesis, transformation and screening.

An alternative partitioning scheme is to employ structural correlation information. Since peptides folding in three-dimensions interact among sequentially distant segments, a structural template or a model can be used to assign structurally correlated sequences for partitioning. For instance, the ends of the loop may be correlated while the apex itself is relatively free of interactions with the ends. In such a case, the variant profile can be partitioned into at least two profiles: one for the two ends and one for the apex.

Either or both approaches can be employed in partitioning a highly variant profile. When partitioning, there should be at least 2, preferably 3 or more residue overlaps between the segments so that some structural correlation is maintained between adjacent segments. Either or both approaches can be employed to achieve operationally optimized oligonucleotide library sizes.

Once the sequence variant profile is determined, its library is computationally screened using a known structural template or a homology-based model and a scoring function (see below). This ranking is used to filter and reduce the variant profile by identifying favorable variants while filtering out unfavorable variants, thereby simultaneously enriching and reducing the size of the experimental library.

2) Structure Space

In structure space, the goal also is to determine the variant profile optimized for the target function but starting with one structure or an ensemble of structures and then scoring the sequences based on the average of the ensemble of structures. The cycle begins with a set of structures and associated sequences that can be computationally screened and evaluated using a scoring function.

For a theoretical, ideal scoring function that accounts for all physicochemical variables, the energy score ranking would correlate perfectly with the functional ranking. This is neither possible nor computationally practical and one must use an imperfect scoring function that will coarsely correlate structure or sequence with function. Since the goal of the design protocol is to identify a set of probable sequences that will possess the desired function, an imperfect scoring function that, nevertheless correlates sequence and structure with function, can be used.

Such a scoring function can involve any combination of computational terms that correlates or maps functional values to a sequence or structural value. A simple case is that of a van der Waals energy that correlates hydrophobic packing function with sequences containing the appropriate density of aliphatic or aromatic sidechains. Another might be an enzymatic hydrolytic activity that correlates with the existence of a nucleophilic sidechain group at a particular position in a sequence.

In general, the scoring function will be based on thermodynamic energy sum that incorporates some or all of the contributing terms that correlate with the structural stability and function of the protein. Most commonly, these will include the electrostatic solvation energy, nonpolar solvation energy and sidechain and backbone entropy. MM-PBSA or MM-GBSA is such a method that combines standard terms calculated using molecular mechanical (MM) forcefields with the solvation terms including electrostatic solvation with continuous solvent model, calculated either by solving the Poisson-Boltzmann (BP) equation or using the Generalized Born (GB) approximation, and solvent-accessible solvation term, based on proportionality to the surface area (SA), together with contribution from the conformational entropy, including backbone and side chains. Good correlation between experimental and MM-PBSA calculated values based on the ensemble structures derived from molecular dynamic simulation has been reported (Wang W, Donini O, Reyes C M, Kollman P A. (2001) Annu Rev Biophys Biomol Struct 30, 211–43). The refined scoring function based on the MM-PBSA was used to evaluate the simple scoring function based on the total energy of Amber94 forcefield implemented in CONGEN, which was used to scan a sequence library for its compatibility with a template structure (see for example, FIG. 12). The comparison between the simple scoring function used here and the refined scoring function for a hit library of the lead sequence using one template structure (1cz8) (FIGS. 12D & E) suggests that the simple scoring function is correlated with the refined scoring function, although significant scattering in the correlation map suggests that some refinement in the simple scoring function can be done to improve its agreement with the refined scoring function.

Compared to other scoring functions used in protein and drug design, MM-PBSA or MM-GBSA is a better physical model for scoring and would handle various problems on an uniform basis, although it is computationally expensive because multiple trajectories from molecular dynamic simulation in explicit water is required to calculate the ensemble averages for the system. This method is useful for studying some of the difficult mutants beyond the simple scoring procedure, and can serve as a control to validate the procedure used in high-throughput computational screening.

3) Optimized Variant Profile

The first result of the design protocol is the optimal variant profile. It embodies the results of both the sequence and structure evaluations so that evolutionary and structural preferences are incorporated into the design. Subsequent steps in the functional space aim to evaluate and refine this profile, and, if necessary, modify earlier steps, so that cyclic enrichment of the resulting library can be accomplished at various steps in the design protocol.

In a preferred embodiment, the method comprises:

the method comprises the steps of:

a) providing an amino acid sequence of the variable region of the heavy chain ($V_H$) or light chain ($V_L$) of a lead antibody, the lead antibody having a known three dimensional structure;

b) identifying the amino acid sequences in the CDRs of the lead antibody;

c) selecting one of the CDRs in the $V_H$ or $V_L$ region of the lead antibody;

d) providing an amino acid sequence that comprises at least 3 consecutive amino acid residues in the selected CDR, the selected amino acid sequence being defined as a lead sequence;

e) comparing the lead sequence with a plurality of tester protein sequences;

f) selecting from the plurality of tester protein sequences at least two peptide segments that have at least 10% sequence identity with lead sequence, the selected peptide segments forming a hit library;

g) building an amino acid positional variant profile of the hit library based on frequency of amino acid variant appearing at each position of the lead sequence;

h) combining the amino acid variants in the hit library to produce a combination of hit variants which form a hit variant library;

i) determining if a member of the hit variant library is structurally compatible with the lead structural template using a scoring function;

j) selecting the members of the hit variant library that score equal to or better than the lead sequence;

k) constructing a degenerate nucleic acid library comprising DNA segments encoding the amino acid sequences of the selected members of the hit variant library;

l) determining the diversity of the nucleic acid library, if the diversity is higher than $1\times10^6$, repeating steps j) through l) until the diversity of the diversity of the nucleic acid library is equal to or lower than $1\times10^6$;

m) introducing the DNA segments in the degenerate nucleic acid library into cells of a host organism;

n) expressing the DNA segments in the host cells such that recombinant antibodies containing the amino acid sequences of the hit library are produced in the cells of the host organism;

o) selecting the recombinant antibody that binds to a target antigen with affinity higher than $10^6$ $M^{-1}$; and p) repeating steps e) through o) if no recombinant antibody is found to bind to the target antigen with affinity higher than $10^6$ $M^{-1}$.

As shown in FIG. 2B, the method is executed starting from the target sequence or sequence profile based on structure-based multiple alignment, searching for variant profile based on evolutionary enriched sequence database, and then evaluating their compatibility with structure template or ensembles, and then selecting sequence ensembles that can be targeted experimentally. This procedure has been exemplified in our examples. First, it utilizes the evolutionary information encoded in sequences or their combinations including expression, folding, etc. that are not yet captured in theoretical calculations. Second, after removing a lot of unrelated random sequences, structure-based screening for the resulting library is amenable to refined computational screening. Also refined computational scoring such as MM-PBSA can be applied to some of them using ensemble structures. The inventors believe this procedure tends to give highly refined sequence library for experimental screening with significant savings in time and cost.

FIG. 2C illustrates another embodiment of the method. The method comprises the steps of:

a) providing an amino acid sequence of the variable region of the heavy chain ($V_H$) or light chain ($V_L$) of a lead antibody, the lead antibody having a known three dimensional structure which is defined as a lead structural template;

b) identifying the amino acid sequences in the CDRs of the lead antibody;

c) selecting one of the CDRs in the $V_H$ or $V_L$ region of the lead antibody;

d) providing an amino acid sequence that comprises at least 3 consecutive amino acid residues in the selected CDR, the selected amino acid sequence being defined as a lead sequence;

e) mutating the lead sequence by substituting one or more of the amino acid residues of the lead sequence with one or more different amino acid residues, resulting in a lead sequence mutant library;

f) determining if a member of the lead sequence mutant library is structurally compatible with the lead structural template using a first scoring function;

g) selecting the lead sequence mutants that score equal to or better than the lead sequence;

h) comparing the lead sequence with a plurality of tester protein sequences;

i) selecting from the plurality of tester protein sequences at least two peptide segments that have at least 10% sequence identity with lead sequence, the selected peptide segments forming a hit library;

j) building an amino acid positional variant profile of the hit library based on frequency of amino acid variant appearing at each position of the lead sequence;

k) combining the amino acid variants in the hit library to produce a combination of hit variants;

l) combining the selected lead sequence mutants with the combination of hit variants to produce a hit variant library;

m) determining if a member of the hit variant library is structurally compatible with the lead structural template using a second scoring function;

n) selecting the members of the hit variant library that score equal to or better than the lead sequence;

o) constructing a degenerate nucleic acid library comprising DNA segments encoding the amino acid sequences of the selected members of the hit variant library;

p) determining the diversity of the nucleic acid library, and if the diversity is higher than $1\times10^6$, repeating steps n) through p) until the diversity of the diversity of the nucleic acid library is equal to or lower than $1\times10^6$;

q) introducing the DNA segments in the degenerate nucleic acid library into cells of a host organism;

r) expressing the DNA segments in the host cells such that recombinant antibodies containing the amino acid sequences of the hit library are produced in the cells of the host organism;

s) selecting the recombinant antibody that binds to a target antigen with affinity higher than $10^6$ $M^{-1}$; and t) repeating steps e) through s) if no recombinant antibody is found to bind to the target antigen with affinity higher than $10^6$ $M^{-1}$.

4) Function Space

In functional space, the goal is to express and screen the library derived from the optimized variant profile. There are two components that comprise the function cycle. An operational component that may not directly affect function but is important in the expression of the protein is the optimization of the oligonucleotide. The determination of the practical limit on the size of the oligonucleotide library is used as a guide to sequence partitioning and reprofiling of the variants.

The other component is the functional screen that directly reflects the results of all previous steps and is the final evaluative portion of the design strategy. The results of the experimental functional screen determine whether the library candidates can be passed on for further evaluation or used to enrich and refine the libraries from previous steps. For instance, a set of sequences exhibiting varying levels of function can be used to narrow the variant profile or to give weights to different residues at indicated positions. In addition, sequence space jumps through the use of degenerate oligonucleotide design may lead to the identification of a novel functional variant that can be used to further enrich the optimized variant profile. Alternatively, the frequency of a particular set of amino acid may reflect either a functional preference of expressional preference. In the latter option, a low expressing sequence that, nevertheless, exhibit good function may prompt a modification in the codon usage that can improve expression levels while maintaining function. It is important to select some second or third “tier” variants, ones that occur at lower frequencies, since selecting only the highest frequency variants only leads closer to concensus and likely leads to “average” functioning sequences. It is possible that exceptional variants are likely to come from combinations not observed in nature. While we use natural evolutionary patterns as our guide, we look for combinations not observed in nature, either because they are unfavorable in evolutionary time scale but possibly useful for our more immediate applications, or, perhaps, because nature has yet to try them out. In this regard, structure-based screening of random mutants or their combinations would potentially yield those mutants are yet observed in nature but nevertheless preferred structurally, although this puts stringent requirements on accuracy of the structure and potential functions as well as computational speed.

5) Iteration, Refinement, and Enrichment

The design protocol is divided according to different spaces that are evaluated but all the operational cycles are inter-related and integrated so that information can be exchanged and cycled freely to and from any space in order to continually refine and enrich the library based on the optimized variant profile. As a result, the pathway from target sequence or structure to candidate sequences is not a single pathway but a series of oscillations among the three cycles, each improving the selection in the optimized variant profile.

In addition, functional evaluation and iterative nature of the design protocol not only help improve the variant selection but also help increase the accuracy of the scoring function, at least for the range of sequences and structures examined. A missed prediction may indicate incompatible template. It may also indicate that a particular contribution may need to be more heavily weighed, for instance, backbone entropy in the context of glycine preference in functional screen. A particular charged residue such as Arg versus Lys in $V_H$ CDR3 may be favored because of its role in orientating a specific conformation (see example section below).

6) Re-Profiling of Sequences According to Scores and Ranking

As described above, sequences in the hit variant library can be evaluated based on their structural compatibility with the lead antibody in the presence and absence of the antigen. According to the scores and rankings obtained from the structural evaluation, the sequences in the hit variant library are re-profiled to optimize the sampling of the sequence and structure space for functional sequences. This step involves the selection of a sub-population of the hit variant library that scores better than the lead sequence(s) and re-profiling them to generate an optimized library. One option is to re-profile all of the sequences scoring better than the leads. However, this is likely to lead to too large a library for experimental screen. A preferred way is to select a subset of sequences in a certain low energy window or several such subsets (FIG. 7). This will reduce the eventual size of the experimental nucleic acid library as will be described in the section below and outlined in FIG. 6. When combined with rational selection and design, this step should enrich the library with better scoring sequences.

The modification and optimization of the profile must take into account the ultimate size of the physical nucleic acid library (FIG. 6). One strategy is to re-profile the best scoring 10–20% of the hit variant library to limit the number of positional variants within certain limit that can be easily targeted in experiments (preferably $<10^6$ for degenerate nucleic acid library). Similarly we might select a set of low energy sequences that contain desired amino acids in certain positions.

7) Partitioning of Sequences into Fragments

Another size controlling strategy is to partition the sequences based on structurally correlated and uncorrelated fragments in structure space. These parsed sequences with the smaller variant profiles can be used for generating several smaller libraries. The rationale for this is that, to a first approximation, structurally distant segments are often uncorrelated so that mutations widely separated can be treated independently, whereas those fragments that couple with each other in space should be targeted simultaneously by the combinatorial nucleic acid libraries. In the case of loops, the sequences forming the base of the loop are generally correlated due to loop closure, but the apex is often uncorrelated from the base of the loop. In such a case the amino acid sequence variant profile is partitioned into three segments and the first and third segments (base of the loop) are used for one profile and library design and the second segment (apex of the loop) is used for the second profile and library design. There should be 2 or 3 positional overlaps between the fragments to maintain a small level of structural correlation among the resulting libraries. In a similar fashion, a longer profile can be partitioned into a chain of overlapping segments to span the length of the sequence and corresponding libraries generated. Simple criteria such as the $C_\alpha$ or $C_\beta$ distance matrix can be examined to identify correlated segments (FIG. 28A). Optionally, a more detailed interaction matrix can be mapped out to explore numbers and types of interactions, but the underlying principle is the same for identifying correlated segments.

The resulting re-profiling can be further modified and enhanced based on observed experimental or structural criteria. These can include varying positions with known hydrogen bonds with additional polar amino acids, region of high van der Waals contacts with bulky aliphatic or aromatic groups, or region which might benefit from increased flexibility with glycine. In an experimental feedback, variants may be added based on assay results from earlier screening as a basis for subsequent design improvement. A more sophisticated analysis might take into account the coupling of amino acid groups such as salt bridges or hydrogen bonds within the sequence. Additional design constraints might include solvent accessible surface area of nonpolar groups of proteins.

With the modified and optimized profile, we generate a new amino acid sequence library designated the "hit variant library II" or a group of libraries (hit variant library IIA, IIB, IIC, etc) and score these using the same energy function. The energy distribution should expand beyond the original energy window since variant recombination and profile modification are intended to expand the sequence and structure space covered (FIGS. 7, 13A, 17A, & 18).

Various embodiments of the inventive methodology are described in detail as follows.

3. Construction of Hit Antibody Library in Silico

As illustrated in FIG. 1A, a hit library can be constructed in silico based on the lead sequence from a region of the lead antibody. Sequences from a database of protein sequences, such as genbank of the NIH or the Kabat database for CDRs of antibodies, are searched based on their alignment with the lead sequence by using a variety of sequence alignment algorithms. FIG. 3 illustrates an exemplary procedure for constructing the hit library, which begins with a search of a protein sequence database of varying identity with the lead sequence or sequence profiles. The lead sequence profile is generated by aligning sequences within the same family of a structural motif. This lead sequence profile can be used to build the HMM to search the sequence database for hit libraries of remote homology to the lead sequence. This approach is taken to find a rich pool of diverse hit sequences (i.e., the hit library) to ensure that all available variants of the lead sequence from the database are included.

The database screened against the lead sequence(s) preferably includes expressed protein sequences, including sequences of all organisms. More preferably, the protein sequences originate from mammals including humans and rodents if the frameworks are targeted. Optionally, the protein sequences may originate from a specific species or a specific population of the same species. For example, the protein sequences collected from a human immunoglobulin sequence database can be used to construct the library of polypeptide segments. Compared to the conventional way of building the library using completely random protein sequences, this approach of the present invention takes advantage of the sequence information derived from the evolution of proteins, thus more closely mimicking the natural process of antibody generation and affinity maturation.

Depending on the region/domain of the protein to be designed, databases of proteins with different evolutionary origins may be exploited. For example, to reduce human immunogenicity of the design antibody, sequences of human origins, more preferably germline sequences, are used for the design purpose. On the other hand, to increase the diversity in the CDRs, extensive sequence search and selection from a wide range of databases and/or structure-based design procedures may be employed to increase the structural and/or functional diversity. Through such sequence and structure-based selections, rare combination of sequences may be found in the CDRs while the sequences in the framework regions are kept as close to the human sequence family as possible.

In addition, some combinations of amino acid residues from sequences of diverse species including human or other non-human species including but not limited to mouse, rabbit, etc., may be preferred at certain regions such as the boundaries between CDRs and frameworks in antibodies. This approach may be taken in order to maintain or optimize the relative orientations among various motifs.

Many sequence alignment methods can be used to align sequences from the database with the lead sequence (or lead sequence profiles) ranging from a high to low sequence identity. A number of sequence-based alignment programs have been developed, including but not limited to Smith-Waterman algorithm, Needleman-Wunsch algorithms, Fasta, Blast, Psi-Blast, Clustalx, and profile Hidden Markov Model.

Optionally, a simple sequence search method such as BLAST (Basic Local Alignment Search Tool) can be used for searching closely related sequences (e.g., >50% sequence homology). BLAST uses a heuristic algorithm with position-independent scoring parameters (e.g., BLOSUM62 etc) to detect similarity between two sequences and is widely used in routine sequence alignment (Altschul S F, Gish W, Miller W, Myers E W, Lipman D J (1990) J Mol Biol 215, 403–410). However, the BLAST analysis may be too restrictive to detect remote homologues of the lead sequence. More advanced tools for sequence alignment can be used to search for remote homologues of the lead sequence.

A profile-based sequence alignment method may be used to search for the variants for the lead sequence, such as PSI-BLAST (Position-Specific Iterated BLAST) and HMM. These profile-based sequence alignment methods can detect more remote homologues of the lead sequence (Altschul, S F, Madden, T L, Schaffer A A, Zhang J, Zhang Z, Miller W, Lipman D J (1997) Nucleic Acids Res 25, 3389–3402; Krogh, A, Brown M, Mian S I, Sjolander K m Haussler D (1994) J. Mol. Biol 235, 1501–1531).

PSI-BLAST is a new generation BLAST program belonging to the profile-based sequence searching methods (Altschul, S F, Madden, T L, Schaffer A A, Zhang J, Zhang Z, Miller W, Lipman D J (1997) Nucleic Acids Res 25, 3389–3402). PSI-BLAST automatically combines the statistically significant alignments produced by BLAST into a position-specific matrix to score sequence alignment in the database. The newly searched sequences are incorporated into the position-specific scoring matrix to start another round of sequence search in the database. This procedure is iterated until no new hits are found or the pre-set criteria are met. Although PSI-BLAST may not be as sensitive as the Profile Hidden Markov Models (HMM), it can be used in the present invention because of its speed and ease of operation in the absence of a pre-built motif profile. The Profile Hidden Markov Models or HMM are statistical models of the primary sequence consensus of a given sequence or sequence alignment family. The sequence family is defined as the multiple sequence alignment resulting from the corresponding multiple sequence and/or structure alignment. The formal probabilistic basis underlying HMM makes it possible to use Bayesian probability theory to guide the setting of the scoring parameters based on the profile of aligned sequences. This same feature also allows the HMM to use a consistent approach, using the position-dependent scores, to score the alignment for both amino acids and gaps. These features in HMM make it a powerful method to search for remote homologues compared to the traditional heuristic methods (Eddy S. R (1996) Curr Opin Struct. Biol 6, 361–365). The pattern in the primary sequence can be detected by the pattern recognition algorithms and therefore can be used to pull out more members related to the target sequence (when one sequence is used) or sequence profile (when multiple sequence alignment is used). To capture the higher order correlation in a sequence, or the interactions between amino acids in three-dimensional space, the multiple sequence alignment resulting from multiple structural alignment is a preferred method to be used in the present invention to generate the hit library.

Optionally, a structure-based sequence alignment may be used to search for a highly diverse hit library. This method is advantageous because it is a gold standard that can be used for comparing various multiple sequence alignments in the absence of any detectable sequence homology (Sauder J M, Arthur J W, Dunbrack R L Jr (2000) Proteins 40, 6–22). The multiple structure alignment can directly yield the corresponding multiple sequence alignment. Alternatively, these closely related structures can be used as structural templates for sequence threading to generate the multiple sequence alignment profile (Jones D T (1999) J Mol Biol 1999, 797–815). Methods combining multiple sequence and structure alignments have been reported to annotate the structural and functional properties of known protein sequences (Al-Lazikani B, Sheinerman F B, Honig B (2001) PNAS 98, 14796–14801).

Also optionally, a reverse threading process may be used to search for of a highly diverse hit library. A reverse threading process is the counter part of the threading process. Threading is a process of assigning the folding of a protein by threading its sequence (i.e., the query sequence) to a library of potential structural templates by using a scoring function that incorporates the sequence side chain interactions as well as the local parameters such as secondary structure and solvent exposure. The threading process starts with a prediction of the secondary structure of an amino acid sequence and solvent accessibility for each residue of the query sequence. The resulting one-dimensional (1D) profile of the predicted structure is threaded into each member of a library of known 3D structures. The optimal threading for each sequence-structure pair is obtained using dynamic programming. The overall best sequence-structure pair constitutes the predicted 3D structure for the query sequence.

In contrast, reverse threading is a process of searching for the optimal sequence(s) from sequence database by threading them onto a given target structure or structure cluster ensembles of the target structure. Various scoring functions may be used to select for the optimal sequence(s) from the library comprising protein sequences with various lengths.

For example, amino acid sequences from a human germline immunoglobulin database can be threaded onto the 3D structure of the lead antibody to search for the sequences with acceptable scores. The selected sequences constitute the hit library. The reverse threading process is the opposite of the threading process in that the former tries to find the best sequences fitting to the target structural template whereas the latter finds the best 3D structure structures that fit the target structure profile.

Additionally, the top hits of the sequences found for the lead antibody may be profiled by reverse threading multiple amino acids at each position in a combinatorial approach to select for the best "consensus" combinatorial sequences compatible with the 3D structure of the lead antibody. This process of searching for a consensus sequence is different from the method of using simple sequence average at each position described in Knappik, et al (2000). The consensus sequence according to the present invention is created using the structurally-based reverse engineering approach using all possible combination of amino acids that are allowed at each position, based on the retrieved sequences and optimized by scoring their compatibility with the structural template.

In addition to the methods used for sequence alignment, the sequence motif and the corresponding database used in the sequence alignment are also of critical importance in the present inventive method. The sequence or sequence profile used here are defined based on structural analysis of the protein functions for antibody regions, such as the CDR motifs (CDR1, CDR2 and CDR3) for antigen binding and the framework regions (FR1, FR2, FR3 and FR4) for supporting the antibody scaffold. As an example, Genbank and Kabat databases can be used to search for sequence hits from various species to increase the diversity of the hit library matching the CDRs of antibodies in order to maximize the binding affinity of a designed antibody. On the other hand, human or even human germline sequence database is preferably used to search for sequence hits for framework design in order to decrease the chance of creating immunogenic epitopes of non human origins in a designed framework. This sequence selection step allows for maximum flexibility and control of the sequence source for design, especially when considering the eventual therapeutic application of the designed antibody.

The hit library can be refined further by eliminating redundant sequences and re-profiled to get a more accurate HMM or PSI-BLAST profile. As described in detail in the Example section, the $V_H$ CDR3 sequence, according to the Kabat classification (and also the structure motif) of a humanized anti-VEGF antibody with or without a few residues flanking them at N- or C-termini, was used as the lead sequence. The utilities (hmmbuild, hmmcalibrate, hmmsearch, hmmalign) in HMMER 2.1.1 software package with default setting (as shown in the website of hmmer.wustl.edu) were used to build the HMM model, to calibrate HMM model against synthesized random sequences, to search the database for hit sequences and align them. Only hit sequences with the same length to the lead sequence are used for alignment and variant profile. Insertion or deletion in aligned sequences can be also used to profile the variants at aligned positions.

As illustrated in FIG. 3, when a single lead sequence of the $V_H$ CDR3 sequence of the anti-VEGF antibody was used as HMM to search the Kabat database, 108 unique sequences were found with sequence identity ranging from 40 to 100% relative to the lead sequence (FIGS. 10A & 19C). When a multiple aligned sequence profile of this lead sequence was used as HMM to search the same Kabat database, 251 unique sequence hits were found with sequence identity ranging from 15 to 100% to the lead sequence (FIG. 19C). These results show that a profile HMM can find sequences with remote homology to the lead sequence. Thus, a sequence profile derived from the multiple structure-alignment would extend the diversity of the hit library.

Sequences of the hit library also depend on the database used. For example, by replacing the Kabat database with Genpept in the above, hits that are different from those in Kabat database were found either when the single lead sequence was used as HMM or when the structure-based sequence profile was used as HMM.

The sequences in the hit library constructed by searching the databases can be analyzed (e.g., by profiling based on the positional frequency of each amino acid residue) and used directly for screening in vitro or in vivo for the desired function(s). See Route I in FIG. 1A and FIG. 3.

Optionally, the sequences in the hit library are profiled and used to construct a hit variant library I which is then screened in vitro or in vivo for the desired function(s). See Route II in FIG. 1B and FIG. 4.

Also optionally, the hit library is filtered based on the scoring of their compatibility with the lead structural template using methods such as reverse threading or forcefield-based full atom representation. Based on the resulting ranking of the scores, a hit variant library II is selected for screening in vitro or in vivo for the desired function(s). See Route III in FIG. 1C and FIG. 5.

Also optionally, the hit variant library I is filtered based on the scoring of their compatibility with the lead structural template using methods such as threading or forcefield-based full atom representation. Based on the the relative ranking of the hits, a subset of multiply aligned sequences are selected to create hit variant library II and screened in vitro or in vivo for the desired function(s). See Route IV in FIG. 1D and FIG. 5.

4. Construction of the Hit Variant Library

To further explore the rich diversity encoded in the structure and sequence spaces of proteins, the hits that are selected based on sequence alignment are profiled at each amino acid position of the sequences to generate a variant profile. A hit variant library is combinatorially enumerated using this variant profile. FIG. 4 illustrates an exemplary process for constructing a hit variant library. The variant profile generated from the hit library (i.e., sequence hits or filtered sequence hits) is listed based on frequency of amino acid appearing at each position in the hit sequences (FIGS. 11 & 19B). The variants profiled provides an excellent starting point for constructing combinatorial libraries.

Some cutoff values based on the frequencies (e.g., a frequency of over 5% or higher) or preferred variants of amino acids at each position, and/or computational results can be applied to reduce the size of this hit variant library (see the lower portion of FIG. 11 for a cutoff at 10% of the totoal number of hits; FIG. 19B uses 5%). The variants based on these highly preferred amino acid residues at each position should offer a good pool of recombinant sequences for fishing out sequences with high affinity or other desired functions.

The informational sequence entropy, calculated based on the variant frequency at each position, provides a quantitative means to measure how significant the residue identities in aligned sequences deviates from a random distribution of amino acid residues. A relative entropy can be used in the present invention to take into account highly variable mutagenesis probabilities of the sequences involving protein variants (Plaxco K W, Larson S, Ruczinski, Riddle D S, Thayer E C, Buchwitz B, Davidson A R, Baker D (2000) J Mol Biol 298, 303–312). The inventors believe that the relative site entropies provide a good guide for the positions and mutants that should be targeted for computational and experimental screening since they are based on real evolutionary data from databases of expressed proteins.

The relative site entropy measures the diversity at each position of amino acid residues accumulated during evolution while maintaining structure and function of the hit sequences. These sites are chosen to recombine for computational and experimental screening. Because the size of the resulting combinatorial hit variant library is much smaller than that generated by a random combination of all 20 amino acids at each position, it is possible to carry out more accurate and detailed computational or even direct experimental screening.

The sequence entropies resulting from the hit library in the present invention are not related to the site entropies which others in the field have used to measure the structural tolerance toward amino acid substitution, using force-field based computational method (Voigt C A, Mayo S L, Arnold F H, Wang Z G (2001) PNAS 98, 3778–3783). Although a forcefield-based method would provide some novel mutants that may not yet have been sampled by evolution, the site entropy derived from the evolutionary sequences (i.e., the sequence entropy) should provide more meaningful statistics on the variation and preferred mutants at each position with all information including structural, kinetic, expression and biological activities incorporated. This may be important for targeting difficult structures such as loop regions in antibodies that are not yet fully understood or predicted by forcefield-based methods, but they can be modeled with some confidence using the database-based methods of the present invention. The homology-based method that relies on the evolutionary information is still one of the most reliable ways to model loop structures that can be augmented with forcefield-based simulations.

As will be described in detail in the Example section, the variant profile for an anti-VEGF antibody (the lead antibody) was searched by using several different approaches. Based on a sequence of $V_H$ CDR3 of this lead antibody, the variant profiles of the hit lists from Kabat, genpept and a non-redundant database, combining Kabat, genpept, imgt, and others, are listed. Important mutants observed by others in affinity matured sequences from this antibody also appear with high frequency in the variant profile searched using the methods of the present invention. For example, it was believed that the single most important mutant was H97 in the lead sequence replaced by Y97 in the matured sequence (FIG. 9B) which is almost 50% in the amino acid variants at this position (FIG. 11). The above-described methods of the present invention have several advantages in protein design and engineering. In any recombinant library, the diversity is necessarily limited by the ability to screen, which means that allocation and, thus design, of diversity is an important factor in the creation of a functionally relevant library. The inventive method is an in silico rational design of protein, in particular, antibody. It begins with the selection of functionally similar “natural” polypeptide fragments from databases of expressed proteins to form the hit library. Analysis of specific positional variations in the “naturally” occurring peptide fragments yields evolutionary data about preferred residues and position—the variant profile. A critical analysis of the variants can identify important residues and combinations. Combinatorial enumeration of the reduced set of select variants leads to the generation of a hit variant library that is focused on the functionally relevant sequences.

Starting with the variant profile, the in silico rational library design of the present invention generates a focused library or libraries of protein fragments based on functional and structural data. To some extent, in silico recombination is similar in principle to DNA shuffling of a family of homologous sequences. But the present inventive approach is a highly efficient sequence recombination procedure for a family of protein sequences with widely distributed sequence homology. Furthermore, in the present invention, the recombinations occur at the amino acid level and can be localized to specific functional region to generate a library whose members are designed rather than randomly recombined. It is not constrained by a homology requirement and can be selectively modified according to structural or experimental data. For example, the sequences in the hit library have sequence identities relative to the lead sequence ranging from 100 to 20, or even lower depending on the searching method and database used. In comparison, the DNA shuffling is DNA recombination process between closely related sequence homologues with stringent requirement on the sequence homology between recombined nucleic acid sequence; DNA shuffling is inefficient in generating beneficial mutant recombination and it is prone to random mutations during experimental recombination.

5. Structure-Based Evaluation of Antibody Variant Library

The hit library or a hit variant library, derived from the recombination of the variant profile from the hit library as described above, may be evaluated based on their structural compatibility with the lead protein. For structure-based evaluation of the antibody variant library, the present invention addresses the following questions: i) how to model conformations of noncanonical loops in the presence of antigen which forms a protein complex with the antibody; (ii) how to place side chains on CDR loop backbones to best fit the antibody and/or antigen structure; and (iii) how to combine CDR loops with the best framework model to allow formation of stable antibody-antigen complex with high affinity. Implementing procedures are described in detail as follows.

1) Antibody Structures and Structure Models

A structural template of the lead antibody can either be taken directly from an X-ray or NMR structure or modeled using structural computational engines described below. As shown in the EXAMPLE section, the structural templates for anti-VEGF antibody are taken from PDB databank, 1BJ1 for the parental antibody and 1CZ8 for the matured antibody. Both templates were used in the presence and absence of the antigen VEGF. The scoring listed in the examples is from 1CZ8 in the presence of the antigen VEGF.

2) Evaluation Based on Structural Template of the Lead Antibody

As an example, an antibody with a known 3D structure serves as the lead protein. This requirement for a well-defined structure (such as one obtained by X-ray crystallography) is not absolute since alternative techniques, such as homology-based modeling, may be applied to generate a reasonably defined template structure for a target protein to be engineered. Generation of the hit variant library requires the determination, modification, and optimization of the amino acid positional variant profile. The lead sequence and sequences in the hit library and the hit variant library are scored in the context of the 3D structure of the lead antibody and scored to obtain the ranking distribution for these sequences. It is noted that, although the scoring in the EXAMPLE section is based on an empirical all-atom energy function, any computationally tractable scoring or fitness function may be applied to structurally evaluate these sequences.

FIG. 5 illustrates an exemplary procedure for structural evaluation of sequences from the lead, the hit library and the hit variant library. For scoring and ranking, these sequences are built into the lead structural template by substituting side chains from a backbone-dependent/independent rotamer library (Dunbrack R L Jr, Karplus M (1993) J Mol Biol 230:543–574). The side chains and the backbone of the substituted segment are then locally energy minimized to relieve local strain. Each structure is scored using a custom energy function that measures the relative stability of the sequence in the lead structural template.

Comparison of the energies for sequences from the lead, the hit library and the hit variant library indicates the degree of structural compatibility of the various sequences with the lead structural template. It is not unreasonable to obtain a very broad distribution with many sequences scoring better or worse than the lead sequence. The focus is not to identify specific sequences (although permissible) but to identify a population of sequences or a sequence ensemble with average scores equal to or better than the lead sequences and share ensemble properties in sequence that can be targeted simultaneously using degenerate nucleic acid libraries. The amino acid sequence ensemble represents a sequence space that is likely to show good structural compatibility with better binding sites and orientation for epitope recognition than a single, specific sequence. The combinatorial libraries of the sequence ensembles distributed around the statistical ensemble average should be targeted experimentally in order to increase the chance of finding good candidates with improved affinity.

3) Evaluation Based on Lead Structural Template in the Presence of its Ligand

Optionally, sequences from the lead, the hit library and the hit variant library can be evaluated based on the lead structural template in the presence of its ligand or antigen, for example, a lead anti-VEGF antibody in complex with VEGF. This approach is useful when structure of the complex formed by the lead protein and its ligand is known or readily ascertained.

In the presence of the antigen, the complete thermodynamic cycle of complex formation between an antibody and an antigen may be included in the calculation. The conformation of the antibody, especially in the combining site, may be modeled based on individual CDR loop conformation from its canonical family with preferred side-chain rotamers as well as the interactions between CDR loops. A wide range of conformations, including those of the side chains of amino acid residues and those of the CDR loops in the antigen combining site, can be sampled and incorporated into a main framework (or a scaffold) of an antibody. With the antigen present, such conformational modeling assures higher physical relevancy in the scoring, using physical-chemical force fields as well as semi-empirical and knowledge-based parameters, and better representation of the natural process of antibody production and maturation in the body.

4) Correlation of the Scores of Antibody Sequences in the Presence and Absence of an Antigen It is desirable to have the complex structure between an antigen and its antibody to focus the antibody library towards sequences with good probability of binding the antigen. Unfortunately, for most antibodies of biomedical interest, the complex structure between the antibody and antigen is not yet available.

The inventors found that many sequences that are favorable in stabilizing target antibody scaffold are also among the selected candidates that can stabilize the specific antibody-antigen complex even for the $V_H$ CDR3 that is involved directly in binding to the antigen. Correlation analysis shows that there is a general correlated trend in the scores of the antibody sequences in the presence and absence of the antigen (FIG. 12C). Further, a large population of sequences selected with good scores is favorable in stabilizing the scaffolding of the binding motifs such as $V_H$ CDR3 for anti-VEGF used here.

It should be noted that, without the complex structure, the antibody structure alone can still give a population of sequences that stabilize the target scaffold while possessing the right binding site for the antigen. Although conformational change upon antigen binding has been observed, it is not clear if conformation change is only one of many possible solutions or is an absolute requirement for the antigen-antibody interaction. The goal is to identify an ensemble of sequences likely to form a functional proteins so the bound structure is not a requirement as long as it does not undergo major conformational shifts. Based on the available structures of antibodies in both bound and unbound states, this is a good assumption. At least, some structure fluctuations are allowed in the approach taken here (see 19A) as far as they belong to the same family of ensemble structures.

Alternatively, if the structure of the lead antibody is not available, a template may be generated by modeling. Antibody structure or structure motifs are among some of the best known examples of proteins for which structural models can be generated, using homology modeling, with a relatively high degree of confidence. Thus, it is still possible to target a sequence library for the lead sequence without using the lead structure template. As will be shown in the EXAMPLE section, stretches of sequence libraries that cover the target motifs can be synthesized and used to screen for antibody with high affinity without relying on the structure of the lead antibody.

5) Structural Computational Engines

Many programs are available for modeling and evaluating the libraries against the lead structural template. For example, a molecular mechanics software may be employed for these purposes, examples of which include, but are not limited to CONGEN, SCWRL, UHBD, GENPOL and AMBER.

CONGEN (CONformation GENerator) is a program for performing conformational searches on segments of proteins (R. E. Bruccoleri (1993) *Molecular Simulations* 10, 151–174 (1993); R. E. Bruccoleri, E. Haber, J. Novotny, (1988) Nature 335, 564–568 (1988); R. Bruccoleri, M. Karplus. (1987) Biopolymers 26, 137–168. It is most suited to problems where one needs to construct undetermined loops or segments in a known structure, i.e. homology modeling. The program is a modification of CHARMM version 16, and has most of the capabilities of that version of CHARMM (Brooks B R, Bruccoleri B E, Olafson B D, States D J, Swaminathan S, Karplus M. (1983) J. Comput. Chem. 4, 187–217).

The basic energy function used includes terms for bonds, angles, torsional angels, improper angles, van der Waals and electrostatic interactions with distance dependent dielectric constant using Amber94 forcefield which can be determined using CONGEN. (see EXAMPLE section).

CONGEN program is used to search for low-energy conformers that are close or correspond to the naturally occurring structure with lowest free energy (Bruccoleri and Karplus (1987) Biopolymers 26:137–168; and Bruccoleri and Novotny (1992) Immunomethods 96–106). Given an accurate Gibbs function and a short loop sequence, all of the stereochemically acceptable structures of the loop can be generated and their energies calculated. The one with the lower energy is selected.

The program can be used to perform both conformational searches and structural evaluation using basic or refined scoring function. The program can calculate other properties of the molecules such as the solvent accessible surface area and conformational entropies, given steric constraints. Each one of these properties in combination with other properties described below can be used to score the digital libraries.

According to the present invention, the defined canonical structures for five of the CDRs ($V_L$ CDR1, 2, and 3, and $V_H$ CDR1, and 2) except for $V_H$ CDR3. $V_H$ CDR3 is known to show large variation in its length and conformations, although progress has been made in modeling its conformation with increasing number of antibody structures becoming available in the PDB (protein data bank) database. CONGEN may be used to generate conformations of a loop region (e.g., $V_H$ CDR3) if no canonical structure is available, to replace the side chains of the template sequence with the corresponding side chain rotamers of the target amino acids. Third, the model can be further optimized by energy minimization or molecular dynamics simulation or other protocols to relieve the steric clashes and strains in the structure model.

SCWRL is a side chain placing program that can be used to generate side chain rotamers and combinations of rotamers using the backbone dependent rotamer library (Dunbrack R L Jr, Karplus M (1993) J Mol Biol 230:543–574; Bower, M J, Cohen F E, Dunbrack R L (1997) J Mol Biol 267, 1268–1282). The library provides lists of chi1-chi2-chi3-chi4 values and their relative probabilities for residues at given phi-psi values. The program can further explore these conformations to minimize sidechain-backbone clashes and sidechain-sidechain clashes. Once the steric clash is minimized, the side chains and the backbone of the substituted segment can be energy minimized to relieve local strain using CONGEN (Bruccoleri and Karplus (1987) Biopolymers 26:137–168).

Several automatic programs that are developed specifically for building antibody structures may be used for structural modeling of antibody in the present invention. The ABGEN program is an automated antibody structure generation algorithm for obtaining structural models of antibody fragments. Mandal et al. (1996) Nature Biotech. 14:323–328. ABGEN utilizes a homology based scaffolding technique and includes the use of invariant and strictly conserved residues, structural motifs of known Fab, canonical features of hypervariable loops, torsional constraints for residue replacements and key inter-residue interactions. Specifically, the ABGEN algorithm consists of two principal modules, ABalign and ABbuild. ABalign is the program that provides the alignment of an antibody sequence with all the V-region sequences of antibodies whose structures are known and computes alignment score scores. The highest scoring library sequence is considered to be the best fit to the test sequence. ABbuild then uses this best fit model output by ABalign to generate the three-dimensional structure and provides Cartesian coordinates for the desired antibody sequence.

WAM (Whitelegg N R J and Rees, A R (2000) Protein Engineering 13, 819–824) is an improved version of ABM which uses a combined algorithm (Martin, A C R, Cheetham, J C, and Rees A R (1989) PNAS 86, 9268–9272) to model the CDR conformations using the canonical conformations of CDRs loops from x-ray PDB database and loop conformations generated using CONGEN. In short, the modular nature of antibody structure makes it possible to model its structure using a combination of protein homology modeling and structure predictions.

In a preferred embodiment, the following procedure will be used to model antibody structure. Because antibody is one of the most conserved proteins in both sequence and structure, homology models of antibodies are relatively straightforward, except for certain CDR loops that are not yet determined within existing canonical structures or those with insertion or deletions. However, these loops can be modeled using algorithms that combine homology modeling with conformational search (for example, CONGEN can be used for such purpose).

The defined canonical structures for five of the CDRs (L1,2,3 and H1,2) are used. H3 in variable heavy chain (i.e., $V_H$ CDR3) is known to show a large variation in its length and conformation, although progress has been made in modeling its conformation as more antibody structures became available. The modeling methods include protein structure prediction methods such as threading, and comparative modeling, which aligns the sequence of unknown structure with at least one known structure based on the similarity modeled sequence. The de novo or ab initio methods also show increasing promise in predicting the structure from sequence alone. The unknown loop conformations can be sampled using CONGEN if no canonical structure is available (Bruccoleri R E, Haber E, Novotny J (1988) Nature 355, 564–568). Alternatively, ab initio methods, including but not limited to Rosetta ab initio method, can be used to predict antibody CDR structures (Bonneau R, Tsai J, Ruczinski I, Chivian D, Rohl C, Strauss C E, Baker D (2001) Proteins Suppl 5, 119–126) without relying on similarity at the fold level between the modeled sequence and any known structures. A more accurate method that uses the state-of-the-art explicit solvent molecular dynamics and implicit solvent free energy calculations can be used to refine and select for native-like structures from models generated from either CONGEN or Rossetta ab initio method (Lee M R, Tsai J, Baker D, Kollman P A (2001) J Mol Biol 313, 417–430).

Either the X-ray structures as used here (1BJ1 and/or 1CZ8) or the modeled structure as described above can be used as the structural template for designing antibody library for experimental screening described below.

6) Scoring Functions for Structural Evaluation

In one embodiment of the present invention, computational analysis is used for structural evaluation of the selected sequences from the sequence evaluation processes described above in Sections 3 and 4. The structural evaluation is based on an empirical and parameterized scoring function and is intended to reduce the number of subsequent in vitro screenings necessary.

This approach uses an existing structural template to score all the amino acid libraries generated. The use of a known structure as a template to assess antibody-antigen interaction assumes that (i) the structures of the antibody and antigen molecules do not change significantly between bound and free states, (ii) the mutations in the CDRs do not significantly alter the global as well as local structures and (iii) the energetic effects due to mutations in the CDRs are localized and can be scored to assess functions directly related to the mutations. An advantage of having a known structure as a template is that it can serve as a good starting point for design improvements rather than compared to the more challenging approach using modeled structures. The energy distribution of these sequence hits should reveal how well they cover the fitness function of the target scaffold in terms of their structural compatibility with the target.

Since the above-described assumptions necessarily introduce errors due to uncertainties in the structures of the mutants, it is likely that a sophisticated scoring function would still fail to give meaningful prediction if the mutant has altered the structure. A generic but well tested forcefield (see below) was used in the initial calculations in the model system of anti-VEGF antibody as shown in the Example section. It may avoid the bias built into the specific systems in general if the preferred region of the fitness landscape can be explored by sampling the ensemble sequences implemented experimentally. However, the present invention does not preclude the use of more sophisticated scoring functions for the structural evaluation.

Many energy functions can be used to score the compatibility between sequences and structures. Typically, four kinds of energy functions can be used: (1) empirical physical chemistry forcefields such as standard molecular mechanic forcefields discussed below that are derived from simple model compounds; (2) knowledge-based statistical forcefields extracted from protein structures, the so called potential of mean force (PMF) or the threading score derived from the structure-based sequence profiling; (3) parameterized forcefield by fitting the forcefield parameters using experimental model system; (4) combinations of one or several terms from (1) to (3) with various weighting factor for each term.

The following are some well-tested physical-chemistry forcefields that can be used or incorporated into the scoring functions. For example, amber 94 forcefield was used in CONGEN to score the sequence-structure compatibility in the examples below. The forcefields include but are not limited to the following forcefields which are widely used by those skilled in the art: Amber 94 (Cornell, W D, Cieplak P, Bayly C I, Gould I R, Merz K M Jr, Ferguson D M, Spellmeyer D C, Fox T, Caldwell J W and Kollman P A. *JACS* (1995) 117, 5179–5197 (1995); CHARMM (Brooks, B. R., Bruccoleri, R. E., Olafson, B. D., States, D. J., Swaminathan, S., Karplus, M. (1983) J. Comp. Chem. 4, 187–217.; MacKerell, A D; Bashford, D; Bellott, M; Dunbrack, R L; Eva seck, J D; Field, M J; Fischer, S; Gao, J; Guo, H; Ha, S; JosephMcCarthy, D; Kuc nir, L; Kuczera, K; Lau, F T K; Mattos, C; Michnick, S; Ngo, T; Nguyen, D T; Pro hom, B; Reiher, W E; Roux, B; Schlenkrich, M; Smith, J C; Stote, R; Straub, J; Watanabe, M; WiorkiewiczKuczera, J; Yin, D; Karplus, M (1998) J. Phys. Chem., B 102, 3586–3617); Discover CVFF (Dauber-Osguthorpe, P.; Roberts, V. A.; Osguthorpe, D. J.; Wolff, J.; Genest, M.; Hagler, A. T. (1988) Proteins: Structure, Function and Genetics, 4, 31–47.); ECEPP (Momany, F. A., McGuire, R. F., Burgess, A. W., & Scheraga, H. A., (1975) J. Phys. Chem. 79, 2361–2381.; Nemethy, G., Pottle, M. S., & Scheraga, H. A., (1983) J. Phys. Chem. 87, 1883–1887.); GROMOS (Hermans, J., Berendsen, H. J. C., van Gunsteren, W. F., & Postma, J. P. M., (1984) Biopolymers 23, 1); MMFF94 (Halgren, T. A. (1992) J. Am. Chem. Soc. 114, 7827–7843.; Halgren, T. A. (1996) J. Comp. Chem 17, 490–519.; Halgren, T. A. (1996) J. Comp. Chem. 17, 520–552.; Halgren, T. A. (1996) J. Comp. Chem. 17, 553–586.; Halgren, T. A., and Nachbar, R. B. (1996) J. Comp. Chem. 17, 587–615.; Halgren, T. A. (1996) J. Comp. Chem. 17, 616–641.); OPLS (see Jorgensen, W. L., & Tirado-Rives, J.,(1988) J. Am. Chem. Soc. 110, 1657–1666.; Damm, W., A. Frontera, J. Tirado-Rives and W. L. Jorgensen (1997) J. Comp. Chem. 18, 1955–1970.); Tripos (Clark, M., Cramer III, R. D., van Opdenhosch, N., (1989) Validation of the General Purpose Tripose 5.2 Force Field, J. Comp. Chem. 10, 982–1012.); MM3 (Lii, J-H., & Allinger, N. L. (1991) J. Comp. Chem. 12, 186–199). Other generic forcefields such as Dreiding (Mayo S L, Olafson B D, Goddard (1990) J Phy Chem 94, 8897–8909) or specific forcefield used for protein folding or simulations like UNRES (United Residue Forcefield; Liwo et al., (1993) Protein Science 2, 1697–1714; Liwo et al., (1993) Protein Science 2, 1715–1731; Liwo et al., (1997) J. Comp. Chem. 18, 849–873; Liwo et al., (1997) J. Comp. Chem. 18:874–884; Liwo et al., (1998) J. Comp. Chem. 19:259–276.), may also be used.

The statistical potentials derived from protein structures can be also used to assess the compatibility between sequences and protein structure using. These potential include but not limited to residue pair potentials (Miyazawa S, Jernigan R (1985) Macromolecules 18, 534–552; Jernigan R L, Bahar, I (1996) Curr. Opin. Struc. Biol. 6, 195–209). The potentials of mean force (Hendlich et al., (1990) J. Mol. Biol. 216, 167–180) has been used to calculate the conformational ensembles of proteins (Sippl M (1990) J Mol Biol. 213, 859–883). However, some limitations of these forcefields are also discussed (Thomas P D, Dill K A (1996) J Mol Biol 257, 457–469; Ben-Naim A (1997) J Chem Phys 107, 3698–3706).

Another methods to score the compatibility between sequences and structure is to use sequence profiling (Bowie J U, Luthy R, Eisenberg D A (1991) Science 253, 164–170) or threading scores (Jones D T, Taylor W R, Thornton J M (1992) Nature 358, 86–89; Bryant, S H, Lawrence, C E (1993) Proteins 16, 92–112; Rost B, Schneider R, Sander C (1997) J Mol Biol 270, 471–480; Xu Y, Xu D (2000) Proteins 40, 343–354). These statistical forcefields based on the quasichemical approximation or Boltzmann statistics or Bayes theorem (Simons K T, Kooperberg C, Huang E, Baker D (1997) J Mol Biol 268, 209–225) are used to assess the goodness of the fit between a sequence and a structure or for protein design (Dima R I, Banavar J R, Maritan A (2000) Protein Science 9, 812–819).

Furthermore, the structure-based thermodynamic parameters related to the thermodynamic stability of the protein structures can be also used to evaluate the fitness between a sequence and a structure. In the structure-based thermodynamic methods, the thermodynamic quantities such as heat capacity, enthalpy, entropy can be calculated based on the structure of a protein to explain the temperature-dependence of the thermal unfolding using the thermodynamic data from model compounds or protein calorimetry studies (Spolar R S, Livingstone J R, Record M T (1992) Biochemistry 31, 3947–3955; Spolar R S, Record M T (1994) Science 263, 777–784; Murphy K P, Freire E (1992) Adv Protein Chem 43, 313–361; Privalov P L, Makhatadze G I (1993) J Mol Biol 232, 660–679; Makhatadze G I, Privalov P L (1993) J Mol Biol 232, 639–659). The structure-based thermodynamic parameters can be used to calculate structural stability of mutant sequences and hydrogen exchange protection factors using ensemble-based statistical thermodynamic approach (Hilser V J, Dowdy D, Oas T G, Freire E (1998) PNAS 95, 9903–9908). Thermodynamic parameters relating to statistical thermodynamic models of the formation of the protein secondary structures have also been determined using experimental model systems with excellent agreement between predictions and experimental data (Rohl C A, Baldwin R L (1998) Methods Enzymol 295, 1–26; Serrano L (2000) Adv Protein Chem 53, 49–85).

A combination of various terms from molecular mechanic forcefields plus some specific components has been used in most protein design programs. In a preferred embodiment, the forcefield is composed of one or several terms such as the vdw, hydrogen bonding and electrostatic interactions from the standard molecular mechanics forcefields such as Amber, Charmm, OPLS, cvff, ECEPP, plus one or several terms that are believed to control the stability of proteins.

To improve the scoring function, additional energy terms are included in later steps that allow tuning of the scoring function to better address deviations from experimental results and influence of specific antibody-antigen interactions of interest. For example, one energy term can penalize arginine mutation to reduce its contribution to the overall score due to the uncertainty of prediction its sidechain conformation and to compensate for the bias in the current scoring function that favors arginine. Another energy term can score the charged and polar group solvent exposure based on surface area calculation so that mutations that lead to charge burial are penalized according to exposed surface.

In practice, there are many scoring functions that can be used to score the compatibility of sequences with a template structure or structure ensemble. The refined scoring function is composed of several terms including contributions from electrostatic and van der Waals interactions, $\Delta G_{MM}$ calculated using molecular mechanics forcefield, contribution from solvation including electrostatic solvation and solvent-accessible surface, $\Delta G_{sol}$, and contribution from the conformational entropy (Sharp K A. (1998) Proteins 33, 39–48; Novotny J, Bruccoleri R E, Davis M, Sharp K A (1997) J Mol Biol 268, 401–411).

A simple fast way for computational screening is to calculate structural stability of a sequence using the total or combination of energy terms using a basic scoring function that includes terms from molecular mechanic forcefield such as Amber94 as implemented in CONGEN.

$$\Delta E_{total}=E_{bond}+E_{angel}+E_{dihed}+E_{impr}+E_{vdw}+E_{elec}+E_{solvation}+E_{other}$$

or alternatively, the binding free energy is calculated as the difference between the bound and unbound states using a refined scoring function $$\Delta G_b=\Delta G_{MM}+\Delta G_{sol}-T\Delta S_{ss}$$

where:

$$\Delta G_{MM}=\Delta G_{ele}+\Delta G_{vdw} \quad (1)$$

$$\Delta G_{sol}=\Delta G_{ele\text{-}sol}+\Delta G_{ASA} \quad (2)$$

The $\Delta G_{ele}$ and $\Delta G_{vdw}$ electrostatic and van der Waals interaction energy are calculated using Amber94 parameters implemented in CONGEN for $\Delta G_{MM}$, whereas the $\Delta G_{ele\text{-}sol}$ is electrostatic solvation energy required to move a heterogeneously distributed charges in a protein with no dielectric boundary into an aqueous phase with dielectric boundary defined by the shape of a protein. This is calculated by solving the Poisson-Boltzmann equation for the electrostatic potential for the reference and mutant structures. $\Delta G_{ASA}$, the nonpolar energy is the energetic cost of moving nonpolar solute groups into an aqueous solvent, resulting in the reorganization of the solvent molecules. This has been shown to correlate linearly with the solvent accessible surface area of the molecule (Sitkoff D, Sharp, K A, Honig B (1994) J Phys Chem 98, 1978–1988; Pascual-Ahir & Silla (1990) J Comp Chem 11, 1047–1060).

The change in the side chain entropy ($\Delta S_{ss}$) is a measure of the effect on the local side chain conformational space, particularly at the binding interface. This is calculated from the ratio of the number of allowed side chain conformations in the bound and unbound states. For general scoring purposes, the independent side chain approximation is applied to the mutated side chains in order to avoid the huge computational demand imposed by sampling conformational space of multiple side chains in various backbone conformations.

The sequences in the hit library or hit variant library are evaluated for their structural compatibility with the target structure and are mapped out on the energy landscape of the target fold. For the anti-VEGF antibody, the scores for the antibody sequences in the presence and absence of antigen are correlated in general trend because a large number of variants are capable of stabilizing the antibody scaffold (see FIG. 12C). Among them, there is a significant fraction of the sequences that are capable of binding the target epitope. As shown in the EXAMPLE section, CDR library sequences are ranked based on their fitness scores, based on the relative stability of the template antibody-antigen complex (1CZ8), and experimentally selected sequences are identified (FIG. 13A).

It is beneficial, if possible, to determine the scores in both the antigen bound and unbound states to eliminate any grossly unfavorable sequences in either state. By doing so, we can avoid the need to accurately score the differences between the bound and unbound states while still effectively reducing the search space.

The scoring function is used to score the sequences in the hit library, hit variant library I or hit variant library II and, optionally, the differences between the lead sequence or lead structural template sequence and the library sequence is calculated to complete a thermodynamic cycle. Consequently, sequences can be selected for further experimental screening based on any of the following criteria: 1) sequences that score better than the lead sequence in stabilizing the antibody structure are selected; 2) sequences that score better than the lead sequence in stabilizing the antibody-antigen complex structure are selected; 3) the difference in the score between the bound and unbound states is better than the lead sequence, provided the scoring function is sensitive enough to discriminate small differences between large numbers. The last criterion should be used only if highly refined scoring functions or high quality ensemble based scoring function is available and prefereably with systems where high quality mutant data are available for calibration of the scoring function.

Sequences that score better than the lead sequence(s) are analyzed and sorted into distinct clusters. A combination of the clusters should cover sufficient sequence and structure space that covers desired regions in the fitness landscape (FIG. 7). This approach of selecting a scoring window by clustering the sequences is taken as an effort to reduce the physical library size. Another benefit of the clustering approach is that combination of the subsequent nucleic acid libraries (e.g., nucleic acid library I, II, III, etc., FIG. 7) from several disjointed scoring windows may still cover a large portion of sequence and structure space with better scores than the lead sequence. A desirable result of this clustering process is that since each of these clusters of sequences requires a much smaller physical library size than the combined library, the nucleic acid library encoding each of the clusters is small enough for a thorough screening in vitro or in vivo.

In one embodiment of the present invention, the scoring of the hit variant library is used to select a population of sequences optimized for the desired function and to formulate the starting design for hit variant library II. Scoring of the resulting hit variant library II is used to determine the effects of modification and design enhancements on variant profile. Hit variant library III, derived from the nucleic acide library (described in detail in Section 7 below), is also scored to determine the fitness of the library and to evaluate the effectiveness of the scoring function in mapping the sequence and structure space onto the fitness landscape of the molecular target.

In a particular embodiment, standard terms from MM terms have been combined with the solvation terms including electrostatic solvation and solvent-accessible solvation term calculated with continuous solvent model for electrostatic salvation; these MM-PBSA or MM-GBSA method, together with contribution from the conformational entropy including backbone and side chains, have shown good correlation between experimental and calculated values in the free energy change (Wang W, Kollman P (2000) J Mol Biol 303, 567–582). Compared to other scoring functions used in protein and drug design, MM-PBSA or MM-GBSA is better physical model for scoring and would handle various problems with a consistent approach, although it is computational expensive because multiple trajectories from molecular dynamic simulation in explicit water are required to calculate the ensemble averages for the system and continuous solvent model is still computationally slow. These accurate methods should provide a benchmark for calibrating the simple scoring function used for library screening or for studying some challenging mutations that elude simple calculations.

7) Examples of Forcefields for Protein Design

An important interaction for scoring the correct packing interactions inside the core of proteins, van der Waals (vdw) interaction was used to design the protein core sequences by testing allowed rotamer sequences in enumeration (Ponder J W, Richards F M (1987) J Mol Biol 193, 775–791. A group of sequences can be selected under a potential function using simulated evolution with stochastic algorithm; the ranking order of the energies of selected sequences for residues in the hydrophobic cores of proteins correlates well with their biological activities (Hellinga H W, Richards F M (1994) PNAS 91, 5803–5807).

Similar approaches were also used to design proteins using stochastic algorithm (Desjarlais J, Handel T, (1995) Protein Science 4, 2006–2018; Kono H, Doi J (1994) Proteins, 19, 244–255). Effect of potential function on the designed sequences of a target scaffold has been evaluated by including van der Waals, electrostatics, and surface-dependent semi-empirical environmental free energy or combinations of terms in an automatic protein design method that keeps the composition of amino acid sequence unchanged. It was shown that each additional term of the energy function increases progressively the performance of the designed sequences with vdw for packing, electrostatics for folding specificity and environmental solvation term for burial of the hydrophobic residues and for exposure of the hydrophilic residue (Koehl P, Levitt M (1999) J Mol Biol 293, 1161–1181).

The self-consistent mean field approach was used to sample the energy surface in order to find the optimal solution, (Delarue M, Koehl. (1997) Pac. Symp. Biocomput. 109–121; Koehl P, Delarue M, (1994) J. Mol. Biol. 239, 249–275; Koehl P, Delarue M (1995) Nat. Struct. Biol. 2,163–170; Koehl P, Delarue M (1996) Curr. Opin. Struct. Biol. 6:222–226; Lee J. (1994) Mol. Biol. 236, 918–939; Vasquez (1995) Biopolymers 36, 53–70). Combination of terms from molecular forcefield, knowledge-based statistical forcefield and other empirical correction has been also used to design protein sequences that are close to the native sequence of the target scaffold (Kuhlman B, Baker D (2000) PNAS 97, 10383–10388). The structure-based thermodynamic terms were included in addition to the steric repulsion in the protein core design (Jiang X, Farid H, Pistor E, Farid R S (2000) Protein Science 9, 403–416). Knowledge-based potentials have been used to design proteins (Rossi A, Micheletti C, Seno F, Maritan A (2001) Biophysical Journal 80, 480–490).

Forcefields have been also optimized specifically for protein design purpose in combination with the dead end elimination algorithm (Dahiyat B I, Mayo S L (1996) Protein Science 5, 895–903). The energy function is decomposed into pairwise functional forms that combine molecular mechanic energy terms with specific solvation term is used for residues at the core, boundary and surface positions; dead end elimination algorithm is used to sip through huge number of combinatorial rotameric sequences. The stringency of force fields and rigid inverse folding protocol with fixed backbone used in protein design has inevitably resulted a significant rate of false negative: rejection of many sequences that might be acceptable if soft energy function or flexible backbone is allowed. Moreover, the energy function used for protein design is quite different from general forcefields such as Amber or Charmm that are widely used and tested for studying protein folding or stability (Gordon D B, Marshall S A, Mayo S L (1999) Curr Opin Stru Biol 9, 509–513). Cautions should be exercised in comparing the sequences designed using specific protocol with others from alternative methods because a direct comparison among them may not be possible due to the false negative issues involved in protein design protocols.

The inventors believe that, although a high false negative rate in protein design is not a problem for designing proteins with few restriction, this will pose serious problems for designing proteins for pharmaceutical application for which only small restrictive region is allowed to have altered sequences to improve protein function. For example, many variants are acceptable for $V_H$ CDR3, even though only one or two residues in the $V_H$ CDR3 in the VEGF antibody would actually improve its binding affinity, but for the framework regions, only a few mutants can be tolerated for humanization. Therefore, it is accuracy rather than the scale or speed of computational screening that matters the most for functional improvement in order to identify those few mutants in the targeted region.

Optionally, molecular dynamics or other computational methods can be used to generate structure ensembles and the ensemble average scores used to rank sequences (Kollman P A, Massova I, Reyes C, Kuhn B, Huo S H, Chong L T, Lee M, Lee T S, Duan Y, Wang W, Donini O, Cieplak P, Srinivasan P, Case D A, and Cheatham T E (2000) Acc. Chem Res. 33, 889–897). The average properties calculated from ensemble structures show better correlation with corresponding data from experimental measurement.

6. Construction of Mutant Antibody Library Based on Lead Structural Template

Alternatively, a mutant antibody library may be constructed directly based on the 3D structure of the lead antibody and then screened for desired function in vitro or vivo. This approach takes a short cut by avoiding the construction of the hit variant library and directly evaluates sequences from the hit library constructed by screening protein databases. This approach is depicted as Route III in FIG. 1C or 1E-H.

As described in detail in section 3, there are several ways to construct the hit library. One way of building the hit library is to search in a protein database to find those segments that match in sequence pattern with the amino acid sequence of the region to be mutated, for example, CDR3 of the heavy chain (CDR H3) of the lead antibody. A conventional BLAST analysis may be employed to search for sequences with high homology to the CDR H3 sequence.

Optionally, PSI-BLAST may be used to search for sequence homologues of the CDR H3 sequence of the template antibody.

Also optionally, single target sequence and/or multiple sequence alignment can be used to build a profile Hidden Markov Model (HMM). This HMM is then be used to search for both close and remote human homologues from a protein sequence database such as Kabat database of proteins and the human germline immunoglobulin database for frameworks. The Kabat database of proteins of immunological interest from various species can be used for designing diverse sequences for CDRs.

The sequences in the hit library selected by using any of the above methods for sequence alignment or combinations thereof can be profiled to compare the type of amino acid and its frequency of appearance in each position of the corresponding region in the template antibody (e.g., CDR H3).

Each member of this hit library is grafted onto the corresponding region in the template antibody (e.g., CDR H3) and tested for its structural compatibility with the rest of the antibody by using scoring functions described in section 5 above.

Using similar approaches, hit libraries can be constructed based on lead sequences from different regions of the lead antibody, such as CDR1, CDR2 of the heavy chain and light chain, and tested for structural compatibility with the rest of the lead antibody. These libraries may be combined to allow simultaneous mutations to different regions of the lead antibody, thereby increasing the diversity of the mutant antibody library.

All of the mutant antibody sequences selected in these processes are pooled and screened for high affinity binding to the target antigen in vitro or in vivo.

7. Construction of Nucleic Acid Library for Experimental Screening

To facilitate functional screening in vitro or in vivo, nucleic acid libraries are constructed to encode the amino acid sequences that are selected by using the above-described methods of the present invention. The size of the nucleic acid library may vary depending on the particular method of selecting and profiling the amino acid sequences. For example, the size of the nucleic acid may reach $>10^6$ if too many amino acid sequences are chosen and recombined. Partitioning and re-profiling of the amino acid sequences may be performed to reduce the size of the nucleic acid library to facilitate efficient and thorough screening experimentally. As described in Section 5 above, the profile used to generate the hit variant library II, for example, is also used to determine the size of the nucleic acid library for experimental screening in vitro or in vivo.

FIG. 6 illustrates an exemplary procedure for constructing a nucleic acid library to encode the amino acid sequences of the selected amino acid variants, e.g., hit variant library II (FIGS. 4 & 5). To construct the nucleic acid library, the variants in the amino acid profile are back translated into corresponding nucleic acids by taking into account of the library size and codon usages (FIG. 6).

For example, to obtain the simplest and smallest nucleic acid library covering the diversity of a given amino acid library, only the preferred codons used in the expression system (e.g., *E. coli*) are selected to encode the amino acid library. The corresponding nucleotide positional variant profile (NT-PVP) is obtained from the back translation of the AA-PVP and the nucleic acid library size is determined from the nucleotide combinatorial enumeration. See example in FIG. 13A-C. If this size is less than $10^6$, synthesis of the nucleic acid library or libraries (e.g., nucleic acid library I, II, III, etc., FIG. 7) is performed and experimental screening is then conducted. If the size is greater than $10^6$, the hit variant library II is partitioned into a shorter library or the scoring distribution is resampled to generate a new AA-PVP to generate a smaller library size, as described in section 2 under sequence space or reprofile.

By using NT-PVP, a degenerate nucleic acid library can be constructed without synthesizing each of the selected nucleic acid sequences individually. This approach reduces cost and time because the synthesis of the nucleic acid libraries can be accomplished in one pass for each library (e.g., nucleic acid I, II, III, etc., FIG. 7) by programming an automated oligonucleotide synthesizer with different mixtures of nucleotides for each position. As a result, the sequence space of the degenerate nucleic acid library is significantly expanded with an increase in diversity. Although the size of the nucleic acid library (translated as hit variant library III) is larger than the one faithfully encoding the designed amino acid sequences (e.g., hit variant library II), this approach of degenerate library construction not only guarantees to include the designed sequences but also promises to increase the chance of finding novel sequences with equivalent or better functions than the originally designed ones.

For reassurance, the nucleic acid library generated by using NT-PVP is translated back to an amino acid sequence library to generate hit variant library III and scored using an energy function to evaluate the sequence and structure space covered by the hit variant library II and the fitness of the library (FIG. 13A). The ultimate comparison requires experimental selection data to validate the fitness of the libraries and the effectiveness of the scoring function in mapping the sequence and structure space onto the fitness landscape.

8. Construction of Mutant Libraries with No Structure Available.

Mutant libraries can be constructed by partitioning sequence libraries into smaller segments. This is advantegious if only low resultion structure or no structure is available. A composite library is designed by partitioning sequences into overlapping consecutive sequence segments. Each fragment can be targeted with a degenerate nucleic acid library. It should be noted that if even low resolution structural model or other structural information is available, the variants that are determined to be structurally coupled should be targeted simultaneously using degenerate nucleic acid libraries (see example below). The idea has been described in 7) of Section 2 and is illustrated in Example below (see FIGS. 28A–D for design and FIGS. 30 and 36 for experimental results).

In brief, sequence variant library can be parsed into smaller fragments as follows: the structurally distant segments are often uncorrelated so that mutations widely separated can be treated independently, whereas those fragments that couple with each other in space should be targeted simultaneously by the combinatorial nucleic acid libraries. It should be noted that the structural information is desirable but not absolutely necessary in this case. (see details in Example below and FIGS. 28A–D).

Advantages of the Present Invention

By sampling a large combinatorial space of amino acid sequence and structural motifs and scoring the intermolecular interactions between proteins, a library of amino acid sequences can be screened computationally. For the specific antibody-antigen complex used here, several libraries of the antibody are designed and constructed based on the lead sequence alone, the antibody structure and the complex structure between the antibody and antigen, respectively. All of the libraries are biased towards the lead antibody, either its sequence and/or structure; some of them are directed towards the specific antigen in the complex. Thus, the antibody libraries are more focused and relevant than a collection of antibodies from a cDNA library or from a random mutagenesis of a specific antibody lead. These libraries are screened experimentally for affinity maturation with the specific antigen. Various sequences different from the lead antibody sequence in CDRs were selected (see FIGS. 16A and 27). Some of the selected sequences show slower off-rate (suggesting higher affinity) than that of the lead antibody (or parental antibody). Among them, two of the mutants (see FIGS. 30 & 36) are identical to the critical mutants in the affinity-matured $V_H$ CDR3 sequence reported in the literature such as (H97Y and/or S101T), whereas one novel mutant (S101R) was found to be even better in off-rate panning, determined by two independent experimental systems, than S101T reported in the literature (Chen Y, Wiesmann C, Fuh G, Li B, Christinger H W, McKay P, de Vos A M (1999) J Mol Biol 293, 865–881).

The present inventions are believed to be advantageous in several aspects. First, this approach utilizes evolutionary data of proteins to expand the hit library in both sequence and structure spaces. The sequence searching methods, ranging from a simple BLAST to the increasingly powerful profile based approaches, such as PSI-BLAST and/or HAMMER, are employed to search for close as well as remote homologues of a lead sequence from the evolutionarily enriched sequence database. The use of sequence profile based on the multiple structure alignment of the available lead structure allows the sampling of a larger sequence space than by traditional, multiple sequence alignment approaches. The methods used here, therefore, increase the diversity as well as the chance to find novel hits or combination of mutants with enhanced binding affinity.

Second, the sampling in sequence space also emphasizes the choice of sequence database suitable for the specific purpose. For example, the use of the diverse sequence database for designing CDRs and the use of the human germlines or sequences of human origins for the framework regions should be exploited in designing proteins for pharmaceutical applications where immunogenicity is a major concern.

Third, sequence design using existing sequences from various databases is simple and highly efficient since only evolutionally enriched sequences or their combinations are used. A refined, yet computationally expensive scoring function can be applied to score the resulting sequence pool of manageable size, that incorporates, implicitly, the information involving folding and expression.

Fourth, the implementation of the structural template and optimized scoring function can efficiently filter and reduce the size of the combinatorial hit variant library prior to any experimental screening. Thus, a large virtual sequence space can be computationally sampled and subsequent selection of ensembles of favorable sequences can direct the experimental synthesis of several small libraries that cover a diverse sequence space.

Fifth, the control of the library size (which is usually around $10^3$ to $10^7$ for nucleic acid library) may make it easier to implement experimentally for direct functional screening. Because the direct functional screening is the ultimate test on the validity and accuracy of the in silico methods, some intrinsic limits related to scoring function and structure template in the computational screening can be tested experimentally.

Sixth, the use of simple structural correlation to partition long sequences allows the control of the library size so that it is experimentally manageable without a significant loss of diversity. It also makes it possible to design sequence libraries for a lead sequence with little structural information available.

Finally, the adaptability and parameterization of the scoring function permits refinement with each experimental cycle. The experimentally screened clones represent an actual positional variant in a profile that can be used as a feedback for refining the scoring function by refining the various scoring terms.

In summary, exploring the function space by combining direct experimental screening, within experimental limit, with indirect computational screening in sequence and structure space of a target protein is a powerful approach to protein engineering and design as we demonstrate here for antibodies.

EXAMPLE

Methods of the present invention were used for in silico construction of antibody libraries. The vascular endothelial growth factor (VEGF) is chosen as the antigen for the present proof-of-principle experiments in order to demonstrate the present invention in antibody design. A rich collection of sequence and structure information is available for VEGF and it receptor (Muller Y A, Christinger H W, Keyt B A, de Vos A M (1997) Structure 5, 1325–1338; Wiesmann C, Fuh G, Christinger H W, Eigenbrot C, Wells J A, de Vos A M (1997) Cell 91, 695–704), a complex between VEGF and its humanized antibody (Muller Y A, Christinger H W, Li B, Cunningham B C, Lowman H B, de Vos A M (1998) Structure 6, 1153–1167, and a complex between VEGF and its matured antibody (Chen Y, Wiesmann C, Fuh G, Li B, Christinger H W, McKay P, de Vos A M (1999) J Mol Biol 293, 865–881). These provide a good platform for testing the methods of the present invention. By using the methods provided by the present invention, several digital libraries of anti-VEGF antibodies were designed in silico by utilizing incrementally enriched information from an antibody sequence, the structure of an antibody, the complex structure between an antibody and its antigen. Populations of the antibody libraries were screened in vitro for high affinity binding to VEGF via two independent novel phage display systems with antibody binding unit in single or double chains.

1. In Silico Design of Anti-VEGF Antibody Libraries

VEGF is a key angiogenic factor in development and is involved in the growth of solid tumor by stimulating endothelial cells. A murine monoclonal antibody was found to block VEGF-dependent cell proliferation and slow the tumor growth in vivo (Kim K J, Li B, Winer J, Armanini M, Gillett N, Phillips H S, Ferrara N (1993) Nature 362, 841–844). This murine antibody was humanized (Presta L G, Chen H, O'Connor S J, Chisholm V, Meng Y G, Krummen L, Winkler M, Ferrara N (1997) Cancer Res. 57, 4593–4599; Baca M, Presta L G, O'Connor S J, Wells J A (1997) J Biol Chem 272, 10678–10684) and affinity-matured by using phage-display and off-rate selection (Chen Y, Wiesmann C, Fuh G, Li B, Christinger H W, McKay P, de Vos A M (1999) J Mol Biol 293, 865–881). X-ray structure for the complex formed between VEGF and the parental antibody was reported (Muller Y A, Chen Y, Christinger H W, Li B, Cunningham, B C, Lowman H B, de Vos A M (1998) Structure 6, 1153–1167.), as well as the one formed between VEGF and the matured antibody (Chen Y, Wiesmann C, Fuh G, Li B, Christinger H W, McKay P, de Vos A M, Lowman H B (1999) J. Mol Biol 293, 865–881).

The amino acid sequences of the variable regions of the humanized anti-VEGF antibody (therein after referred to as "parental anti-VEGF antibody") are listed in the Sequence List as SEQ ID NO: 1. for $V_H$ and SEQ ID NO:2 for $V_L$; and the antibody affinity matured from the humanized anti-VEGF antibody (therein after referred to as "matured anti-VEGF antibody") SEQ ID NO:3 for $V_H$ and SEQ ID NO:4 for $V_L$. FIG. 9A is an alignment of the parental and matured anti-VEGF antibody in the $V_H$ CDRs. The framework and CDRs are designated according to the Kabat criteria (Kabat E A, Redi-Miller M, Perry H M, Gottesman K S (1987) Sequences of Proteins of Immunological Interest 4$^{th}$ edit, National Institutes of Health, Bethesda, Md.). As described in Kabat et al. (1987) ibid., "the variable regions . . . of immunoglobulins have been shown to contain hypervariable segments in their light . . . and heavy chains, which certain residues have been affinity labled . . . . Three hypervariable segments of light chain were delineated from a statistical examination of sequences of human $V_\kappa$, human $V_\lambda$, and mouse $V_\kappa$ light chains aligned for maximum homology . . . These and the three corresponding segments of the heavy chains . . . were hypothesized . . . to be the complementarity-determining regions or segments (CDR) containing the residues which make contact with various antigenic determinants, that this has been verified by X-ray diffraction studies at high resolution . . . . The rest of the V-region constitutes the framework . . . . It is convenient to identify the framework segments (FR1, FR2, FR3, and FR4) and the complementarity-determining segments (CDR1, CDR2, and CDR3) with the three CDRs separating the four FRs. Kabat et al. (1987) ibid. page viii, last paragraph. In the table that follows, Kabat et al. numbered residues of these segments: FR1, CDR1, FR2, CDR2, FR3, CDR3 and FR4. Kabat et al. (1987) ibid. page ix, table. In FIG. 9A, differences in amino acid residues are highlighted in bold letter. As shown in FIG. 9A, the matured antibody only has two amino acid residues that are different from the parental one in both $V_H$ CDR1 (T28D and N31H) and $V_H$ CDR3 (H97Y and S100aT). There is no change in CDR2 after the affinity maturation.

The matured anti-VEGF antibody has a 135 times higher binding affinity to VEGF than the parental one with 4 mutations in the $V_H$ chain (T28D, N31H, H97Y, and S100aT). The two of the mutations in $V_H$ CDR3 individually improve binding affinity by 14-fold (from H97Y) and 2-fold (from S100aT) relative to the parental antibody (see Table 6 of Chen Y, Wiesmann C, Fuh G, Li B, Christinger H W, McKay P, de Vos A M, Lowman H B (1999) J. Mol Biol 293, 865–881). The 14-fold affinity improvement by H97Y alone in $V_H$ CDR3 makes it the single most important mutation for affinity maturation, which is consistent with observation in the x-ray complex structure that two additional H-bonds are made by H97Y mutant between the antigen and antibody.

According to the present invention, each motif such as CDR and framework of the antibody can be targeted using a modular in silico evolutionary design approach. This modular design is depicted in FIG. 8. It has been understood that there are only a limited number of conformations (called canonical structures) for each CDR. These structural features of an antibody provide an excellent system for testing the evolutionary sequence design by using structured motifs at various regions of an antibody, such as CDR1, CDR2, and CDR3 in $V_L$ & $V_H$ as well as the framework regions from the extensive analysis of antibody structures. These structure and sequence conservation are observed across different species. In fact, the scaffolding of antibodies, or the immunoglobin fold, is one of the most abundant structure observed in nature and is highly conserved among various antibodies and related molecules.

The inventors believe that parental anti-VEGF antibody described above can serve as a lead protein in a model system for directed antibody affinity maturation using the methods of the present invention. The matured anti-VEGF antibody (Chen et al., supra) can serve as a reference or positive control to validate the results obtained by using the inventive methods.

In addition, structural superposition revealed that the structure of the complex formed between VEGF and the parental antibody almost overlaps with that formed between VEGF and the matured antibody. Since the antibody structures before and after affinity maturation remain substantially the same, structures of both parental and matured antibodies were used in the design of digital libraries of anti-VEGF antibodies using the inventive methods. The inventive method can be also used to design antibodies with induced fit upon antigen binding using sequence-based approach or structure ensembles that contain the induced structure changes.

Using parental anti-VEGF antibody as the lead protein and its $V_H$ CDR3 as the lead sequence, digital libraries of $V_H$ CDR3 were constructed by following the procedure outlined as Route IV in FIG. 1D and the diagram in FIG. 2.

The lead sequence included $V_H$ CDR3 of parental anti-VEGF antibody and a few amino acid residues from the adjacent framework regions (FIG. 9B). As an overview, a hit library was constructed by searching and selecting hit amino acid sequences with remote homology to $V_H$ CDR3. Variant profile was built to list all variants at each position based on the hit library and filtered with certain cutoff value to reduce of the size of the resulting hit variant library within computational or experimental limit. Variant profileswere also built in order to facilitate i) the sampling of the sequence space that covers the preferred region in the fitness landscape; ii) the partitioning and synthesis of degenerate nucleic acid libraries that target the preferred peptide ensemble sequences; iii) the experimental screening of the antibody libraries for the desired function; and iv) the analysis of experimental results with feedback for further design and optimization.

The lead structural templates were obtained from the available X-ray structures of the complexes formed between VEGF and anti-VEGF antibodies. The complex structure of VEGF and parental anti-VEGF antibody is designated as 1BJ1, and that formed between VEGF and matured anti-VEGF antibody 1CZ8. The results from 1CZ8 structural template were similar to those from 1BJ1 in the relative ranking order of the scanned sequences.

1) Lead Sequence

The lead sequence for $V_H$ CDR3 is taken from the parental anti-VEGF antibody according to Kabat classification with amino acid residues CAK and WG from the adjacent framework regions flanking the $V_H$ CDR3 sequence at N- and C-terminus, respectively (FIG. 9B). As shown in FIG. 9B, $V_H$ CDR3 of the parental and matured antibodies differ only at two amino acid positions. Only $V_H$ CDR3 sequence of the parental antibody was used to build the HMM for searching the protein databases.

2) Hit Library and Variant Profile

The HMM built using the single lead sequence, SEQ ID NO: 5 (FIG. 9B), was calibrated and used to search the Kabat database (Johnson, G and Wu, T T (2001) Nucleic Acids Research, 29, 205–206). All sequence hits that are above expectation value or E-value are listed and aligned using HAMMER 2.1.1 package. After removing the redundant and the matured sequence (i.e., SEQ ID NO: 6 by assuming that no matured sequence is available) from the hit list, the remaining 107 hit sequences for the lead HMM form the hit library.

As shown in FIG. 10A, the 107 hits have sequence identities ranging from 35 to 95% of the lead sequence from the Kabat database. The evolutionary distances between the hits are displayed in a phylogram in FIG. 10B by using the program TreeView 1.6.5 (as shown in the website of taxonomy.zoology.gla.ac.uk/rod). The phylogenetic tree was analyzed using the neighbor-joining method (Saitou N, Nei M (1987) Mol Biol Evol 4, 406–425) in ClustaiW 1.81 (Thompson J D, Higgins D G, Gibson T J (1994) Nucleic Acids Research 22, 4673–4680).

The variant profile at each position is shown in FIG. 11. The AA-PVP table in FIG. 11 gives the number of occurrence of each amino acid residue at each position. The variant profile below the table lists, in the order of decreasing occurrence at each position, all variants found from the database with the lead sequence as the reference sequence. The dot indicates that the same amino acid as in the reference is found at that position.

The diversity of the 107 hit sequences from the hit library can be seen in the AA-PVP table that shows both the frequency and variability of amino acids at each position. Comparing the difference between sequences of the parental and matured anti-VEGF antibody in $V_H$ CDR3, two different amino acids (H97Y and S100aT using the numbering in the Kabat system) are included in variants listed at each position. The H97Y which was reported to be the most important mutant to increase the binding affinity of the matured sequence (Chen Y, Wiesmann C, Fuh G, Li B, Christinger H W, McKay P, de Vos A M, Lowman H B (1999) J. Mol Biol 293, 865–881) is readily identified as the most frequent residue (~27%) in that position. The S100aT accounts for ~5% of the variants identified in that position. The right lower portion of FIG. 11 shows the variant profile after filtering variants that occur at or less than the cutoff frequency of 10. After the filtering, it becomes clear that only a limited numbers of variants are allowed at each position of the sequence; however some important mutants such as S100aT in the matured sequence might be missed at such a cutoff although energy scoring would keep it.

The variant profile from the evolutionary sequence pool provides informative data to identify the positions in the lead sequence that can be either varied or fixed. The sites can be divided into three categories: i) Structurally conserved sites remain conserved over evolution. The high frequency residues can be used to maintain the scaffold of the target motif at these positions; ii) variable functional hot spots should be targeted with focused mutagenesis; iii) combination of both i) and ii) to stabilize the target scaffold while simultaneously providing variability in the functional hot spots.

A set of the amino acids from the functional variants should be included at the functional hot spots according to their frequencies in the variant profile because they are evolutionarily selected or optimized. Furthermore, the variants at each position can be filtered or prioritized to include other potentially beneficial mutants or exclude potentially undesirable mutants to meet the computational and experimental constraints.

3) Structure-Based Evaluation of Combinatorial Sequences of the Hit Library

Although the variant profile is informative on the preferred amino acid residues at each position and specific mutants in a preferred order, unmodified, it embodies an enormous number of recombinants. Some filtering using frequency cutoff can reduce the combinatorial sequences that need to be evaluated by computational screening or targeted directly by experimental libraries. Even with the cutoff applied to the variant profile, there is still a large number of combinatorial sequences that needs to be scored and evaluated in the final sequences for experimental screening (as shown in FIG. 13A-C and 28A-D).

A structure-based scoring is applied to screen the hit library and its combinatorial sequences that form a hit variant library. Side chains of $V_H$ CDR3 of the parental anti-VEGF antibody were substituted by rotamers of corresponding amino acid variants from the hit variant library at each residue position. The conformations of rotamers were built and optimized by using the program SCWRL® (version 2.1) using backbone-dependent rotamer library (Bower M J, Cohen F E, Dunbrack R L (1997) JMB 267, 1268–82).

The scoring was done by searching the optimal rotamers and minimizing the energy by 100 steps using the Amber94 force field in CONGEN [Bruccoleri and Karplus (1987) Biopolymers 26:137–168] in the presence and absence of the structure of the antigen VEGF. FIGS. 12A & B shows the energy scores of an anti-VEGF variant library based on the total energy calculated with CONGEN with and/without VEGF antigen, using the structures of the parental (1bj1) and matured (1cz8) anti-VEGF antibodies, respectively. The scores of the parental and matured sequences are marked in FIGS. 12A and B. The matured sequence scores better than the parental sequence in both structures with/without antigen, suggesting that the mutants of the matured sequence stabilize both the antibody structure as well as its complex with VEGF antigen. FIG. 12C shows that the scoring of the sequences in the presence and absence of antigen is in general correlated, which suggests that screening sequences based on a antibody structure alone would also provide good candidate sequences with good binding affinity with its antigen.

As shown in FIGS. 12A and 12B, there are a large number of sequences for various variant libraries with higher scores than the parental and matured sequences. The distribution of the energy scoring in the energy diagram is shown in FIG. 13A for 10 selected sequences from the hit variant library of $V_H$ CDR3, its combinatorial peptides, combinatorial library of the degenerate nucleic acid library, and the experimentally selected sequnences. The scoring shows that Y97 in the matured sequence always scores better than H97, consistent with the experimental observation (Chen Y, Wiesmann C, Fuh G, Li B, Christinger H W, McKay P, de Vos A M, Lowman H B (1999) J. Mol Biol 293, 865–881). T100a is preferred over S100a as found in the matured sequences, whereas both T and S are equally preferred in 100b position. Thus, the structure-based energy scoring provides another independent way to reprofile the occurrence of variants at each position for the hit variant library which was originally built based on profiling of evolutionary sequences selected from protein databases.

In order to gauge the accuracy of the scoring function using the simple energy function implemented in CONGEN, the energies of a randomly selected set of sequences were calculated using a refined custom scoring function that includes sidechain entropy, nonpolar solvation energy and electrostatic salvation energy. Three energy terms were calculated: sidechain entropy, nonpolar solvation energy and electrostatic solvation energy. There was an additional option to calculate the backbone entropy for loops. The sidechain entropy was calculated using the conformational search command CGEN in CONGEN. Options under CGEN were defined to perform individual sidechain conformational tree search using the torsion space at each bond (node) to expand the tree. These included the SEARCH DEPTH and SIDE option for each sidechain with the SGRID parameter set to AUTO so that each torsion angle was rotated at discrete intervals. Specifically, the AUTO setting used torsion grid angle of 30 degrees for bonds with rotational symmetry such as in the phenyl, tyrosyl, carboxyl, and amino groups, and 10 degrees for all others. MIN option set rotational sampling to start at a local energy minimum for each specified torsion. Also VAVOID option was included to turn on van der Waals repulsion avoidance. MAXEVDW parameter was set to a relatively high 100 kcal/mol so as to relax the van der Waals repulsion, leading to a higher number of conformers in the enumeration.

This sidechain conformational search was repeated for each mutant residue sidechain. The code outputs the "number of bottom leaves" reached by the tree search in conformational space which is the number of completed tree search. As an approximation, the sidechain conformational search treats each residue independently, so that computational time can be minimized. For residues that do not contact one another, this is a good approximation. For residues that can potentially contact one another, the conformational enumeration will tend to overestimate the number of conformations. Since we use a relatively high van der Waals repulsion in order to obtain a larger sampling, the error due to residue contacts should be reduced in the context of this artificial gauge of the conformational space. Furthermore, the significance of the error due to residue contacts will tend to diminish with greater number of conformations since the relative change in entropy is a difference of the logarithms of the number of conformations in the mutant and the reference structures.

The nonelectrostatic solvation energy is made proportional to the molecular surface, as calculated by the GEPOL93 algorithm, with the scaling constant of 70 cal/mol/$A^2$ (Tunon I, Silla E, Pascual-Ahuir J L (1992) Prot Eng 5, 715–716) using GEPOL (Pascual-Ahuir J L, Silla E (1993) J Comput Chem 11, 1047–1060) command as implemented in CONGEN. NDIV which specifies the division level for the triangles on the surface is set to 3. Values range from 1 to 5 with 5 giving the highest accuracy but with significant increase in CPU time requirement. RGRID is set to 2.5A and describes the space grid used to find neighbor.

The electrostatic solvation energy is calculated using the finite-difference PB (FDPB) method as implemented in UHBD program (Davis M E, Madura J D, Luty B A, McCammon J A (1991) Comput Phys Commun 62, 187–197). The focusing method is used for the region surrounding the mutation. An automated protocol generates three grids: coarse, fine, and focus grids. The grid units are 1.5, 0.5, and 0.25 angstroms, respectively. The focusing grid is a cubic grid that spans the Cartesian volume occupied by the mutated residues. The fine grid is a cubic grid that spans the entire volume of the protein or the complex. The coarse grid is a cubic grid that is set to approximately twice the size of the fine grid in each axis and covers approximately 8 times the volume of the fine grid. The coarse grid serves to account for the long-range solvent effects and sets the boundary conditions for the fine grid. Similarly, the fine grid accounts for the electrostatic contributions of the protein interior and sets the boundary condition for the focus grid. The focus grid accounts for finer details of the localized effects due to the mutation. The dielectric constants for the protein interior and exterior are set to 4 and 78, respectively. Temperature is set to 300 Kelvin and ionic strength is set to 150 mM. Maximum iteration is set to 200. The calculations are repeated with a uniform dielectric so that both the interior and exterior dielectrics are set to 4 and the difference between the two energies is computed. The latter calculations represent the energies due to bringing the charges onto the grids.

It was shown that the custom scoring function or the molecular mechanics energy using Amber94 forcefield in CONGEN plus the solvation terms from PB in UHBD used here is similar to MM-PBSA or MM-GBSA. The energy function shows better agreement with experimental data (Sharp K A. (1998) Proteins 33, 39–48; Novotny J, Bruccoleri R E, Davis M, Sharp K A (1997) J Mol Biol 268, 401–411), especially when structure ensembles by molecular dynamics calculations are used to provide more accurate methods to score sequence and its variants based on the ensemble averages of the energy functions (Kollman P A, Massova I, Reyes C, Kuhn B, Huo S H, Chong L T, Lee M, Lee T S, Duan Y, Wang W, Donini O, Cieplak P, Srinivasan P, Case D A, and Cheatham T E (2000) Acc. Chem Res. 33, 889–897).

4) Reduction of the Variant Profile of the Hit Variant Library

The variant profile from the hit variant library as described above was filtered in order to reduce the potential library size while maintaining most of the preferred residues. The upper portion of FIG. 13A shows the reduced variant profile of 10 selected sequences with top ranking from a hit variant library after eliminating amino acids with occurrences lower than the cutoff value and structure-based evaluation. The list was chosen as a blind test on the validation of the current method in selecting for diverse sequences that can bind with a target antigen. There are some common features shared among 10 selected sequences from one computationally screening variant library: R94, Y97 and R100a are found always better than the corresponding residues at K94, H97 and S100a, for example for the top ranked 200 sequences using either 1bj1 or 1cz8 as the template structure in the presence or absence of VEGF antigen. As shown in the experimental selection later that H97Y is indeed a good mutant for affinity maturation. However, mutation such as K94R and S100aR into arginine is an interesting case: on the one hand, K94R is not a good mutant for affinity maturation although K94R lies in the boundary between CDR and framework according to Kabat classification and is preferred evolutionally for human framework sequence. K94 is favored over R94 as shown in experimental selection of the current invention (FIGS. 30 & 36), consistent with the observation in literature that R94K mutation increases the binding affinity of anti-VEGF antibody (Baca M, Presta L G, O'Connor S J, Wells J A (1997) J Biol Chem 272, 10678–10684). One the other hand, S100aR turns out to be one of the most important single mutation for $V_H$ CDR3 maturation, it is favored over S100aT as reported in the literature and persist many rounds of panning under harsh washing conditions in phage display (see FIGS. 30 & 36).

In order to avoid missing some important mutants in a variant profile, some residues such as lysine (such as K94R) from the wild type might be included even though they are below the cutoff value used in filtering hit library or they somehow score less well as arginine because of the problems associated with assumption in computation involving charged residues with long side chains or conformational change etc. Therefore, for charged residues with long side chains, such as arginine and lysine, the predicted residues as well as the wild type residue at the same position might be included in the design libraries. The reduced variant profile was used to enumerate hit variant library II as the blind test on the inventive method used here for designing functional library with diverse sequences from the lead sequence.

5) Hit Variant Library II—an Amino Acid Library Designed from Scoring Selection and Optimization A strategy that selects top sequences based on favorable score and/or the presence of residues likely to participate in favorable interactions was employed to identify a cluster or clusters of amino acid sequences for the nucleic acid library design (FIG. 7). As described above, a cluster of sequences (e.g., 10 sequences) in FIGS. 13A–C for $V_H$ CDR3, CDR1 and CDR2, respectively, from computational evaluation was chosen for further experimental test in vitro. The peptide sequence and variants at each position are listed in upper left portion of FIG. 13A. A combinatorial library was generated based on the filtered variant profile, forming hit variant library II. For $V_H$ CDR3 of anti-VEGF (FIG. 13A), the size of hit variant library II is 72 based on the variant profile of the selected top 10 sequences with scores better than the lead sequence (the top 10 ranked sequences among the variant library used). See FIGS. 13B and C for $V_H$ CDR1 and CDR2.

6) Construction of Degenerate Nucleic Acid Library Based on Hit Variant Library II The hit variant library constructed above was targeted with a single degenerate nucleic acid library. The lower portion of FIG. 13A shows a nucleic acid sequence profile resulting from back-translation using the optimal *E. coli* codons for $V_H$ CDR3. Based on this profile, a degenerate nucleic acid library was synthesized by incorporating a mixture of bases into each degenerate position. As a result of the combinatorial effect of the synthesis, this degenerate nucleic acid library encodes an expanded amino acid library (designated "hit variant library III") with a size of 4608. See FIGS. 13B and C for $V_H$ CDR1 and CDR2.

The degenerate nucleic acid library constructed above was cloned into a phage display system and the phage-displayed antibodies (ccFv) were selected based on their binding to immobilized VEGF coated onto 96-well plates. As will be described in more detail in section 2 below, with a small nucleic acid library size, one to three round of washing and selection (i.e., panning) were performed and clones showing positive ELISA reaction were selected and sequenced as shown in FIG. 14B for $V_H$ CDR3. The positive clones show a diverse variant profile at targeted position with the incorporation of degenerate codons into the nucleic acid library.

The results of the designed versus the experimentally screened antibody sequences are analyzed in FIGS. 14–18. In brief, the sequences for $V_H$ CDR1,2,3 have been designed based on the inventive method described above in detail for $V_H$ CDR3. Top 10 sequences and their variant profiles selected from the computationally screened libraries for $V_H$ CRD3, CDR2 and CDR2, respectively, are shown FIGS. 13A–C. FIG. 16A is a table that lists the experimentally selected amino acids sequences from $V_H$ CDR1, CDR2 and CDR3 libraries of degenerate nucleic acids shown in FIGS. 13A–C. FIG. 16B shows the distribution of the sequence identities of selected sequences from $V_H$ CDR1, CDR2 and CDR3 libraries relative to the corresponding parental sequence of anti-VEGF $V_H$ CDR1,2,3 respectively. FIG. 17A shows the relationship among 4 different libraries (designed amino acid sequences, the combinatorial library of amino acid variant of the designed sequences, and combinatorial degenerate nucleic acid libraries encoding the unique amino acid sequences and the entire degenerate nucleic acid library) and the distribution of the experimentally selected positive clones shown in X, using anti-VEGF $V_H$ CDR3 library from round 3 as an example (see table in FIG. 17B). The distribution among different libraries depends on selection conditions, the effectiveness of library design, the relative size of the selected colons versus library or number of sequenced clones etc. FIG. 17B shows a table delineating the relationships among the four libraries (FIG. 17A) and the distribution of the experimentally selected sequences of the positive clones for anti-VEGF $V_H$ CDR1, 2, 3 library.

Detailed analysis for $V_H$ CDR3 is discussed below. FIG. 14A shows UV reading of the ELISA positive clones identified in round 1 and round 3 selections of functional anti-VEGF ccFv antibodies with $V_H$ CDR3 encoded by the designed nucleic acid library FIG. 13A). FIG. 14B shows $V_H$ CDR3 sequences of the positive clones from round 1 and 3 selection via phage display of the nucleic acid library shown in FIG. 13A. It is clear that many diverse sequences are selected with large variations at several positions that are different from $V_H$ CDR3 of parental and matured anti-VEGF antibody FIGS. 9A & B). FIG. 14C illustrates a phylogenic tree of the positive clones showing the diversity of the screened sequences. The sequence identities of the selected positive clones from $V_H$ CDR3 shown in FIG. 14B ranged from 57 to 73 percent relative to the parental $V_H$ CDR3 sequence. FIGS. 15A–B are pie charts showing the breakdown of the origins of the screened sequences in the first and third rounds into three groups: designed amino acid sequences, combinatorial amino acid sequences from the designed sequences, and the unique combinatorial amino acid sequences encoded by the synthesized degenerate nucleic acid library. Because only limited number of positive clones from each round are selected for sequence analysis, the figures are only used to illustrate percentage of the selected sequences from designed, its combinatorial amino acid and nucleic acid libraries.

These experiments demonstrated that by using the methods of the present invention, antibodies could be selected, not only with diverse sequences and phylogenic distances, but also with relevant biological function, e.g., ability to bind to the target antigen such as VEGF.

FIG. 18 summarizes the progressive evolution of the sequence design using the scoring results for amino acid sequences at each stage for $V_H$ CDR3 as an example. From left to right, the diagram shows the energy spectra for the lead sequence, the hit library generated from the database search, computationally screened combinatorial sequences in the hit variant library I, a selected group of designed amino acid sequences (hit variant library II), a degenerate nucleic acid library derived from library II profile, and experimentally screened positive clones and sequences. The process can be iterated with feedback from experiments until the sequences with enhanced or desired properties are selected experimentally.

FIG. 19A-D show the comparison of the sequence homology distribution based on a lead sequence or a lead sequence derived from a multiple structure-based alignment. FIG. 19A shows the lead profile generated from structure-based mutiple seqeuce alignment. The structural motif of the lead sequence is used to search protein structure database (PDB databank) for similar structures within certain distance cutoff. The five structures are superimposed using Ca atoms of the $V_H$ CDR3. The average root mean squire difference (RMSD) between each structure and $V_H$ CDR3 structure motif (colored in magenta) is within 2 Å. The corresponding mutiple sequence alignment is shown in the right of FIG. 19A, together with their PDB IDs and color of the corresponding structure.

FIG. 19B shows a variant profile for the 251 unique sequences of the hit library generated based on the lead sequence profile of $V_H$ CDR3 of parental anti-VEGF antibody. The lower portion of the figure shows a filtered variant profile obtained by using a 5% cutoff of the frequency or 12 in this case. Interestingly, important mutants (H97Y and S100aR or S100aT, see FIGS. 30 & 36) are also observed in the variant profile generated from the lead sequence profile.

FIG. 19C shows the distribution of the sequences from the hit library relative to the parental $V_H$ CDR3 sequence. The circles indicate the sequence identity up to 36% can be identified using the single parental sequence for HMM search. The triangles indicate that even lower sequence identity up to ~20% can be found using the lead sequence profile from a structure-based multiple sequence alignment. The sequence searching strategy used here can find diverse hits with remote homology (as low as 20%) to the lead sequence.

FIG. 19D shows the conceptual evolution of the inventive methods used here to search for promising candidates in sequence, structure and function spaces. The basic idea here is to expand the diversity of hits and variant libraries in sequence and structure space in order to find the candidates with improved function in function space. While the diversity and/or the size of the hit and variant library is increased by, for example, finding remote homologues of the lead sequence or sequence profile (as shown in FIG. 19A), the intersection among the sequence, structure and function spaces can be focused into a smaller region with increased probability of finding sequences with enhanced function.

It is clear that using structurally-based multiple sequence alignment as the profile to build the HMM model makes it possible to find remote homologues (to 20% sequence identity of the query sequence) of a lead sequence. The inventive method described here will become more powerful for designing antibody CDR libraries with the increase in available sequence and structure information and improvement in the accuracy of the scoring functions.

2. Functional Screening of Designed Antibody Libraries in Vitro

The antibody libraries that were designed in silico, based on a lead sequence of the parental anti-VEGF antibody by using the methods described above were tested for their ability to bind to the antigen, VEGF, by using a novel phage display system. The structure of either the parental antibody or matured antibody would be used for structure-based computational screening. In contrast to the popular approach of screening antibodies adopting a form of single chain antibody (scFv) (see another novel method shown in FIGS. 20 & 32), a two-chain antibody library was expressed and displayed on the surface of bacteriophage. The two-chain antibody is formed by heterodimerization of $V_H$ and $V_L$ to functionally mimic the Fab of antibody. This two-chain antibody is designated as "ccFv". The ccFv library was constructed based on the degenerate nucleic acid library encoding sequences of the antibodies designed in silico as described above.

Described in detail below are the rationale for designing the ccFv, construction and expression of the ccFv library, and functional screening of the ccFv library.

1) ccFv—a Heterodimeric Coiled-Coil Stabilized Antibody

The antibody Fv fragment is the smallest antibody fragment containing the whole antigen-binding site. The Fv fragments have very low interaction energy between their two $V_H$ and $V_L$ fragments, and are often too unstable for many applications at physiological condition. Naturally, $V_H$ and $V_L$ domain are linked by an interchain disulfide bond located in the constant domains, $C_H1$ and $C_L$, to form a Fab fragment. It has also been shown that the $V_H$ and $V_L$ fragments can also be artificially held together by a short peptide linker between the carboxy-terminus of one fragment and amino-terminus of another to form a single-chain Fv antibody fragment (scFv).

The present invention provides a new strategy to stabilize $V_H$ and $V_L$ heterodimer. A unique heterodimerization sequence pair was designed and used to create a Fab-like, functional artificial Fv fragment ccFv (FIG. 20). Each of the heterodimeric sequence pair was derived from heterodimeric receptors $GABA_B$ R1 and R2, respectively. This sequence pair specifically forms a coiled-coil structure and mediates the functional heterodimerization of $GABA_B$-R1 and $GABA_B$-R2 receptors. For the purpose of engineering a heterodimer of $V_H$ and $V_L$ of an antibody, $GABA_B$-R1 and $GABA_B$-R2 coiled coil domains (GR1 and GR2, respectively) are fused to the carboxy-terminus of $V_H$ and $V_L$ fragment, respectively. Thus, the functional pairing of $V_H$ and $V_L$, ccFv (coiled coil Fv), is mediated by specific heterodimerization of GR1 and GR2. Furthermore, the carboxy-termini of GR1 and GR2 domains were modified by adding a flexible spacer or flexon "SerArgGlyGlyGlyGly" [SEQ ID NO: 7] (or "GlyGlyGlyGlySer"" [SEQ ID NO: 18]) To further stabilize the heterodimeric ccFv, a pair of cysteine residues were introduced by adding "ValGlyGlyCys" [SEQ ID NO: 8] spacer at the C-termini of the GR1 and GR2 coiled coils so that the coiled-coil GR1 & GR2 mediated heterodimer can be linked covalently by disulfide bond (FIG. 20-21). ccFv were expressed in *E.coli* with a molecular weight 35 kDa.

2) Anti-VEGF (AM2-ccFv) and its Display on Phage Surface $V_H$ and $V_L$ sequences of an anti-VEGF antibody AM2 are shown in FIG. 22A-B. This is an antibody designed by modifying the parental anti-VEGF antibody. Unique restriction sites were introduced in both $V_H$ and $V_L$ genes of the parental anti-VEGF antibody to facilitate an efficient cloning of designed CDR sequence libraries. Both AM2 $V_H$ and $V_L$ genes were cloned into a phagemid vector to construct the phage display vector pABMD 12. FIGS. 23A and 23B show the vector map and sequence [SEQ ID NO: 17], respectively. This vector will express two fusion proteins: $V_H$-GR1 and $V_L$-GR2-pIII fusions. The expressed $V_H$-GR1 and $V_L$-GR2-pIII fusions are secreted into periplasmic space, where they heterodimerize to form a stable ccFv antibody (designated as "AM2-ccFv") via the coiled-coil domain.

To display AM2-ccFv on phage, pABMD12 vector was transformed into bacterial TG1 cells. The TG1 cells carrying the pABMD12 vector were further superinfected with KO7 helper phage. The infected TG1 cells were grown in 2×YT/Amp/Kan at 30° C. overnight. The phagemid particles were precipitated twice by PEG/NaCl from culture supernatants, and resuspended in PBS for library selection against immobilized VEGF. After 2 hours of binding, unbound phages were washed away and bound phages were eluted and amplified for the next round of panning.

Binding of the ccFv displayed on phage particles was detected by antigen binding activity via phage ELISA. Briefly, the antigen (e.g., VEGF) was first coated onto the ELISA plates. After blocking with 5% milk/PBS, the phage solution was added to the ELISA plates. The phages bound to the immobilized antigen were detected by incubation with HRP-conjugated anti-M13 antibody against phage coat protein pVIII. The substrate ABTS [2,2'Azino-bis(3-ethylbenzthiazoline-6-sulfonic acid)] was used for measurement of HRP activity. The assay was shown to be highly specific for AM2.

The single-chain AM2 antibody (AM2-scFv) phage was also prepared for comparison with the AM2-ccFv in phage ELISA described above. As indicated in FIG. 24, the apparent binding affinity of AM2-ccFv phage to immobilized VEGF is almost one order of magnitude higher than AM2-scFv phage. Thus, it is concluded that both AM2-ccFv and AM2-scFv are functional when displayed on a phage particle.

3) Enrichment of ccFv Phages from a Model Antibody Library

To prove that AM2-ccFv displayed phages can be enriched from background phages, we performed panning experiments to select for AM2-ccFv phage from "model libraries". The model libraries were prepared by mixing of AM2-ccFv phages with an unrelated AM1-ccFv displayed phage at a ratio of $1:10^6$ or $1:10^7$. Two round of panning on immobilized VEGF antigen were carried out. 100 ul of 2 ug/ml VEGF was coated on each well in a 96-wells plate. After blocking with 5% milk in PBS, $1\times10^{12}$ library phages in 2% milk/PBS were added to the well, and incubated for 2 hours at room temperature. Phage solution was discarded and wells were washed 5 times with PBST (0.05% Tween-20 in PBS) and 5 times with PBS. Bound phages were eluted with 100 mM triethylamine, and were added to TG1 culture for infection. The phages prepared from infected TG1 cells were used for the next round panning and phage ELISA described above. After each round of panning, the ratio of AM2-ccFv phage to AM1-ccFv phage recovered was also determined by analysis of infected TG1 colonies via PCR. Due to the difference in the sequences of AM2-ccFv gene and AM1-ccFv gene, a pair of primers was designed to specifically amplify only AM2-ccFv gene, but not AM1-ccFv. As shown in FIG. 25A, phages from the second round panning yielded very high ELISA reading, suggesting that a high enrichment of AM2-ccFv phages was achieved from both the $1:10^6$ and the $1:10^7$ libraries after 2 rounds of panning. PCR analysis confirmed that the occurrence rate of AM2-ccFv phage was 4.4% from $1:10^7$ library after the first round panning, and 100% after the second round of panning (FIG. 25B).

4) Construction and Panning of Phage Library of Designed ccFv Antibodies

As diagramed in FIG. 8, a modular, evolutionary approach was employed to construct an antibody library for computational and experimental screening. The oligos encoding a library of designed CDR sequences were synthesized and amplified by PCR. The primers for amplification contain the restriction sites to clone the synthetic CDR sequences into the pABMD12 vector. Three $V_H$ libraries were prepared for AM2-ccFv, using restriction sites of NheI and XmaI, XmaI and SpelI, and PstI and StyI for the insertion of CDR1, CDR2 and CDR3, respectively. After ligation, DNA was transformed into TG1 cells. Phages were prepared from TG1 cells by KO7 helper phage infection. Three rounds of panning against immobilized VEGF were carried out as described below. 100 ul of 2 ug/ml VEGF was first coated onto each well of a 96-well plate. After blocking with 5% milk in PBS, $1\times10^{12}$ library phages in 2% milk/PBS were added to the well and incubated for 2 hours at room temperature. The phage containing solution was then discarded, and the wells were washed 5 times with PBST (0.05% Tween-20 in PBS) and 5 times with PBS. Bound phages were finally eluted with 100 mM triethylamine, and were added to TG1 culture for infection. The phages prepared from infected TG1 cells were consequently used for the next round of panning. For each round of panning, 94 to 376 clones were picked for phage ELISA (FIGS. 26A and B). Positive clones from the phage ELISA were amplified by PCR and sequenced. DNA sequences were then translated to amino acid sequences. The coding amino acid sequences from the three libraries ware listed in a table in FIG. 27.

5) Library Design Based on the Sequence with and without Constraints from Tertiary Structure or Structural Model Another strategy for designing CDR libraries is to partition the CDR sequences into uncorrelated and correlated segments in structure space in order to detect the covariant mutants at structurally coupled positions such as the N- and C-termini regions of the CDR loops (low resolution structure should be enough in most cases). For example, FIG. 28A shows a composite variant profile for $V_H$ CDR3 of anti-VEGF antibody obtained by combining a filtered hit variant profile for $V_H$ CDR3 with other variants from experimental selection. We would like to demonstrate that variants from diverse sources can be combined to generate a composite variant profile for library construction. This variant profile is parsed into several segments of smaller variant profile in order to make sure that each smaller variant profile can be covered by a nucleic acid library with a diversity around $10^{6-107}$. Note, the combination of the $V_H$ CDR3 mature sequence with H97Y and S101T (S100aT in Kabat) is deliberately avoided in the parsed segment libraries (see FIGS. 28A–D).

FIG. 28A-D show the sequence library of anti-VEGF $V_H$ CDR3. The library is parsed into 3 segments: FIG. 28B covers the N- and C-termini that might contain coupled variants (1–3), FIG. 28C contains segment (4) and FIG. 28D contains another segment (5). All three segments are covered by nucleic acid libraries with a size around $10^6$: (1–3) in FIG. 28B are targeted by 3 degenerate nucleic acid libraries, whereas (4) and (5) in FIGS. 28C–D are targeted by a separate degenerate nucleic acid library.

The rationale for designing these segment libraries is as follows. Structurally distant segments are often uncorrelated so that mutations widely separated in space can be treated independently. For the CDR3 loop, the sequence is partitioned into three segments: the first and third segments (base of the loop) form one profile for library design, whereas apex of the loop is parsed into two profiles for library design with a size of $10^6$ in the degenerate nucleic acid libraries. As shown in FIG. 28B, fragments at N- and C-termini that couple with each other in space (the sequences forming the base of the loop are generally correlated due to loop closure) should be targeted simultaneously by the combinatorial nucleic acid libraries with only three degenerate oligonucleotides (1–3). Simple criteria such as the $C_\alpha$ or $C_\beta$ distance matrix can be examined to identify correlated segments (see FIG. 28A for the structure and distance contact matrix among $C_\alpha$ atoms within 8A). Optionally, a more detailed interaction matrix can be mapped out to explore number and types of interactions, but the underlying principle is the same for identifying correlated segments.

Libraries for the apex, such as (4) and (5) in FIGS. 28C and 28D, are often uncorrelated. They are targeted by degenerate oligonucleotide libraries along the primary sequence in a consecutive fashion as long as each library is limited to the size range that can be managed easily by experiment ($<10^6$ in FIGS. 28C–D). There should be positional overlaps between the fragments to maintain a small level of local correlation among the resulting libraries. In a similar fashion, longer segments can be partitioned into overlapping segments to span the length of the sequence and the corresponding libraries can be generated.

The resulting re-profiling can be further modified and enhanced based on observed experimental or structural or computational criteria. These can include varying positions with known hydrogen bonds with additional polar amino acids, region of high van der Waals contacts with bulky aliphatic or aromatic groups, or region which might benefit from increased flexibility with glycine. In an experimental feedback, variants may be added based on assay results from earlier screening as a basis for subsequent design improvement as shown the variant profile in FIG. 28A. A more sophisticated analysis might take into account the coupling of amino acid groups such as salt bridges or hydrogen bonds within the sequence.

6) Off-Rate Panning for ccFv Library L14

In order to select high affinity antibodies, off-rate panning process was carried out for selection in library L14 (see FIG. 28A-D). The strength of the interaction between an antibody fragment on phage surface and an immobilized antigen is measured by their interacting affinity, which is determined by its on-rate (the rate of association) and off-rate (the rate of dissociation). According to previous studies, antibody of high affinity usually bears slow off-rate whereas antibody of low affinity usually bears fast off-rate, whereas their on-rates are similar. The off-rate panning was designed to facilitate the dissociation of those antibodies with lower affinities from immobilized antigen with gradual increase in harshness (stringency) of wash conditions. By applying washes of increasing stringency, phages with lower affinities will be washed away, leaving behind phages with increasingly higher affinities (i.e., the slower off-rates). Therefore, those phages that survive increasingly harsh washing conditions should have higher affinities and those whose occurrence becomes dominant must have higher affinities than those of low occurrence rate. We also demonstrate comparable off-rate panning at the phage level using two independent display platforms (FIGS. 20 and 32) under various panning conditions (FIGS. 29 and 35A–B). The resulting positive clones or consensus of clones from phage panning should suggest strongly that some sequences or variants should possess enhanced affinity with antigen relative to the parental sequences.

L14 was prepared as anti-VEGF $V_H$ CDR3 library by parsing the $V_H$ CDR3 sequence into short overlapping segments (see FIG. 28A-D). In order to discriminate slow off-rates, a number of panning conditions were manipulated. During the first two rounds of panning, wells were briefly washed 6 times with PBST and PBS to remove phages with lower affinities. Starting from panning 3, the bound phages were further washed with additional hours to remove those with faster off-rates (dissociation). The duration and stringency of such a dissociation period were increased with the number of panning (FIG. 29) so that more and more phages were allowed to dissociate and to be removed; in contrast, those with slow off-rate (higher affinity) would remain bound and are eventually enriched. As listed in FIG. 29, panning 3 was performed in PBS for 1 hour at 37° C. (PBS was refreshed every 10 min. and a brief wash was applied in between to remove the dissociated phages); panning 4 was performed in PBS for 2 hours at 37° C.; panning 5 was performed in PBST for 1 hour at room temperature followed by PBS for 2 hours at 37° C.; panning 6 applied an overnight wash in a large volume (20 ml) of PBS at room temperature; panning 7 further increased the temperature (30° C.), volume (50 ml), and duration (24 hrs) of the wash. As indicated in FIG. 29, in addition to changing the wash stringency described above, by lowering the concentration of antigen, the concentration of the phage input, and increasing the temperature of the binding period, dissociation is further enhanced. The surviving clones from the panning were randomly picked and assayed in phage ELISA to confirm their abilities to bind to VEGF. 100% ELISA positive rate was obtained from clones in both panning 5 and 7, suggesting that after panning 5, all survival phages were able to bind to VEGF, and therefore, phages being washed away had faster off-rates. Among the clones that were positive in phage ELISA, 20 clones from panning 5 and 10 clones from panning 7 were randomly picked for DNA sequencing. The coding amino acid sequences for VH CDR3 are summarized in FIG. 30. The frequency of the wild-type anti-VEGF antibody was 20% in panning 5. After two additional rounds of off-rate panning with high stringency, the frequency of the wild-type sequence dropped to zero in panning 7. In contrast, the HR (H97, R101 or R100a in Kabat) mutant was continuously enriched from 35% in panning 5 to 70% in panning 7 (FIG. 30), which became the sole dominant clone in the end. The presence of the HT (H97, T101 or T100a in Kabat) mutant (30%) remained unchanged in panning 5 and 7. The enrichment of HR mutant from P0 to P7 is shown in FIG. 31. These data suggest that both HR and HT mutant have higher affinity than that of wild-type antibody. The affinity of HR mutant should be higher than that of HT mutant, which has a threonine, rather than arginine, at position 101 (or 100a in Kabat), as reported for the matured sequence (Chen Y, Wiesmann C, Fuh G, Li B, Christinger H W, McKay P, de Vos A M, Lowman H B (1999) J. Mol Biol 293, 865–881).

8) Panning of Single-Chain (scFv) Anti-VEGF Antibody Library by Adapter-Mediated Phage Display System.

The off-rate panning strategy was further tested using an independent system as described below.

In the conventional phage display system, a protein of interest is fused to a phage capsid protein such as pIII in order to be displayed on the surface of phage. This fusion protein will be assembled into phage particles with the wild-type phage proteins provided by a helper phage such as KO7. We have developed a new phage display system named 'adaptor-directed display system'. In general, a protein of interest is carried to the surface of the phage particle by a pair of adaptors that specifically form a heterodimer, one being fused with the displayed protein in an expression vector and the other being fused with a phage capsid protein in a helper vector. The present example for the pair of adaptors is GR1 and GR2, as described above. As illustrated in FIG. 32, the protein of interest (scFv anti-VEGF) is expressed as a fusion with an adaptor (GR1) to form a construct of scFv-GR1 in an expression vector (FIGS. 33A and B). GR2 was inserted in the genome of a helper phage to form a fusion with pIII capsid protein (GR2-CT of pIII, FIGS. 33A and B). As a result, the helper phage with the modified genome is then designated the GMCT Ultra-Helper phage (FIGS. 34A and B). In TG1 cells, the expression vector expresses scFv-GR1, which is then secreted into bacterial periplasmid space. The cells are further infected with GMCT Ultra-Helper phage, which expresses GR2-CT of pIII, also secreted into the bacterial periplasmic space. Therefore, scFv-GR1 and GR2-CT of pIII specifically form a heterodimer through a coiled-coil interaction between GR1 and GR2, which ultimately assembles the scFv onto the surface of the phage.

Using this system, we constructed an anti-VEGF scFv library L17, equivalent to ccFv library L14 described above (anti-VEGF CDR3 $V_H$ synthetic library). Similar to the selection of library L14, off-rate panning was applied. Library DNA was transformed into TG1 cells and then rescued with GMCT Ultra-Helper phage. Phages were prepared following standard protocol and tested for binding against immobilized VEGF in 96-well plate. As indicated in FIG. 35A, wells from panning 1 and 2 were first washed 10 times with PBST and then 10 times with PBS at room temperature, followed by a dissociation period in PBST for 1 hour at room temperature (PBST was refreshed every 10 min. and a brief wash was applied in between to remove the dissociated phages); the dissociation period was increased to 2 hours in panning 3. Using phages recovered from panning 3, two parallel pannings (FIG. 35B), panning 4 and panning 5, were carried out in order to further enhance the dissociation of phages with lower affinities: 150 ml PBST for 18 hrs at 25° C. for panning 4, and at 37° C. for panning 5. Ten clones of ELISA positives from panning 4 and 8 clones from panning 5 were picked randomly for sequencing. The data are shown in FIG. 36. In panning 4, the presence of WT sequence was 10%. The frequencies of both HT mutant (30%) and HA mutant (30%) were equal. Note that there is no arginine residue shown in position 101 (100a Kabat) among the 10 clones analyzed (FIG. 36), suggesting its low occurrence at this stage. In contrast, by increasing the dissociation stringency at panning 5, the occurrence of arginine in position 101 (100a Kabat) increases to 50% (4 out of 8 clones) and becomes dominant in panning 5. In comparison, the HT mutant drops from 30% to 12.5% and the WT drops from 10% to 0, consistent with the observation in FIG. 30. This result suggests strongly that the HR mutant has a higher affinity than either the HT mutant or the WT.

9) Summary of the Library Design, Diversity and Affinity Maturation

Results shown in both FIGS. 30 and 36 suggest that the off-rate panning of two independent novel phage display systems used here are able to select out a novel mutant, HR (H97,R101 or R100a Kabat). The HR mutant has a higher binding affinity than the corresponding HT (H97, T101 or T100a Kabat) mutant in the reported matured sequence (FIG. 9B). Moreover, HR mutant binds the antigen better than the YS (Y97, S101 or S101a Kabat) mutant (see Panning 4 of FIG. 36). The YS mutant was reported previously to improve the binding affinity 14-fold relative to the WT and was believed to be the single most important mutant in $V_H$ CDR3 of the matured anti-VEGF antibody (FIG. 9B and see Chen Y, Wiesmann C, Fuh G, Li B, Christinger H W, McKay P, de Vos A M (1999) J Mol Biol 293, 865–881). This mutant H97Y is also found to be important in the designed library both by database searching (FIG. 11) and computational screening (FIG. 13A).

K94 is an interesting case and deserves some discussion. Strictly speaking, K94 does not belong to $V_H$ CDR3 according to the Kabat nomenclature. However, the sequence CAK at the N-terminal of $V_H$ CDR3 are included in building the HMM motif because this sequence puts a strong constraint on the boundary of the sequence motif. Because CAK is the boundary region between framework and $V_H$ CDR3, we consider it here to test the impact of the mutation in this region on the binding affinity. Although R94 is found to be favorable in both the database search and computational screening (FIGS. 11 and 13A), K94 binds tighter than R94 in experimental screening (FIGS. 30 and 36). Only K94 was selected when both K94 and R94 were included in the libraries (FIGS. 28B, 30 and 36), although the R94 is still active in binding to VEGF (see FIGS. 13A and 14B). The reason for this might be that R94 in the joint region would change the orientation of the $V_H$ CDR3 in binding to the antigen by interacting with other regions of the antibody, thereby invalidating the original K94 x-ray structure (matured antibody) used for computational screening. It was reported that R94 would reduce the binding affinity of the anti-VEGF antibody by ~5-fold during humanization (Presta L G, O'Connor S J, Wells J A (1997) J Biol Chem 272, 10678–10684). Several approaches can be used to avoid this problem: (1) avoid designing the boundary residues if only CDRs should be designed; (2) combine both parental and preferred residues (e.g. both K and R at 94) in the experimental library. These should be reasonable and straightforward in this case because R and K are the two major residues (~90% for R94 and ~10% for K94) preferred at this position from the database search (see FIG. 11); (3) sampling the conformations at this position for R94 computationally by molecular dynamics simulation and see if altered structure or structure ensemble should be used with R94.

To summarize, the three important sites around $V_H$ CDR3 region of the anti-VEGF antibody have been found to have a direct impact on the binding affinity of the antibody for VEGF. Two of the mutations (Y97 and R101 or R100a Kabat) in the three positions (K94, H97 and S101) were found to be important for improved binding with antigen using either the parental or matured antibody structure in the presence and/or absence of antigen, whereas R94 was not predicted correctly because of the potential structural changes induced by the mutation at the joint region. Y97 is known to be an important mutation for affinity improvement as shown in our own experimental screening. R101 (R100a Kabat) is a novel mutant confirmed by two independent phage display systems and may confer potentially higher affinity than that by Y97.

Most of these mutants including R94, Y97 and R101 are among the dominant variants in the hit variant profile (see FIG. 11) (>5%). So a simple sequence search would have found them from the hit variant library. In structure-based screening of the variant library, these mutants are also ranked higher in the selected sequence profile as shown in FIG. 13A. From an ensemble sequence scoring point of view, the pooling and reprofiling of the sequences scoring higher than the parental sequence, also ranks the observed variants at 94 (88% R, 12% K), 97 (60% Y, 17% H), and 101 (60% R, 17% T, 13% S) highly. Except for the problem associated with R94, the statistical preference for Y97 and R101 or T101 is apparent in our design. We have demonstrated our library design, using sequence searching and/or structure-based scoring to generate variant profiles. The experimental screening or selection using the two independent novel phage display systems have shown the utility of the inventive methods described here in designing sequences different from the parental sequence in $V_H$. Some of the mutants found here, such as Y97 and/or R101 or T101, have affinity higher than that of the parental sequence by at least 10-fold (Y97 is reported to account for a 14-fold improvement in affinity while R101 is shown in our experiments to have a higher affinity (see FIG. 36). By extraploatoin, a combination of the mutants, such as Y97 and R101, is likely to have a higher affinity than that reported for the matured sequence.

It should be noted that the antibody libraries designed by using the methods of the present invention can not only be expressed and screened in a bacteriophage system, but also in cells of other organisms, including but not limited to yeast, insect, plant, and mammalian cells. A designed antibody, including the antigen binding fragments and other antibody forms, may be produced by a variety of recombinant DNA or other techniques. For example, the DNA segment(s) encoding the designed antibody may be cloned into an expression vector and transferred into the host cells by well-known methods, which varies depending on the type of the cellular host, including but not limited to calcium chloride transfection, electroporation, lipofection, and viral transfection. The antibody may be purified according to standard procedures of the art, including but not limited to ammonium sulfate precipitation, affinity columns, column chromatography, gel electrophoresis, and the like. Various modifications may occur to those skilled in the art without departing from the spirit and scope of the invention as defined by the appended claims.

The antibodies designed by using the methods of present invention may be used for diagnosing or therapeutic treatment of various diseases, including but not limited to, cancer, autoimmune diseases such as multiple sclerosis, rheumatoid arthritis, systemic lupus erythematosus, Type I diabetes, and myasthenia gravis, graft-versus-host disease, cardiovascular diseases, viral infection such as HIV, hepatitis viruses, and herpes simplex virus, bacterial infection, allergy, Type II diabetes, hematological disorders such as anemia.

The antibodies can also be used as conjugates that are linked with diagnostic or therapeutic moieties, or in combination with chemotherapeutic or biological agents. The antibodies can also be formulated for delivery via a wide variety of routes of administration. For example, the antibodies may be administered or coadministered orally, topically, parenterally, intraperitoneally, intravenously, intraarterially, transdermally, sublingually, intramuscularly, rectally, transbuccally, intranasally, via inhalation, vaginally, intraoccularly, via local delivery (for example by a catheter or a stent), subcutaneously, intraadiposally, intraarticularly, or intrathecally.

The methods of present invention for designing protein libraries in silico can be implemented in various configurations in any computing systems, including but not limited to supercomputers, personal computers, personal digital assistants (PDAs), networked computers, distributed computers on the internet or other microprocessor systems. The methods and systems described herein above is amenable to execution on various types of executable mediums other than a memory device such as a random access memory (RAM). Other types of executable mediums can used, including but not limited to, a computer readable storage medium which can be any memory device, compact disc, zip disk or floppy disk.

The patents, patent applications and publications cited above are incorporated herein by reference in their entirety.

What is claimed is:

1. A method for constructing a library of antibodies based on a structure of a lead antibody, the method comprising:

providing an amino acid sequence of the variable region of the heavy chain ($V_H$) or light chain ($V_L$) of a lead antibody, the lead antibody having a known three dimensional structure which is defined as a lead structural template;

identifying the amino acid sequences in the complementarity determining regions (CDRs) of the lead antibody;

selecting one of the CDRs in the $V_H$ or $V_L$ region of the lead antibody;

providing an amino acid sequence that comprises at least 3 consecutive amino acid residues in the selected CDR, the selected amino acid sequence being a lead sequence;

comparing the lead sequence with a plurality of tester protein sequences;

selecting from the plurality of tester protein sequences at least two peptide segments that have at least 10% sequence identity with the lead sequence, the selected peptide segments forming a hit library;

determining if each of the selected peptide segments in the hit library is structurally compatible with the lead structural template using an energy-based scoring function;

selecting the peptide segments in the hit library that have an equal or lower energy score than that of the lead sequence, which indicates that the selected peptide segments are structurally compatible with the lead structural template displaying the selected peptide segments in the hit library ; and constructing a library of antibodies based on the selected peptide segments in the hit library.

2. The method of claim 1, wherein the length of the lead sequence is between 5–100 aa.

3. The method of claim 1, wherein the length of the lead sequence is between 6–80 aa.

4. The method of claim 1, wherein the length of the lead sequence is between 8–50 aa.

5. The method of claim 1, wherein the amino sequences in the CDRs are identified based on Kabat criteria or Chothia criteria.

6. The method of claim 1, wherein the lead sequence comprises an amino acid sequence from a region within the $V_H$ or $V_L$ of the lead antibody selected from the group consisting of CDR1, CDR2, CDR3, FR1-CDR1, CDR1-FR2, FR2-CDR2, CDR2-FR3, FR3-CDR3, CDR3-FR4, FR1-CDR1-FR2, FR2-CDR2-FR3, and FR3-CDR3-FR4, FR being defined as a framework region in an antibody variable region.

7. The method of claim 1, wherein the lead sequence comprises at least 6 consecutive amino acid residues in the selected CDR.

8. The method of claim 1, wherein the lead sequence comprises at least 7 consecutive amino acid residues in the selected CDR.

9. The method of claim 1, wherein the lead sequence comprises all of the amino acid residues in the selected CDR.

10. The method of claim 1, wherein the lead sequence further comprises at least one of the amino acid residues immediately adjacent to the selected CDR.

11. The method of claim 1, wherein the lead sequence further comprises at least one of the amino acid residues in the FRs flanking the selected CDR.

12. The method of claim 1, wherein the lead sequence further comprises one or more CDRs or FRs adjacent the C-terminus or N-terminus of the selected CDR.

13. The method of claim 1, wherein the plurality of tester protein sequences comprises antibody sequences.

14. The method of claim 1, wherein the plurality of tester protein sequences comprises human antibody sequences.

15. The method of claim 1, wherein the plurality of tester protein sequences comprises humanized antibody sequences having at least 70% human sequences in $V_H$ or $V_L$.

16. The method of claim 1, wherein the plurality of tester protein sequences comprises human germline antibody sequences.

17. The method of claim 1, wherein the plurality of tester protein sequences is retrieved from a database consisting of Genbank of the National Institutes of Health (NIH), Swiss-Prot database, and the Kabat database for CDRs of antibodies.

18. The method of claim 1, wherein the step of comparing the lead sequence with the plurality of tester protein sequences is implemented by an algorithm selected from the group consisting of BLAST, PSI-BLAST, profile Hidden Markov Model (HMM), and COBLATH.

19. The method of claim 1, wherein the sequence identity of the selected peptide segments in the hit library with the lead sequence is at least 25%.

20. The method of claim 1, wherein the sequence identity of the selected peptide segments in the hit library with the lead sequence is at least 35%.

21. The method of claim 1, wherein the sequence identity of the selected peptide segments in the hit library with the lead sequence is at least 45%.

22. The method of claim 1, wherein the scoring function is an energy scoring function selected from the group consisting of electrostatic interactions, van der Waals interactions, electrostatic solvation energy, solvent-accessible surface solvation energy, and conformational entropy.

23. The method of claim 1, wherein the scoring function is a scoring function that incorporates a forcefield selected from the group consisting of the Amber forcefield, Charmm forcefield, the Discover cvff forcefields, the ECEPP forcefields, the GROMOS forcefields, the OPLS forcefields, the MMFF94 forcefield, the Tripos forcefield, the MM3 forcefield, the Dreiding forcefield, and UNRES forcefield.

24. The method of claim 1, wherein the step of selecting the peptide segments in the hit library includes selecting the peptide segments in the hit library that have a lower or equal total energy than that of the lead sequence calculated based on a formula of $$\Delta E_{total}=E_{vdw}+E_{bond}+E_{angle}+E_{electrostatics}+E_{solvation}$$

Wherein $\Delta E_{total}$ is total energy; $E_{vdw}$ energy of van der Waals interactions; $E_{bond}$ bond energy; $E_{angle}$ bond angle energy; $E_{electrostatics}$ electrostatic energy; $E_{solvation}$ solvent-accessible surface solvation energy calculated for the peptide segment in the hit library.

25. The method of claim 1, wherein the step of selecting the peptide segments in the hit library includes selecting the peptide segments in the hit library that have a lower binding free energy than that of the lead sequence calculated as the difference between the bound and unbound states using a refined scoring function $$\Delta G_b=\Delta G_{MM}+\Delta G_{sol}-T\Delta S_{ss}$$

where $$\Delta G_{MM}=\Delta G_{ele}+\Delta G_{vdw} \quad (1)$$

$$\Delta G_{sol}=\Delta G_{ele\text{-}sol}+\Delta G_{ASA} \quad (2)$$

wherein $\Delta G_b$ is binding free energy; $\Delta G_{MM}$ free energy calculated using molecular dynamics forcefield; $\Delta G_{sol}$ is free energy contributed by solvation; T temperature; $\Delta S_{ss}$ conformational entropy; $\Delta G_{ele}$ free energy contributed by electrostatic interactions; $\Delta G_{vdw}$ free energy contributed by van der Waals interactions; $\Delta G_{ele\text{-}sol}$ free energy contributed by electrostatic solvation; $\Delta G_{ASA}$ free energy contributed by solvent-accessible surface solvation calculated for the peptide segments in the hit library.

26. The method of claim 1, wherein the lead structural template is a 3D structure of a fully assembled lead antibody.

27. The method of claim 1, wherein the lead structural template is a 3D structure of $V_H$ or $V_L$ of the lead antibody.

28. The method of claim 1, wherein the lead structural template is a 3D structure of a CDR or FR of the lead antibody, or combination thereof.

29. The method of claim 1, wherein the lead structural template is a structure derived from X-crystallography, nuclear magnetic resonance (NMR) spectroscopy or theoretical structural modeling.

30. The method of claim 1, further comprising the step of:

constructing a nucleic acid library comprising DNA segments encoding the amino acid sequences of the hit library.

31. The method of claim 1, further comprising the steps of:

building an amino acid positional variant profile of the hit library;

converting amino acid positional variant profile of the hit library into a nucleic acid positional variant profile by back-translating the amino acid positional variants into their corresponding genetic codons; and constructing a degenerate nucleic acid library of DNA segments by combinatorially combining the nucleic acid positional variants.

32. The method of claim 31, wherein the genetic codons are the ones that are preferred for expression in bacteria.

33. The method of claim 31, wherein the genetic codons are chosen such that the diversity of the degenerate nucleic acid library of DNA segments is below $1\times^{107}$.

34. The method of claim 31, wherein the genetic codons are chosen such that the diversity of the degenerate nucleic acid library of DNA segments is below $1\times10^6$.

35. The method of claim 31, further comprising the steps of:

introducing the DNA segments in the degenerate nucleic acid library into cells of a host organism;

expressing the DNA segments in the host cells such that recombinant antibodies containing the amino acid sequences encoded by the degenerate nucleic acid library are produced in the cells of the host organism; and selecting the recombinant antibody that binds to a target antigen with affinity higher than $10^6$ $M^{-1}$.

36. The method of claim 35, wherein the affinity of the selected recombinant antibody is higher than $10^8$ $M^{-1}$.

37. The method of claim 35, wherein the affinity of the selected recombinant antibody is higher than $10^9$ $M^{-1}$.

38. The method of claim 35, wherein the host organism is selected from the group consisting of bacteria, yeast, plants, insects, and mammals.

39. The method of claim 35, wherein the recombinant antibodies are selected from the group consisting of fully assembled antibodies, Fab fragments, Fv fragments, and single chain antibodies.

40. The method of claim 35, wherein the recombinant antibodies are displayed on the surface of phage particles.

41. The method of claim 40, wherein the recombinant antibodies displayed on the surface of phage particles are double-chain heterodimers formed between $V_H$ and $V_L$.

42. The method of claim 41, wherein heterodimerization of $V_H$ and $V_L$ chains is facilitated by a heterodimer formed between two non-antibody polypeptide chains fused to the $V_H$ and $V_L$ chains, respectively.

43. The method of claim 42, wherein the non-antibody polypeptide chains are derived from heterodimeric receptors $GABA_B$ R1 (GR1) and R2 (GR2), respectively.

44. The method of claim 40, wherein the recombinant antibodies displayed on the surface of phage particles are single-chain antibodies containing $V_H$ and $V_L$ linked by a peptide linker.

45. The method of claim 44, wherein display of the single chain antibody on the surface of phage particles is facilitated by a heterodimer formed between a fusion of the single chain antibody with GR1 and a fusion of phage pIII capsid protein with GR2.

46. The method of claim 35, wherein the target antigen is selected from the group consisting of small organic molecules, proteins, peptides, nucleic acids and polycarbohydrates.

* * * * *

SEQUENCE LISTING

```
<160> NUMBER OF SEQ ID NOS: 125

<210> SEQ ID NO 1
<211> LENGTH: 123
<212> TYPE: PRT
<213> ORGANISM: Artificial Sequence
<220> FEATURE:
<223> OTHER INFORMATION: VH of parental anti-VEGF antibody

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120


<210> SEQ ID NO 2
<211> LENGTH: 108
<212> TYPE: PRT
<213> ORGANISM: Artificial Sequence
<220> FEATURE:
<223> OTHER INFORMATION: VL of parental anti-VEGF antibody

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg
            100                 105
```

-continued

```
<210> SEQ ID NO 3
<211> LENGTH: 123
<212> TYPE: PRT
<213> ORGANISM: Artificial Sequence
<220> FEATURE:
<223> OTHER INFORMATION: VH of matured anti-VEGF antibody

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser
        115                 120


<210> SEQ ID NO 4
<211> LENGTH: 108
<212> TYPE: PRT
<213> ORGANISM: Artificial Sequence
<220> FEATURE:
<223> OTHER INFORMATION: VL of matured anti-VEGF antibody

<400> SEQUENCE: 4

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg
            100                 105


<210> SEQ ID NO 5
<211> LENGTH: 19
<212> TYPE: PRT
<213> ORGANISM: Artificial Sequence
<220> FEATURE:
<223> OTHER INFORMATION: VH CDR3 of parental anti-VEGF antibody

<400> SEQUENCE: 5

Cys Ala Lys Tyr Pro His Tyr Tyr Gly Ser Ser His Trp Tyr Phe Asp
1               5                   10                  15

Val Trp Gly
```

<210> SEQ ID NO 6
<211> LENGTH: 19
<212> TYPE: PRT
<213> ORGANISM: Artificial Sequence
<220> FEATURE:
<223> OTHER INFORMATION: VH CDR3 of matured anti-VEGF antibody

<400> SEQUENCE: 6

Cys Ala Lys Tyr Pro Tyr Tyr Tyr Gly Thr Ser His Trp Tyr Phe Asp
1 5 10 15

Val Trp Gly

<210> SEQ ID NO 7
<211> LENGTH: 6
<212> TYPE: PRT
<213> ORGANISM: Artificial Sequence
<220> FEATURE:
<223> OTHER INFORMATION: Flexon sequence

<400> SEQUENCE: 7

Ser Arg Gly Gly Gly Gly
1 5

<210> SEQ ID NO 8
<211> LENGTH: 4
<212> TYPE: PRT
<213> ORGANISM: Artificial Sequence
<220> FEATURE:
<223> OTHER INFORMATION: Spacer

<400> SEQUENCE: 8

Val Gly Gly Cys
1

<210> SEQ ID NO 9
<211> LENGTH: 146
<212> TYPE: DNA
<213> ORGANISM: Artificial Sequence
<220> FEATURE:
<223> OTHER INFORMATION: GR1 domain

<400> SEQUENCE: 9
tctagaggtg gaggaggtga ggagaagtcc cggctgttgg agaaggagaa ccgtgaactg 60
gaaaagatca ttgctgagaa agaggagcgt gtctctgaac tgcgccatca actccagtct 120
gtaggaggtt gttaataggg cgcgcc 146

<210> SEQ ID NO 10
<211> LENGTH: 44
<212> TYPE: PRT
<213> ORGANISM: Artificial Sequence
<220> FEATURE:
<223> OTHER INFORMATION: GR1 domain

<400> SEQUENCE: 10

Ser Arg Gly Gly Gly Gly Glu Glu Lys Ser Arg Leu Leu Glu Lys Glu
1 5 10 15

Asn Arg Glu Leu Glu Lys Ile Ile Ala Glu Lys Glu Glu Arg Val Ser
20 25 30

Glu Leu Arg His Gln Leu Gln Ser Val Gly Gly Cys
35 40

<210> SEQ ID NO 11
<211> LENGTH: 141

-continued

<212> TYPE: DNA
<213> ORGANISM: Artificial Sequence
<220> FEATURE:
<223> OTHER INFORMATION: GR2 domain

<400> SEQUENCE: 11
tctcgaggag gtggtggaac atcccgcctg gagggcctac agtcagaaaa ccatcgcctg 60
cgaatgaaga tcacagagct ggataaagac ttggaagaag tcaccatgca gctgcaagac 120
gttggcggtt gcgcggccgc t 141

<210> SEQ ID NO 12
<211> LENGTH: 47
<212> TYPE: PRT
<213> ORGANISM: Artificial Sequence
<220> FEATURE:
<223> OTHER INFORMATION: GR2 domain

<400> SEQUENCE: 12

Ser Arg Gly Gly Gly Gly Thr Ser Arg Leu Glu Gly Leu Gln Ser Glu
1 5 10 15

Asn His Arg Leu Arg Met Lys Ile Thr Glu Leu Asp Lys Asp Leu Glu
20 25 30

Glu Val Thr Met Gln Leu Gln Asp Val Gly Gly Cys Ala Ala Ala
35 40 45

<210> SEQ ID NO 13
<211> LENGTH: 369
<212> TYPE: DNA
<213> ORGANISM: Artificial Sequence
<220> FEATURE:
<223> OTHER INFORMATION: VH of AM2-ccFv

<400> SEQUENCE: 13
gaggtgcagc tggtggagtc tgggggaggc ctggtccagc ctgggggtc cctgagactc 60 tcctgtgcag ctagcggcta caccttcact aactatggca tgaactgggt ccgccaggct 120
cccgggaagg ggctggagtg ggttggctgg ataaacacat atactggaga gccaacttat 180
gcagctgact tcaaaagacg attcaccttt tccctcgaca ctagtaagtc cacggcatat 240
ctgcaaatga acagcctgag agccgaggac actgcagtgt attactgtgc gaagtaccct 300
cactactacg gtagttccca ctggtacttc gacgtctggg gccaagggac ccttgtcacc 360
gtctcctca 369

<210> SEQ ID NO 14
<211> LENGTH: 123
<212> TYPE: PRT
<213> ORGANISM: Artificial Sequence
<220> FEATURE:
<223> OTHER INFORMATION: VH of AM2-ccFv

<400> SEQUENCE: 14

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Thr Phe Thr Asn Tyr
20 25 30

Gly Met Asn Trp Val Arg Gln Ala Pro Gly Lys Gly Leu Glu Trp Val
35 40 45

Gly Trp Ile Asn Thr Tyr Thr Gly Glu Pro Thr Tyr Ala Ala Asp Phe
50 55 60

Lys Arg Arg Phe Thr Phe Ser Leu Asp Thr Ser Lys Ser Thr Ala Tyr

```
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120


<210> SEQ ID NO 15
<211> LENGTH: 324
<212> TYPE: DNA
<213> ORGANISM: Artificial Sequence
<220> FEATURE:
<223> OTHER INFORMATION: VL of AM2-ccFv

<400> SEQUENCE: 15

gacatccaga tgacacagtc tccatcctcc ctgtctgcat ctgtaggaga cagggtcacc      60

atcacttgca gcgcaagtca ggacattagt aactatttaa attggtatca gcagaaacca     120

ggtaaggcgc ctaaggtcct gatctatttc acatccagtt tgcactccgg agtcccatca     180

aggttcagtg gcagtggatc tgggacagat ttcactctca ccatcagcag tctgcaaccc     240

gaagactttg caacttacta ctgtcaacag tacagtactg tcccctggac tttcggtcag     300

ggtaccaaag tggagatcaa acgt                                            324


<210> SEQ ID NO 16
<211> LENGTH: 108
<212> TYPE: PRT
<213> ORGANISM: Artificial Sequence
<220> FEATURE:
<223> OTHER INFORMATION: VL of AM2-ccFv

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg
            100                 105


<210> SEQ ID NO 17
<211> LENGTH: 5251
<212> TYPE: DNA
<213> ORGANISM: Artificial Sequence
<220> FEATURE:
<223> OTHER INFORMATION: pABMD12 vector

<400> SEQUENCE: 17

gcgcaacgca attaatgtga gttagctcac tcattaggca ccccaggctt tacactttat      60

gcttccggct cgtatgttgt gtggaattgt gagcggataa caatttaccg gttcttttaa     120

ctttagtaag gaggaattaa aaaatgaaaa agtctttagt cctcaaagcc tccgtagccg     180
```

-continued

```
ttgctaccct cgttccgatg ctaagcttcg ctgaggtgca gctggtggag tctgggggag    240
gcctggtcca gcctgggggg tccctgagac tctcctgtgc agctagcggc tacaccttca    300
ctaactatgg catgaactgg gtccgccagg ctcccgggaa ggggctggag tgggttggct    360
ggataaacac atatactgga gagccaactt atgcagctga cttcaaaaga cgattcacct    420
tttccctcga cactagtaag tccacggcat atctgcaaat gaacagcctg agagccgagg    480
acactgcagt gtattactgt gcgaagtacc ctcactacta cggtagttcc cactggtact    540
tcgacgtctg gggccaaggg acccttgtca ccgtctcctc atctagaggt ggaggaggtg    600
aggagaagtc ccggctgttg gagaaggaga accgtgaact ggaaaagatc attgctgaga    660
aagaggagcg tgtctctgaa ctgcgccatc aactccagtc tgtaggaggt tgttaatagg    720
gcgcgccaca atttcacagt aaggaggttt aacttatgaa aaaattatta ttcgcaattc    780
ctttagttgt tcctttctat tctcactccg ctacgcgtga catccagatg acacagtctc    840
catcctccct gtctgcatct gtaggagaca gggtcaccat cacttgcagc gcaagtcagg    900
acattagtaa ctatttaaat tggtatcagc agaaaccagg taaggcgcct aaggtcctga    960
tctatttcac atccagtttg cactccggag tcccatcaag gttcagtggc agtggatctg   1020
ggacagattt cactctcacc atcagcagtc tgcaacccga agactttgca acttactact   1080
gtcaacagta cagtactgtc ccctggactt tcggtcaggg taccaaagtg gagatcaaac   1140
gttctcgagg aggtggtgga acatcccgcc tggagggcct acagtcagaa aaccatcgcc   1200
tgcgaatgaa gatcacagag ctggataaag acttggaaga agtcaccatg cagctgcaag   1260
acgttggcgg ttgcgcggcc gcttatccat acgacgtacc agactacgca ggaggtcatc   1320
accatcatca ccattagaga tctggaggcg gtactgttga aagttgttta gcaaaacctc   1380
atacagaaaa ttcatttact aacgtctgga aagacgacaa aactttagat cgttacgcta   1440
actatgaggg ctgtctgtgg aatgctacag gcgttgtggt ttgtactggt gacgaaactc   1500
agtgttacgg tacatgggtt cctattgggc ttgctatccc tgaaaatgag ggtggtggct   1560
ctgagggtgg cggttctgag ggtggcggtt ctgagggtgg cggtactaaa cctcctgagt   1620
acggtgatac acctattccg ggctatactt atatcaaccc tctcgacggc acttatccgc   1680
ctggtactga gcaaaacccc gctaatccta atccttctct tgaggagtct cagcctctta   1740
atactttcat gtttcagaat aataggttcc gaaataggca gggtgcatta actgtttata   1800
cgggcactgt tactcaaggc actgaccccg ttaaaactta ttaccagtac actcctgtat   1860
catcaaaagc catgtatgac gcttactgga acggtaaatt cagagactgc gctttccatt   1920
ctggctttaa tgaggatcca ttcgtttgtg aatatcaagg ccaatcgtct gacctgcctc   1980
aacctcctgt caatgctggc ggcggctctg gtggtggttc tggtggcggc tctgagggtg   2040
gcggctctga gggtggcggt tctgagggtg gcggctctga gggtggcggt tccggtggcg   2100
gctccggttc cggtgatttt gattatgaaa aaatggcaaa cgctaataag gggggctatga  2160
ccgaaaatgc cgatgaaaac gcgctacagt ctgacgctaa aggcaaactt gattctgtcg   2220
ctactgatta cggtgctgct atcgatggtt tcattggtga cgtttccggc cttgctaatg   2280
gtaatggtgc tactggtgat tttgctggct ctaattccca aatggctcaa gtcggtgacg   2340
gtgataattc acctttaatg aataatttcc gtcaatattt accttccctc cctcaatcgg   2400
ttgaatgtcg cccttttgtc tttagcgctg gtaaaccata tgaattttct attgattgtg   2460
acaaaataaa cttattccgt ggtgtctttg cgtttctttt atatgttgcc acctttatgt   2520
```

-continued

```
atgtattttc tacgtttgct aacatactgc gtaataagga gtcttaagtc gacctcgacc   2580
aattcgccct atagtgagtc gtattacaat tcactggccg tcgttttaca acgtcgtgac   2640
tgggaaaacc ctggcgttac ccaacttaat cgccttgcag cacatccccc tttcgccagc   2700
tggcgtaata gcgaagaggc ccgcaccgat cgcccttccc aacagttgcg cagcctgaat   2760
ggcgaatggg acgcgccctg tagcggcgca ttaagcgcgg cgggtgtggt ggttacgcgc   2820
agcgtgaccg ctacacttgc cagcgcccta gcgcccgctc ctttcgcttt cttcccttcc   2880
tttctcgcca cgttcgccgg ctttccccgt caagctctaa atcgggggct ccctttaggg   2940
ttccgattta gtgctttacg gcacctcgac cccaaaaaac ttgattaggg tgatggttca   3000
cgtagtgggc catcgccctg atagacggtt tttcgccctt tgacgttgga gtccacgttc   3060
tttaatagtg gactcttgtt ccaaactgga acaacactca accctatctc ggtctattct   3120
tttgatttat aagggatttt gccgatttcg gcctattggt taaaaaatga gctgatttaa   3180
caaaaattta acgcgaattt taacaaaata ttaacgctta caatttaggt ggcacttttc   3240
ggggaaatgt gcgcggaacc cctatttgtt tatttttcta aatacattca aatatgtatc   3300
cgctcatgag acaataaccc tgataaatgc ttcaataata ttgaaaaagg aagagtatga   3360
gtattcaaca tttccgtgtc gcccttattc ccttttttgc ggcattttgc cttcctgttt   3420
ttgctcaccc agaaacgctg gtgaaagtaa aagatgctga agatcagttg ggtgcacgag   3480
tgggttacat cgaactggat ctcaacagcg gtaagatcct tgagagtttt cgccccgaag   3540
aacgttttcc aatgatgagc acttttaaag ttctgctatg tggcgcggta ttatcccgta   3600
ttgacgccgg gcaagagcaa ctcggtcgcc gcatacacta ttctcagaat gacttggttg   3660
agtactcacc agtcacagaa aagcatctta cggatggcat gacagtaaga gaattatgca   3720
gtgctgccat aaccatgagt gataacactg cggccaactt acttctgaca acgatcggag   3780
gaccgaagga gctaaccgct tttttgcaca acatggggga tcatgtaact cgccttgatc   3840
gttgggaacc ggagctgaat gaagccatac caaacgacga gcgtgacacc acgatgcctg   3900
tagcaatggc aacaacgttg cgcaaactat taactggcga actacttact ctagcttccc   3960
ggcaacaatt aatagactgg atggaggcgg ataaagttgc aggaccactt ctgcgctcgg   4020
cccttccggc tggctggttt attgctgata aatctggagc cggtgagcgt gggtctcgcg   4080
gtatcattgc agcactgggg ccagatggta agccctcccg tatcgtagtt atctacacga   4140
cggggagtca ggcaactatg gatgaacgaa atagacagat cgctgagata ggtgcctcac   4200
tgattaagca ttggtaactg tcagaccaag tttactcata tatactttag attgatttaa   4260
aacttcattt ttaatttaaa aggatctagg tgaagatcct ttttgataat ctcatgacca   4320
aaatccctta acgtgagttt tcgttccact gagcgtcaga ccccgtagaa aagatcaaag   4380
gatcttcttg agatcctttt tttctgcgcg taatctgctg cttgcaaaca aaaaaaccac   4440
cgctaccagc ggtggtttgt ttgccggatc aagagctacc aactcttttt ccgaaggtaa   4500
ctggcttcag cagagcgcag ataccaaata ctgtccttct agtgtagccg tagttaggcc   4560
accacttcaa gaactctgta gcaccgccta catacctcgc tctgctaatc ctgttaccag   4620
tggctgctgc cagtggcgat aagtcgtgtc ttaccgggtt ggactcaaga cgatagttac   4680
cggataaggc gcagcggtcg ggctgaacgg ggggttcgtg cacacagccc agcttggagc   4740
gaacgaccta caccgaactg agatacctac agcgtgagct atgagaaagc gccacgcttc   4800
ccgaagggag aaaggcggac aggtatccgg taagcggcag ggtcggaaca ggagagcgca   4860
cgagggagct tccaggggga aacgcctggt atctttatag tcctgtcggg tttcgccacc   4920
```

```
tctgacttga gcgtcgattt ttgtgatgct cgtcaggggg gcggagccta tggaaaaacg   4980

ccagcaacgc ggccttttta cggttcctgg ccttttgctg gccttttgct cacatgttct   5040

ttcctgcgtt atcccctgat tctgtggata accgtattac cgcctttgag tgagctgata   5100

ccgctcgccg cagccgaacg accgagcgca gcgagtcagt gagcgaggaa gcggaagagc   5160

gcccaatacg caaaccgcct ctccccgcgc gttggccgat tcattaatgc agctggcacg   5220

acaggtttcc cgactggaaa gcgggcagtg a                                  5251


<210> SEQ ID NO 18
<211> LENGTH: 5
<212> TYPE: PRT
<213> ORGANISM: Artificial Sequence
<220> FEATURE:
<223> OTHER INFORMATION: Flexon

<400> SEQUENCE: 18

Gly Gly Gly Gly Ser
1               5


<210> SEQ ID NO 19
<211> LENGTH: 9
<212> TYPE: PRT
<213> ORGANISM: Artificial Sequence
<220> FEATURE:
<223> OTHER INFORMATION: VH CDR1 Variant

<400> SEQUENCE: 19

Gly Tyr Asn Phe Thr Arg Tyr Gly Ile
1               5


<210> SEQ ID NO 20
<211> LENGTH: 9
<212> TYPE: PRT
<213> ORGANISM: Artificial Sequence
<220> FEATURE:
<223> OTHER INFORMATION: VH CDR1 Variant

<400> SEQUENCE: 20

Gly Tyr Asn Phe Thr Arg Tyr Gly Met
1               5


<210> SEQ ID NO 21
<211> LENGTH: 9
<212> TYPE: PRT
<213> ORGANISM: Artificial Sequence
<220> FEATURE:
<223> OTHER INFORMATION: VH CDR1 Variant

<400> SEQUENCE: 21

Gly Tyr Asn Phe Asn Arg Tyr Gly Ile
1               5


<210> SEQ ID NO 22
<211> LENGTH: 9
<212> TYPE: PRT
<213> ORGANISM: Artificial Sequence
<220> FEATURE:
<223> OTHER INFORMATION: VH CDR1 Variant

<400> SEQUENCE: 22

Gly Tyr Asp Phe Thr Arg Tyr Gly Val
1               5
```

```
<210> SEQ ID NO 23
<211> LENGTH: 9
<212> TYPE: PRT
<213> ORGANISM: Artificial Sequence
<220> FEATURE:
<223> OTHER INFORMATION: VH CDR1 Variant

<400> SEQUENCE: 23

Gly Tyr Asp Phe Thr Arg Tyr Gly Met
1               5


<210> SEQ ID NO 24
<211> LENGTH: 9
<212> TYPE: PRT
<213> ORGANISM: Artificial Sequence
<220> FEATURE:
<223> OTHER INFORMATION: VH CDR1 Variant

<400> SEQUENCE: 24

Gly Tyr Asp Phe Asn Arg Tyr Gly Ile
1               5


<210> SEQ ID NO 25
<211> LENGTH: 9
<212> TYPE: PRT
<213> ORGANISM: Artificial Sequence
<220> FEATURE:
<223> OTHER INFORMATION: VH CDR1 Variant

<400> SEQUENCE: 25

Gly Tyr Asp Phe Asp Arg Tyr Gly Met
1               5


<210> SEQ ID NO 26
<211> LENGTH: 9
<212> TYPE: PRT
<213> ORGANISM: Artificial Sequence
<220> FEATURE:
<223> OTHER INFORMATION: VH CDR1 Variant

<400> SEQUENCE: 26

Gly Tyr Asp Phe Asp Arg Tyr Gly Ile
1               5


<210> SEQ ID NO 27
<211> LENGTH: 9
<212> TYPE: PRT
<213> ORGANISM: Artificial Sequence
<220> FEATURE:
<223> OTHER INFORMATION: VH CDR1 Variant

<400> SEQUENCE: 27

Gly Tyr Asp Phe Asp Arg Tyr Gly Val
1               5


<210> SEQ ID NO 28
<211> LENGTH: 9
<212> TYPE: PRT
<213> ORGANISM: Artificial Sequence
<220> FEATURE:
<223> OTHER INFORMATION: VH CDR1 Variant

<400> SEQUENCE: 28

Gly Tyr Thr Phe Asn Arg Tyr Gly Ile
1               5


<210> SEQ ID NO 29
```

```
<211> LENGTH: 9
<212> TYPE: PRT
<213> ORGANISM: Artificial Sequence
<220> FEATURE:
<223> OTHER INFORMATION: VH CDR1 Variant

<400> SEQUENCE: 29

Gly Tyr Ala Phe Asn Arg Tyr Gly Ile
1               5


<210> SEQ ID NO 30
<211> LENGTH: 9
<212> TYPE: PRT
<213> ORGANISM: Artificial Sequence
<220> FEATURE:
<223> OTHER INFORMATION: VH CDR1 Variant

<400> SEQUENCE: 30

Gly Tyr Ala Phe Asn Arg Tyr Gly Met
1               5


<210> SEQ ID NO 31
<211> LENGTH: 17
<212> TYPE: PRT
<213> ORGANISM: Artificial Sequence
<220> FEATURE:
<223> OTHER INFORMATION: VH CDR2 Variant

<400> SEQUENCE: 31

Trp Ile Asn Thr Asn Asn Gly Glu Ser Thr Tyr Ala Gln Gly Phe Thr
1               5                   10                  15

Arg


<210> SEQ ID NO 32
<211> LENGTH: 17
<212> TYPE: PRT
<213> ORGANISM: Artificial Sequence
<220> FEATURE:
<223> OTHER INFORMATION: VH CDR2 Variant

<400> SEQUENCE: 32

Trp Ile Asn Thr Asn Asn Gly Asp Thr Thr Tyr Ala Gln Glu Phe Thr
1               5                   10                  15

Arg


<210> SEQ ID NO 33
<211> LENGTH: 17
<212> TYPE: PRT
<213> ORGANISM: Artificial Sequence
<220> FEATURE:
<223> OTHER INFORMATION: VH CDR2 Variant

<400> SEQUENCE: 33

Trp Ile Asn Thr Asn Asn Gly Asn Ser Thr Tyr Ala Gln Glu Phe Thr
1               5                   10                  15

Arg


<210> SEQ ID NO 34
<211> LENGTH: 17
<212> TYPE: PRT
<213> ORGANISM: Artificial Sequence
<220> FEATURE:
<223> OTHER INFORMATION: VH CDR2 Variant

<400> SEQUENCE: 34
```

-continued

```
Trp Ile Asn Thr Asn Asn Gly Asp Thr Thr Tyr Val Gln Asp Phe Thr
1               5                   10                  15

Arg


<210> SEQ ID NO 35
<211> LENGTH: 16
<212> TYPE: PRT
<213> ORGANISM: Artificial Sequence
<220> FEATURE:
<223> OTHER INFORMATION: VH CDR2 Variant

<400> SEQUENCE: 35

Trp Val Asn Thr Asn Asn Gly Asp Ser Thr Tyr Ala Gln Gly Phe Thr
1               5                   10                  15


<210> SEQ ID NO 36
<211> LENGTH: 15
<212> TYPE: PRT
<213> ORGANISM: Artificial Sequence
<220> FEATURE:
<223> OTHER INFORMATION: VH CDR3 Variant

<400> SEQUENCE: 36

Arg Tyr Pro Tyr Tyr Tyr Ser Arg Ser Ser Trp Tyr Phe Asp Leu
1               5                   10                  15


<210> SEQ ID NO 37
<211> LENGTH: 15
<212> TYPE: PRT
<213> ORGANISM: Artificial Sequence
<220> FEATURE:
<223> OTHER INFORMATION: VH CDR3 Variant

<400> SEQUENCE: 37

Arg Tyr Pro Tyr Tyr Tyr Ser Arg Ser Asn Trp Tyr Phe Asp Leu
1               5                   10                  15


<210> SEQ ID NO 38
<211> LENGTH: 15
<212> TYPE: PRT
<213> ORGANISM: Artificial Sequence
<220> FEATURE:
<223> OTHER INFORMATION: VH CDR3 Variant

<400> SEQUENCE: 38

Arg Tyr Pro Tyr Tyr Tyr Gly Arg Ser Asn Trp Tyr Phe Asp Leu
1               5                   10                  15


<210> SEQ ID NO 39
<211> LENGTH: 15
<212> TYPE: PRT
<213> ORGANISM: Artificial Sequence
<220> FEATURE:
<223> OTHER INFORMATION: VH CDR3 Variant

<400> SEQUENCE: 39

Arg Tyr Pro Tyr Tyr Tyr Gly Arg Ser Ser Trp Tyr Phe Asp Leu
1               5                   10                  15


<210> SEQ ID NO 40
<211> LENGTH: 15
<212> TYPE: PRT
<213> ORGANISM: Artificial Sequence
<220> FEATURE:
<223> OTHER INFORMATION: VH CDR3 Variant

<400> SEQUENCE: 40
```

-continued

Arg Tyr Pro Tyr Tyr Tyr Gly Arg Thr Ser Trp Tyr Phe Asp Leu
1 5 10 15

<210> SEQ ID NO 41
<211> LENGTH: 15
<212> TYPE: PRT
<213> ORGANISM: Artificial Sequence
<220> FEATURE:
<223> OTHER INFORMATION: VH CDR3 Variant

<400> SEQUENCE: 41

Arg Tyr Pro Tyr Tyr Tyr Ser Arg Thr Ser Trp Tyr Phe Asp Leu
1 5 10 15

<210> SEQ ID NO 42
<211> LENGTH: 15
<212> TYPE: PRT
<213> ORGANISM: Artificial Sequence
<220> FEATURE:
<223> OTHER INFORMATION: VH CDR3 Variant

<400> SEQUENCE: 42

Arg Tyr Pro Tyr Tyr Ser Gly Arg Ser Ser Trp Tyr Phe Asp Leu
1 5 10 15

<210> SEQ ID NO 43
<211> LENGTH: 15
<212> TYPE: PRT
<213> ORGANISM: Artificial Sequence
<220> FEATURE:
<223> OTHER INFORMATION: VH CDR3 Variant

<400> SEQUENCE: 43

Arg Ala Pro Tyr Tyr Cys Gly Arg Ser Cys Trp Tyr Phe Asp Leu
1 5 10 15

<210> SEQ ID NO 44
<211> LENGTH: 15
<212> TYPE: PRT
<213> ORGANISM: Artificial Sequence
<220> FEATURE:
<223> OTHER INFORMATION: VH CDR3 Variant

<400> SEQUENCE: 44

Arg Tyr Pro Tyr Tyr Asp Gly Arg Ser Asn Trp Tyr Phe Asp Leu
1 5 10 15

<210> SEQ ID NO 45
<211> LENGTH: 15
<212> TYPE: PRT
<213> ORGANISM: Artificial Sequence
<220> FEATURE:
<223> OTHER INFORMATION: VH CDR3 Variant

<400> SEQUENCE: 45

Arg Tyr Pro Tyr Tyr Cys Gly Arg Ser Asn Trp Tyr Phe Asp Leu
1 5 10 15

<210> SEQ ID NO 46
<211> LENGTH: 15
<212> TYPE: PRT
<213> ORGANISM: Artificial Sequence
<220> FEATURE:
<223> OTHER INFORMATION: VH CDR3 Variant

<400> SEQUENCE: 46

```
Arg Asp Pro Tyr Tyr Cys Ser Arg Ser Cys Trp Tyr Phe Asp Leu
1               5                   10                  15


<210> SEQ ID NO 47
<211> LENGTH: 15
<212> TYPE: PRT
<213> ORGANISM: Artificial Sequence
<220> FEATURE:
<223> OTHER INFORMATION: VH CDR3 Variant

<400> SEQUENCE: 47

Arg Tyr Pro Tyr Tyr Ser Gly Arg Ser Tyr Trp Tyr Phe Asp Leu
1               5                   10                  15


<210> SEQ ID NO 48
<211> LENGTH: 15
<212> TYPE: PRT
<213> ORGANISM: Artificial Sequence
<220> FEATURE:
<223> OTHER INFORMATION: VH CDR3 Variant

<400> SEQUENCE: 48

Arg Pro Pro Tyr Tyr Tyr Gly Ser Ser His Trp Tyr Phe Asp Val
1               5                   10                  15


<210> SEQ ID NO 49
<211> LENGTH: 19
<212> TYPE: PRT
<213> ORGANISM: Artificial Sequence
<220> FEATURE:
<223> OTHER INFORMATION: Variant #61

<400> SEQUENCE: 49

Cys Ala Arg Asp Pro Tyr Tyr Tyr Gly Arg Ser Tyr Trp Tyr Phe Asp
1               5                   10                  15

Leu Trp Gly


<210> SEQ ID NO 50
<211> LENGTH: 19
<212> TYPE: PRT
<213> ORGANISM: Artificial Sequence
<220> FEATURE:
<223> OTHER INFORMATION: Variant #181

<400> SEQUENCE: 50

Cys Ala Arg Asp Pro Tyr Tyr Tyr Ser Arg Ser Tyr Trp Tyr Phe Asp
1               5                   10                  15

Leu Trp Gly


<210> SEQ ID NO 51
<211> LENGTH: 19
<212> TYPE: PRT
<213> ORGANISM: Artificial Sequence
<220> FEATURE:
<223> OTHER INFORMATION: Variant #19501

<400> SEQUENCE: 51

Cys Ala Arg Tyr Pro Tyr Tyr Tyr Gly Arg Ser Tyr Trp Tyr Phe Asp
1               5                   10                  15

Leu Trp Gly


<210> SEQ ID NO 52
<211> LENGTH: 19
<212> TYPE: PRT
<213> ORGANISM: Artificial Sequence
```

<220> FEATURE:
<223> OTHER INFORMATION: Variant #13165

<400> SEQUENCE: 52

Cys Ala Arg Thr Pro Tyr Tyr Tyr Ser Arg Thr Tyr Trp Tyr Phe Asp
1 5 10 15

Leu Trp Gly

<210> SEQ ID NO 53
<211> LENGTH: 19
<212> TYPE: PRT
<213> ORGANISM: Artificial Sequence
<220> FEATURE:
<223> OTHER INFORMATION: Variant #19525

<400> SEQUENCE: 53

Cys Ala Arg Tyr Pro Tyr Tyr Tyr Gly Arg Thr Tyr Trp Tyr Phe Asp
1 5 10 15

Leu Trp Gly

<210> SEQ ID NO 54
<211> LENGTH: 19
<212> TYPE: PRT
<213> ORGANISM: Artificial Sequence
<220> FEATURE:
<223> OTHER INFORMATION: Variant #13021

<400> SEQUENCE: 54

Cys Ala Arg Thr Pro Tyr Tyr Tyr Gly Arg Ser Tyr Trp Tyr Phe Asp
1 5 10 15

Leu Trp Gly

<210> SEQ ID NO 55
<211> LENGTH: 19
<212> TYPE: PRT
<213> ORGANISM: Artificial Sequence
<220> FEATURE:
<223> OTHER INFORMATION: Variant #19647

<400> SEQUENCE: 55

Cys Ala Arg Tyr Pro Tyr Tyr Tyr Ser Arg Thr Ser Trp Tyr Phe Asp
1 5 10 15

Leu Trp Gly

<210> SEQ ID NO 56
<211> LENGTH: 19
<212> TYPE: PRT
<213> ORGANISM: Artificial Sequence
<220> FEATURE:
<223> OTHER INFORMATION: Variant #20005

<400> SEQUENCE: 56

Cys Ala Arg Tyr Pro Tyr Tyr Ser Gly Arg Thr Tyr Trp Tyr Phe Asp
1 5 10 15

Leu Trp Gly

<210> SEQ ID NO 57
<211> LENGTH: 19
<212> TYPE: PRT
<213> ORGANISM: Artificial Sequence
<220> FEATURE:
<223> OTHER INFORMATION: Variant #301

<400> SEQUENCE: 57

-continued

```
Cys Ala Arg Asp Pro Tyr Tyr Gly Gly Arg Ser Tyr Trp Tyr Phe Asp
1               5                   10                  15

Leu Trp Gly


<210> SEQ ID NO 58
<211> LENGTH: 19
<212> TYPE: PRT
<213> ORGANISM: Artificial Sequence
<220> FEATURE:
<223> OTHER INFORMATION: Variant #541

<400> SEQUENCE: 58

Cys Ala Arg Asp Pro Tyr Tyr Ser Gly Arg Ser Tyr Trp Tyr Phe Asp
1               5                   10                  15

Leu Trp Gly


<210> SEQ ID NO 59
<211> LENGTH: 19
<212> TYPE: PRT
<213> ORGANISM: Artificial Sequence
<220> FEATURE:
<223> OTHER INFORMATION: Variant profile lead sequence

<400> SEQUENCE: 59

Cys Ala Arg Asp Pro Tyr Tyr Tyr Gly Arg Ser Tyr Trp Tyr Phe Asp
1               5                   10                  15

Leu Trp Gly


<210> SEQ ID NO 60
<211> LENGTH: 57
<212> TYPE: DNA
<213> ORGANISM: Artificial Sequence
<220> FEATURE:
<223> OTHER INFORMATION: DNA encoding variant profile lead sequence

<400> SEQUENCE: 60

tgcgcgcgta acccgtacta caacggtcgt agctactggt acttcgatct gtggggt        57


<210> SEQ ID NO 61
<211> LENGTH: 57
<212> TYPE: DNA
<213> ORGANISM: Artificial Sequence
<220> FEATURE:
<223> OTHER INFORMATION: Degenerate nucleic acid sequence

<400> SEQUENCE: 61

tgcgcgcgtd myccgtacta cdryrgycgt ascwrctggt acttcgatct gtggggc        57


<210> SEQ ID NO 62
<211> LENGTH: 26
<212> TYPE: PRT
<213> ORGANISM: Artificial Sequence
<220> FEATURE:
<223> OTHER INFORMATION: Matured VH CDR3

<400> SEQUENCE: 62

Thr Ala Val Tyr Tyr Cys Ala Lys Tyr Pro Tyr Tyr Tyr Gly Thr Ser
1               5                   10                  15

His Trp Tyr Phe Asp Val Trp Gly Gln Gly
            20                  25


<210> SEQ ID NO 63
<211> LENGTH: 26
```

```
<212> TYPE: PRT
<213> ORGANISM: Artificial Sequence
<220> FEATURE:
<223> OTHER INFORMATION: pVGD9-1-1B8

<400> SEQUENCE: 63

Thr Ala Val Tyr Tyr Cys Ala Arg Tyr Pro Tyr Tyr Cys Gly Arg Thr
1               5                   10                  15

Cys Trp Tyr Phe Asp Leu Trp Gly Gln Gly
            20                  25


<210> SEQ ID NO 64
<211> LENGTH: 26
<212> TYPE: PRT
<213> ORGANISM: Artificial Sequence
<220> FEATURE:
<223> OTHER INFORMATION: pVGD9-1-1D7

<400> SEQUENCE: 64

Thr Ala Val Tyr Tyr Cys Ala Arg Tyr Pro Tyr Tyr Cys Gly Arg Thr
1               5                   10                  15

Cys Trp Tyr Phe Asp Leu Trp Gly Gln Gly
            20                  25


<210> SEQ ID NO 65
<211> LENGTH: 26
<212> TYPE: PRT
<213> ORGANISM: Artificial Sequence
<220> FEATURE:
<223> OTHER INFORMATION: pVGD9-1-2A6

<400> SEQUENCE: 65

Thr Ala Val Tyr Tyr Cys Ala Arg Tyr Pro Tyr Tyr Cys Gly Arg Thr
1               5                   10                  15

Cys Trp Tyr Phe Asp Leu Trp Gly Gln Gly
            20                  25


<210> SEQ ID NO 66
<211> LENGTH: 26
<212> TYPE: PRT
<213> ORGANISM: Artificial Sequence
<220> FEATURE:
<223> OTHER INFORMATION: pVGD9-1-3D10

<400> SEQUENCE: 66

Thr Ala Val Tyr Tyr Cys Ala Arg Tyr Pro Tyr Tyr Cys Gly Arg Thr
1               5                   10                  15

Cys Trp Tyr Phe Asp Leu Trp Gly Gln Gly
            20                  25


<210> SEQ ID NO 67
<211> LENGTH: 26
<212> TYPE: PRT
<213> ORGANISM: Artificial Sequence
<220> FEATURE:
<223> OTHER INFORMATION: pVGD9-1-2A12

<400> SEQUENCE: 67

Thr Ala Val Tyr Tyr Cys Ala Arg Tyr Pro Tyr Tyr Cys Gly Arg Thr
1               5                   10                  15

Cys Trp Tyr Phe Asp Leu Trp Gly Gln Gly
            20                  25


<210> SEQ ID NO 68
```

<211> LENGTH: 26
<212> TYPE: PRT
<213> ORGANISM: Artificial Sequence
<220> FEATURE:
<223> OTHER INFORMATION: pVGD9-1-1F8

<400> SEQUENCE: 68

Thr Ala Val Tyr Tyr Cys Ala Arg Tyr Pro Tyr Tyr Cys Gly Arg Ser
1 5 10 15

Cys Trp Tyr Phe Asp Leu Trp Gly Gln Gly
20 25

<210> SEQ ID NO 69
<211> LENGTH: 26
<212> TYPE: PRT
<213> ORGANISM: Artificial Sequence
<220> FEATURE:
<223> OTHER INFORMATION: pVGD9-1-3B5

<400> SEQUENCE: 69

Thr Ala Val Tyr Tyr Cys Ala Arg Tyr Pro Tyr Tyr Cys Gly Arg Ser
1 5 10 15

Cys Trp Tyr Phe Asp Leu Trp Gly Gln Gly
20 25

<210> SEQ ID NO 70
<211> LENGTH: 26
<212> TYPE: PRT
<213> ORGANISM: Artificial Sequence
<220> FEATURE:
<223> OTHER INFORMATION: pVGD9-1-1C4

<400> SEQUENCE: 70

Thr Ala Val Tyr Tyr Cys Ala Arg Tyr Pro Tyr Tyr Cys Ser Arg Ser
1 5 10 15

Cys Trp Tyr Phe Asp Leu Trp Gly Gln Gly
20 25

<210> SEQ ID NO 71
<211> LENGTH: 26
<212> TYPE: PRT
<213> ORGANISM: Artificial Sequence
<220> FEATURE:
<223> OTHER INFORMATION: pVGD9-1-3F1

<400> SEQUENCE: 71

Thr Ala Val Tyr Tyr Cys Ala Arg Tyr Pro Tyr Tyr Cys Ser Arg Ser
1 5 10 15

Cys Trp Tyr Phe Asp Leu Trp Gly Gln Gly
20 25

<210> SEQ ID NO 72
<211> LENGTH: 26
<212> TYPE: PRT
<213> ORGANISM: Artificial Sequence
<220> FEATURE:
<223> OTHER INFORMATION: pVGD9-1-2F7

<400> SEQUENCE: 72

Thr Ala Val Tyr Tyr Cys Ala Arg Tyr Pro Tyr Tyr Cys Gly Arg Ser
1 5 10 15

Asn Trp Tyr Phe Asp Leu Trp Gly Gln Gly
20 25

<210> SEQ ID NO 73
<211> LENGTH: 26
<212> TYPE: PRT
<213> ORGANISM: Artificial Sequence
<220> FEATURE:
<223> OTHER INFORMATION: pVGD9-1-3B11

<400> SEQUENCE: 73

```
Thr Ala Val Tyr Tyr Cys Ala Arg Tyr Pro Tyr Tyr Gly Ser Arg Thr
1               5                   10                  15

Cys Trp Tyr Phe Asp Leu Trp Gly Gln Gly
            20                  25
```

<210> SEQ ID NO 74
<211> LENGTH: 26
<212> TYPE: PRT
<213> ORGANISM: Artificial Sequence
<220> FEATURE:
<223> OTHER INFORMATION: pVGD9-1-3B10

<400> SEQUENCE: 74

```
Thr Ala Val Tyr Tyr Cys Ala Arg Tyr Pro Tyr Tyr Ser Gly Arg Ser
1               5                   10                  15

Tyr Trp Tyr Phe Asp Leu Trp Gly Gln Gly
            20                  25
```

<210> SEQ ID NO 75
<211> LENGTH: 26
<212> TYPE: PRT
<213> ORGANISM: Artificial Sequence
<220> FEATURE:
<223> OTHER INFORMATION: pVGD9-1-1A11

<400> SEQUENCE: 75

```
Thr Ala Val Tyr Tyr Cys Ala Arg Asp Pro Tyr Tyr Asp Ser Arg Ser
1               5                   10                  15

Ser Trp Tyr Phe Asp Leu Trp Gly Gln Gly
            20                  25
```

<210> SEQ ID NO 76
<211> LENGTH: 26
<212> TYPE: PRT
<213> ORGANISM: Artificial Sequence
<220> FEATURE:
<223> OTHER INFORMATION: pVGD9-1-2A1

<400> SEQUENCE: 76

```
Thr Ala Val Tyr Tyr Cys Ala Arg Asp Pro Tyr Tyr Asp Ser Arg Ser
1               5                   10                  15

Tyr Trp Tyr Phe Asp Leu Trp Gly Gln Gly
            20                  25
```

<210> SEQ ID NO 77
<211> LENGTH: 26
<212> TYPE: PRT
<213> ORGANISM: Artificial Sequence
<220> FEATURE:
<223> OTHER INFORMATION: pVGD9-1-3A6

<400> SEQUENCE: 77

```
Thr Ala Val Tyr Tyr Cys Ala Arg Asp Pro Tyr Tyr Gly Gly Arg Ser
1               5                   10                  15

Tyr Trp Tyr Phe Asp Leu Trp Gly Gln Gly
            20                  25
```

-continued

<210> SEQ ID NO 78
<211> LENGTH: 26
<212> TYPE: PRT
<213> ORGANISM: Artificial Sequence
<220> FEATURE:
<223> OTHER INFORMATION: pVGD9-1-2G8

<400> SEQUENCE: 78

```
Thr Ala Val Tyr Tyr Cys Ala Arg Asp Pro Tyr Tyr Gly Gly Arg Thr
1               5                   10                  15

Ser Trp Tyr Phe Asp Leu Trp Gly Gln Gly
            20                  25
```

<210> SEQ ID NO 79
<211> LENGTH: 26
<212> TYPE: PRT
<213> ORGANISM: Artificial Sequence
<220> FEATURE:
<223> OTHER INFORMATION: pVGD9-1-3B8

<400> SEQUENCE: 79

```
Thr Ala Val Tyr Tyr Cys Ala Arg Asp Pro Tyr Tyr Cys Gly Arg Ser
1               5                   10                  15

Asn Trp Tyr Phe Asp Leu Trp Gly Gln Gly
            20                  25
```

<210> SEQ ID NO 80
<211> LENGTH: 26
<212> TYPE: PRT
<213> ORGANISM: Artificial Sequence
<220> FEATURE:
<223> OTHER INFORMATION: pVGD9-1-1B7

<400> SEQUENCE: 80

```
Thr Ala Val Ser Tyr Cys Ala Arg Asp Pro Tyr Tyr Tyr Gly Arg Ser
1               5                   10                  15

Asn Trp Tyr Phe Asp Leu Trp Gly Gln Gly
            20                  25
```

<210> SEQ ID NO 81
<211> LENGTH: 26
<212> TYPE: PRT
<213> ORGANISM: Artificial Sequence
<220> FEATURE:
<223> OTHER INFORMATION: pVGD9-1-3H3

<400> SEQUENCE: 81

```
Thr Ala Val Tyr Tyr Cys Ala Arg Asp Pro Tyr Tyr Tyr Gly Arg Thr
1               5                   10                  15

Ser Trp Tyr Phe Asp Leu Trp Gly Gln Gly
            20                  25
```

<210> SEQ ID NO 82
<211> LENGTH: 26
<212> TYPE: PRT
<213> ORGANISM: Artificial Sequence
<220> FEATURE:
<223> OTHER INFORMATION: pVGD9-1-1D2

<400> SEQUENCE: 82

```
Thr Ala Val Tyr Tyr Cys Ala Arg Ala Pro Tyr Tyr Cys Ser Arg Thr
1               5                   10                  15

Cys Trp Tyr Phe Asp Leu Trp Gly Gln Gly
            20                  25
```

```
<210> SEQ ID NO 83
<211> LENGTH: 26
<212> TYPE: PRT
<213> ORGANISM: Artificial Sequence
<220> FEATURE:
<223> OTHER INFORMATION: pVGD9-1-2A2

<400> SEQUENCE: 83

Thr Ala Val Tyr Tyr Cys Ala Arg Ala Pro Tyr Tyr Cys Ser Arg Thr
1               5                   10                  15

Cys Trp Tyr Phe Asp Leu Trp Gly Gln Gly
            20                  25


<210> SEQ ID NO 84
<211> LENGTH: 26
<212> TYPE: PRT
<213> ORGANISM: Artificial Sequence
<220> FEATURE:
<223> OTHER INFORMATION: pVGD9-1-2A11

<400> SEQUENCE: 84

Thr Ala Val Tyr Tyr Cys Ala Arg Ala Pro Tyr Tyr Cys Gly Arg Ser
1               5                   10                  15

Cys Trp Tyr Phe Asp Leu Trp Gly Gln Gly
            20                  25


<210> SEQ ID NO 85
<211> LENGTH: 26
<212> TYPE: PRT
<213> ORGANISM: Artificial Sequence
<220> FEATURE:
<223> OTHER INFORMATION: pVGD9-1-3A12

<400> SEQUENCE: 85

Thr Ala Val Tyr Tyr Cys Ala Arg Ala Pro Tyr Tyr Cys Gly Arg Ser
1               5                   10                  15

Cys Trp Tyr Phe Asp Leu Trp Gly Gln Gly
            20                  25


<210> SEQ ID NO 86
<211> LENGTH: 26
<212> TYPE: PRT
<213> ORGANISM: Artificial Sequence
<220> FEATURE:
<223> OTHER INFORMATION: pVGD9-1-1C2

<400> SEQUENCE: 86

Thr Ala Val Tyr Tyr Tyr Ala Arg Ala Pro Tyr Tyr Cys Gly Arg Ser
1               5                   10                  15

Tyr Trp Tyr Phe Asp Leu Trp Gly Gln Gly
            20                  25


<210> SEQ ID NO 87
<211> LENGTH: 26
<212> TYPE: PRT
<213> ORGANISM: Artificial Sequence
<220> FEATURE:
<223> OTHER INFORMATION: pVGD9-1-1B12

<400> SEQUENCE: 87

Thr Ala Val Tyr Tyr Tyr Ala Arg Ala Pro Tyr Tyr Cys Gly Arg Ser
1               5                   10                  15

Tyr Trp Tyr Phe Asp Leu Trp Gly Gln Gly
```

-continued

```
            20                  25


<210> SEQ ID NO 88
<211> LENGTH: 26
<212> TYPE: PRT
<213> ORGANISM: Artificial Sequence
<220> FEATURE:
<223> OTHER INFORMATION: pVGD9-1-2A3

<400> SEQUENCE: 88

Thr Ala Val Tyr Tyr Cys Ala Arg Ser Pro Tyr Tyr Cys Gly Arg Ser
1               5                   10                  15

Cys Trp Tyr Phe Asp Leu Trp Gly Gln Gly
            20                  25


<210> SEQ ID NO 89
<211> LENGTH: 26
<212> TYPE: PRT
<213> ORGANISM: Artificial Sequence
<220> FEATURE:
<223> OTHER INFORMATION: pVGD9-1-2G5

<400> SEQUENCE: 89

Thr Ala Val Tyr Tyr Cys Ala Arg Ser Pro Tyr Tyr Cys Gly Arg Ser
1               5                   10                  15

Cys Trp Tyr Phe Asp Leu Trp Gly Gln Gly
            20                  25


<210> SEQ ID NO 90
<211> LENGTH: 26
<212> TYPE: PRT
<213> ORGANISM: Artificial Sequence
<220> FEATURE:
<223> OTHER INFORMATION: pVGD9-1-2A8

<400> SEQUENCE: 90

Thr Ala Val Tyr Tyr Cys Ala Arg Ser Pro Tyr Tyr Cys Ser Arg Thr
1               5                   10                  15

Cys Trp Tyr Phe Asp Leu Trp Gly Gln Gly
            20                  25


<210> SEQ ID NO 91
<211> LENGTH: 26
<212> TYPE: PRT
<213> ORGANISM: Artificial Sequence
<220> FEATURE:
<223> OTHER INFORMATION: pVGD9-1-3A7

<400> SEQUENCE: 91

Thr Ala Val Tyr Tyr Cys Ala Arg Ser Pro Tyr Tyr Gly Gly Arg Ser
1               5                   10                  15

Tyr Trp Tyr Phe Asp Leu Trp Gly Gln Gly
            20                  25


<210> SEQ ID NO 92
<211> LENGTH: 26
<212> TYPE: PRT
<213> ORGANISM: Artificial Sequence
<220> FEATURE:
<223> OTHER INFORMATION: pVGD9-1-2B7

<400> SEQUENCE: 92

Thr Ala Val Tyr Tyr Cys Ala Arg Asn Pro Tyr Tyr Cys Gly Arg Thr
1               5                   10                  15
```

```
Cys Trp Tyr Phe Asp Leu Trp Gly Gln Gly
            20                  25


<210> SEQ ID NO 93
<211> LENGTH: 26
<212> TYPE: PRT
<213> ORGANISM: Artificial Sequence
<220> FEATURE:
<223> OTHER INFORMATION: pVGD9-1-2G6

<400> SEQUENCE: 93

Thr Ala Val Tyr Tyr Cys Ala Arg Asn Pro Tyr Tyr Cys Gly Arg Thr
1               5                   10                  15

Cys Trp Tyr Phe Asp Leu Trp Gly Gln Gly
            20                  25


<210> SEQ ID NO 94
<211> LENGTH: 26
<212> TYPE: PRT
<213> ORGANISM: Artificial Sequence
<220> FEATURE:
<223> OTHER INFORMATION: pVGD9-1-3A11

<400> SEQUENCE: 94

Thr Ala Val Tyr Tyr Cys Ala Arg Thr Pro Tyr Tyr Gly Gly Arg Thr
1               5                   10                  15

Asn Trp Tyr Phe Asp Leu Trp Gly Gln Gly
            20                  25


<210> SEQ ID NO 95
<211> LENGTH: 26
<212> TYPE: PRT
<213> ORGANISM: Artificial Sequence
<220> FEATURE:
<223> OTHER INFORMATION: pVGD9-1-3H2

<400> SEQUENCE: 95

Thr Ala Val Tyr Tyr Cys Ala Arg Thr Pro Tyr Tyr Tyr Gly Arg Thr
1               5                   10                  15

Ser Trp Tyr Phe Asp Leu Trp Gly Gln Gly
            20                  25


<210> SEQ ID NO 96
<211> LENGTH: 26
<212> TYPE: PRT
<213> ORGANISM: Artificial Sequence
<220> FEATURE:
<223> OTHER INFORMATION: Library9
<220> FEATURE:
<221> NAME/KEY: MISC_FEATURE
<222> LOCATION: (9)..(9)
<223> OTHER INFORMATION: X = Y, D, A, S, N, or T
<220> FEATURE:
<221> NAME/KEY: MISC_FEATURE
<222> LOCATION: (13)..(13)
<223> OTHER INFORMATION: X = Y, C, G, S, or D.
<220> FEATURE:
<221> NAME/KEY: MISC_FEATURE
<222> LOCATION: (14)..(14)
<223> OTHER INFORMATION: X = G or S.
<220> FEATURE:
<221> NAME/KEY: MISC_FEATURE
<222> LOCATION: (16)..(16)
<223> OTHER INFORMATION: X = S or T.
<220> FEATURE:
<221> NAME/KEY: MISC_FEATURE
<222> LOCATION: (17)..(17)
<223> OTHER INFORMATION: X = H, C, N, Y, or S.
```

-continued

<400> SEQUENCE: 96

```
Thr Ala Val Tyr Tyr Cys Ala Arg Xaa Pro Tyr Tyr Xaa Xaa Arg Xaa
1               5                   10                  15

Xaa Trp Tyr Phe Asp Leu Trp Gly Gln Gly
            20                  25
```

<210> SEQ ID NO 97
<211> LENGTH: 26
<212> TYPE: PRT
<213> ORGANISM: Artificial Sequence
<220> FEATURE:
<223> OTHER INFORMATION: PVG9-3-1G6

<400> SEQUENCE: 97

```
Thr Ala Val Tyr Tyr Cys Ala Arg Tyr Pro Tyr Tyr Tyr Ser Arg Ser
1               5                   10                  15

Ser Trp Tyr Phe Asp Leu Trp Gly Gln Gly
            20                  25
```

<210> SEQ ID NO 98
<211> LENGTH: 26
<212> TYPE: PRT
<213> ORGANISM: Artificial Sequence
<220> FEATURE:
<223> OTHER INFORMATION: PVG9-3-2A1

<400> SEQUENCE: 98

```
Thr Ala Val Tyr Tyr Cys Ala Arg Tyr Pro Tyr Tyr Tyr Ser Arg Ser
1               5                   10                  15

Ser Trp Tyr Phe Asp Leu Trp Gly Gln Gly
            20                  25
```

<210> SEQ ID NO 99
<211> LENGTH: 26
<212> TYPE: PRT
<213> ORGANISM: Artificial Sequence
<220> FEATURE:
<223> OTHER INFORMATION: PVG9-3-1D3

<400> SEQUENCE: 99

```
Thr Ala Val Tyr Tyr Cys Ala Arg Tyr Pro Tyr Tyr Tyr Ser Arg Ser
1               5                   10                  15

Ser Trp Tyr Phe Asp Leu Trp Gly Gln Gly
            20                  25
```

<210> SEQ ID NO 100
<211> LENGTH: 26
<212> TYPE: PRT
<213> ORGANISM: Artificial Sequence
<220> FEATURE:
<223> OTHER INFORMATION: PVG9-3-1D5

<400> SEQUENCE: 100

```
Thr Ala Val Tyr Tyr Cys Ala Arg Tyr Pro Tyr Tyr Tyr Ser Arg Ser
1               5                   10                  15

Ser Trp Tyr Phe Asp Leu Trp Gly Gln Gly
            20                  25
```

<210> SEQ ID NO 101
<211> LENGTH: 26
<212> TYPE: PRT
<213> ORGANISM: Artificial Sequence
<220> FEATURE:
<223> OTHER INFORMATION: PVG9-3-1G4

<400> SEQUENCE: 101

Thr Ala Val Tyr Tyr Cys Ala Arg Tyr Pro Tyr Tyr Tyr Ser Arg Ser
1 5 10 15

Ser Trp Tyr Phe Asp Leu Trp Gly Gln Gly
20 25

<210> SEQ ID NO 102
<211> LENGTH: 26
<212> TYPE: PRT
<213> ORGANISM: Artificial Sequence
<220> FEATURE:
<223> OTHER INFORMATION: PVG9-3-2E1

<400> SEQUENCE: 102

Thr Ala Val Tyr Tyr Cys Ala Arg Tyr Pro Tyr Tyr Tyr Ser Arg Ser
1 5 10 15

Ser Trp Tyr Phe Asp Leu Trp Gly Gln Gly
20 25

<210> SEQ ID NO 103
<211> LENGTH: 26
<212> TYPE: PRT
<213> ORGANISM: Artificial Sequence
<220> FEATURE:
<223> OTHER INFORMATION: PVG9-3-1E5

<400> SEQUENCE: 103

Thr Ala Val Tyr Tyr Cys Ala Arg Tyr Pro Tyr Tyr Tyr Ser Arg Ser
1 5 10 15

Ser Trp Tyr Phe Asp Leu Trp Gly Gln Gly
20 25

<210> SEQ ID NO 104
<211> LENGTH: 26
<212> TYPE: PRT
<213> ORGANISM: Artificial Sequence
<220> FEATURE:
<223> OTHER INFORMATION: PVG9-3-1A5

<400> SEQUENCE: 104

Thr Ala Val Tyr Tyr Cys Ala Arg Tyr Pro Tyr Tyr Tyr Ser Arg Ser
1 5 10 15

Ser Trp Tyr Phe Asp Leu Trp Gly Gln Gly
20 25

<210> SEQ ID NO 105
<211> LENGTH: 26
<212> TYPE: PRT
<213> ORGANISM: Artificial Sequence
<220> FEATURE:
<223> OTHER INFORMATION: PVG9-3-1A10

<400> SEQUENCE: 105

Thr Ala Val Tyr Tyr Cys Ala Arg Tyr Pro Tyr Tyr Tyr Ser Arg Ser
1 5 10 15

Ser Trp Tyr Phe Asp Leu Trp Gly Gln Gly
20 25

<210> SEQ ID NO 106
<211> LENGTH: 26
<212> TYPE: PRT
<213> ORGANISM: Artificial Sequence
<220> FEATURE:

-continued

```
<223> OTHER INFORMATION: PVG9-3-2E6

<400> SEQUENCE: 106

Thr Ala Val Tyr Tyr Cys Ala Arg Tyr Pro Tyr Tyr Tyr Ser Arg Ser
1               5                   10                  15

Asn Trp Tyr Phe Asp Leu Trp Gly Gln Gly
            20                  25


<210> SEQ ID NO 107
<211> LENGTH: 26
<212> TYPE: PRT
<213> ORGANISM: Artificial Sequence
<220> FEATURE:
<223> OTHER INFORMATION: PVG9-3-1B10

<400> SEQUENCE: 107

Thr Ala Val Tyr Tyr Cys Ala Arg Tyr Pro Tyr Tyr Tyr Ser Arg Ser
1               5                   10                  15

Asn Trp Tyr Phe Asp Leu Trp Gly Gln Gly
            20                  25


<210> SEQ ID NO 108
<211> LENGTH: 26
<212> TYPE: PRT
<213> ORGANISM: Artificial Sequence
<220> FEATURE:
<223> OTHER INFORMATION: PVG9-3-1D6

<400> SEQUENCE: 108

Thr Ala Val Tyr Tyr Cys Ala Arg Tyr Pro Tyr Tyr Tyr Ser Arg Ser
1               5                   10                  15

Asn Trp Tyr Phe Asp Leu Trp Gly Gln Gly
            20                  25


<210> SEQ ID NO 109
<211> LENGTH: 26
<212> TYPE: PRT
<213> ORGANISM: Artificial Sequence
<220> FEATURE:
<223> OTHER INFORMATION: PVG9-3-2F4

<400> SEQUENCE: 109

Thr Ala Val Tyr Tyr Cys Ala Arg Tyr Pro Tyr Tyr Tyr Gly Arg Ser
1               5                   10                  15

Asn Trp Tyr Phe Asp Leu Trp Gly Gln Gly
            20                  25


<210> SEQ ID NO 110
<211> LENGTH: 26
<212> TYPE: PRT
<213> ORGANISM: Artificial Sequence
<220> FEATURE:
<223> OTHER INFORMATION: PVG9-3-1E3

<400> SEQUENCE: 110

Thr Ala Val Tyr Tyr Cys Ala Arg Tyr Pro Tyr Tyr Tyr Gly Arg Ser
1               5                   10                  15

Asn Trp Tyr Phe Asp Leu Trp Gly Gln Gly
            20                  25


<210> SEQ ID NO 111
<211> LENGTH: 26
<212> TYPE: PRT
<213> ORGANISM: Artificial Sequence
```

<220> FEATURE:
<223> OTHER INFORMATION: PVG9-3-2A2

<400> SEQUENCE: 111

Thr Ala Val Tyr Tyr Cys Ala Arg Tyr Pro Tyr Tyr Tyr Gly Arg Ser
1               5                   10                  15

Asn Trp Tyr Phe Asp Leu Trp Gly Gln Gly
            20                  25

<210> SEQ ID NO 112
<211> LENGTH: 26
<212> TYPE: PRT
<213> ORGANISM: Artificial Sequence
<220> FEATURE:
<223> OTHER INFORMATION: PVG9-3-1G7

<400> SEQUENCE: 112

Thr Ala Val Tyr Tyr Cys Ala Arg Tyr Pro Tyr Tyr Tyr Gly Arg Ser
1               5                   10                  15

Ser Trp Tyr Phe Asp Leu Trp Gly Gln Gly
            20                  25

<210> SEQ ID NO 113
<211> LENGTH: 26
<212> TYPE: PRT
<213> ORGANISM: Artificial Sequence
<220> FEATURE:
<223> OTHER INFORMATION: PVG9-3-1E2

<400> SEQUENCE: 113

Thr Ala Val Tyr Tyr Cys Ala Arg Tyr Pro Tyr Tyr Tyr Gly Arg Ser
1               5                   10                  15

Ser Trp Tyr Phe Asp Leu Trp Gly Gln Gly
            20                  25

<210> SEQ ID NO 114
<211> LENGTH: 26
<212> TYPE: PRT
<213> ORGANISM: Artificial Sequence
<220> FEATURE:
<223> OTHER INFORMATION: PVG9-3-2B12

<400> SEQUENCE: 114

Thr Ala Val Tyr Tyr Cys Ala Arg Tyr Pro Tyr Tyr Tyr Gly Arg Thr
1               5                   10                  15

Ser Trp Tyr Phe Asp Leu Trp Gly Gln Gly
            20                  25

<210> SEQ ID NO 115
<211> LENGTH: 26
<212> TYPE: PRT
<213> ORGANISM: Artificial Sequence
<220> FEATURE:
<223> OTHER INFORMATION: PVG9-3-2D6

<400> SEQUENCE: 115

Thr Ala Val Tyr Tyr Cys Ala Arg Tyr Pro Tyr Tyr Tyr Gly Arg Thr
1               5                   10                  15

Ser Trp Tyr Phe Asp Leu Trp Gly Gln Gly
            20                  25

<210> SEQ ID NO 116
<211> LENGTH: 26
<212> TYPE: PRT

<213> ORGANISM: Artificial Sequence
<220> FEATURE:
<223> OTHER INFORMATION: PVG9-3-2F2

<400> SEQUENCE: 116

Thr Ala Val Tyr Tyr Cys Ala Arg Tyr Pro Tyr Tyr Ser Gly Arg Ser
1 5 10 15

Ser Trp Tyr Phe Asp Leu Trp Gly Gln Gly
20 25

<210> SEQ ID NO 117
<211> LENGTH: 26
<212> TYPE: PRT
<213> ORGANISM: Artificial Sequence
<220> FEATURE:
<223> OTHER INFORMATION: PVG9-3-1D1

<400> SEQUENCE: 117

Thr Ala Val Tyr Tyr Cys Ala Arg Tyr Pro Tyr Tyr Ser Gly Arg Ser
1 5 10 15

Ser Trp Tyr Phe Asp Leu Trp Gly Gln Gly
20 25

<210> SEQ ID NO 118
<211> LENGTH: 26
<212> TYPE: PRT
<213> ORGANISM: Artificial Sequence
<220> FEATURE:
<223> OTHER INFORMATION: PVG9-3-1A11

<400> SEQUENCE: 118

Thr Ala Val Tyr Tyr Cys Ala Arg Tyr Pro Tyr Tyr Ser Gly Arg Ser
1 5 10 15

Ser Trp Tyr Phe Asp Leu Trp Gly Gln Gly
20 25

<210> SEQ ID NO 119
<211> LENGTH: 26
<212> TYPE: PRT
<213> ORGANISM: Artificial Sequence
<220> FEATURE:
<223> OTHER INFORMATION: PVG9-3-1E7

<400> SEQUENCE: 119

Thr Ala Val Tyr Tyr Cys Ala Arg Tyr Pro Tyr Tyr Tyr Ser Arg Thr
1 5 10 15

Ser Trp Tyr Phe Asp Leu Trp Gly Gln Gly
20 25

<210> SEQ ID NO 120
<211> LENGTH: 26
<212> TYPE: PRT
<213> ORGANISM: Artificial Sequence
<220> FEATURE:
<223> OTHER INFORMATION: PVG9-3-1C10

<400> SEQUENCE: 120

Thr Ala Val Tyr Tyr Cys Ala Arg Ala Pro Tyr Tyr Cys Gly Arg Ser
1 5 10 15

Cys Trp Tyr Phe Asp Leu Trp Gly Gln Gly
20 25

<210> SEQ ID NO 121
<211> LENGTH: 26

-continued

<212> TYPE: PRT
<213> ORGANISM: Artificial Sequence
<220> FEATURE:
<223> OTHER INFORMATION: PVG9-3-1F9

<400> SEQUENCE: 121

Thr Ala Val Tyr Tyr Cys Ala Arg Tyr Pro Tyr Tyr Cys Gly Arg Ser
1               5                   10                  15

Cys Trp Tyr Phe Asp Leu Trp Gly Gln Gly
            20                  25

<210> SEQ ID NO 122
<211> LENGTH: 26
<212> TYPE: PRT
<213> ORGANISM: Artificial Sequence
<220> FEATURE:
<223> OTHER INFORMATION: PVG9-3-1F8

<400> SEQUENCE: 122

Thr Ala Val Tyr Tyr Cys Ala Arg Tyr Pro Tyr Tyr Asp Gly Arg Ser
1               5                   10                  15

Asn Trp Tyr Phe Asp Leu Trp Gly Gln Gly
            20                  25

<210> SEQ ID NO 123
<211> LENGTH: 26
<212> TYPE: PRT
<213> ORGANISM: Artificial Sequence
<220> FEATURE:
<223> OTHER INFORMATION: PVG9-3-2G5

<400> SEQUENCE: 123

Thr Ala Val Tyr Tyr Cys Ala Arg Tyr Pro Tyr Tyr Cys Gly Arg Ser
1               5                   10                  15

Asn Trp Tyr Phe Asp Leu Trp Gly Gln Gly
            20                  25

<210> SEQ ID NO 124
<211> LENGTH: 26
<212> TYPE: PRT
<213> ORGANISM: Artificial Sequence
<220> FEATURE:
<223> OTHER INFORMATION: PVG9-3-2B11

<400> SEQUENCE: 124

Thr Ala Val Tyr Tyr Cys Ala Arg Asp Pro Tyr Tyr Cys Ser Arg Ser
1               5                   10                  15

Cys Trp Tyr Phe Asp Leu Trp Gly Gln Gly
            20                  25

<210> SEQ ID NO 125
<211> LENGTH: 26
<212> TYPE: PRT
<213> ORGANISM: Artificial Sequence
<220> FEATURE:
<223> OTHER INFORMATION: PVG9-3-2G9

<400> SEQUENCE: 125

Thr Ala Val Tyr Tyr Cys Ala Arg Tyr Pro Tyr Tyr Ser Gly Arg Ser
1               5                   10                  15

Tyr Trp Tyr Phe Asp Leu Trp Gly Gln Gly
            20                  25